(12) United States Patent
Kaner et al.

(10) Patent No.: US 11,541,153 B2
(45) Date of Patent: ***Jan. 3, 2023

(54) BIOFOULING RESISTANT COATINGS AND METHODS OF MAKING AND USING THE SAME

(71) Applicants: The Regents of the University of California, Oakland, CA (US); Silq Technologies Corporation, Los Angeles, CA (US)

(72) Inventors: Richard B. Kaner, Los Angeles, CA (US); Dayong Chen, Los Angeles, CA (US); Brian T. McVerry, Laguna Hills, CA (US); Ethan Rao, Venice, CA (US); Alexandra L. Polasko, Santa Monica, CA (US)

(73) Assignees: The Regents of the University of California, Oakland, CA (US); Silq Technologies Corporation, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/924,523

(22) Filed: Jul. 9, 2020

(65) Prior Publication Data

US 2020/0338240 A1 Oct. 29, 2020

Related U.S. Application Data

(63) Continuation of application No. 16/206,596, filed on Nov. 30, 2018, now Pat. No. 10,729,822.
(Continued)

(51) Int. Cl.
*A61L 31/10* (2006.01)
*A61L 27/34* (2006.01)
(Continued)

(52) U.S. Cl.
CPC .............. *A61L 31/10* (2013.01); *A01N 33/00* (2013.01); *A01N 33/12* (2013.01); *A01N 33/20* (2013.01);
(Continued)

(58) Field of Classification Search
CPC combination set(s) only.
See application file for complete search history.

(56) References Cited

U.S. PATENT DOCUMENTS 3,796,314 A 3/1974 Kolek
4,767,645 A 8/1988 Linder et al.
(Continued)

FOREIGN PATENT DOCUMENTS

CN 1481928 A 3/2004
CN 102067365 A 5/2011
(Continued)

OTHER PUBLICATIONS

Seo "Simultaneous patterning of proteins and cells through bioconjugation with photoreactable phospholipid polymers", RSC Adv. 2017, 7, 40669-40672 (Year: 2017).*
(Continued)

*Primary Examiner* — Nicole M. Buie-Hatcher
(74) *Attorney, Agent, or Firm* — Foley Hoag LLP; David P. Halstead; Lawrence P. Tardibono

(57) ABSTRACT

Disclosed herein are compositions to use in biofouling-resistant coatings, biofouling-resistant coatings, methods of making biofouling-resistant coatings, biofouling-resistant devices, and methods of making biofouling-resistant devices.

19 Claims, 13 Drawing Sheets

Related U.S. Application Data

(60) Provisional application No. 62/593,645, filed on Dec. 1, 2017.

(51) Int. Cl.

| | |
|---|---|
| *A61L 29/08* | (2006.01) |
| *A61L 27/54* | (2006.01) |
| *A61L 29/16* | (2006.01) |
| *A61L 31/16* | (2006.01) |
| *C09D 5/00* | (2006.01) |
| *C09D 133/14* | (2006.01) |
| *A61L 17/14* | (2006.01) |
| *A01N 41/06* | (2006.01) |
| *A01N 33/00* | (2006.01) |
| *C08J 7/04* | (2020.01) |
| *C08F 220/38* | (2006.01) |
| *C08J 7/056* | (2020.01) |
| *A01N 33/12* | (2006.01) |
| *C09D 183/04* | (2006.01) |
| *C08J 3/24* | (2006.01) |
| *A01N 33/20* | (2006.01) |
| *A61L 17/00* | (2006.01) |

(52) U.S. Cl.
CPC .......... *A01N 41/06* (2013.01); *A61L 17/005* (2013.01); *A61L 17/145* (2013.01); *A61L 27/34* (2013.01); *A61L 27/54* (2013.01); *A61L 29/085* (2013.01); *A61L 29/16* (2013.01); *A61L 31/16* (2013.01); *C08F 220/387* (2020.02); *C08J 3/245* (2013.01); *C08J 7/0427* (2020.01); *C08J 7/056* (2020.01); *C09D 5/00* (2013.01); *C09D 133/14* (2013.01); *C09D 183/04* (2013.01); *A61L 2300/404* (2013.01); *A61L 2300/408* (2013.01); *A61L 2420/02* (2013.01); *C08F 2800/10* (2013.01); *C08F 2810/20* (2013.01); *C08J 2383/04* (2013.01); *C08J 2433/14* (2013.01)

(56) References Cited

U.S. PATENT DOCUMENTS

| | | | |
|---|---|---|---|
| 5,753,008 | A | 5/1998 | Friesen et al. |
| 7,670,720 | B1 | 3/2010 | Buerger et al. |
| 8,029,857 | B2 | 10/2011 | Hoek et al. |
| 8,132,677 | B2 | 3/2012 | Liu et al. |
| 8,530,269 | B2 | 9/2013 | Chua et al. |
| 8,550,256 | B1 | 10/2013 | Diep et al. |
| 9,662,617 | B2 | 5/2017 | Hoek et al. |
| 10,315,169 | B2 | 6/2019 | Hoek et al. |
| 10,629,880 | B2 | 4/2020 | McVerry et al. |
| 10,729,822 | B2 | 8/2020 | Kaner et al. |
| 11,084,002 | B2 | 8/2021 | Hoek et al. |
| 11,258,134 | B2 | 2/2022 | McVerry et al. |
| 2002/0122872 | A1 | 9/2002 | Leukel et al. |
| 2005/0276419 | A1 | 12/2005 | Eggert et al. |
| 2006/0141273 | A1 | 6/2006 | Kino et al. |
| 2007/0254006 | A1 | 11/2007 | Loose et al. |
| 2008/0017512 | A1 | 1/2008 | Bordunov et al. |
| 2009/0155335 | A1 | 6/2009 | O'Shaughnessey et al. |
| 2009/0308804 | A1 | 12/2009 | Cohen et al. |
| 2010/0075101 | A1 | 3/2010 | Tang |
| 2011/0005997 | A1 | 1/2011 | Kurth et al. |
| 2011/0104573 | A1 | 5/2011 | Gogichev et al. |
| 2012/0201972 | A1 | 8/2012 | Hayashi et al. |
| 2012/0258313 | A1 | 10/2012 | Wen et al. |
| 2014/0206251 | A1 | 7/2014 | Stokes |
| 2014/0251897 | A1 | 9/2014 | Livingston et al. |
| 2015/0025168 | A1 | 1/2015 | Lienkamp et al. |
| 2016/0001236 | A1 | 1/2016 | Hoek et al. |
| 2016/0152008 | A1 | 6/2016 | Ogata et al. |
| 2017/0296986 | A1 | 10/2017 | Hoek et al. |
| 2017/0355799 | A1 | 12/2017 | Veiseh et al. |
| 2018/0159106 | A1 | 6/2018 | McVerry et al. |
| 2019/0185776 | A1 | 6/2019 | Kuramoto et al. |
| 2020/0203692 | A1 | 6/2020 | McVerry et al. |
| 2020/0338240 | A1 | 10/2020 | Kaner et al. |
| 2020/0385506 | A1 | 12/2020 | McVerry et al. |
| 2021/0095122 | A1 | 4/2021 | Freeman et al. |
| 2021/0245111 | A1 | 8/2021 | Lee et al. |

FOREIGN PATENT DOCUMENTS

| | | | |
|---|---|---|---|
| CN | 102099099 A | 6/2011 | |
| CN | 103068476 A | 4/2013 | |
| CN | 103582520 A | 2/2014 | |
| CN | 105854628 A | 8/2016 | |
| CN | 105932317 A | 9/2016 | |
| FR | 2989215 A1 | 10/2013 | |
| JP | 56067848 A | 7/1981 | |
| JP | 2007/527542 A | 9/2007 | |
| JP | 2009/147369 A | 7/2009 | |
| JP | 2010059346 A | 3/2010 | |
| JP | 48-41863 B2 | 12/2011 | |
| JP | 2012/055858 A | 3/2012 | |
| JP | 2017177754 A | 10/2017 | |
| TW | 201311750 A | 3/2013 | |
| TW | 201720848 A * | 6/2017 | ............. A61L 33/00 |
| WO | WO-00/076641 A1 | 12/2000 | |
| WO | WO-2004/100282 A2 | 11/2004 | |
| WO | WO-2009/039467 A1 | 3/2009 | |
| WO | WO-2009/099126 A1 | 8/2009 | |
| WO | WO-2010/006196 A2 | 1/2010 | |
| WO | WO-2010/036452 A2 | 4/2010 | |
| WO | WO-2011/060202 A1 | 5/2011 | |
| WO | WO-2012/071461 A2 | 5/2012 | |
| WO | WO-2013/109810 A1 | 7/2013 | |
| WO | WO-2014/001795 A1 | 1/2014 | |
| WO | WO-2014/032005 A1 | 2/2014 | |
| WO | WO-2014/113618 A1 | 7/2014 | |
| WO | WO-2016/083314 A1 | 6/2016 | |
| WO | WO-2017170210 A1 | 10/2017 | |
| WO | WO-2018/102517 A1 | 6/2018 | |
| WO | WO-2019/094685 A1 | 5/2019 | |
| WO | WO-2019/108871 A1 | 6/2019 | |
| WO | WO-2020/247629 A1 | 12/2020 | |

OTHER PUBLICATIONS

Machine translation of JP 2017177754 A, retrieved Mar. 2022 (Year: 2022).*
EIC search report for U.S. Appl. No. 16/404,372 (2020).
International Search Report and Written Opinion for International Application No. PCT/US2020/036121 dated Aug. 19, 2020.
Tanaka et al., "Synthesis and structures of zwitterionic polymers to induce electrostatic interaction with PDMS surface treated by air-plasma," Organic Chemistry, part ii:330-343 (2018).
Extended European Search Report for EP Application No. 18876572.1 dated Jul. 9, 2021.
Extended European Search Report for EP Application No. 18882865.1 dated Jul. 23, 2021.
Anderson et al., "Conjugated Polymer Films for Gas Separations," Sci 252(5011):1412-1415 (1991).
Batool et al., "Fabrication of covalently bonded nanostructured thin films of epoxy resin and polydimethylsiloxane for oil adsorption," Polymer Bulletin, 74(12):4827-4840 (2017).
Extended European Search Report issued by the European Patent Office in corresponding Application No. EP 14753770, dated Oct. 24, 2016.
Extender European Search Report for EP Application No. 17876218.3 dated Mar. 24, 2020.
Freger et al., "TFC polyamide membranes modified by grafting of hydrophilic polymers: an FT-IR/AFM/TEM study," J Mem Sci, 209:283-292 (2002).

(56) References Cited

OTHER PUBLICATIONS

Gerard et al., "Surface modification of poly(butylene terephthalate) nonwoven by photochemistry and biofunctionalization with peptides for blood filtration," Polymer Chemistry, 49(23): 5087-5099 (2011).
International Search Report and Written Opinion for International Application No. PCT/US14/17758 dated May 30, 2014.
International Search Report and Written Opinion for International Application No. PCT/US17/63887 dated Jan. 26, 2018.
International Search Report and Written Opinion for International Application No. PCT/US2018/059967 dated Feb. 17, 2019.
International Search Report and Written Opinion for International Application No. PCT/US2018/063196 dated Mar. 10, 2019.
Khong et al., "General Photo-Patterning of Polyelectrolyte Thin Films via Efficient Ionic Bis(Fluorinated Phenyl Azide) Photo-Crosslinkers and their Post-Deposition Modification," Advanced Functional Materials, 17(14): 2490-2499 (2007).
Khulbe et al., "The art of surface modification of synthetic polymeric membranes," J Appl Ploymer Sci, 115(2): 855-895 (2010).
Kuo et al., "Surface modification with poly(sulfobetaine methacrylate-co-acrylic acid) to reduce fibrinogen adsorption, platelet adhesion, and plasma coagulation," Biomacromolecules, 12(12):4348-4356 (2011).
Li et al., "Influence of polybenzimidazole main chain structure on H2/CO2 separation at elevated temperatures," Journal of Membrane Science, 461:59-68 (2014).
Liu et al., "Perfluorophenyl Azides: New Applications in Surface Functionalization and Nanomaterial Synthesis," Acc Chem Res, 43(11):1434-1443 (2010).
Liu et al., "Photoinitiated coupling of unmodified monosaccharides to iron oxide nanoparticles for sensing proteins and bacteria," Bioconjugate Chem, 20(7): 1349-1355 (2009).
Mandwar et al., "Perfluorophenyl azide immobilization chemistry for single molecule force spectroscopy ofthe concanavalin A/mannose interaction," Langmuir, 26(22): 16677-16680 (2010).
Mizutani et al., "Liquid, phenylazide-end-capped copolymers of epsilon-caprolactone and trimethylene carbonate: preparation, photocuring characteristics, and surface layering," Biomacromolecules, 3(4):668-675 (2002).
Mosnacek et al., "Photochemical grafting of polysulfobetaine onto polyethylene and polystyrene surfaces and investigation of long-term stability ofthe polysulfobetaine layer in seawater," Polymers for Advanced Technologies, 29(7):1930-1938 (2018).
Puleo et al., "Gas sorption and transport in substituted polystyrenes," Journal of Polymer Science Part B: Polymer Physics, 27(11):2385-2406 (1989).
Qureshi et al., "Nanoprotective layer-by-layer coatings with epoxy components for enhancing abrasion resistance: toward robust multimaterial nanoscale films," Acs Nano, 7(10):9336-9344 (2013).
Sakuragi et al., "A photoimmobilizable sulfobetaine-based polymer for a nonbiofouling surface," Materials Science and Engineering:C, 30(2):316-322 (2010).
Seo et al., "Simultaneous patterning of proteins and cells through bioconjugation with photoreactable phospholipid polymers," RSC Advances, 7(64):40669-40672 (2017).
Sivakumar et al., "Novel Microarrays for Simultaneous of Multiple Antiviral Antibodies," Plos One, 8(12):e81726/1-e81726/9 (2013).
Sundhoro et al., "Fabrication of carbohydrate microarrays on a poly (2-hydroxyethyl methacrylate)-based photoactive substrate," Organic & Biomolecular Chemistry, 14(3):1124-1130 (2015).
Sundhoro et al., "Poly(HEMA-co-HEMA-PFA): Synthesis and preparation of stable micelles encapsulating imaging nanoparticles," Journal of Colloid and Interface Science, 500:1-8 (2017).
Yuwen, "Polymer-based photoactive surface for the efficient immobilization of nanoparticles, polymers, graphene and; carbohydrates," PDXScholar, Dissertation, Portland State University (2011).

\* cited by examiner

BIOFOULING RESISTANT COATINGS AND METHODS OF MAKING AND USING THE SAME

CROSS-REFERENCE

This application is a continuation of U.S. patent application Ser. No. 16/206,596 filed on Nov. 30, 2018, which claims the benefit of U.S. Provisional Application No. 62/593,645 filed on Dec. 1, 2017, the contents of each of which are fully incorporated by reference herein.

BACKGROUND

Hospital acquired infections (HAIs) cause over 100,000 deaths per year and over $30 billion in direct healthcare cost. In some cases, medical devices implanted into the body are the source of the HAI. Planktonic bacteria adhere to the surface of the medical devices and begin to grow into resilient biofilms that become more resistant to antibiotics and disinfecting agents than in the planktonic state.

SUMMARY

Described herein, in certain embodiments, are compositions to use in biofouling-resistant coatings, biofouling-resistant coatings, methods of making biofouling-resistant coatings, biofouling-resistant devices, and methods of making biofouling-resistant devices.

In one aspect, described herein is a compound of Formula (I):

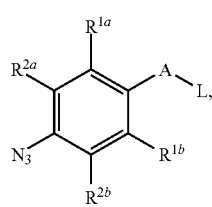

Formula (I)

wherein
A is selected from $-C(=O)-$, $-S(=O)-$, $-S(=O)_2-$, and $-S(=O)(-NR^3)-$;
L is selected from $-OQ$, $-NR^3Q$, and $-N(R^3)_2Q^+$;
Q is a structure represented by a formula:

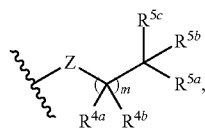

Z is selected from $-CR^{6a}R^{6b}-$, $-C(=O)-$, $-C(=NH)-$, and $-C(=NH)NR^7-$;
m is an integer selected from 0, 1, 2, 3, 4, 5, 6, 7, and 8;
each $R^{1a}$ and $R^{1b}$ is independently selected from hydrogen and halogen;
each $R^{2a}$ and $R^{2b}$ is independently selected from halogen, $-CN$, and optionally substituted C1-C6fluoroalkyl;
each $R^3$ is independently selected from hydrogen, optionally substituted C1-C4 alkyl, $-X$-optionally substituted C1-C4 alkyl, optionally substituted aryl, and $-X$-optionally substituted aryl;

X is $-C(=O)-$, $-S(=O)-$, or $-S(=O)_2-$;
each $R^{4a}$, $R^{4b}$, $R^{5a}$, $R^{5c}$, $R^{6a}$, and $R^{6b}$ is independently selected from hydrogen, halogen, $-CN$, $-OH$, optionally substituted C1-C4 alkyl, optionally substituted C1-C4 fluoroalkyl, optionally substituted aryl, $-NR^{8a}R^{8b}$, $-NR^{8a}R^{8b}R^{8c+}$, $-S(=O)_2O^-$, $-S(=O)_2OR^9$, $-C(=O)O^-$, and $-C(=O)OR^9$;
$R^{5b}$ is $-NR^{10a}R^{10b}$ or $-NR^{10a}R^{10b}R^{10c+}$;
each $R^7$, $R^{8a}$, $R^{8b}$, $R^{8c}$, and $R^9$ is independently selected from hydrogen and optionally substituted C1-C4 alkyl, and optionally substituted aryl;
each $R^{10a}$ and $R^{10c}$ is independently selected from hydrogen, optionally substituted C1-C4 alkyl, optionally substituted aryl, -(optionally substituted C1-C8alkylene)$S(=O)_2O^-$, -(optionally substituted C1-C8alkylene)$S(=O)_2OH$, -(optionally substituted C1-C8alkylene)$C(=O)O^-$, and -(optionally substituted C1-C8alkylene)$C(=O)OH$; and
$R^{10b}$ is $-(C=O)-C2-C6alkenyl$, $(S=O)-C2-C6alkenyl$, or $(S=O)_2-C2-C6alkenyl$.

In another aspect, described herein is a compound of Formula (II):

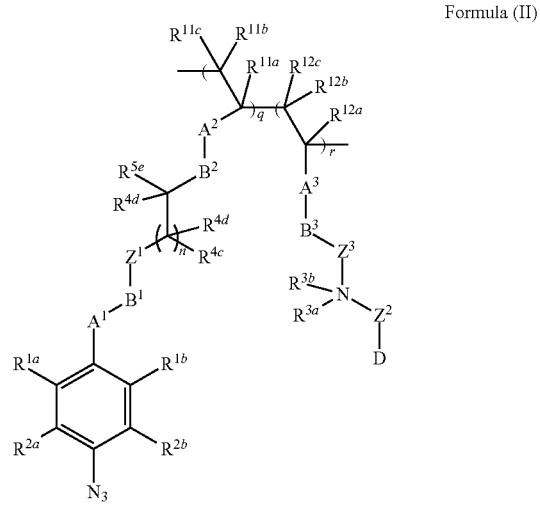

Formula (II)

wherein
each $R^{1a}$ and $R^{1b}$ is independently selected from hydrogen and halogen;
each $R^{2a}$ and $R^{2b}$ is independently selected from halogen, $-CN$, and optionally substituted C1-C6fluoroalkyl;
each $A^1$, $A^2$, and $A^3$ is independently selected from $-C(=O)-$, $-S(=O)-$, $-S(=O)_2-$, and $-S(=O)(=NR^{3c})-$;
each $B^1$, $B^2$, and $B^3$ is independently selected from $-O-$ and $-NR^{3c}-$;
D is $-S(=O)_2O^-$, $-S(=O)_2OR^{9a}$, $-C(=O)O^-$, or $-C(=O)OR^{9a}$;
$Z^1$ is $-(CR^{6c}R^{6d})_s-$;
$Z^2$ is $-(CR^{6c}R^{6d})_t-$;
$Z^3$ is $-(CR^{6c}R^{6d})_p-$;
each $R^{3a}$ and $R^{3b}$ is independently selected from hydrogen, optionally substituted C1-C4 alkyl, and optionally substituted benzyl;
each $R^{3c}$ and $R^{3d}$ is independently selected from hydrogen, optionally substituted C1-C4 alkyl, $-X$-optionally substituted C1-C4 alkyl, optionally substituted C2-C6 alkenyl, and optionally substituted aryl;

X is —C(=O)—, —S(=O)—, or —S(=O)$_2$—;

each $R^{4c}$, $R^{4d}$, $R^{5d}$, $R^{5e}$, $R^{6c}$, and $R^{6d}$ is independently selected from hydrogen, halogen, —CN, —OH, optionally substituted C1-C4 alkyl, optionally substituted C1-C4 fluoroalkyl, optionally substituted C2-C6 alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;

each $R^{9a}$, $R^{11a}$, $R^{11b}$, $R^{11c}$, $R^{12a}$, $R^{12b}$, and $R^{12c}$ is independently selected from hydrogen, optionally substituted C1-C4 alkyl, and optionally substituted aryl;

n is an integer selected from 0, 1, 2, 3, 4, 5, and 6;
s is an integer selected from 1, 2, 3, 4, or 5;
t is an integer selected from 1, 2, 3, 4, or 5;
p is an integer selected from 1, 2, 3, 4, or 5;
q is an integer selected from 40-60;
r is an integer selected from 1-10; and
wherein the compounds of Formula (II) is charged or zwitterionic.

In another aspect, described herein is a compound of Formula (III):

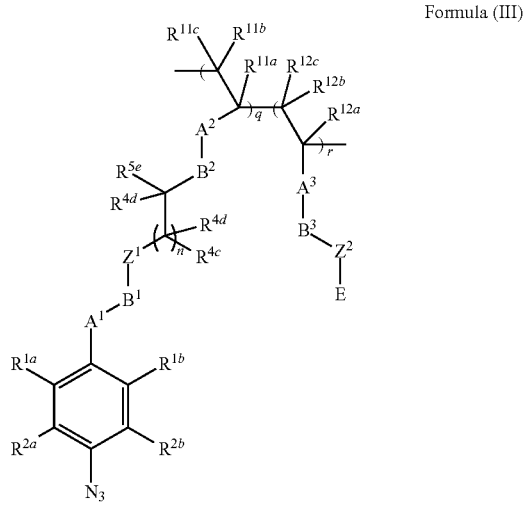

Formula (III)

wherein
each $R^{1a}$ and $R^{1b}$ is independently selected from hydrogen and halogen;
each $R^{2a}$ and $R^{2b}$ is independently selected from halogen, —CN, and optionally substituted C1-C6fluoroalkyl;
each $A^1$, $A^2$, and $A^3$ is independently selected from —C(=O)—, —S(=O)—, —S(=O)$_2$—, and —S(=O)(=NR$^{3c}$)—;
each $B^1$, $B^2$, and $B^3$ is independently selected from —O— and —NR$^{3c}$—;
$Z^1$ is —(CR$^{6c}$R$^{6d}$)$_s$—;
$Z^2$ is —(CR$^{6c}$R$^{6d}$)$_t$—;
E is —CN, —OR$^{9a}$, —NR$^{9a}$R$^{9b}$, —NR$^{9a}$R$^{9b}$R$^{9c+}$, optionally substituted C1-C4 alkyl, optionally substituted C1-C6fluoroalkyl, —S(=O)$_2$O$^-$, —S(=O)$_2$OR$^{9a}$, —C(=O)O$^-$, or —C(=O)OR$^{9a}$;
each $R^{4c}$, $R^{4d}$, $R^{5d}$, $R^{5e}$, $R^{6c}$, and $R^{6d}$ is independently selected from hydrogen, halogen, —CN, —OR$^{9a}$, optionally substituted C1-C4 alkyl, optionally substituted C1-C4 fluoroalkyl, optionally substituted C2-C6 alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;
each $R^{3c}$ and $R^{3d}$ is independently selected from hydrogen, optionally substituted C1-C4 alkyl, —X-optionally substituted C1-C4 alkyl, optionally substituted C2-C6 alkenyl, and optionally substituted aryl;
X is —C(=O)—, —S(=O)—, or —S(=O)$_2$—;
each $R^{9a}$, $R^{11a}$, $R^{11b}$, $R^{11c}$, $R^{12a}$, $R^{12b}$ and $R^{12c}$ is independently selected from hydrogen, optionally substituted C1-C4 alkyl, and optionally substituted aryl;
n is an integer selected from 0, 1, 2, 3, 4, 5, and 6;
s is an integer selected from 1, 2, 3, 4, or 5;
t is an integer selected from 1, 2, 3, 4, or 5;
q is an integer selected from 40-60; and
r is an integer selected from 1-10.

Any combination of the groups described above or below for the various variables is contemplated herein. Throughout the specification, groups and substituents thereof are chosen by one skilled in the field to provide stable moieties and compounds.

In another aspect, described herein is a medical device coated with a compound of Formula (I), (II), or (III).

In another aspect, described herein is a biofouling-resistant medical device, wherein a surface of the medical device is coated with a phenyl azide-based copolymer having a number-average molecular weight of between about 10,000 and about 250,000.

In another aspect, described herein is a biofouling-resistant medical device, wherein a surface of the medical device is coated with a phenyl azide-based copolymer having a number-average molecular weight of between about 14,000 and about 21,000.

In another aspect, described herein is a biofouling-resistant medical device, wherein a surface of the medical device is coated with a phenyl azide-based copolymer having a polydispersity index (PDI) of between about 1 and 1.5.

In another aspect, described herein is a method of preparing a biofouling-resistant medical device, comprising:
a) contacting a surface of a medical device with a mixture comprising a charged or zwitterion copolymer; and
b) treating the surface of the medical device of step a) with a light source for a time sufficient to undergo photografting of the charged or zwitterion copolymer onto the surface of the medical device, thereby making the biofouling-resistant medical device;
wherein the charged or zwitterion copolymer comprises a phenyl azide-based copolymer; and wherein the charged or zwitterion copolymer has a number-average molecular weight of between about 10,000 and about 250,000.

In another aspect, described herein is a method of preparing a biofouling-resistant medical device, comprising:
c) contacting a surface of a medical device with a mixture (e.g., a solution) comprising a charged or zwitterion copolymer; and
d) treating the surface of the medical device of step a) with a light source for a time sufficient to undergo photografting of the charged or zwitterion copolymer onto the surface of the medical device, thereby making the biofouling-resistant medical device;
wherein the charged or zwitterion copolymer comprises a phenyl azide-based copolymer; and wherein the charged or zwitterion copolymer has a number-average molecular weight of between about 14,000 and about 21,000.

In another aspect, described herein is a method of preparing a charged or zwitterion copolymer modified biofouling-resistant device comprising:
a) contacting a surface of a silicon-based device with a mixture (e.g., a solution) comprising a charged or zwitterion copolymer; and b) treating the surface of the device of step a) with a light source for a time sufficient to undergo photografting of the charged or zwitterion copolymer onto the surface of the silicon-based device, thereby generating the charged or zwitterion copolymer modified device;

wherein the charged or zwitterion copolymer comprises a phenyl azide-based copolymer.

In another aspect, described herein is a method of preparing a charged or zwitterion copolymer modified biofouling-resistant device comprising:

a) contacting a surface of a device with a mixture (e.g., a solution) comprising a charged or zwitterion copolymer; and b) treating the surface of the device of step a) with a light source for a time sufficient to undergo photografting of the charged or zwitterion copolymer onto the surface of the device, thereby generating the charged or zwitterion copolymer modified device;

wherein the charged or zwitterion copolymer comprises a phenyl azide-based copolymer; and wherein the charged or zwitterion copolymer has a number-average molecular weight of between about 10,000 and about 250,000.

In another aspect, described herein is a method of preparing a charged or zwitterion copolymer modified biofouling-resistant device comprising:

c) contacting a surface of a device with a mixture (e.g., a solution) comprising a charged or zwitterion copolymer; and d) treating the surface of the device of step a) with a light source for a time sufficient to undergo photografting of the charged or zwitterion copolymer onto the surface of the device, thereby generating the charged or zwitterion copolymer modified device;

wherein the charged or zwitterion copolymer comprises a phenyl azide-based copolymer; and wherein the charged or zwitterion copolymer has a number-average molecular weight of between about 14,000 and about 21,000.

In yet another aspect, described herein is a method for synthesizing a compound of Formula (II) comprising: reacting a compound of Formula (IV) or a salt or solvate thereof with a compound of Formula (V):

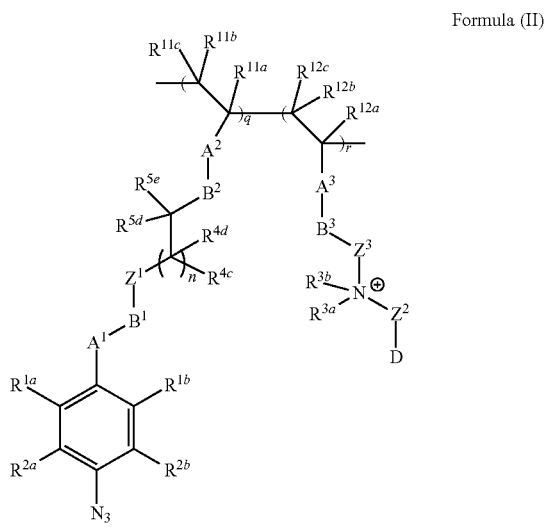

Formula (II)

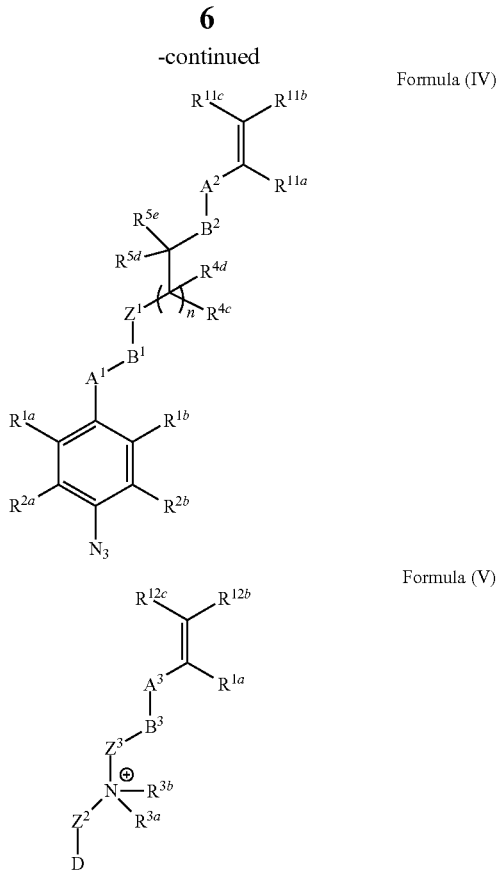

Formula (IV)

Formula (V)

wherein
each $R^{1a}$ and $R^{1b}$ is independently selected from hydrogen and halogen;
each $R^{2a}$ and $R^{2b}$ is independently selected from halogen, —CN, and optionally substituted C1-C6 fluoroalkyl;
each $A^1$, $A^2$, and $A^3$ is independently selected from —C(=O)—, —S(=O)—, —S(=O)$_2$—, and —S(=O)(=NR$^{3c}$)—;
each $B^1$, $B^2$, and $B^3$ is independently selected from —O— and —NR$^{3c}$—;
D is —S(=O)$_2$O$^-$, —S(=O)$_2$OR$^{9a}$, —C(=O)O$^-$, or —C(=O)OR$^{9a}$;
$Z^1$ is —(CR$^{6c}$R$^{6d}$)$_s$—;
$Z^2$ is —(CR$^{6c}$R$^{6d}$)$_t$—;
$Z^3$ is —(CR$^{6c}$R$^{6d}$)$_p$—;
each $R^{3a}$ and $R^{3b}$ is independently selected from hydrogen, optionally substituted C1-C4 alkyl, and optionally substituted benzyl;
each $R^{3c}$ and $R^{3d}$ is independently selected from hydrogen, optionally substituted C1-C4 alkyl, —X-optionally substituted C1-C4 alkyl, optionally substituted C2-C6 alkenyl, and optionally substituted aryl;
X is —C(=O)—, —S(=O)—, or —S(=O)$_2$—;
each $R^{4c}$, $R^{4d}$, $R^{5d}$, $R^{5e}$, $R^{6c}$, and $R^{6d}$ is independently selected from hydrogen, halogen, —CN, —OH, optionally substituted C1-C4 alkyl, optionally substituted C1-C4 fluoroalkyl, optionally substituted C2-C6 alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;
each $R^{9a}$, $R^{11a}$, $R^{11b}$, $R^{11c}$, $R^{12a}$, $R^{12b}$, and $R^{12c}$ is independently selected from hydrogen, optionally substituted C1-C4 alkyl, and optionally substituted aryl;
n is an integer selected from 0, 1, 2, 3, 4, 5, and 6;
s is an integer selected from 1, 2, 3, 4, or 5;

t is an integer selected from 1, 2, 3, 4, or 5;
p is an integer selected from 1, 2, 3, 4, or 5;
q is an integer selected from 40-60;
r is an integer selected from 1-10; and
wherein the compounds of Formula (II) and Formula (V) are each independently charged or zwitterionic.

In another aspect, described herein is a method for synthesizing a compound of Formula (III) comprising: reacting a compound of Formula (IV) or a salt or solvate thereof with a compound of Formula (VI):

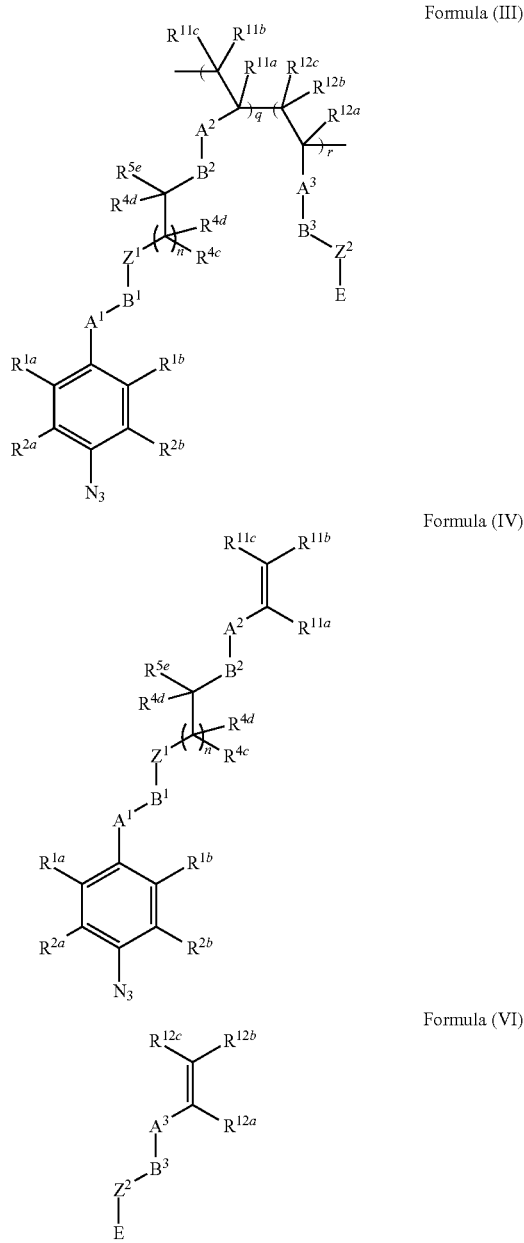

Formula (III)

Formula (IV)

Formula (VI)

wherein
each $R^{1a}$ and $R^{1b}$ is independently selected from hydrogen and halogen;
each $R^{2a}$ and $R^{2b}$ is independently selected from halogen, —CN, and optionally substituted C1-C6fluoroalkyl;

each $A^1$, $A^2$, and $A^3$ is independently selected from —C(=O)—, —S(=O)—, —S(=O)$_2$—, and —S(=O)(=NR$^{3c}$)—;
each $B^1$, $B^2$, and $B^3$ is independently selected from —O— and —NR$^{3c}$—;
$Z^1$ is —(CR$^{6c}$R$^{6d}$)$_s$—;
$Z^2$ is —(CR$^{6c}$R$^{6d}$)$_t$—;
E is —CN, —OR$^{9a}$, —NR$^{9a}$R$^{9b}$, —NR$^{9a}$R$^{9b}$R$^{9c+}$, optionally substituted C1-C4 alkyl, optionally substituted C1-C6fluoroalkyl, —S(=O)$_2$O$^-$, —S(=O)$_2$OR$^{9a}$, —C(=O)O$^-$, or —C(=O)OR$^{9a}$;
each $R^{4c}$, $R^{4d}$, $R^{5d}$, $R^{5e}$, $R^{6c}$, and $R^{6d}$ is independently selected from hydrogen, halogen, —CN, —OR$^{9a}$, optionally substituted C1-C4 alkyl, optionally substituted C1-C4 fluoroalkyl, optionally substituted C2-C6 alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;
each $R^{3c}$ and $R^{3d}$ is independently selected from hydrogen, optionally substituted C1-C4 alkyl, —X-optionally substituted C1-C4 alkyl, optionally substituted C2-C6 alkenyl, and optionally substituted aryl;
X is —C(=O)—, —S(=O)—, or —S(=O)$_2$—;
each $R^{9a}$, $R^{11a}$, $R^{11b}$, $R^{11c}$, $R^{12a}$, $R^{12b}$, and $R^{12c}$ is independently selected from hydrogen, optionally substituted C1-C4 alkyl, and optionally substituted aryl;
n is an integer selected from 0, 1, 2, 3, 4, 5, and 6;
s is an integer selected from 1, 2, 3, 4, or 5;
t is an integer selected from 1, 2, 3, 4, or 5;
q is an integer selected from 40-60; and
r is an integer selected from 1-10.

In one aspect, also described herein is a charged or zwitterion copolymer modified biofouling-resistant device prepared by the method comprising:
a) contacting a surface of a silicon-based device with a mixture (e.g., a solution) comprising a charged or zwitterion copolymer; and
b) treating the surface of the device of step a) with a light source for a time sufficient to undergo photografting of the charged or zwitterion copolymer onto the surface of the silicon-based device, thereby generating the charged or zwitterion copolymer modified device;
wherein the charged or zwitterion copolymer comprises a phenyl azide-based copolymer.

In another aspect, described herein is a charged or zwitterion copolymer modified biofouling-resistant device prepared by the method comprising:
a) contacting a surface of a device with a mixture (e.g., a solution) comprising a charged or zwitterion copolymer; and
b) treating the surface of the device of step a) with a light source for a time sufficient to undergo photografting of the charged or zwitterion copolymer onto the surface of the device, thereby generating the charged or zwitterion copolymer modified device;
wherein the charged or zwitterion copolymer comprises a phenyl azide-based copolymer; and wherein the charged or zwitterion copolymer has a number-average molecular weight of between about 10,000 and about 250,000.

In another aspect, described herein is a charged or zwitterion copolymer modified biofouling-resistant device prepared by the method comprising:
c) contacting a surface of a device with a mixture (e.g., a solution) comprising a charged or zwitterion copolymer; and
d) treating the surface of the device of step a) with a light source for a time sufficient to undergo photografting of the charged or zwitterion copolymer onto the surface of the device, thereby generating the charged or zwitterion copolymer modified device;

wherein the charged or zwitterion copolymer comprises a phenyl azide-based copolymer; and wherein the charged or zwitterion copolymer has a number-average molecular weight of between about 14,000 and about 21,000.

BRIEF DESCRIPTION OF THE FIGURES

The accompanying figures, which are incorporated in and constitute a part of this specification, illustrate several aspects and together with the description serve to explain and not to limit the scope of current disclosure.

Figure 1:
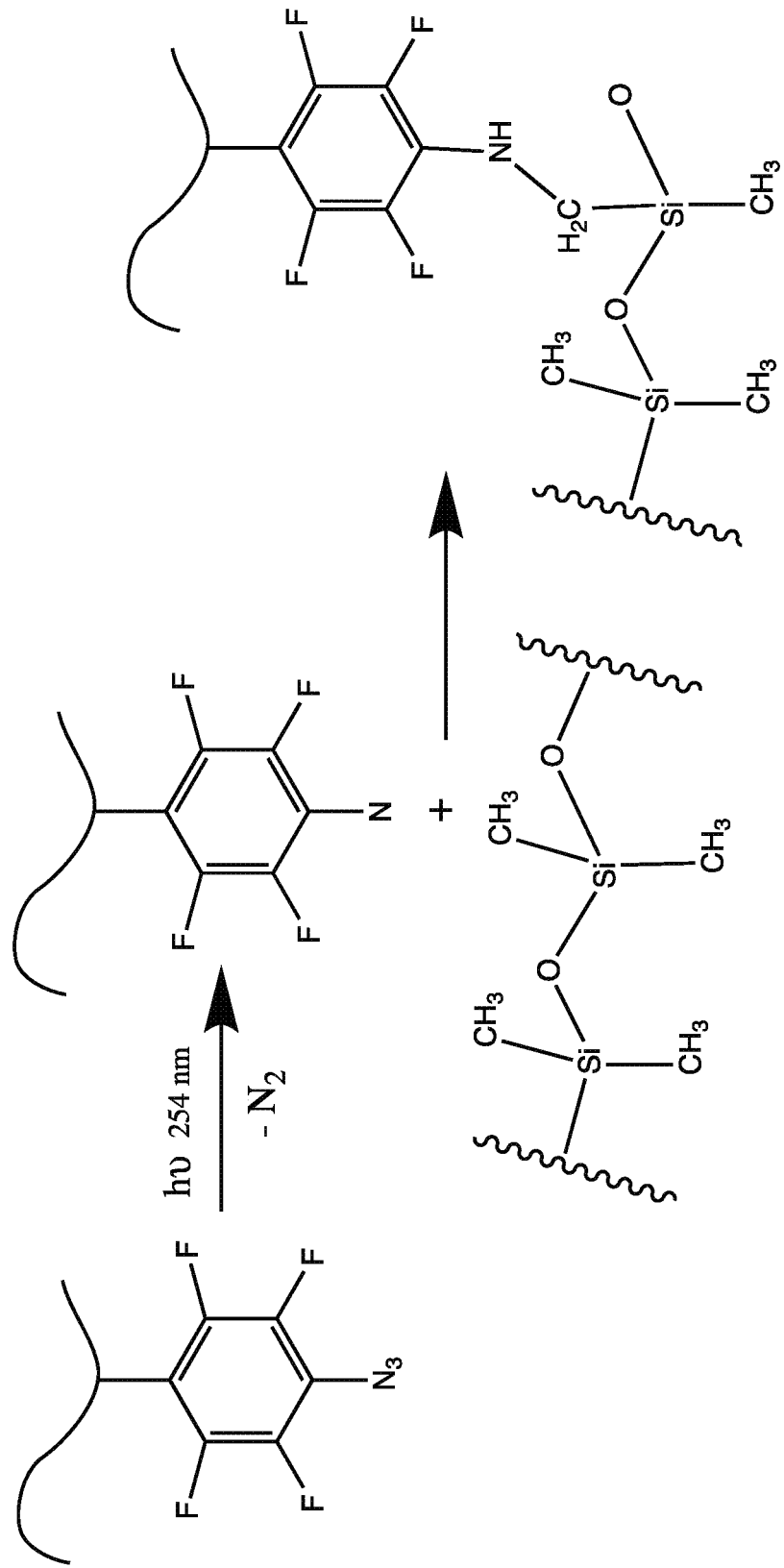
FIG. 1 illustrates representative photografting of poly (sulfobetaine methacrylate-co-perfluorophenylazide methacrylate) (PFPA-PSB copolymer) to a silicone surface.
Figure 2A:
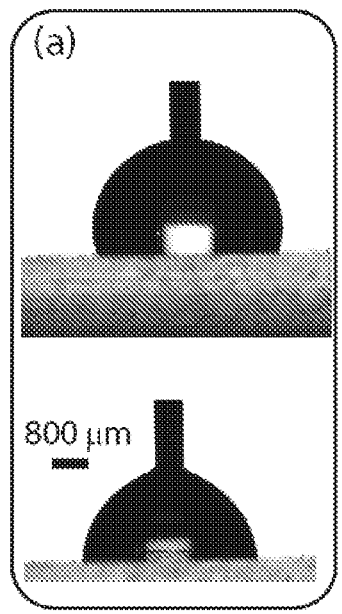
FIG. 2A illustrates representative water advancing contact angle (upper image) and receding contact angle (lower image) on an unmodified silicone surface and (b) PFPA-PSB copolymer modified silicone surface.
Figure 2B:
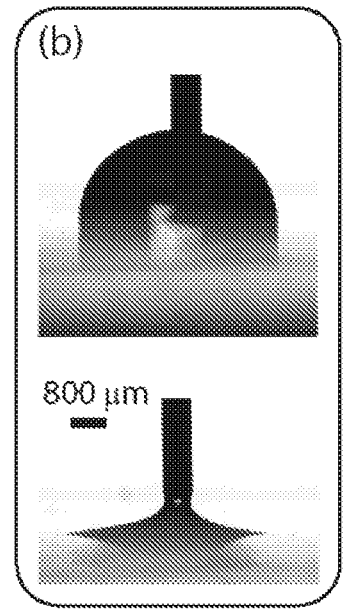
FIG. 2B illustrates representative water advancing contact angle (upper image) and receding contact angle (lower image) on a PFPA-PSB copolymer modified silicone surface.
Figure 3A:
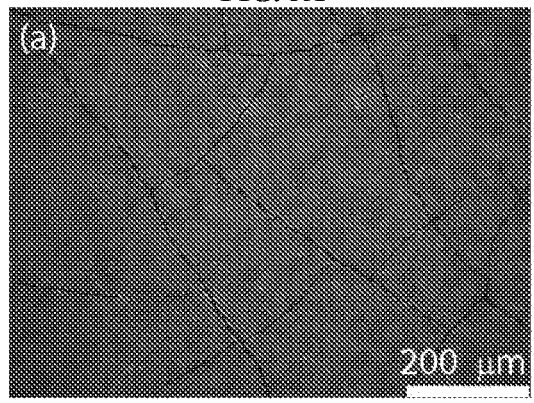
FIG. 3A illustrates high density of *Escherichia coli* adhesion to unmodified silicone surface forming an elastic film, which fractured upon surface drying.
Figure 3B:
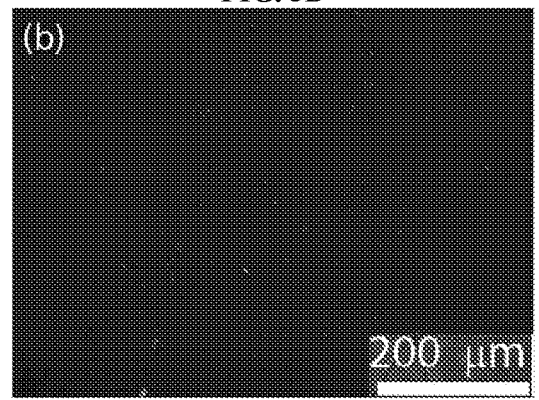
FIG. 3B illustrates very low density of *Escherichia coli* adhesion to poly(sulfobetaine methacrylate-co-perfluorophenylazide methacrylate)-modified silicone surface.
Figure 4:
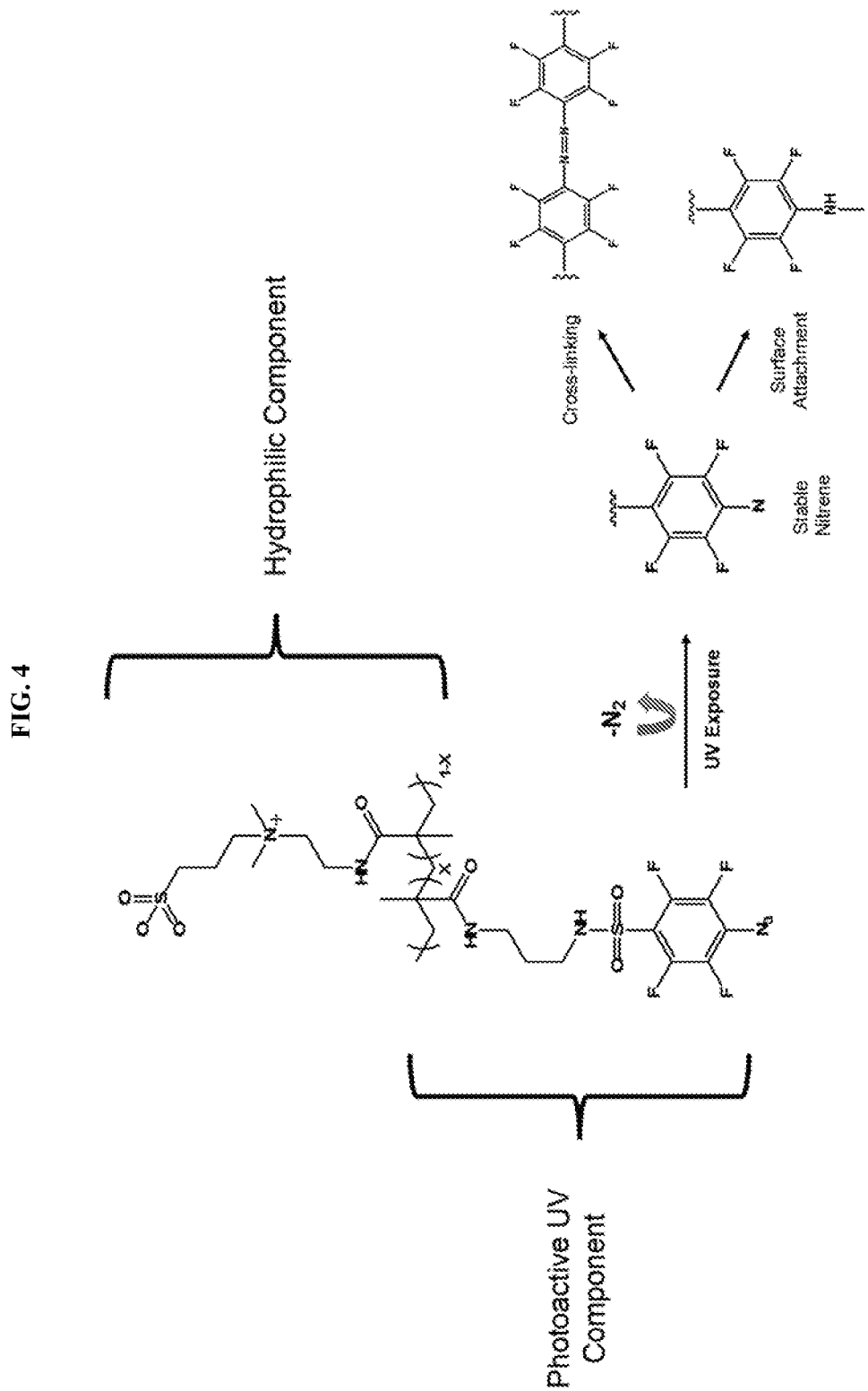
FIG. 4 illustrates the structure of PFPA-PSB copolymer.
Figure 5A:
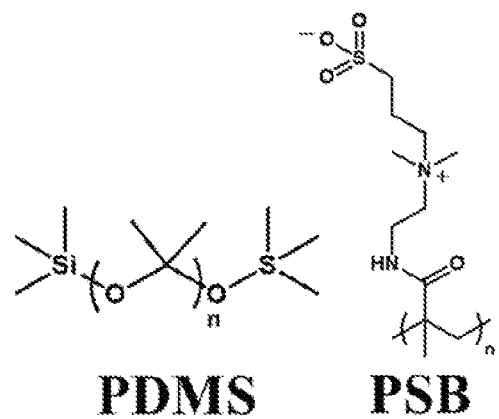
FIG. 5A illustrates chemical structure of polydimethylsiloxane and polysulfobetaine.
Figure 5B:
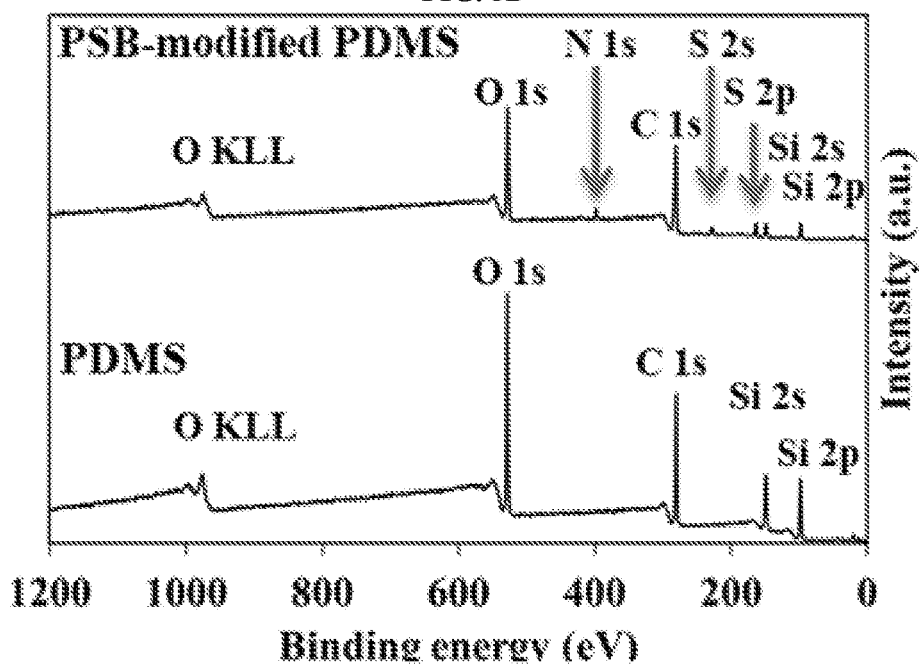
FIG. 5B illustrates XPS spectra of a PFPA-PSB modified PDMS substrate, showing the successful grafting of PSB on the organic substrate.
Figure 5C:
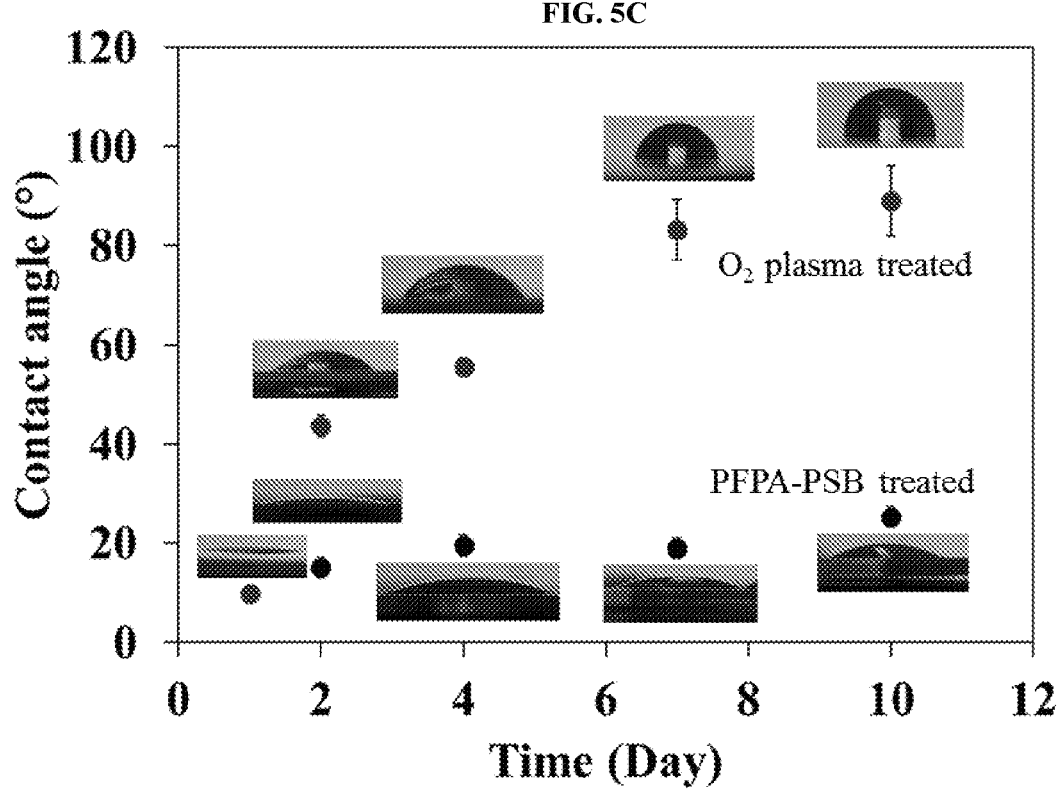
FIG. 5C illustrates evolution of water contact angle on PDMS substrates treated with $O_2$ plasma or coated with PSB. The plasma treated PDMS substrate shows a rapid hydrophobic recovery, whereas, the PSB-modified PDMS substrate remains hydrophilic for an extended time.
Figure 5D:
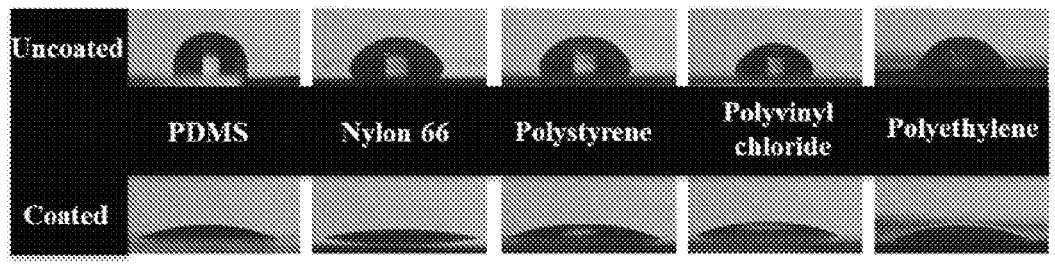
FIG. 5D illustrates superhydrophilic properties of a wide spectrum of hydrophobic organic substrates coated with PFPA-PSB copolymer, including PDMS, Nylon 66, Polystyrene, polyvinyl chloride, and polyethylene.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Hospital acquired infections (HAIs) cause over 100,000 deaths per year and over $30 billion in direct healthcare cost. Despite reduction of HAIs in recent years through improved antiseptic technique, surgical procedure, and diagnosis, HAIs declines are slowing down indicating the need for new preventative methods. In some instances, medical devices implanted into the body are the source of infection. It is estimated that 60-70% of HAIs are associated with the use of implantable medical devices. Planktonic bacteria adhere to the surface of the medical devices and begin to grow into resilient biofilms that become more resistant to antibiotics and disinfecting agents than in the planktonic state. As the biofilm grows and the cells continue to proliferate, the extracellular matrix scaffolding (made up of proteins and polysaccharides) bursts open, releasing more bacteria into the body. The body can no longer stave off infection and strong antibiotics must be used to fight the infectious cells. The use of strong antibiotics has led to the existence of antibiotic resistant bacteria, also known as superbugs, which can no longer be treated with conventional antibiotics.

Without the initial adhesion of planktonic cells to the surface of a material, the biofilm formation is prevented or reduced. Several researchers have identified the attractive forces that cause organic material to adhere to polymeric surfaces: hydrophobic interactions and electrostatic interactions (van der Waals forces) between the organic materials and polymer surface. Using self-assembled monolayers, Whitesides et al. surveyed several functional groups to determine surface functionalities that promote or hinder the non-specific adsorption of proteins. (Whitesides, G. M. A survey of structureproperty relationships of surfaces that resist the adsorption of protein. *Langmuir*, 2001, 17 (18), pp 5605-5620). The functional groups that exhibited the lowest adhesion were electrostatically neutral hydrophilic moieties that contained hydrogen bond donating groups. From these design rules, many material coatings have been developed and shown to reduce adhesion of proteins and microorganisms. However, these coating are substrate dependent and/or require exotic reaction conditions that are not compatible for wide-scale use. In some cases, several polymers coatings and surface modifications have been developed to repel these interactions to reduce/prevent the formation of biofilms on surfaces. In some instances, the coating should have the following chemical requirements to be used as an anti-fouling surface: a) the coating should be hydrophilic; b) the coating should consist of mostly of hydrogen bond acceptors; and c) the coating should be electrostatically neutral. However, due to the water-solubility of hydrophilic coatings, the coating material should be covalently bound to the polymeric material for long-term effects.

In some instances, medical grade silicone is used in medical and health care industry. Its market currently undergoes a rapid growth and is projected to reach $7.23 billion by 2021. Medical grade silicone generally includes polydimethylsiloxane (PDMS) fluids and elastomers. Due to their good chemical stability, matching mechanical properties with human tissues, and no-requirements for plasticizers, PDMS elastomers generally have excellent biocompatibility, and are used in medical devices and biomedical implants such as catheters and pacemakers. PDMS elastomers also have high transparency and easy processability. Therefore, PDMS elastomers have found broad applications in fabricating microfluidic devices, which provide low-cost, simple, and robust systems for diagnosing diseases (Whitesides, G. M. The origins and the future of microfluidics. *Nature* 2006, 442 (7101), 368-373). However, PDMS elastomers also have a low surface energy of about 20 mN/m. Bacteria, platelets, proteins, and other biomolecules tend to adhere to the hydrophobic surfaces of PDMS elastomers (Hron, P. Hydrophilisation of silicone rubber for medical applications. *Polymer international* 2003, 52 (9), 1531-1539). For silicone medical implants, bacterial adhesion and biofilm formation may lead to the failure of medical devices, severe infection, and even death of patients. For disease diagnosis devices based on PDMS microfluidics, proteins and other biomolecules fouling on the PDMS surfaces can significantly reduce the sensitivity of these devices, and may even lead to complete device-failure if blocking of the microfluidic channels occurs (Zhou, J. et al. Recent developments in PDMS surface modification for microfluidic devices. *Electrophoresis* 2010, 31 (1), 2-16).

Hydrophilic treatment of the PDMS surfaces was found to be one of the strategies to alleviate or prevent the problem of biofouling (Keefe, A. J. et al. Suppressing surface reconstruction of superhydrophobic PDMS using a superhydrophilic zwitterionic polymer. *Biomacromolecules* 2012, 13 (5), 1683-1687). Some conventional methods of making PDMS surfaces hydrophilic include oxidation of the surfaces by oxygen plasma, UV-ozone, or corona discharge. However, these modifications are only temporary because PDMS has an extremely low glass transition temperature of about −120° C. and therefore the PDMS chains are highly mobile at room temperature. The PDMS chains are able to rearrange and recover the hydrophobic surface of PDMS elastomers within a time window of a few hours. In some cases, other methods seeking to make long-lasting hydrophilic PDMS surfaces take many steps and involve radical reaction or polymerization. These steps have to be performed in closed containers, and/or under the protection of inert gas. Due to the higher solubility of oxygen relative to nitrogen in PDMS, in some instances it takes long time to remove oxygen from PDMS so that the radical reaction can proceed efficiently. These strict reaction conditions significantly increase the cost and limit industrial applicability of these reactions.

In some embodiments, provided herein are biofouling-resistant coatings comprising charged or zwitterion compounds comprising phenyl-azide moieties. In some instances, biofouling comprises microfouling or macrofouling. Microfouling comprises formation of microorganism adhesion (e.g., bacteria adhesion) and/or biofilm. Biofilm is a group of microorganism which adheres to a surface. In some instances, the adhered microorganisms are further embedded in a self-produced matrix of extracellular polymeric substance, which comprises a polymeric conglomeration of extracellular DNA, protein, and polysaccharides. Macrofouling comprises attachment of larger organisms.

Charged and/or zwitterionic compounds bind water molecules via electrostatically induced hydration. In such cases, charged and/or zwitterionic materials exhibit surface resistance to protein/cell/bacterial adhesion, biofilm formation, and/or macrofouling. In some embodiments, the charged or zwitterion compounds comprise copolymers. In some embodiments, also provided herein are methods of making biofouling-resistant coatings comprising charged or zwitterion copolymers via polymerization reaction. In some embodiments, the polymerization reaction is addition polymerization, atomic transfer radical polymerization (ATRP), coordination polymerization, free-radical polymerization, nitroxide-mediated radical polymerization (NMP), reversible addition fragmentation chain-transfer polymerization (RAFT), or ring-opening metathesis polymerization (ROMP). In some embodiments, the ionic polymerization is anionic polymerization or cationic polymerization. In some embodiments, the polymerization reaction is reversible-deactivation polymerization (RDP). In some embodiments, the polymerization reaction is free-radical polymerization. In some embodiments, the polymerization reaction is atomic transfer radical polymerization (ATRP). In some embodiments, biofouling-resistant coatings comprising charged or zwitterion copolymers are grafted onto a polymer surface of a device under a UV exposure. In some other embodiments, charged or zwitterion copolymers are grafted onto a silicone-comprising surface of a device under a UV exposure. In some embodiments, charged or zwitterion copolymers are grafted onto a surface of a medical device under a UV exposure. In some other embodiments, charged or zwitterion copolymers are grafted onto a silicone-comprising surface of a medical device under a UV exposure. In some embodiments, charged or zwitterion are grafted onto a polymer surface of a medical device under a UV exposure. In some other embodiments, charged or zwitterion copolymers are grafted onto a silicone-comprising polymer surface of a medical device under a UV exposure.

In some embodiments, a charged or zwitterion copolymer modified device comprises anti-fouling properties and is used to prevent and/or to reduce the development of biofouling. In some embodiments, a charged or zwitterion copolymer modified medical device comprises anti-fouling properties and is used to prevent and/or to reduce the development of biofouling. In some embodiments, the charged or zwitterion coatings prevent and/or reduce the attachment of microorganisms, plants, algae, or animals to a surface.

In additional embodiments, disclosed herein are compounds to be used to prepare charged or zwitterion copolymers of the disclosure as well as the charged or zwitterion copolymers themselves to be used within the methods disclosed herein.

I. Compounds

In one aspect, described herein is a compound that has the structure of Formula (I) or a salt or solvate thereof:

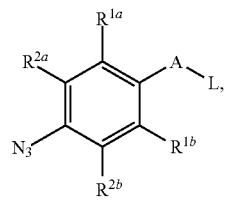

Formula (I)

wherein
A is selected from —C(=O)—, —S(=O)—, —S(=O)$_2$—, and —S(=O)(—NR$^3$)—;
L is selected from —OQ, —NR$^3$Q, and —N(R$^3$)$_2$Q$^+$;
Q is a structure represented by a formula:

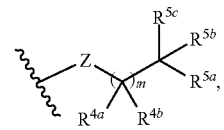

Z is selected from —CR$^{6a}$R$^{6b}$—, —C(=O)—, —C(=NH)—, and —C(=NH)NR$^7$—;
m is an integer selected from 0, 1, 2, 3, 4, 5, 6, 7, and 8;
each R$^{1a}$ and R$^{1b}$ is independently selected from hydrogen and halogen;
each R$^{2a}$ and R$^{2b}$ is independently selected from halogen, —CN, and optionally substituted C1-C6fluoroalkyl;
each R$^3$ is independently selected from hydrogen, optionally substituted C1-C4 alkyl, —X-optionally substituted C1-C4 alkyl, optionally substituted aryl, and —X-optionally substituted aryl;
X is —C(=O)—, —S(=O)—, or —S(=O)$_2$—;
each R$^{4a}$, R$^{4b}$, R$^{5a}$, R$^{5c}$, R$^{6a}$, and R$^{6b}$ is independently selected from hydrogen, halogen, —CN, —OR$^9$, optionally substituted C1-C4 alkyl, optionally substituted C1-C4 fluoroalkyl, optionally substituted aryl, —NR$^{8a}$R$^{8b}$, —NR$^{8a}$R$^{8b}$R$^{8c+}$, —S(=O)$_2$O$^-$, —S(=O)$_2$ OR$^9$, —C(=O)O$^-$, and —C(=O)OR$^9$;
R$^{5b}$ is —NR$^{10a}$R$^{10b}$ or —NR$^{10a}$R$^{10b}$R$^{10c+}$;
each R$^7$, R$^{8a}$, R$^{8b}$, R$^{8c}$, and R$^9$ is independently selected from hydrogen and optionally substituted C1-C4 alkyl, and optionally substituted aryl;
each R$^{10a}$ and R$^{10c}$ is independently selected from hydrogen, optionally substituted C1-C4 alkyl, optionally substituted aryl, -(optionally substituted C1-C8alkylene)S(=O)$_2$O$^-$, -(optionally substituted C1-C8alkylene)S(=O)$_2$OH, -(optionally substituted C1-C8alkylene)C(=O)O$^-$, and -(optionally substituted C1-C8alkylene)C(=O)OH; and
R$^{10b}$ is —(C=O)—C2-C6alkenyl, (S=O)—C2-C6alkenyl, or (S=O)$_2$—C2-C6alkenyl.

In some embodiments, the compound of Formula (I) has a structure selected from:

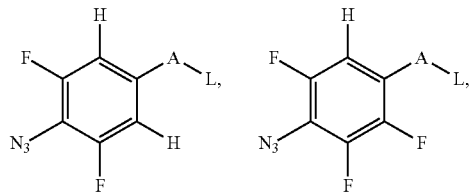

-continued
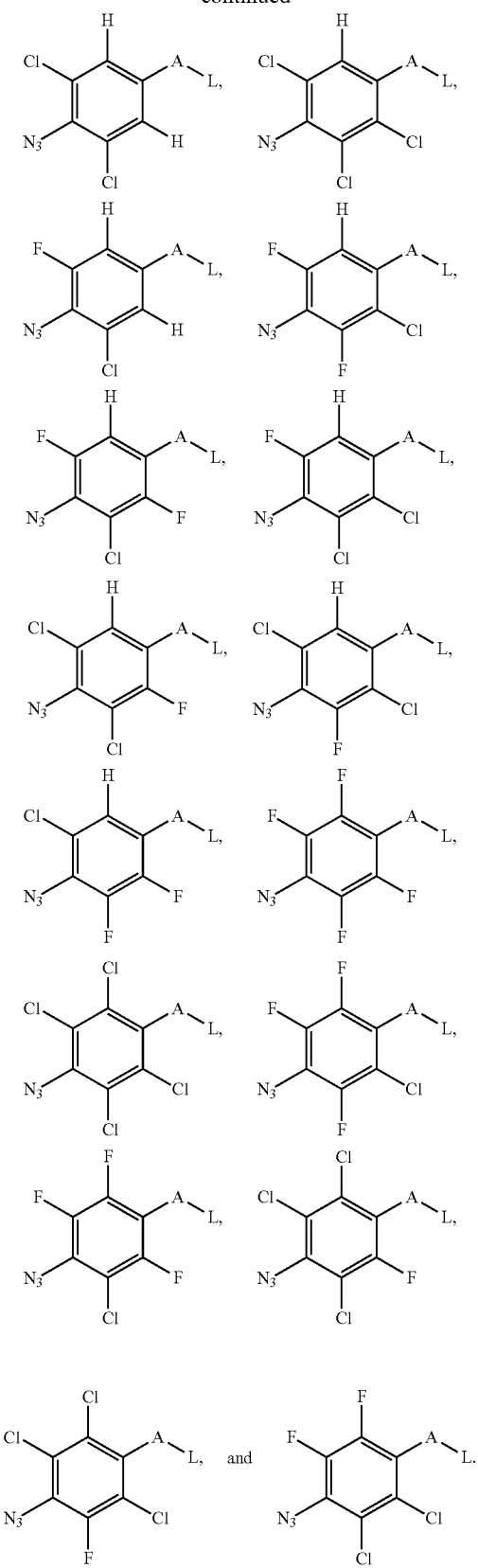
In some embodiments, the compound of Formula (I) has the structure selected from:
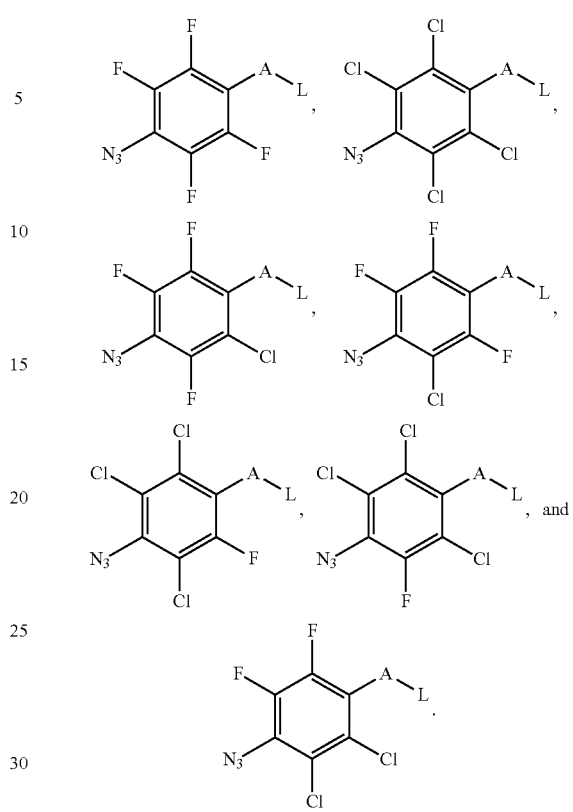
In some embodiments, the compound of Formula (I) has the following structure:
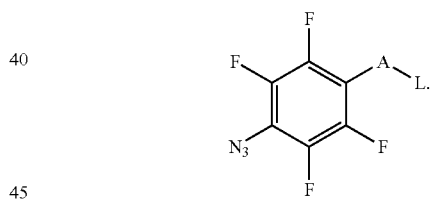
In some embodiments, the compound of Formula (I) has a structure selected from:
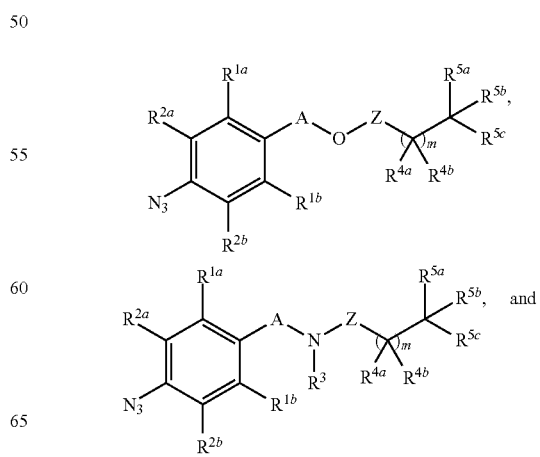

-continued

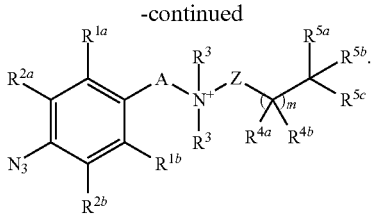

In some embodiments, the compound of Formula (I) has a structure selected from:

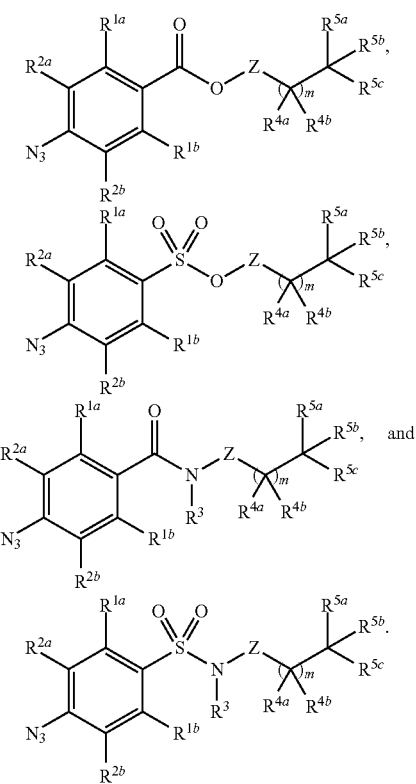

In some embodiments, each $R^{1a}$ and $R^{1b}$ is independently halogen. In some embodiments, each $R^{1a}$ and $R^{1b}$ is independently F or Cl. In some embodiments, each $R^{1a}$ and $R^{1b}$ is F. In some embodiments, each $R^{2a}$ and $R^{2b}$ is independently selected from halogen, —CN, and optionally substituted C1-C6fluoroalkyl. In some embodiments, each $R^{2a}$ and $R^{2b}$ is independently halogen. In some embodiments, each $R^{2a}$ and $R^{2b}$ is —CN. In some embodiments, each $R^{2a}$ and $R^{2b}$ is independently substituted C1-C6fluoroalkyl. In some embodiments, each $R^{2a}$ and $R^{2b}$ is —CF$_3$.

In some embodiments, each $R^{1a}$, $R^{1b}$, $R^{2a}$, and $R^{2b}$ is F.

In some embodiments, Z is selected from —CR$^{6a}$R$^{6b}$—, —C(=O)—, —C(=NH)—, and —C(=NH)NR$^7$—. In some embodiments, Z is —CR$^{6a}$R$^{6b}$—. In some embodiments, Z is —C(=O)—. In some embodiments, Z is —C(=NH)—. In some embodiments, Z is —C(=NH)NR$^7$—.

In some embodiments, each $R^3$ is independently selected from hydrogen, optionally substituted C1-C4 alkyl, —X-optionally substituted C1-C4 alkyl, optionally substituted aryl, and —X-optionally substituted aryl. In some embodiments, $R^3$ is hydrogen. In some embodiments, $R^3$ is optionally substituted C1-C4 alkyl. In some embodiments, $R^3$ is —X-optionally substituted C1-C4 alkyl. In some embodiments, $R^3$ is optionally substituted aryl. In some embodiments, $R^3$ is —X-optionally substituted aryl.

In some embodiments, X is —C(=O)—, —S(=O)—, or —S(=O)$_2$—. In some embodiments, X is —C(=O)—. In some embodiments, X is —S(=O)—. In some embodiments, X is —S(=O)$_2$—.

In some embodiments, each $R^{6a}$ and $R^{6b}$ is hydrogen.

In some embodiments, m is 0, 1, 2, 3, 4, or 5. In some embodiments, m is 0. In some embodiments, m is 1. In some embodiments, m is 2. In some embodiments, m is 3. In some embodiments, m is 4. In some embodiments, m is 5.

In some embodiments, $R^{5a}$ is hydrogen; $R^{5b}$ is —NR$^{10a}$R$^{10b}$; and $R^{5c}$ is hydrogen.

In some embodiments, the compound of Formula (I) has a structure of Formula (Ia):

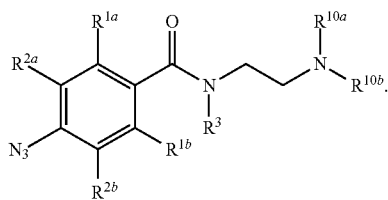

In some embodiments, the compound of Formula (I) has a structure of Formula (Ib):

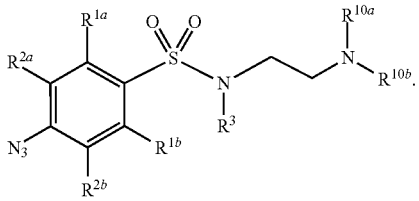

In some embodiments, $R^{10a}$ is hydrogen, optionally substituted C1-C4 alkyl, or optionally substituted aryl. In some embodiments, $R^{10a}$ is hydrogen. In some embodiments, $R^{10a}$ is optionally substituted C1-C4 alkyl. In some embodiments, $R^{10a}$ is CH$_3$. In some embodiments, $R^{10a}$ is CH$_2$CH$_3$. In some embodiments, $R^{10a}$ is optionally substituted aryl. In some embodiments, $R^{10a}$ is phenyl.

In some embodiments, $R^{10b}$ is —(C=O)—C2-C6alkenyl, (S=O)—C2-C6alkenyl, or (S=O)$_2$—C2-C6alkenyl. In some embodiments, $R^{10b}$ is —(C=O)—C2-C6alkenyl. In some embodiments, $R^{10b}$ is —(S=O)—C2-C6alkenyl. In some embodiments, $R^{10b}$ is —(S=O)$_2$—C2-C6alkenyl.

In some embodiments, the compound of Formula (I) has the structure of:

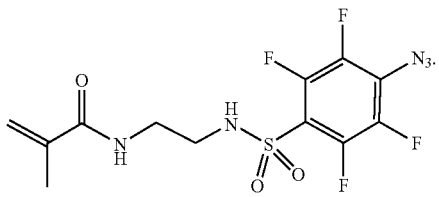 [SMILES: C=C(C)C(=O)NCCNS(=O)(=O)c1c(F)c(F)c(N=[N+]=[N-])c(F)c1F]

In another aspect, described herein is a compound that has the structure of Formula (II) or a salt or solvate thereof:

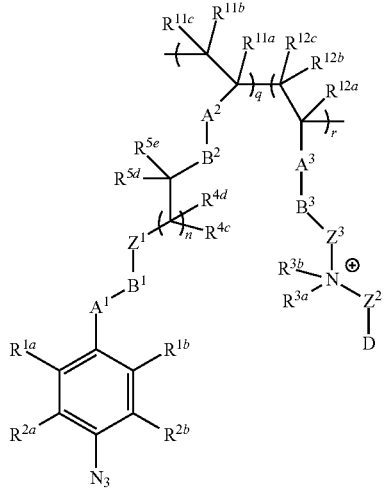

Formula (II)

wherein
each $R^{1a}$ and $R^{1b}$ is independently selected from hydrogen and halogen;
each $R^{2a}$ and $R^{2b}$ is independently selected from halogen, —CN, and optionally substituted C1-C6fluoroalkyl;
each $A^1$, $A^2$, and $A^3$ is independently selected from —C(=O)—, —S(=O)—, —S(=O)$_2$—, and —S(=O)(=NR$^{3c}$)—;
each $B^1$, $B^2$, and $B^3$ is independently selected from —O— and —NR$^{3c}$—;
D is —S(=O)$_2$O$^-$, —S(=O)$_2$OR$^{9a}$, —C(=O)O$^-$, or —C(=O)OR$^{9a}$;
$Z^1$ is —(CR$^{6c}$R$^{6d}$)$_s$—;
$Z^2$ is —(CR$^{6c}$R$^{6d}$)$_t$—;
$Z^3$ is —(CR$^{6c}$R$^{6d}$)$_p$—;
each $R^{3a}$ and $R^{3b}$ is independently selected from hydrogen, optionally substituted C1-C4 alkyl, and optionally substituted benzyl;
each $R^{3c}$ and $R^{3d}$ is independently selected from hydrogen, optionally substituted C1-C4 alkyl, —X-optionally substituted C1-C4 alkyl, optionally substituted C2-C6 alkenyl, and optionally substituted aryl;
X is —C(=O)—, —S(=O)—, or —S(=O)$_2$—;
each $R^{4c}$, $R^{4d}$, $R^{5c}$, $R^{5e}$, $R^{6c}$, and $R^{6d}$ is independently selected from hydrogen, halogen, —CN, —OR$^{9a}$, optionally substituted C1-C4 alkyl, optionally substituted C1-C4 fluoroalkyl, optionally substituted C2-C6 alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;
each $R^{9a}$, $R^{11a}$, $R^{11b}$, $R^{11c}$, $R^{12a}$, $R^{12b}$, and $R^{12c}$ is independently selected from hydrogen, optionally substituted C1-C4 alkyl, and optionally substituted aryl;
n is an integer selected from 0, 1, 2, 3, 4, 5, and 6;
s is an integer selected from 1, 2, 3, 4, or 5;
t is an integer selected from 1, 2, 3, 4, or 5;
p is an integer selected from 1, 2, 3, 4, or 5;
q is an integer selected from 40-60;
r is an integer selected from 1-10; and
wherein the compounds of Formula (II) is charged or zwitterionic.

In some embodiments, each $R^{1a}$ and $R^{1b}$ is independently halogen. In some embodiments, each $R^{1a}$ and $R^{1b}$ is independently F or Cl. In some embodiments, each $R^{1a}$ and $R^{1b}$ is F. In some embodiments, each $R^{2a}$ and $R^{2b}$ is independently selected from halogen, —CN, and optionally substituted C1-C6fluoroalkyl. In some embodiments, each $R^{2a}$ and $R^{2b}$ is independently halogen. In some embodiments, each $R^{2a}$ and $R^{2b}$ is —CN. In some embodiments, each $R^{2a}$ and $R^{2b}$ is independently substituted C1-C6fluoroalkyl. In some embodiments, each $R^{2a}$ and $R^{2b}$ is —CF$_3$.

In some embodiments, each $R^{1a}$, $R^{1b}$, $R^{2a}$, and $R^{2b}$ is F.
In some embodiments, $A^1$ is —S(=O)$_2$—. In some embodiments, $A^1$ is —C(=O)—.
In some embodiments, $A^2$ is —S(=O)$_2$—. In some embodiments, $A^2$ is —C(=O)—.
In some embodiments, $A^3$ is —S(=O)$_2$—. In some embodiments, $A^3$ is —C(=O)—.
In some embodiments, each $B^1$ and $B^2$ is —NR$^{3c}$—.
In some embodiments, each $R^{3c}$ is independently hydrogen, optionally substituted C1-C4 alkyl, or optionally substituted aryl. In some embodiments, $R^{3c}$ is hydrogen. In some embodiments, $R^{3c}$ is optionally substituted C1-C4 alkyl. In some embodiments, $R^{3c}$ is —CH$_3$. In some embodiments, $R^{3c}$ is optionally substituted aryl. In some embodiments, $R^{3c}$ is optionally substituted phenyl.
In some embodiments, $B^3$ is —O—.
In some embodiments, D is —S(=O)$_2$OR$^{9a}$ or —C(=O)OR$^{9a}$. In some embodiments, D is —S(=O)$_2$OR$^{9a}$. In some embodiments, D is —C(=O)OR$^{9a}$.
In some embodiments, $R^{9a}$ is hydrogen or —CH$_3$. In some embodiments, $R^{9a}$ is hydrogen. In some embodiments, $R^{9a}$ is —CH$_3$.
In some embodiments, D is —S(=O)$_2$O$^-$ or —C(=O)O$^-$. In some embodiments, D is —S(=O)$_2$O$^-$. In some embodiments, D is —C(=O)O$^-$.
In some embodiments, each $R^{6c}$ and $R^{6d}$ is hydrogen.
In some embodiments, each $R^{3a}$ and $R^{3b}$ is —CH$_3$.
In some embodiments, $R^{11a}$ is hydrogen or —CH$_3$. In some embodiments, $R^{11a}$ is hydrogen. In some embodiments, $R^{11a}$ is —CH$_3$.
In some embodiments, $R^{12a}$ is hydrogen or —CH$_3$. In some embodiments, $R^{11a}$ is hydrogen. In some embodiments, $R^{12a}$ is —CH$_3$.
In some embodiments, each $R^{11b}$, $R^{11c}$, $R^{12b}$, and $R^{12c}$ is hydrogen.
In some embodiments, n is 0, 1, 2, 3, 4, or 5. In some embodiments, n is 0. In some embodiments, n is 1. In some embodiments, m is 2. In some embodiments, n is 3. In some embodiments, n is 4. In some embodiments, n is 5.
In some embodiments, s is 1, 2, 3, or 4. In some embodiments, s is 1. In some embodiments, s is 2. In some embodiments, s is 3. In some embodiments, s is 4.
In some embodiments, t is 1, 2, 3, or 4. In some embodiments, t is 1. In some embodiments, t is 2. In some embodiments, t is 3. In some embodiments, t is 4.
In some embodiments, p is 1, 2, 3, or 4. In some embodiments, p is 1. In some embodiments, p is 2. In some embodiments, p is 3. In some embodiments, p is 4.
In some embodiments, q is 45, 46, 47, 48, 49, 50, 51, 52, 53, 54, or 55. In some embodiments, q is 45. In some embodiments, q is 46. In some embodiments, q is 47. In some embodiments, q is 48. In some embodiments, q is 49. In some embodiments, q is 50. In some embodiments, q is 51. In some embodiments, q is 52. In some embodiments, q is 53. In some embodiments, q is 54. In some embodiments, q is 55.
In some embodiments, r is 1, 2, 3, 4, 5, 6, 7, 8, 9, or 10. In some embodiments, r is 1. In some embodiments, r is 2. In some embodiments, r is 3. In some embodiments, r is 4.

In some embodiments, r is 5. In some embodiments, r is 6. In some embodiments, r is 7. In some embodiments, r is 8. In some embodiments, r is 9. In some embodiments, r is 10.

In another aspect, described herein is a compound that has the structure of Formula (III) or a salt or solvate thereof:

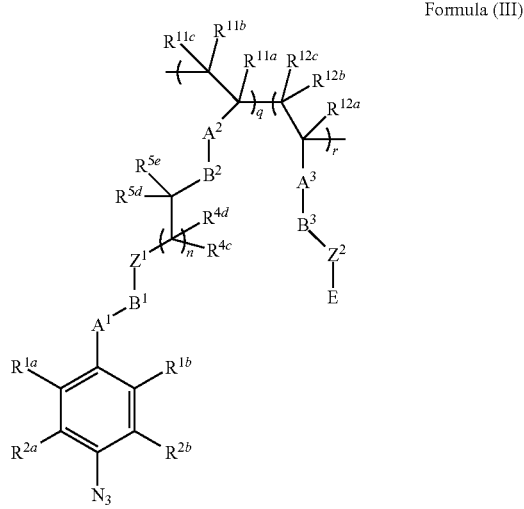

Formula (III)

wherein
each $R^{1a}$ and $R^{1b}$ is independently selected from hydrogen and halogen;
each $R^{2a}$ and $R^{2b}$ is independently selected from halogen, —CN, and optionally substituted C1-C6fluoroalkyl;
each $A^1$, $A^2$, and $A^3$ is independently selected from —C(=O)—, —S(=O)—, —S(=O)$_2$—, and —S(=O)(=NR$^{3c}$)—;
each $B^1$, $B^2$, and $B^3$ is independently selected from —O— and —NR$^{3c}$—;
$Z^1$ is —(CR$^{6c}$R$^{6d}$)$_s$—;
$Z^2$ is —(CR$^{6c}$R$^{6d}$)$_t$—;
E is —CN, —OR$^{9a}$, —NR$^{9a}$R$^{9b}$, —NR$^{9a}$R$^{9b}$R$^{9c+}$, optionally substituted C1-C4 alkyl, optionally substituted C1-C6fluoroalkyl, —S(=O)$_2$O$^-$, —S(=O)$_2$OR$^{9a}$, —C(=O)O$^-$, or —C(=O)OR$^{9a}$;
each $R^{4c}$, $R^{4d}$, $R^{5d}$, $R^{5e}$, $R^{6c}$, and $R^{6d}$ is independently selected from hydrogen, halogen, —CN, —OR$^{9a}$, optionally substituted C1-C4 alkyl, optionally substituted C1-C4 fluoroalkyl, optionally substituted C2-C6 alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;
each $R^{3c}$ and $R^{3d}$ is independently selected from hydrogen, optionally substituted C1-C4 alkyl, —X-optionally substituted C1-C4 alkyl, optionally substituted C2-C6 alkenyl, and optionally substituted aryl;
X is —C(=O)—, —S(=O)—, or —S(=O)$_2$—;
each $R^{9a}$, $R^{11a}$, $R^{11b}$, $R^{11c}$, $R^{12a}$, $R^{12b}$, and $R^{12c}$ is independently selected from hydrogen, optionally substituted C1-C4 alkyl, and optionally substituted aryl;
n is an integer selected from 0, 1, 2, 3, 4, 5, and 6;
s is an integer selected from 1, 2, 3, 4, or 5;
t is an integer selected from 1, 2, 3, 4, or 5;
q is an integer selected from 40-60; and
r is an integer selected from 1-10.

In some embodiments, each $R^{1a}$ and $R^{1b}$ is independently halogen. In some embodiments, each $R^{1a}$ and $R^{1b}$ is independently F or Cl. In some embodiments, each $R^{1a}$ and $R^{1b}$ is F. In some embodiments, each $R^{2a}$ and $R^{2b}$ is independently selected from halogen, —CN, and optionally substituted C1-C6fluoroalkyl. In some embodiments, each $R^{2a}$ and $R^{2b}$ is independently halogen. In some embodiments, each $R^{2a}$ and $R^{2b}$ is CN. In some embodiments, each $R^{2a}$ and $R^{2b}$ is independently substituted C1-C6fluoroalkyl. In some embodiments, each $R^{2a}$ and $R^{2b}$ is —CF$_3$.

In some embodiments, each $R^{1a}$, $R^{1b}$, $R^{2a}$, and $R^{2b}$ is F.
In some embodiments, $A^1$ is —S(=O)$_2$—. In some embodiments, $A^1$ is —C(=O)—.
In some embodiments, $A^2$ is —S(=O)$_2$—. In some embodiments, $A^2$ is —C(=O)—.
In some embodiments, $A^3$ is —S(=O)$_2$—. In some embodiments, $A^3$ is —C(=O)—.
In some embodiments, each $B^1$, $B^2$, and $B^3$ is —NR$^{3c}$—.
In some embodiments, each $R^{3c}$ is independently hydrogen, optionally substituted C1-C4 alkyl, or optionally substituted aryl. In some embodiments, $R^{3c}$ is hydrogen. In some embodiments, $R^{3c}$ is optionally substituted C1-C4 alkyl. In some embodiments, $R^{3c}$ is —CH$_3$. In some embodiments, $R^{3c}$ is optionally substituted aryl. In some embodiments, $R^{3c}$ is optionally substituted phenyl.
In some embodiments, E is —NR$^{9a}$R$^{9b}$R$^{9c+}$ or —S(=O)$_2$OR$^{9a}$.
In some embodiments, E is —NR$^{9a}$R$^{9b}$R$^{9c+}$. In some embodiments, each $R^{9a}$, $R^{9b}$, or $R^{9c}$ is independently H or —CH$_3$. In some embodiments, $R^{9a}$ is H. In some embodiments, $R^{9a}$ is —CH$_3$. In some embodiments, $R^{9b}$ is H. In some embodiments, $R^{9b}$ is —CH$_3$. In some embodiments, $R^{9c}$ is H. In some embodiments, $R^{9c}$ is —CH$_3$.
In some embodiments, E is —S(=O)$_2$OR$^{9a}$. In some embodiments, each $R^{9a}$ is H or —CH$_3$. In some embodiments, $R^{9a}$ is H. In some embodiments, $R^{9a}$ is —CH$_3$.
In some embodiments, each $R^{6c}$ and $R^{6d}$ is independently selected from hydrogen and —CH$_3$.
In some embodiments, each $R^{3a}$ and $R^{3b}$ is —CH$_3$.
In some embodiments, $R^{11a}$ is hydrogen or —CH$_3$. In some embodiments, $R^{11a}$ is hydrogen. In some embodiments, $R^{11a}$ is —CH$_3$.
In some embodiments, $R^{12a}$ is hydrogen or —CH$_3$. In some embodiments, $R^{12a}$ is hydrogen. In some embodiments, $R^{12a}$ is —CH$_3$.
In some embodiments, each $R^{11b}$, $R^{11c}$, $R^{12b}$, and $R^{12c}$ is hydrogen.

Any combination of the groups described above or below for the various variables is contemplated herein. Throughout the specification, groups and substituents thereof are chosen by one skilled in the field to provide stable moieties and compounds.

Further Forms of Compounds

In one aspect, the compound of Formula (I), (II) or (III), possesses one or more stereocenters and each stereocenter exists independently in either the R or S configuration. The compounds presented herein include all diastereomeric, enantiomeric, and epimeric forms as well as the appropriate mixtures thereof. The compounds and methods provided herein include all cis, trans, syn, anti, entgegen (E), and zusammen (Z) isomers as well as the appropriate mixtures thereof. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In one aspect, stereoisomers are obtained by stereoselective synthesis.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine and chlorine, such as, for example, $^2H$, $^3H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^3H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

Compounds described herein might be formed as, and/or used as, salts. The type of salts, include, but are not limited to: (1) acid addition salts, formed by reacting the free base form of the compound with: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a salt includes the solvent addition forms, particularly solvates. Solvates contain either stoichiometric or non-stoichiometric amounts of a solvent, such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Synthesis of Compounds

Compounds described herein are synthesized using standard synthetic techniques or using methods known in the art in combination with methods described herein.

Unless otherwise indicated, conventional methods of mass spectroscopy, NMR, HPLC, protein chemistry, biochemistry, recombinant DNA techniques and pharmacology are employed.

Compounds are prepared using standard organic chemistry techniques such as those described in, for example, March's Advanced Organic Chemistry, 6th Edition, John Wiley and Sons, Inc. Alternative reaction conditions for the synthetic transformations described herein may be employed such as variation of solvent, reaction temperature, reaction time, as well as different chemical reagents and other reaction conditions. The starting materials are available from commercial sources or are readily prepared.

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3 527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates:

An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

In the reactions described, it may be necessary to protect reactive functional groups, for example hydroxy, amino, imino, thio or carboxy groups, where these are desired in the final product, in order to avoid their unwanted participation in reactions. A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

In some embodiments, compounds are synthesized as described in the Examples section.

II. Biofouling-Resistant Coatings

In one aspect, described herein is a biofouling-resistant coating comprising a compound of Formula (I):

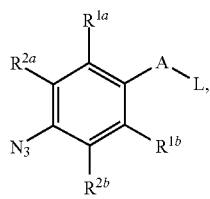

Formula (I)

wherein
A is selected from —C(=O)—, —S(=O)—, —S(=O)$_2$—, and —S(=O)(—NR$^3$)—; L is selected from —OQ, —NR$^3$Q, and —N(R$^3$)$_2$Q$^+$;
Q is a structure represented by a formula:

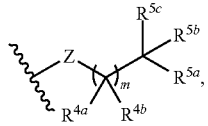

Z is selected from —CR$^{6a}$R$^{6b}$—, —C(=O)—, —C(=NH)—, and —C(=NH)NR$^7$—;
m is an integer selected from 0, 1, 2, 3, 4, 5, 6, 7, and 8;
each R$^{1a}$ and R$^{1b}$ is independently selected from hydrogen and halogen;
each R$^{2a}$ and R$^{2b}$ is independently selected from halogen, —CN, and optionally substituted C1-C6fluoroalkyl;
each R$^3$ is independently selected from hydrogen, optionally substituted C1-C4 alkyl, —X-optionally substituted C1-C4 alkyl, optionally substituted aryl, and —X-optionally substituted aryl;
X is —C(=O)—, —S(=O)—, or —S(=O)$_2$—;
each R$^{4a}$, R$^{4b}$, R$^{5a}$, R$^{5c}$, R$^{6a}$, and R$^{6b}$ is independently selected from hydrogen, halogen, —CN, —OR$^9$, optionally substituted C1-C4 alkyl, optionally substituted C1-C4 fluoroalkyl, optionally substituted aryl, —NR$^{8a}$R$^{8b}$, —NR$^{8a}$R$^{8b}$R$^{8c+}$, —S(=O)$_2$O$^-$, —S(=O)$_2$ OR$^9$, —C(=O)O$^-$, and —C(=O)OR$^9$;

R$^{5b}$ is —NR$^{10a}$R$^{10b}$ or —NR$^{10a}$R$^{10b}$R$^{10c+}$,
each R$^7$, R$^{8a}$, R$^{8b}$, R$^{8c}$, and R$^9$ is independently selected from hydrogen and optionally substituted C1-C4 alkyl, and optionally substituted aryl;
each R$^{10a}$ and R$^{10c}$ is independently selected from hydrogen, optionally substituted C1-C4 alkyl, optionally substituted aryl, -(optionally substituted C1-C8alkylene)S(=O)$_2$O$^-$, -(optionally substituted C1-C8alkylene)S(=O)$_2$OH, -(optionally substituted C1-C8alkylene)C(=O)O$^-$, and -(optionally substituted C1-C8alkylene)C(=O)OH; and
R$^{10b}$ is —(C=O)—C2-C6alkenyl, (S=O)—C2-C6alkenyl, or (S=O)$_2$—C2-C6alkenyl.

In some embodiments, the compound of Formula (I) has a structure selected from:

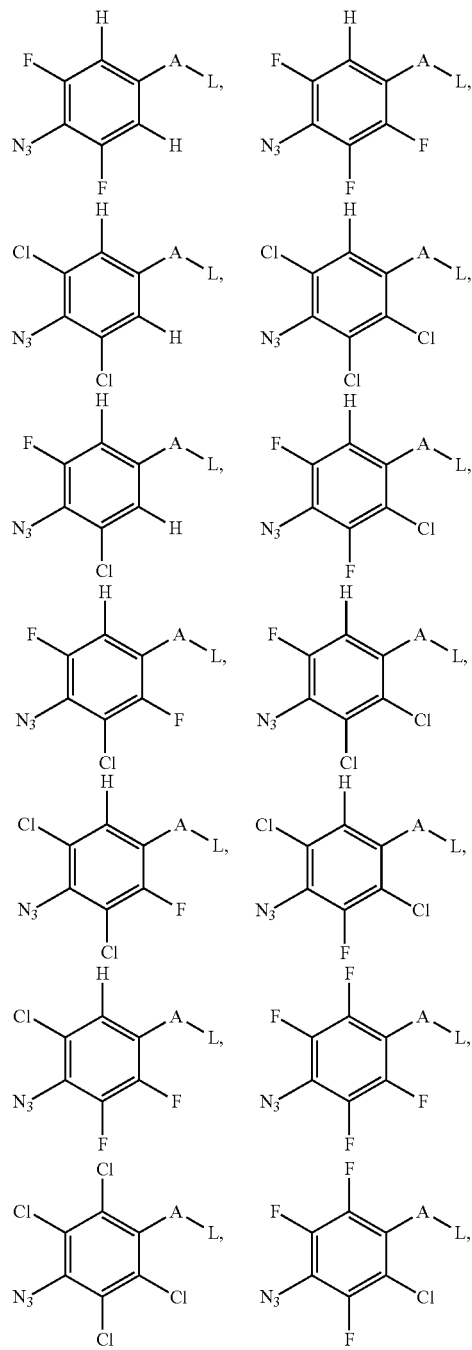

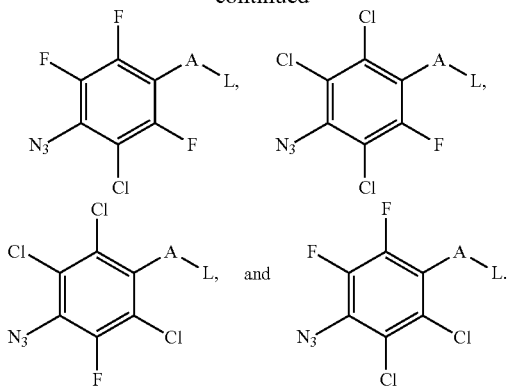

In some embodiments, the compound of Formula (I) has the structure selected from:

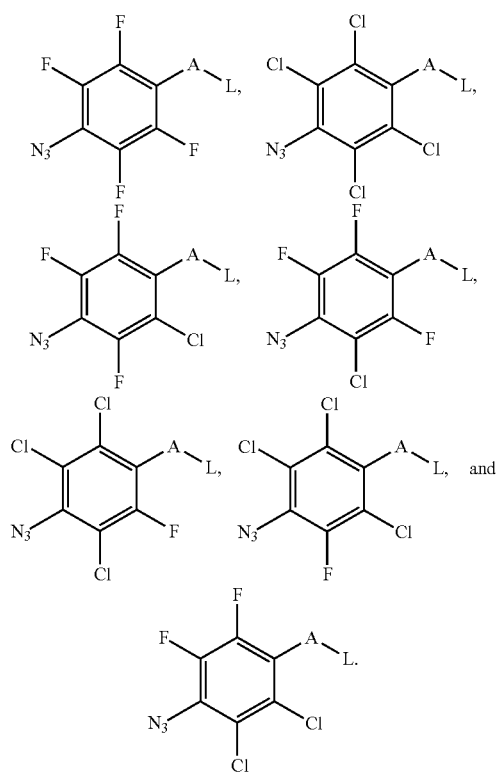

In some embodiments, the compound of Formula (I) has the following structure:

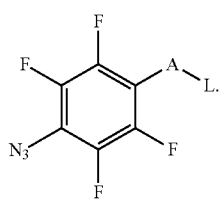

In some embodiments, the compound of Formula (I) has a structure selected from:

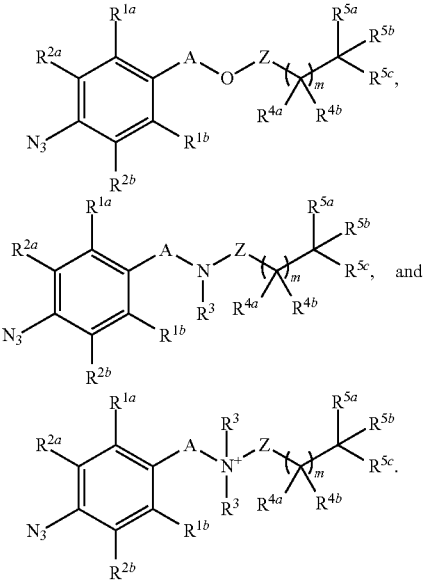

In some embodiments, the compound of Formula (I) has a structure selected from:

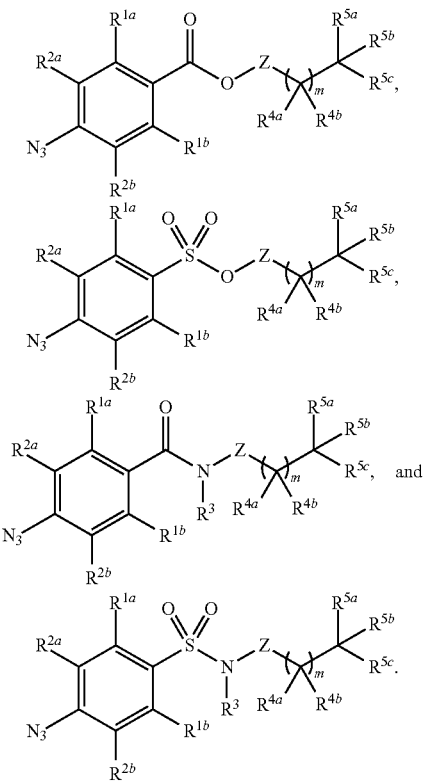

In some embodiments, each $R^{1a}$ and $R^{1b}$ is independently halogen. In some embodiments, each $R^{1a}$ and $R^{1b}$ is independently F or Cl. In some embodiments, each $R^{1a}$ and $R^{1b}$ is F. In some embodiments, each $R^{2a}$ and $R^{2b}$ is independently selected from halogen, —CN, and optionally substituted C1-C6fluoroalkyl. In some embodiments, each $R^{2a}$ and $R^{2b}$ is independently halogen. In some embodiments, each $R^{2a}$ and $R^{2b}$ is —CN. In some embodiments, each $R^{2a}$ and $R^{2b}$ is independently substituted C1-C6fluoroalkyl. In some embodiments, each $R^{2a}$ and $R^{2b}$ is —$CF_3$.

In some embodiments, each $R^{1a}$, $R^{1b}$, $R^{2a}$, and $R^{2b}$ is F.

In some embodiments, Z is selected from —$CR^{6a}R^{6b}$—, —C(=O)—, —C(=NH)—, and —C(=NH)$NR^7$—. In some embodiments, Z is —$CR^{6a}R^{6b}$—. In some embodiments, Z is —C(=O)—. In some embodiments, Z is —C(=NH)—. In some embodiments, Z is —C(=NH)$NR^7$—.

In some embodiments, each $R^3$ is independently selected from hydrogen, optionally substituted C1-C4 alkyl, —X-optionally substituted C1-C4 alkyl, optionally substituted aryl, and —X-optionally substituted aryl. In some embodiments, $R^3$ is hydrogen. In some embodiments, $R^3$ is optionally substituted C1-C4 alkyl. In some embodiments, $R^3$ is —X-optionally substituted C1-C4 alkyl. In some embodiments, $R^3$ is optionally substituted aryl. In some embodiments, $R^3$ is —X-optionally substituted aryl.

In some embodiments, X is —C(=O)—, —S(=O)—, or —S(=O)$_2$—. In some embodiments, X is —C(=O)—. In some embodiments, X is —S(=O)—. In some embodiments, X is —S(=O)$_2$—.

In some embodiments, each $R^{6a}$ and $R^{6b}$ is hydrogen.

In some embodiments, m is 0, 1, 2, 3, 4, or 5. In some embodiments, m is 0. In some embodiments, m is 1. In some embodiments, m is 2. In some embodiments, m is 3. In some embodiments, m is 4. In some embodiments, m is 5.

In some embodiments, $R^{5a}$ is hydrogen; $R^{5b}$ is —$NR^{10a}R^{10b}$, and $R^{5c}$ is hydrogen.

In some embodiments, the compound of Formula (I) has a structure of Formula (Ia):

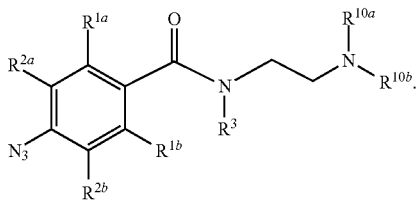

In some embodiments, the compound of Formula (I) has a structure of Formula (Ib):

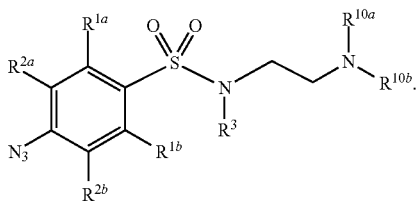

In some embodiments, $R^{10a}$ is hydrogen, optionally substituted C1-C4 alkyl, or optionally substituted aryl. In some embodiments, $R^{10a}$ is hydrogen. In some embodiments, $R^{10a}$ is optionally substituted C1-C4 alkyl. In some embodiments, $R^{10a}$ is —$CH_3$. In some embodiments, $R^{10a}$ is $CH_2CH_3$. In some embodiments, $R^{10a}$ is optionally substituted aryl. In some embodiments, $R^{10a}$ is phenyl.

In some embodiments, $R^{10b}$ is —(C=O)—C2-C6alkenyl, (S=O)—C2-C6alkenyl, or (S=O)$_2$—C2-C6alkenyl. In some embodiments, $R^{10b}$ is —(C=O)—C2-C6alkenyl. In some embodiments, $R^{10b}$ is (S=O)—C2-C6alkenyl. In some embodiments, $R^{10b}$ is —(S=O)$_2$—C2-C6alkenyl.

In another aspect, described herein is a biofouling-resistant coating comprising a compound of Formula (II):

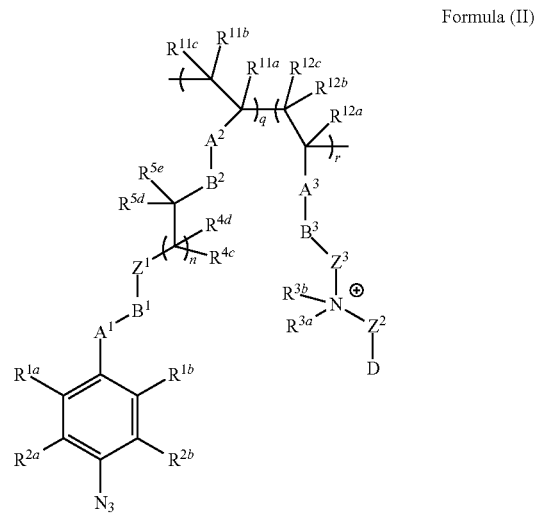

Formula (II)

wherein each $R^{1a}$ and $R^{1b}$ is independently selected from hydrogen and halogen;

each $R^{2a}$ and $R^{2b}$ is independently selected from halogen, —CN, and optionally substituted C1-C6fluoroalkyl;

each $A^1$, $A^2$, and $A^3$ is independently selected from —C(=O)—, —S(=O)—, —S(=O)$_2$—, and —S(=O)(=$NR^{3c}$)—;

each $B^1$, $B^2$, and $B^3$ is independently selected from —O— and —$NR^{3c}$—;

D is —S(=O)$_2$O$^-$, —S(=O)$_2$$OR^{9a}$, —C(=O)O$^-$, or —C(=O)$OR^{9a}$;

$Z^1$ is —$(CR^{6c}R^{6d})_s$—;

$Z^2$ is —$(CR^{6c}R^{6d})_t$—;

$Z^3$ is —$(CR^{6c}R^{6d})_p$—;

each $R^{3a}$ and $R^{3b}$ is independently selected from hydrogen, optionally substituted C1-C4 alkyl, and optionally substituted benzyl;

each $R^{3c}$ and $R^{3d}$ is independently selected from hydrogen, optionally substituted C1-C4 alkyl, —X-optionally substituted C1-C4 alkyl, optionally substituted C2-C6 alkenyl, and optionally substituted aryl;

X is —C(=O)—, —S(=O)—, or —S(=O)$_2$—;

each $R^{4c}$, $R^{4d}$, $R^{5d}$, $R^{5e}$, $R^{6c}$, and $R^{6d}$ is independently selected from hydrogen, halogen, —CN, —$OR^{9a}$, optionally substituted C1-C4 alkyl, optionally substituted C1-C4 fluoroalkyl, optionally substituted C2-C6 alkenyl, —$NR^{3c}R^{3d}$, —S(=O)$_2$O$^-$, —S(=O)$_2$$OR^{9a}$, —C(=O)O$^-$, and —C(=O)$OR^{9a}$;

each $R^{9a}$, $R^{11a}$, $R^{11b}$, $R^{11c}$, $R^{12a}$, $R^{12b}$, and $R^{12c}$ is independently selected from hydrogen, optionally substituted C1-C4 alkyl, and optionally substituted aryl;

n is an integer selected from 0, 1, 2, 3, 4, 5, and 6;

s is an integer selected from 1, 2, 3, 4, or 5;

t is an integer selected from 1, 2, 3, 4, or 5;

p is an integer selected from 1, 2, 3, 4, or 5;

q is an integer selected from 40-60;

r is an integer selected from 1-10; and wherein the compounds of Formula (II) is charged or zwitterionic.

In some embodiments, each $R^{1a}$ and $R^{1b}$ is independently halogen. In some embodiments, each $R^{1a}$ and $R^{1b}$ is independently F or Cl. In some embodiments, each $R^{1a}$ and $R^{1b}$ is F. In some embodiments, each $R^{2a}$ and $R^{2b}$ is independently selected from halogen, —CN, and optionally substituted C1-C6fluoroalkyl. In some embodiments, each $R^{2a}$ and $R^{2b}$ is independently halogen. In some embodiments, each $R^{2a}$ and $R^{2b}$ is —CN. In some embodiments, each $R^{2a}$ and $R^{2b}$ is independently substituted C1-C6fluoroalkyl. In some embodiments, each $R^{2a}$ and $R^{2b}$ is —CF$_3$.

In some embodiments, each $R^{1a}$, $R^{1b}$, $R^{2a}$, and $R^{2b}$ is F.

In some embodiments, $A^1$ is —S(=O)$_2$—. In some embodiments, $A^1$ is —C(=O)—.

In some embodiments, $A^2$ is —S(=O)$_2$—. In some embodiments, $A^2$ is —C(=O)—.

In some embodiments, $A^3$ is —S(=O)$_2$—. In some embodiments, $A^3$ is —C(=O)—.

In some embodiments, each $B^1$ and $B^2$ is —NR$^{3c}$—.

In some embodiments, each $R^{3c}$ is independently hydrogen, optionally substituted C1-C4 alkyl, or optionally substituted aryl. In some embodiments, $R^{3c}$ is hydrogen. In some embodiments, $R^{3c}$ is optionally substituted C1-C4 alkyl. In some embodiments, $R^{3c}$ is —CH$_3$. In some embodiments, $R^{3c}$ is optionally substituted aryl. In some embodiments, $R^{3c}$ is optionally substituted phenyl.

In some embodiments, $B^3$ is —O—.

In some embodiments, D is —S(=O)$_2$OR$^{9a}$ or —C(=O)OR$^{9a}$. In some embodiments, D is —S(=O)$_2$OR$^{9a}$. In some embodiments, D is —C(=O)OR$^{9a}$.

In some embodiments, $R^{9a}$ is hydrogen or —CH$_3$. In some embodiments, $R^{9a}$ is hydrogen. In some embodiments, $R^{9a}$ is —CH$_3$.

In some embodiments, D is —S(=O)$_2$O$^-$ or —C(=O)O$^-$. In some embodiments, D is —S(=O)$_2$O$^-$.

In some embodiments, D is —C(=O)O$^-$.

In some embodiments, each $R^{6c}$ and $R^{6d}$ is hydrogen.

In some embodiments, each $R^{3a}$ and $R^{3b}$ is —CH$_3$.

In some embodiments, $R^{11a}$ is hydrogen or —CH$_3$. In some embodiments, $R^{11a}$ is hydrogen. In some embodiments, $R^{11a}$ is —CH$_3$.

In some embodiments, $R^{12a}$ is hydrogen or —CH$_3$. In some embodiments, $R^{11a}$ is hydrogen. In some embodiments, $R^{12a}$ is —CH$_3$.

In some embodiments, each $R^{11b}$, $R^{11c}$, $R^{12b}$, and $R^{12c}$ is hydrogen.

In some embodiments, n is 0, 1, 2, 3, 4, or 5. In some embodiments, n is 0. In some embodiments, n is 1. In some embodiments, m is 2. In some embodiments, n is 3. In some embodiments, n is 4. In some embodiments, n is 5.

In some embodiments, s is 1, 2, 3, or 4. In some embodiments, s is 1. In some embodiments, s is 2. In some embodiments, s is 3. In some embodiments, s is 4.

In some embodiments, t is 1, 2, 3, or 4. In some embodiments, t is 1. In some embodiments, t is 2. In some embodiments, t is 3. In some embodiments, t is 4.

In some embodiments, p is 1, 2, 3, or 4. In some embodiments, p is 1. In some embodiments, p is 2. In some embodiments, p is 3. In some embodiments, p is 4.

In some embodiments, q is 45, 46, 47, 48, 49, 50, 51, 52, 53, 54, or 55. In some embodiments, q is 45. In some embodiments, q is 46. In some embodiments, q is 47. In some embodiments, q is 48. In some embodiments, q is 49. In some embodiments, q is 50. In some embodiments, q is 51. In some embodiments, q is 52. In some embodiments, q is 53. In some embodiments, q is 54. In some embodiments, q is 55.

In some embodiments, r is 1, 2, 3, 4, 5, 6, 7, 8, 9, or 10. In some embodiments, r is 1. In some embodiments, r is 2. In some embodiments, r is 3. In some embodiments, r is 4. In some embodiments, r is 5. In some embodiments, r is 6. In some embodiments, r is 7. In some embodiments, r is 8. In some embodiments, r is 9. In some embodiments, r is 10.

In another aspect, described herein is a biofouling-resistant coating comprising a compound of Formula (III):

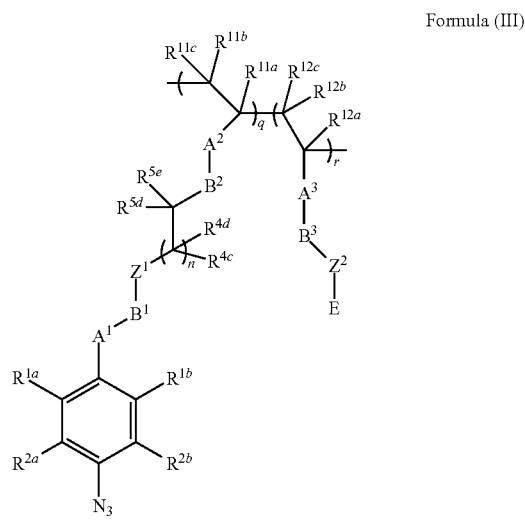

Formula (III)

wherein
each $R^{1a}$ and $R^{1b}$ is independently selected from hydrogen and halogen;
each $R^{2a}$ and $R^{2b}$ is independently selected from halogen, —CN, and optionally substituted C1-C6fluoroalkyl;
each $A^1$, $A^2$, and $A^3$ is independently selected from —C(=O)—, —S(=O)—, —S(=O)$_2$—, and —S(=O)(=NR$^{3c}$)—;
each $B^1$, $B^2$, and $B^3$ is independently selected from —O— and —NR$^{3c}$—;
$Z^1$ is —(CR$^{6c}$R$^{6d}$)$_s$—;
$Z^2$ is —(CR$^{6c}$R$^{6d}$)$_t$—;
E is —CN, —OR$^{9a}$, —NR$^{9a}$R$^{9b}$, —NR$^{9a}$R$^{9b}$R$^{9c+}$, optionally substituted C1-C4 alkyl, optionally substituted C1-C6fluoroalkyl, —S(=O)$_2$O$^-$, —S(=O)$_2$OR$^{9a}$, —C(=O)O$^-$, or —C(=O)OR$^{9a}$;
each $R^{4c}$, $R^{4d}$, $R^{5d}$, $R^{5e}$, $R^{6c}$, and $R^{6d}$ is independently selected from hydrogen, halogen, —CN, —OR$^{9a}$, optionally substituted C1-C4 alkyl, optionally substituted C1-C4 fluoroalkyl, optionally substituted C2-C6 alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;
each $R^{3c}$ and $R^{3d}$ is independently selected from hydrogen, optionally substituted C1-C4 alkyl, —X-optionally substituted C1-C4 alkyl, optionally substituted C2-C6 alkenyl, and optionally substituted aryl;
X is —C(=O)—, —S(=O)—, or —S(=O)$_2$—;
each $R^{9a}$, $R^{11a}$, $R^{11b}$, $R^{11c}$, $R^{12a}$, $R^{12b}$ and $R^{12c}$ is independently selected from hydrogen, optionally substituted C1-C4 alkyl, and optionally substituted aryl;
n is an integer selected from 0, 1, 2, 3, 4, 5, and 6;
s is an integer selected from 1, 2, 3, 4, or 5;
t is an integer selected from 1, 2, 3, 4, or 5;
q is an integer selected from 40-60; and
r is an integer selected from 1-10.

In some embodiments, each $R^{1a}$ and $R^{1b}$ is independently halogen. In some embodiments, each $R^{1a}$ and $R^{1b}$ is independently F or Cl. In some embodiments, each $R^{1a}$ and $R^{1b}$ is F. In some embodiments, each $R^{2a}$ and $R^{2b}$ is independently selected from halogen, —CN, and optionally substituted C1-C6fluoroalkyl. In some embodiments, each $R^{2a}$ and $R^{2b}$ is independently halogen. In some embodiments, each $R^{2a}$ and $R^{2b}$ is —CN. In some embodiments, each $R^{2a}$ and $R^{2b}$ is independently substituted C1-C6fluoroalkyl. In some embodiments, each $R^{2a}$ and $R^{2b}$ is —CF$_3$.

In some embodiments, each $R^{1a}$, $R^{1b}$, $R^{2a}$, and $R^{2b}$ is F.

In some embodiments, $A^1$ is —S(=O)$_2$—. In some embodiments, $A^1$ is —C(=O)—.

In some embodiments, $A^2$ is —S(=O)$_2$—. In some embodiments, $A^2$ is —C(=O)—.

In some embodiments, $A^3$ is —S(=O)$_2$—. In some embodiments, $A^3$ is —C(=O)—.

In some embodiments, each $B^1$, $B^2$, and $B^3$ is —NR$^{3c}$—.

In some embodiments, each $R^{3c}$ is independently hydrogen, optionally substituted C1-C4 alkyl, or optionally substituted aryl. In some embodiments, $R^{3c}$ is hydrogen. In some embodiments, $R^{3c}$ is optionally substituted C1-C4 alkyl. In some embodiments, $R^{3c}$ is —CH$_3$. In some embodiments, $R^{3c}$ is optionally substituted aryl. In some embodiments, $R^{3c}$ is optionally substituted phenyl.

In some embodiments, E is —NR$^{9a}$R$^{9b}$R$^{9c+}$ or —S(=O)$_2$OR$^{9a}$.

In some embodiments, E is —NR$^{9a}$R$^{9b}$R$^{9c+}$. In some embodiments, each $R^{9a}$, $R^{9b}$, or $R^{9c}$ is independently H or —CH$_3$. In some embodiments, $R^{9a}$ is H. In some embodiments, $R^{9a}$ is —CH$_3$. In some embodiments, $R^{9b}$ is H. In some embodiments, $R^{9b}$ is —CH$_3$. In some embodiments, $R^{9c}$ is H. In some embodiments, $R^{9c}$ is —CH$_3$.

In some embodiments, E is —S(=O)$_2$OR$^{9a}$. In some embodiments, each $R^{9a}$ is H or —CH$_3$. In some embodiments, $R^{9a}$ is H. In some embodiments, $R^{9a}$ is —CH$_3$.

In some embodiments, each $R^{6c}$ and $R^{6d}$ is independently selected from hydrogen and —CH$_3$.

In some embodiments, each $R^{3a}$ and $R^{3b}$ is —CH$_3$.

In some embodiments, $R^{11a}$ is hydrogen or —CH$_3$. In some embodiments, $R^{11a}$ is hydrogen. In some embodiments, $R^{11a}$ is —CH$_3$.

In some embodiments, $R^{12a}$ is hydrogen or —CH$_3$. In some embodiments, $R^{12a}$ is hydrogen. In some embodiments, $R^{12a}$ is —CH$_3$.

In some embodiments, each $R^{11b}$, $R^{11c}$, $R^{12b}$, and $R^{12c}$ is hydrogen.

Any combination of the groups described above or below for the various variables is contemplated herein. Throughout the specification, groups and substituents thereof are chosen by one skilled in the field to provide stable moieties and compounds.

In some embodiments, the biofouling-resistant coating described herein comprises one or more compounds of Formula (I), (II), or (III).

In some embodiments, the biofouling-resistant coating described herein comprises one or more copolymers of Formula (II) or (III).

In some embodiments, the biofouling-resistant coating comprising one or more compounds of Formula (I), (II), and (III) is applied onto a surface of the device. In some embodiments, the surface of the device comprises a polymer. In some embodiments, the polymer is selected from polysiloxanes, polyurethanes, polyamides, polyimides, epoxy resins, polyesters, polyolefins, polysulfones, polycarbonates, polyvinylchloride, polyvinylidene difluoride, polyethers, polyether terpthalate, or a mixture thereof.

III. Devices

In certain embodiments, provided herein are devices coated by one or more compounds described herein. In some instances, provided herein are medical devices coated by one or more compounds described herein. In other instances, provided herein are non-medical devices coated by one or more compounds described herein. In additional instances, provided herein are devices coated by one or more compounds described herein in which the coated device reduces the potential for infection.

In some embodiments, the device comprises a polymer-based device. In some embodiments, the polymer-based device comprises a polyolefinic device. In some embodiments, the polyolefinic device comprises a device modified with polyethylene (PE), polypropylene (PP), polyamide (PA), polytetrafluoroethylene (PTFE), polyvinylidene fluoride (PVdF), polyvinyl chloride (PVC), or a combination thereof. In some embodiments, the device comprises a microporous device or a nonwoven device. In some embodiments, the device comprises a carbon-based device comprising a moiety capable of binding with a compound that has a structure of Formula (I), (II), or (III). In some embodiments, the carbon-based device comprises a polymer moiety. In some embodiments, the carbon-based device comprises a carbon-based polymer. In some embodiments, the carbon-based device comprises a polyolefin moiety. In some embodiments, the polyolefin moiety comprises a polyethylene (PE) moiety, a polypropylene (PP) moiety, a polyamide (PA) moiety, a polytetrafluoroethylene (PTFE) moiety, a polyvinylidene fluoride (PVdF) moiety, or a polyvinyl chloride (PVC) moiety.

In some embodiments, the device comprises a carbon-based device. In some embodiments, the carbon-based device comprises a carbon-based polymer. In some embodiments, the carbon-based device comprises a polyolefin moiety. In some embodiments, the polyolefin moiety comprises polyethylene moiety, polypropylene moiety, polyvinyl chloride moiety, polyvinylidene fluoride moiety, polytetrafluoroethylene moiety, polychlorotrifluoroethylene moiety, or polystyrene moiety. In some embodiments, the carbon-based polymer comprises polyamide moiety, polyurethane moiety, phenol-formaldehyde resin moiety, polycarbonate moiety, polychloroprene moiety, polyacrylonitrile moiety, polimide moiety, or polyester moiety. In some embodiments, the carbon-based polymer comprises nylon. In some embodiments, the carbon-based polymer comprises polyethylene terephthalate.

In some embodiments, the device comprises a silicon-based device. In some embodiments, the silicon-based device comprises a silicon-based polymer moiety. In some embodiments, the device comprises a silicon-based device comprising a moiety capable of binding with a compound that has a structure of Formula (I), (II), or (III). In some embodiments, the silicon-based device comprises a polymer moiety. In some embodiments, the silicon-based device comprises a siloxane polymer moiety, a sesquisiloxane polymer moiety, a siloxane-silarylene polymer moiety, a silalkylene polymer moiety, a polysilane moiety, a polysilylene moiety, or a polysilazane moiety.

In some embodiments, the silicon-based device comprises a siloxane polymer moiety. In some embodiments, the silicon-based device comprises silicone polymer. In some embodiments, the silicon-based device comprises a silicone-based device.

In some embodiments, the device comprises a carbon-based device or a silicon-based device.

In some embodiments, a device described herein coated by a compound described herein leads to a reduced potential for infection relative to a device not coated by the compound. In some instances, the reduced potential for infection is by about 10%, 20%, 30%, 40%, 50%, 60%, 70%, 80%, 90%, 95%, 99%, 99.5%, 99.9%, or more relative to a device not coated by the compound. In some instances, the reduced potential for infection is by about 10%, or more relative to a device not coated by the compound. In some instances, the reduced potential for infection is by about 20%, or more relative to a device not coated by the compound. In some instances, the reduced potential for infection is by about 30%, or more relative to a device not coated by the compound. In some instances, the reduced potential for infection is by about 40%, or more relative to a device not coated by the compound. In some instances, the reduced potential for infection is by about 50%, or more relative to a device not coated by the compound. In some instances, the reduced potential for infection is by about 60%, or more relative to a device not coated by the compound. In some instances, the reduced potential for infection is by about 70%, or more relative to a device not coated by the compound. In some instances, the reduced potential for infection is by about 80%, or more relative to a device not coated by the compound. In some instances, the reduced potential for infection is by about 90%, or more relative to a device not coated by the compound. In some instances, the reduced potential for infection is by about 95%, or more relative to a device not coated by the compound. In some instances, the reduced potential for infection is by about 99%, or more relative to a device not coated by the compound. In some instances, the reduced potential for infection is by about 99.5%, or more relative to a device not coated by the compound. In some instances, the reduced potential for infection is by about 99.9%, or more relative to a device not coated by the compound.

Medical Devices

In some embodiments, a device described herein is a medical device. In some cases, a medical device described herein comprises a dental instrument or a medical instrument. In some instances, a medical device comprises an implant, an IV, a prosthesis, a suturing material, a valve, a stent, a catheter, a rod, a shunt, a scope, a contact lens, a tubing, a wiring, an electrode, a clip, a fastener, a syringe, a container, or a combination thereof. In some embodiments, a medical device comprises an implant. In some embodiments, a medical device comprises an IV. In some embodiments, a medical device comprises a prosthesis. In some embodiments, a medical device comprises a suturing material. In some embodiments, a medical device comprises a valve. In some embodiments, a medical device comprises a stent. In some embodiments, a medical device comprises a catheter. In some embodiments, a medical device comprises a rod. In some embodiments, a medical device comprises a shunt. In some embodiments, a medical device comprises a scope. In some embodiments, a medical device comprises a contact lens. In some embodiments, a medical device comprises a tubing. In some embodiments, a medical device comprises a wiring. In some embodiments, a medical device comprises an electrode. In some embodiments, a medical device comprises a clip. In some embodiments, a medical device comprises a fastener. In some embodiments, a medical device comprises a syringe. In some embodiments, a medical device comprises a container. In some instances, a device described herein comprises a dental instrument or a medical instrument. In some instances, a device described herein comprises an implant, an IV, a prosthesis, a suturing material, a valve, a stent, a catheter, a rod, a shunt, a scope, a contact lens, a tubing, a wiring, an electrode, a clip, a fastener, a syringe, a container, or a combination thereof. In some embodiments, a device comprises an implant. In some embodiments, a device comprises an IV. In some embodiments, a device comprises a prosthesis. In some embodiments, a device comprises a suturing material. In some embodiments, a device comprises a valve. In some embodiments, a device comprises a stent. In some embodiments, a device comprises a catheter. In some embodiments, a device comprises a rod. In some embodiments, a device comprises a shunt. In some embodiments, a device comprises a scope. In some embodiments, a device comprises a contact lens. In some embodiments, a device comprises a tubing. In some embodiments, a device comprises a wiring. In some embodiments, a device comprises an electrode. In some embodiments, a device comprises a clip. In some embodiments, a device comprises a fastener. In some embodiments, a device comprises a syringe. In some embodiments, a device comprises a container.

In some embodiments, a compound described herein is coated onto a medical device. In some instances, a compound described herein is coated onto a medical device to prevent and/or reduce biofouling (e.g., microfouling such as bacteria adhesion or biofilm). In some instances, a compound described herein is coated onto a dental instrument or a medical instrument to prevent and/or reduce biofouling (e.g., microfouling such as bacteria adhesion or biofilm). In some instances, a compound described herein is coated onto an implant, an IV, a prosthesis, a suturing material, a valve, a stent, a catheter, a rod, a shunt, a scope, a contact lens, a tubing, a wiring, an electrode, a clip, a fastener, a syringe, a container, or a combination thereof to prevent and/or reduce biofouling (e.g., microfouling such as bacteria adhesion or biofilm).

In some cases, a device described herein comprises a catheter. In some cases, a catheter comprises an indwelling catheter. In some instances, a catheter comprises a permcath. In some instances, a catheter comprises a uretic catheter or a Foley catheter.

In some instances, a compound described herein is coated onto a catheter to prevent and/or reduce biofouling (e.g., microfouling such as bacteria adhesion or biofilm). In some instances, a compound described herein is coated onto an indwelling catheter to prevent and/or reduce biofouling (e.g., microfouling such as bacteria adhesion or biofilm). In some instances, a compound described herein is coated onto a permcath to prevent and/or reduce biofouling (e.g., microfouling such as bacteria adhesion or biofilm). In some instances, a compound described herein is coated onto a uretic catheter to prevent and/or reduce biofouling (e.g., microfouling such as bacteria adhesion or biofilm). In some instances, a compound described herein is coated onto a Foley catheter to prevent and/or reduce biofouling (e.g., microfouling such as bacteria adhesion or biofilm).

In some instances, a device described herein comprises an implant. In some instances, an implant comprises a dental implant or an orthopedic implant. In some cases, a device described herein comprises a dental implant. In other cases, a device described herein comprises an orthopedic implant.

In some instances, a compound described herein is coated onto an implant to prevent and/or reduce biofouling (e.g., microfouling such as bacteria adhesion or biofilm). In some instances, a compound described herein is coated onto a dental implant to prevent and/or reduce biofouling (e.g., microfouling such as bacteria adhesion or biofilm). In some instances, a compound described herein is coated onto an orthopedic implant to prevent and/or reduce biofouling (e.g., microfouling such as bacteria adhesion or biofilm).

In some embodiments, a device described herein comprises an IV. In some instances, a compound described herein is coated onto an IV to prevent and/or reduce biofouling (e.g., microfouling such as bacteria adhesion or biofilm).

In some embodiments, a device described herein comprises a prosthesis. In some cases, a prosthesis comprises an artificial bone, an artificial joint, an artificial organ, or a denture. In some cases, an artificial organ comprises an artificial pancreas, an artificial heart, an artificial limb, or a heart valve. In some embodiments, a device described herein comprises an artificial bone, an artificial joint, an artificial organ or a denture. In some embodiments, a device described herein comprises an artificial pancreas, an artificial heart, an artificial limb, or a heart valve.

In some instances, a compound described herein is coated onto prosthesis to prevent and/or reduce biofouling (e.g., microfouling such as bacteria adhesion or biofilm). In some instances, a compound described herein is coated onto an artificial bone, an artificial joint, an artificial organ, or a denture to prevent and/or reduce biofouling (e.g., microfouling such as bacteria adhesion or biofilm). In some instances, a compound described herein is coated onto an artificial pancreas, an artificial heart, an artificial limb, or a heart valve to prevent and/or reduce biofouling (e.g., microfouling such as bacteria adhesion or biofilm).

In some embodiments, a device described herein comprises a stent. In some instances, a stent is a small expandable tube used to the passageway of a blood vessel or duct remains open. In some cases, a stent comprises a coronary stent, a vascular stent, or a biliary stent. In some instances, a coronary stent is also referred to as a cardiac stent or a heart stent. In some embodiments, a device described herein comprises a coronary stent, a vascular stent, or a biliary stent.

In some instances, a compound described herein is coated onto stent to prevent and/or reduce biofouling (e.g., microfouling such as bacteria adhesion or biofilm). In some instances, a compound described herein is coated onto a coronary stent, a vascular stent, or a biliary stent to prevent and/or reduce biofouling (e.g., microfouling such as bacteria adhesion or biofilm).

In some instances, a device described herein comprises shunt. In some instances, a shunt is a hole or a small passage which allows fluid movement from one part of a body to another. In some instances, a shunt differs from a stent in that a shunt connects two previously unconnected portions. In some instances, a shunt is an acquired shunt. In some cases, a shunt comprises a cardiac shunt, a cerebral shunt, a lumbar-peritoneal shunt, a peritoneovenous shunt, a pulmonary shunt, a portosystemic shunt (PSS), a portacaval shunt, or a vesico-amniotic shunt. In some cases, a cardiac shunt comprises a right-to-left, left-to-right, or bidirectional shunt. In some cases, a cerebral shunt comprises drainage of excess cerebrospinal fluid from the brain into the chest or abdomen cavity. In some cases, a lumbar-peritoneal shunt comprises channeling cerebrospinal fluid from the lumbar thecal sac into the peritoneal cavity. In some instances, a peritoneovenous shunt (also referred to as Denver shunt) drains peritoneal fluid from the peritoneum into the veins. In some cases, a portosystemic shunt (PSS) is a liver shunt which allows bypass of the liver by the circulatory system. In some cases, a portacaval shunt connects the portal vein with the inferior vena cava, for treatment of high blood pressure in the liver. In some cases, a vesico-amniotic shunt is for drainage of excess fluid in a fetus bladder into the surrounding area. In some cases, a device described herein comprises a cardiac shunt, a cerebral shunt, a lumbar-peritoneal shunt, a peritoneovenous shunt, a pulmonary shunt, a portosystemic shunt (PSS), a portacaval shunt, or a vesico-amniotic shunt.

In some instances, a compound described herein is coated onto shunt to prevent and/or reduce biofouling (e.g., microfouling such as bacteria adhesion or biofilm). In some instances, a compound described herein is coated onto a cardiac shunt, a cerebral shunt, a lumbar-peritoneal shunt, a peritoneovenous shunt, a pulmonary shunt, a portosystemic shunt (PSS), a portacaval shunt, or a vesico-amniotic shunt to prevent and/or reduce biofouling (e.g., microfouling such as bacteria adhesion or biofilm).

In some instances, a device described herein comprises a scope. In some cases, a scope is a medical instrument used in an image-guided surgery. In some cases, a scope comprises endoscope or laparoscope. Endoscopy is a medical procedure for examining the GI tract with the aid of an endoscope. In some cases, endoscopy further comprises sigmoidoscopy and colonoscopy. Laparoscopy is a diagnostic procedure for examining internal organs utilizing a laparoscope. In some instances, a device described herein comprises a scope used in endoscopy. In other instances, a device described herein comprises a scope used in laparoscopy.

In some instances, a compound described herein is coated onto scope to prevent and/or reduce biofouling (e.g., microfouling such as bacteria adhesion or biofilm). In some instances, a compound described herein is coated onto endoscope to prevent and/or reduce biofouling (e.g., microfouling such as bacteria adhesion or biofilm). In some instances, a compound described herein is coated onto laparoscope to prevent and/or reduce biofouling (e.g., microfouling such as bacteria adhesion or biofilm).

In some embodiments, a device described herein comprises suturing material, valve, rod, tubing, wiring, electrode, clip, fastener, or a combination thereof. In some instances, a compound described herein is coated onto suturing material, valve, rod, tubing, wiring, electrode, clip, fastener, or a combination thereof to prevent and/or reduce biofouling (e.g., microfouling such as bacteria adhesion or biofilm).

In some embodiments, a device described herein comprises a syringe. In some cases, a syringe further comprises a needle. In some instances, a compound described herein is coated onto a syringe to prevent and/or reduce biofouling (e.g., microfouling such as bacteria adhesion or biofilm).

In some embodiments, a device described herein comprises a container, such as for storage of one or more medical devices. In some instances, a compound described herein is coated onto a container to prevent and/or reduce biofouling (e.g., microfouling such as bacteria adhesion or biofilm).

In some embodiments, a device described herein comprises a bandage or a patch. In some cases, a device described herein comprises a bandage. In other cases, a device described herein comprises a patch.

In some instances, a compound described herein is coated onto a bandage to prevent and/or reduce biofouling (e.g., microfouling such as bacteria adhesion or biofilm). In some instances, a compound described herein is coated onto patch to prevent and/or reduce biofouling (e.g., microfouling such as bacteria adhesion or biofilm).

In some embodiments, a compound described above is a compound that has a structure represented by a Formula (I):

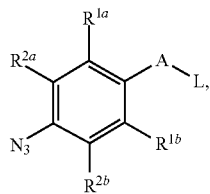

Formula (I)

wherein
A is selected from —C(=O)—, —S(=O)—, —S(=O)$_2$—, and —S(=O)(—NR$^3$)—;
L is selected from —OQ, —NR$^3$Q, and —N(R$^3$)$_2$Q$^+$;
Q is a structure represented by a formula:

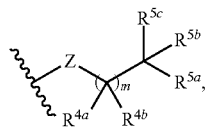

Z is selected from —CR$^{6a}$R$^{6b}$—, —C(=O)—, —C(=NH)—, and —C(=NH)NR$^7$—;
m is an integer selected from 0, 1, 2, 3, 4, 5, 6, 7, and 8;
each R$^{1a}$ and R$^{1b}$ is independently selected from hydrogen and halogen;
each R$^{2a}$ and R$^{2b}$ is independently selected from halogen, —CN, and optionally substituted C1-C6fluoroalkyl;
each R$^3$ is independently selected from hydrogen, optionally substituted C1-C4 alkyl, —X-optionally substituted C1-C4 alkyl, optionally substituted aryl, and —X-optionally substituted aryl;
X is —C(=O)—, —S(=O)—, or —S(=O)$_2$—;
each R$^{4a}$, R$^{4b}$, R$^{5a}$, R$^{5c}$, R$^{6a}$, and R$^{6b}$ is independently selected from hydrogen, halogen, —CN, —OR$^9$, optionally substituted C1-C4 alkyl, optionally substituted C1-C4 fluoroalkyl, optionally substituted aryl, —NR$^{8a}$R$^{8b}$, —NR$^{8a}$R$^{8b}$R$^{8c+}$, —S(=O)$_2$O$^-$, —S(=O)$_2$ OR$^9$, —C(=O)O$^-$, and —C(=O)OR$^9$;
R$^{5b}$ is —NR$^{10a}$R$^{11b}$ or —NR$^{10a}$R$^{10b}$R$^{10c+}$;
each R$^7$, R$^{8a}$, R$^{8b}$, and R$^9$ is independently selected from hydrogen and optionally substituted C1-C4 alkyl, and optionally substituted aryl;
each R$^{10a}$ and R$^{10c}$ is independently selected from hydrogen, optionally substituted C1-C4 alkyl, optionally substituted aryl, -(optionally substituted C1-C8alkylene)S(=O)$_2$O$^-$, -(optionally substituted C1-C8alkylene)S(=O)$_2$OH, -(optionally substituted C1-C8alkylene)C(=O)O$^-$, and -(optionally substituted C1-C8alkylene)C(=O)OH; and R$^{10b}$ is —(C=O)—C2-C6alkenyl, —(S=O)—C2-C6alkenyl, or —(S=O)$_2$—C2-C6alkenyl.

In some embodiments, the compound of Formula (I) has a structure selected from:

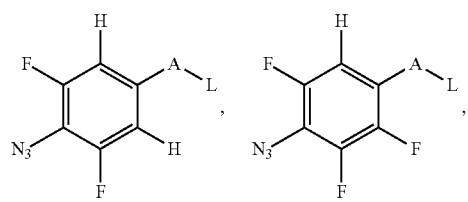

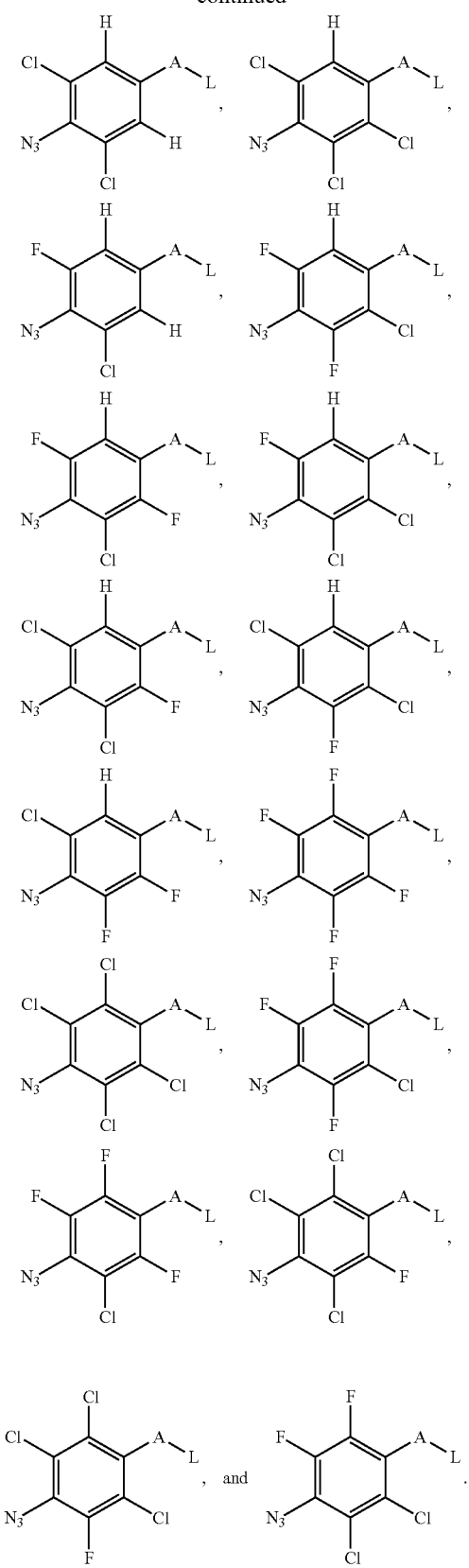

In some embodiments, the compound of Formula (I) has the structure selected from:

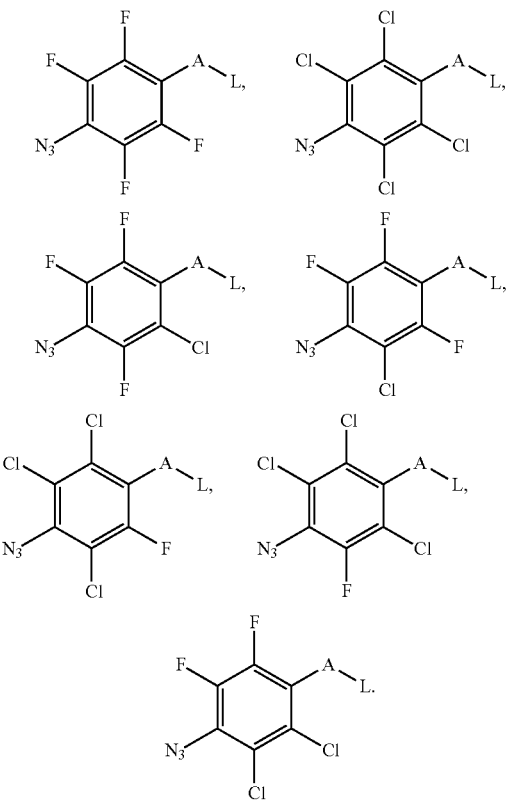

In some embodiments, the compound of Formula (I) has the following structure:

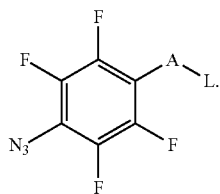

In some embodiments, the compound of Formula (I) has a structure selected from:

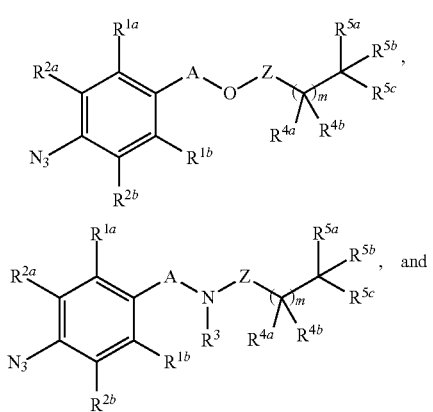

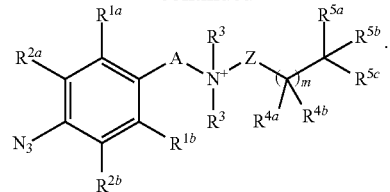

In some embodiments, the compound of Formula (I) has a structure selected from:

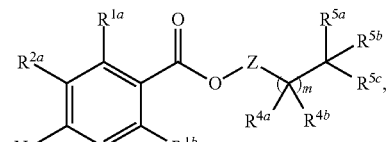

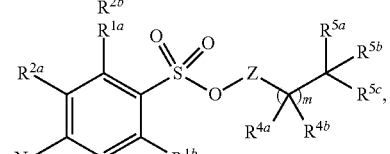

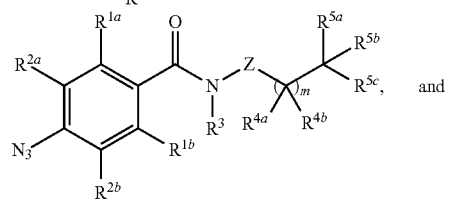

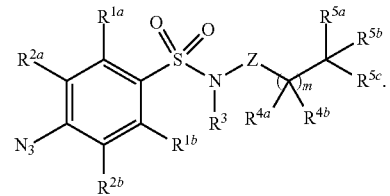

In some embodiments, each $R^{1a}$ and $R^{1b}$ is independently halogen. In some embodiments, each $R^{1a}$ and $R^{1b}$ is independently F or Cl. In some embodiments, each $R^{1a}$ and $R^{1b}$ is F. In some embodiments, each $R^{2a}$ and $R^{2b}$ is independently selected from halogen, —CN, and optionally substituted C1-C6fluoroalkyl. In some embodiments, each $R^{2a}$ and $R^{2b}$ is independently halogen. In some embodiments, each $R^{2a}$ and $R^{2b}$ is —CN. In some embodiments, each $R^{2a}$ and $R^{2b}$ is independently substituted C1-C6fluoroalkyl. In some embodiments, each $R^{2a}$ and $R^{2b}$ is —CF$_3$.

In some embodiments, each $R^{1a}$, $R^{1b}$, $R^{2a}$, and $R^{2b}$ is F.

In some embodiments, Z is selected from —CR$^{6a}$R$^{6b}$—, —C(=O)—, —C(=NH)—, and —C(=NH)NR$^7$—. In some embodiments, Z is —CR$^{6a}$R$^{6b}$—. In some embodiments, Z is —C(=O)—. In some embodiments, Z is —C(=NH)—. In some embodiments, Z is —C(=NH)NR$^7$—.

In some embodiments, each $R^3$ is independently selected from hydrogen, optionally substituted C1-C4 alkyl, —X-optionally substituted C1-C4 alkyl, optionally substituted aryl, and —X-optionally substituted aryl. In some embodiments, $R^3$ is hydrogen. In some embodiments, $R^3$ is optionally substituted C1-C4 alkyl. In some embodiments, $R^3$ is —X-optionally substituted C1-C4 alkyl. In some embodiments, $R^3$ is optionally substituted aryl. In some embodiments, $R^3$ is —X-optionally substituted aryl.

In some embodiments, X is —C(=O)—, —S(=O)—, or —S(=O)$_2$—. In some embodiments, X is —C(=O)—. In some embodiments, X is —S(=O)—. In some embodiments, X is —S(=O)$_2$—.

In some embodiments, each $R^{6a}$ and $R^{6b}$ is hydrogen.

In some embodiments, m is 0, 1, 2, 3, 4, or 5. In some embodiments, m is 0. In some embodiments, m is 1. In some embodiments, m is 2. In some embodiments, m is 3. In some embodiments, m is 4. In some embodiments, m is 5.

In some embodiments, $R^{5a}$ is hydrogen, $R^{5b}$ is —NR$^{10a}$R$^{10b}$, and $R^{5c}$ is hydrogen.

In some embodiments, the compound of Formula (I) has a structure of Formula (Ia):

In some embodiments, the compound of Formula (I) has a structure of Formula (Ib):

In some embodiments, $R^{10a}$ is hydrogen, optionally substituted C1-C4 alkyl, or optionally substituted aryl. In some embodiments, $R^{11a}$ is hydrogen. In some embodiments, $R^{10a}$ is optionally substituted C1-C4 alkyl. In some embodiments, $R^{10a}$ is —CH$_3$. In some embodiments, $R^{10a}$ is CH$_2$CH$_3$. In some embodiments, $R^{10a}$ is optionally substituted aryl. In some embodiments, $R^{10a}$ is phenyl.

In some embodiments, $R^{10b}$ is —(C=O)—C2-C6alkenyl, (S=O)—C2-C6alkenyl, or (S=O)$_2$—C2-C6alkenyl. In some embodiments, $R^{a}$m is —(C=O)—C2-C6alkenyl. In some embodiments, $R^{10b}$ is (S=O)—C2-C6alkenyl. In some embodiments, $R^{10b}$ is —(S=O)$_2$—C2-C6alkenyl.

In some embodiments, a compound described above is a compound that has a structure represented by a Formula (II):

Formula (II)

wherein
each $R^{1a}$ and $R^{1b}$ is independently selected from hydrogen and halogen;
each $R^{2a}$ and $R^{2b}$ is independently selected from halogen, —CN, and optionally substituted C1-C6fluoroalkyl;
each $A^1$, $A^2$, and $A^3$ is independently selected from —C(=O)—, —S(=O)—, —S(=O)$_2$—, and —S(=O)(=NR$^{3c}$)—;
each $B^1$, $B^2$, and $B^3$ is independently selected from —O— and —NR$^{3c}$—;
D is —S(=O)$_2$O$^-$, —S(=O)$_2$OR$^{9a}$, —C(=O)O$^-$, or —C(=O)OR$^{9a}$;
$Z^1$ is —(CR$^{6c}$R$^{6d}$)$_s$—;
$Z^2$ is —(CR$^{6c}$R$^{6d}$)$_t$—;
$Z^3$ is —(CR$^{6c}$R$^{6d}$)$_p$—;
each $R^{3a}$ and $R^{3b}$ is independently selected from hydrogen, optionally substituted C1-C4 alkyl, and optionally substituted benzyl;
each $R^{3c}$ and $R^{3d}$ is independently selected from hydrogen, optionally substituted C1-C4 alkyl, —X-optionally substituted C1-C4 alkyl, optionally substituted C2-C6 alkenyl, and optionally substituted aryl;
X is —C(=O)—, —S(=O)—, or —S(=O)$_2$—;
each $R^{4c}$, $R^{4d}$, $R^{5d}$, $R^{5c}$, $R^{6c}$, and $R^{6d}$ is independently selected from hydrogen, halogen, —CN, —OR$^{9a}$, optionally substituted C1-C4 alkyl, optionally substituted C1-C4 fluoroalkyl, optionally substituted C2-C6 alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;
each $R^{9a}$, $R^{11a}$, $R^{11b}$, $R^{11c}$, $R^{12a}$, $R^{12b}$ and $R^{12c}$ is independently selected from hydrogen, optionally substituted C1-C4 alkyl, and optionally substituted aryl;
n is an integer selected from 0, 1, 2, 3, 4, 5, and 6;
s is an integer selected from 1, 2, 3, 4, or 5;
t is an integer selected from 1, 2, 3, 4, or 5;
p is an integer selected from 1, 2, 3, 4, or 5;
q is an integer selected from 40-60;
r is an integer selected from 1-10; and
wherein the compounds of Formula (II) is charged or zwitterionic.

In some embodiments, each $R^{1a}$ and $R^{1b}$ is independently halogen. In some embodiments, each $R^{1a}$ and $R^{1b}$ is independently F or Cl. In some embodiments, each $R^{1a}$ and $R^{1b}$ is F. In some embodiments, each $R^{2a}$ and $R^{2b}$ is independently selected from halogen, —CN, and optionally substituted C1-C6fluoroalkyl. In some embodiments, each $R^{2a}$ and $R^{2b}$ is independently halogen. In some embodiments, each $R^{2a}$ and $R^{2b}$ is —CN. In some embodiments, each $R^{2a}$ and $R^{2b}$ is independently substituted C1-C6fluoroalkyl. In some embodiments, each $R^{2a}$ and $R^{2b}$ is —CF$_3$.

In some embodiments, each $R^{1a}$, $R^{1b}$, $R^{2a}$, and $R^{2b}$ is F.

In some embodiments, $A^1$ is —S(=O)$_2$—. In some embodiments, $A^1$ is —C(=O)—.

In some embodiments, $A^2$ is —S(=O)$_2$—. In some embodiments, $A^2$ is —C(=O)—.

In some embodiments, $A^3$ is —S(=O)$_2$—. In some embodiments, $A^3$ is —C(=O)—.

In some embodiments, each $B^1$ and $B^2$ is —NR$^{3c}$—.

In some embodiments, each $R^{3c}$ is independently hydrogen, optionally substituted C1-C4 alkyl, or optionally substituted aryl. In some embodiments, $R^{3c}$ is hydrogen. In some embodiments, $R^{3c}$ is optionally substituted C1-C4 alkyl. In some embodiments, $R^{3c}$ is —CH$_3$. In some embodiments, $R^{3c}$ is optionally substituted aryl. In some embodiments, $R^{3c}$ is optionally substituted phenyl.

In some embodiments, $B^3$ is —O—.

In some embodiments, D is —S(=O)$_2$OR$^{9a}$ or —C(=O)OR$^{9a}$. In some embodiments, D is —S(=O)$_2$OR$^{9a}$. In some embodiments, D is —C(=O)OR$^{9a}$.

In some embodiments, $R^{9a}$ is hydrogen or —CH$_3$. In some embodiments, $R^{9a}$ is hydrogen. In some embodiments, $R^{9a}$ is —CH$_3$.

In some embodiments, D is —S(=O)$_2$O$^-$ or —C(=O)O$^-$. In some embodiments, D is —S(=O)$_2$O$^-$. In some embodiments, D is —C(=O)O$^-$.

In some embodiments, each $R^{6c}$ and $R^{6d}$ is hydrogen.

In some embodiments, each $R^{3a}$ and $R^{3b}$ is —CH$_3$.

In some embodiments, $R^{11a}$ is hydrogen or —CH$_3$. In some embodiments, $R^{11a}$ is hydrogen. In some embodiments, $R^{11a}$ is —CH$_3$.

In some embodiments, $R^{12a}$ is hydrogen or —CH$_3$. In some embodiments, $R^{11a}$ is hydrogen. In some embodiments, $R^{12a}$ is —CH$_3$.

In some embodiments, each $R^{11b}$, $R^{11c}$, $R^{12b}$, and $R^{12c}$ is hydrogen.

In some embodiments, n is 0, 1, 2, 3, 4, or 5. In some embodiments, n is 0. In some embodiments, n is 1. In some embodiments, m is 2. In some embodiments, n is 3. In some embodiments, n is 4. In some embodiments, n is 5.

In some embodiments, s is 1, 2, 3, or 4. In some embodiments, s is 1. In some embodiments, s is 2. In some embodiments, s is 3. In some embodiments, s is 4.

In some embodiments, t is 1, 2, 3, or 4. In some embodiments, t is 1. In some embodiments, t is 2. In some embodiments, t is 3. In some embodiments, t is 4.

In some embodiments, p is 1, 2, 3, or 4. In some embodiments, p is 1. In some embodiments, p is 2. In some embodiments, p is 3. In some embodiments, p is 4.

In some embodiments, q is 45, 46, 47, 48, 49, 50, 51, 52, 53, 54, or 55. In some embodiments, q is 45. In some embodiments, q is 46. In some embodiments, q is 47. In some embodiments, q is 48. In some embodiments, q is 49. In some embodiments, q is 50. In some embodiments, q is 51. In some embodiments, q is 52. In some embodiments, q is 53. In some embodiments, q is 54. In some embodiments, q is 55.

In some embodiments, r is 1, 2, 3, 4, 5, 6, 7, 8, 9, or 10. In some embodiments, r is 1. In some embodiments, r is 2. In some embodiments, r is 3. In some embodiments, r is 4. In some embodiments, r is 5. In some embodiments, r is 6. In some embodiments, r is 7. In some embodiments, r is 8. In some embodiments, r is 9. In some embodiments, r is 10.

In some embodiments, a compound described above is a compound that has a structure represented by a Formula (III):

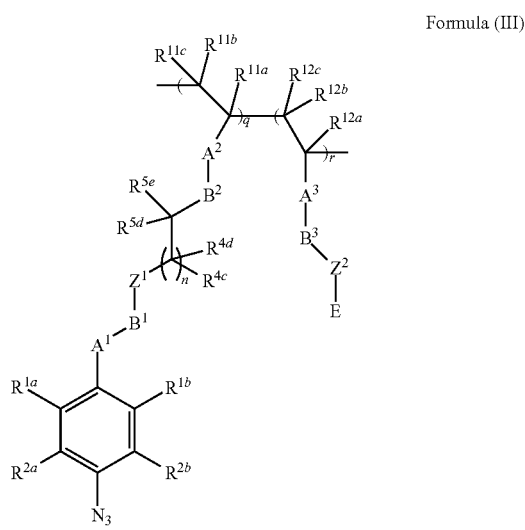

Formula (III)

wherein
each $R^{1a}$ and $R^{1b}$ is independently selected from hydrogen and halogen;
each $R^{2a}$ and $R^{2b}$ is independently selected from halogen, —CN, and optionally substituted C1-C6fluoroalkyl;
each $A^1$, $A^2$, and $A^3$ is independently selected from —C(=O)—, —S(=O)—, —S(=O)$_2$—, and —S(=O)(=NR$^{3c}$)—;
each $B^1$, $B^2$, and $B^3$ is independently selected from —O— and —NR$^{3c}$—;
$Z^1$ is —(CR$^{6c}$R$^{6d}$)$_s$—;
$Z^2$ is —(CR$^{6c}$R$^{6d}$)$_t$—;
E is —CN, —OR$^{9a}$, —NR$^{9a}$R$^{9b}$, —NR$^{9a}$R$^{9b}$R$^{9c+}$, optionally substituted C1-C4 alkyl, optionally substituted C1-C6fluoroalkyl, —S(=O)$_2$O$^-$, —S(=O)$_2$OR$^{9a}$, —C(=O)O$^-$, or —C(=O)OR$^{9a}$;
each $R^{4c}$, $R^{4d}$, $R^{5d}$, $R^{5e}$, $R^{6c}$, and $R^{6d}$ is independently selected from hydrogen, halogen, —CN, —OR$^{9a}$, optionally substituted C1-C4 alkyl, optionally substituted C1-C4 fluoroalkyl, optionally substituted C2-C6 alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;
each $R^{3c}$ and $R^{3d}$ is independently selected from hydrogen, optionally substituted C1-C4 alkyl, —X-optionally substituted C1-C4 alkyl, optionally substituted C2-C6 alkenyl, and optionally substituted aryl;
X is —C(=O)—, —S(=O)—, or —S(=O)$_2$—;
each $R^{9a}$, $R^{11a}$, $R^{11b}$, $R^{11c}$, $R^{12a}$, $R^{12b}$, and $R^{12c}$ is independently selected from hydrogen, optionally substituted C1-C4 alkyl, and optionally substituted aryl;
n is an integer selected from 0, 1, 2, 3, 4, 5, and 6;
s is an integer selected from 1, 2, 3, 4, or 5;
t is an integer selected from 1, 2, 3, 4, or 5;
q is an integer selected from 40-60; and
r is an integer selected from 1-10.

In some embodiments, each $R^{1a}$ and $R^{1b}$ is independently halogen. In some embodiments, each $R^{1a}$ and $R^{1b}$ is independently F or Cl. In some embodiments, each $R^{1a}$ and $R^{1b}$ is F. In some embodiments, each $R^{2a}$ and $R^{2b}$ is independently selected from halogen, —CN, and optionally substituted C1-C6fluoroalkyl. In some embodiments, each $R^{2a}$ and $R^{2b}$ is independently halogen. In some embodiments, each $R^{2a}$ and $R^{2b}$ is —CN. In some embodiments, each $R^{2a}$ and $R^{2b}$ is independently substituted C1-C6fluoroalkyl. In some embodiments, each $R^{2a}$ and $R^{2b}$ is —$CF_3$.

In some embodiments, each $R^{1a}$, $R^{1b}$, $R^{2a}$, and $R^{2b}$ is F.

In some embodiments, $A^1$ is —$S(=O)_2$—. In some embodiments, $A^1$ is —$C(=O)$—.

In some embodiments, $A^2$ is —$S(=O)_2$—. In some embodiments, $A^2$ is —$C(=O)$—.

In some embodiments, $A^3$ is —$S(=O)_2$—. In some embodiments, $A^3$ is —$C(=O)$—.

In some embodiments, each $B^1$, $B^2$, and $B^3$ is —$NR^{3c}$—.

In some embodiments, each $R^{3c}$ is independently hydrogen, optionally substituted C1-C4 alkyl, or optionally substituted aryl. In some embodiments, $R^{3c}$ is hydrogen. In some embodiments, $R^{3c}$ is optionally substituted C1-C4 alkyl. In some embodiments, $R^{3c}$ is —$CH_3$. In some embodiments, $R^{3c}$ is optionally substituted aryl. In some embodiments, $R^{3c}$ is optionally substituted phenyl.

In some embodiments, E is —$NR^{9a}R^{9b}R^{9c+}$ or —$S(=O)_2OR^{9a}$.

In some embodiments, E is —$NR^{9a}R^{9b}R^{9c+}$. In some embodiments, each $R^{9a}$, $R^{9b}$, or $R^{9c}$ is independently H or —$CH_3$. In some embodiments, $R^{9a}$ is H. In some embodiments, $R^{9a}$ is —$CH_3$. In some embodiments, $R^{9b}$ is H. In some embodiments, $R^{9b}$ is —$CH_3$. In some embodiments, $R^{9c}$ is H. In some embodiments, $R^{9c}$ is —$CH_3$.

In some embodiments, E is —$S(=O)_2OR^{9a}$. In some embodiments, each $R^{9a}$ is H or —$CH_3$. In some embodiments, $R^{9a}$ is H. In some embodiments, $R^{9a}$ is —$CH_3$.

In some embodiments, each $R^{6c}$ and $R^{6d}$ is independently selected from hydrogen and —$CH_3$.

In some embodiments, each $R^{3a}$ and $R^{3b}$ is —$CH_3$.

In some embodiments, $R^{11a}$ is hydrogen or —$CH_3$. In some embodiments, $R^{11a}$ is hydrogen. In some embodiments, $R^{11a}$ is —$CH_3$.

In some embodiments, $R^{12a}$ is hydrogen or —$CH_3$. In some embodiments, $R^{11a}$ is hydrogen. In some embodiments, $R^{12a}$ is —$CH_3$.

In some embodiments, each $R^{11b}$, $R^{11c}$, $R^{12b}$, and $R^{12c}$ is hydrogen.

Biofouling-Resistant Medical Devices

In some embodiments, disclosed herein is a biofouling-resistant medical device, wherein a surface of the medical device is coated with one or more compounds of Formula (I), (II), or (III) described herein having a number-average molecular weight of between about 10,000 and about 250,000.

In some embodiments, the phenyl azide-based copolymer has a number-average molecular weight of at least about 10,000, about 20,000, about 30,000, about 40,000, about 50,000, about 60,000, about 70,000, about 80,000, about 90,000, about 100,000, about 110,000, about 120,000, about 130,000, about 140,000, about 150,000, about 160,000, about 170,000, about 180,000, about 190,000, or about 200,000. In some embodiments, the phenyl azide-based copolymer has a number-average molecular weight of no more than about 10,000, about 20,000, about 30,000, about 40,000, about 50,000, about 60,000, about 70,000, about 80,000, about 90,000, about 100,000, about 110,000, about 120,000, about 130,000, about 140,000, about 150,000, about 160,000, about 170,000, about 180,000, about 190,000, or about 200,000.

In some embodiments, the phenyl azide-based copolymer has a number-average molecular weight of between about 10,000 and about 20,000. In some embodiments, the phenyl azide-based copolymer has a number-average molecular weight of between about 10,000 and about 40,000. In some embodiments, the phenyl azide-based copolymer has a number-average molecular weight of between about 10,000 and about 60,000. In some embodiments, the phenyl azide-based copolymer has a number-average molecular weight of between about 10,000 and about 80,000. In some embodiments, the phenyl azide-based copolymer has a number-average molecular weight of between about 10,000 and about 100,000. In some embodiments, the phenyl azide-based copolymer has a number-average molecular weight of between about 10,000 and about 120,000. In some embodiments, the phenyl azide-based copolymer has a number-average molecular weight of between about 10,000 and about 140,000. In some embodiments, the phenyl azide-based copolymer has a number-average molecular weight of between about 10,000 and about 160,000. In some embodiments, the phenyl azide-based copolymer has a number-average molecular weight of between about 10,000 and about 200,000. In some embodiments, the phenyl azide-based copolymer has a number-average molecular weight of between about 20,000 and about 40,000. In some embodiments, the phenyl azide-based copolymer has a number-average molecular weight of between about 20,000 and about 60,000. In some embodiments, the phenyl azide-based copolymer has a number-average molecular weight of between about 20,000 and about 80,000. In some embodiments, the phenyl azide-based copolymer has a number-average molecular weight of between about 20,000 and about 100,000. In some embodiments, the phenyl azide-based copolymer has a number-average molecular weight of between about 20,000 and about 120,000. In some embodiments, the phenyl azide-based copolymer has a number-average molecular weight of between about 20,000 and about 140,000. In some embodiments, the phenyl azide-based copolymer has a number-average molecular weight of between about 20,000 and about 160,000. In some embodiments, the phenyl azide-based copolymer has a number-average molecular weight of between about 20,000 and about 200,000. In some embodiments, the phenyl azide-based copolymer has a number-average molecular weight of between about 20,000 and about 250,000. In some embodiments, the phenyl azide-based copolymer has a number-average molecular weight of between about 40,000 and about 60,000. In some embodiments, the phenyl azide-based copolymer has a number-average molecular weight of between about 40,000 and about 80,000. In some embodiments, the phenyl azide-based copolymer has a number-average molecular weight of between about 40,000 and about 100,000. In some embodiments, the phenyl azide-based copolymer has a number-average molecular weight of between about 40,000 and about 120,000. In some embodiments, the phenyl azide-based copolymer has a number-average molecular weight of between about 40,000 and about 140,000. In some embodiments, the phenyl azide-based copolymer has a number-average molecular weight of between about 40,000 and about 160,000. In some embodiments, the phenyl azide-based copolymer has a number-average molecular weight of between about 40,000 and about 200,000. In some embodiments, the phenyl azide-based copolymer has a number-average molecular weight of between about 40,000 and about 250,000. In some embodiments, the phenyl azide-based copolymer has a number-average molecular weight of between about 60,000 and about 80,000. In some embodiments, the phenyl azide-based copolymer has a number-average molecular weight of between about 60,000 and about 100,000. In some embodiments, the phenyl azide-based copolymer has a number-average molecular weight of between about 60,000 and about 120,000. In some embodiments, the phenyl azide-based copolymer has a number-average molecular weight of between about 60,000 and about 140,000. In some embodiments, the phenyl azide-based copolymer has a number-average molecular weight of between about 60,000 and about 160,000. In some embodiments, the phenyl azide-based copolymer has a number-average molecular weight of between about 60,000 and about 200,000. In some embodiments, the phenyl azide-based copolymer has a number-average molecular weight of between about 60,000 and about 250,000. In some embodiments, the phenyl azide-based copolymer has a number-average molecular weight of between about 80,000 and about 100,000. In some embodiments, the phenyl azide-based copolymer has a number-average molecular weight of between about 80,000 and about 120,000. In some embodiments, the phenyl azide-based copolymer has a number-average molecular weight of between about 80,000 and about 140,000. In some embodiments, the phenyl azide-based copolymer has a number-average molecular weight of between about 80,000 and about 160,000. In some embodiments, the phenyl azide-based copolymer has a number-average molecular weight of between about 80,000 and about 200,000. In some embodiments, the phenyl azide-based copolymer has a number-average molecular weight of between about 80,000 and about 250,000. In some embodiments, the phenyl azide-based copolymer has a number-average molecular weight of between about 100,000 and about 120,000. In some embodiments, the phenyl azide-based copolymer has a number-average molecular weight of between about 100,000 and about 140,000. In some embodiments, the phenyl azide-based copolymer has a number-average molecular weight of between about 100,000 and about 160,000. In some embodiments, the phenyl azide-based copolymer has a number-average molecular weight of between about 100,000 and about 200,000. In some embodiments, the phenyl azide-based copolymer has a number-average molecular weight of between about 100,000 and about 250,000. In some embodiments, the phenyl azide-based copolymer has a number-average molecular weight of between about 120,000 and about 140,000. In some embodiments, the phenyl azide-based copolymer has a number-average molecular weight of between about 120,000 and about 160,000. In some embodiments, the phenyl azide-based copolymer has a number-average molecular weight of between about 120,000 and about 200,000. In some embodiments, the phenyl azide-based copolymer has a number-average molecular weight of between about 120,000 and about 250,000. In some embodiments, the phenyl azide-based copolymer has a number-average molecular weight of between about 140,000 and about 160,000. In some embodiments, the phenyl azide-based copolymer has a number-average molecular weight of between about 140,000 and about 200,000. In some embodiments, the phenyl azide-based copolymer has a number-average molecular weight of between about 140,000 and about 250,000. In some embodiments, the phenyl azide-based copolymer has a number-average molecular weight of between about 160,000 and about 200,000. In some embodiments, the phenyl azide-based copolymer has a number-average molecular weight of between about 160,000 and about 250,000. In some embodiments, the phenyl azide-based copolymer has a number-average molecular weight of between about 200,000 and about 250,000. In some embodiments, the phenyl azide-based copolymer has a number-average molecular weight of about 10,000. In some embodiments, the phenyl azide-based copolymer has a number-average molecular weight of about 20,000. In some embodiments, the phenyl azide-based copolymer has a number-average molecular weight of about 40,000. In some embodiments, the phenyl azide-based copolymer has a number-average molecular weight of about 60,000. In some embodiments, the phenyl azide-based copolymer has a number-average molecular weight of about 80,000. In some embodiments, the phenyl azide-based copolymer has a number-average molecular weight of about 100,000. In some embodiments, the phenyl azide-based copolymer has a number-average molecular weight of about 120,000. In some embodiments, the phenyl azide-based copolymer has a number-average molecular weight of about 140,000. In some embodiments, the phenyl azide-based copolymer has a number-average molecular weight of about 160,000. In some embodiments, the phenyl azide-based copolymer has a number-average molecular weight of about 200,000. In some embodiments, the phenyl azide-based copolymer has a number-average molecular weight of about 250,000.

In some embodiments, disclosed herein is a biofouling-resistant medical device, wherein a surface of the medical device is coated with one or more compounds of Formula (I), (II), or (III) described herein having a number-average molecular weight of between about 14,000 and about 21,000.

In some embodiments, the phenyl azide-based copolymer has a number-average molecular weight of between about 14,000 and about 15,000. In some embodiments, the phenyl azide-based copolymer has a number-average molecular weight of between about 14,000 and about 16,000. In some embodiments, the phenyl azide-based copolymer has a number-average molecular weight of between about 14,000 and about 17,000. In some embodiments, the phenyl azide-based copolymer has a number-average molecular weight of between about 14,000 and about 18,000. In some embodiments, the phenyl azide-based copolymer has a number-average molecular weight of between about 14,000 and about 19,000. In some embodiments, the phenyl azide-based copolymer has a number-average molecular weight of between about 14,000 and about 20,000. In some embodiments, the phenyl azide-based copolymer has a number-average molecular weight of between about 15,000 and about 16,000. In some embodiments, the phenyl azide-based copolymer has a number-average molecular weight of between about 15,000 and about 17,000. In some embodiments, the phenyl azide-based copolymer has a number-average molecular weight of between about 15,000 and about 18,000. In some embodiments, the phenyl azide-based copolymer has a number-average molecular weight of between about 15,000 and about 19,000. In some embodiments, the phenyl azide-based copolymer has a number-average molecular weight of between about 15,000 and about 20,000. In some embodiments, the phenyl azide-based copolymer has a number-average molecular weight of between about 15,000 and about 21,000. In some embodiments, the phenyl azide-based copolymer has a number-average molecular weight of between about 16,000 and about 17,000. In some embodiments, the phenyl azide-based copolymer has a number-average molecular weight of between about 16,000 and about 18,000. In some embodiments, the phenyl azide-based copolymer has a number-average molecular weight of between about 16,000 and about 19,000. In some embodiments, the phenyl azide-based copolymer has a number-average molecular weight of between about 16,000 and about 20,000. In some embodiments, the phenyl azide-based copolymer has a number-average molecular weight of between about 16,000 and about 21,000. In some embodiments, the phenyl azide-based copolymer has a number-average molecular weight of between about 17,000 and about 18,000. In some embodiments, the phenyl azide-based copolymer has a number-average molecular weight of between about 17,000 and about 19,000. In some embodiments, the phenyl azide-based copolymer has a number-average molecular weight of between about 17,000 and about 20,000. In some embodiments, the phenyl azide-based copolymer has a number-average molecular weight of between about 17,000 and about 21,000. In some embodiments, the phenyl azide-based copolymer has a number-average molecular weight of between about 18,000 and about 19,000. In some embodiments, the phenyl azide-based copolymer has a number-average molecular weight of between about 18,000 and about 20,000. In some embodiments, the phenyl azide-based copolymer has a number-average molecular weight of between about 18,000 and about 21,000. In some embodiments, the phenyl azide-based copolymer has a number-average molecular weight of between about 19,000 and about 20,000. In some embodiments, the phenyl azide-based copolymer has a number-average molecular weight of between about 19,000 and about 21,000. In some embodiments, the phenyl azide-based copolymer has a number-average molecular weight of between about 20,000 and about 21,000. In some embodiments, the phenyl azide-based copolymer has a number-average molecular weight of about 14,000. In some embodiments, the phenyl azide-based copolymer has a number-average molecular weight of about 15,000. In some embodiments, the phenyl azide-based copolymer has a number-average molecular weight of about 16,000. In some embodiments, the phenyl azide-based copolymer has a number-average molecular weight of about 17,000. In some embodiments, the phenyl azide-based copolymer has a number-average molecular weight of about 18,000. In some embodiments, the phenyl azide-based copolymer has a number-average molecular weight of about 19,000. In some embodiments, the phenyl azide-based copolymer has a number-average molecular weight of about 20,000. In some embodiments, the phenyl azide-based copolymer has a number-average molecular weight of about 21,000.

In some embodiments, disclosed herein is a biofouling-resistant medical device, wherein a surface of the medical device is coated with one or more compounds of Formula (I), (II), or (III) described herein having a polydispersity index (PDI) of between about 1 and 1.5.

In some embodiments, the surface of the medical device is coated with a phenyl azide-based copolymer having a polydispersity index (PDI) of at least about 1, about 1.1, about 1.2, about 1.3, about 1.4, or about 1.5. In some embodiments, the surface of the medical device is coated with a phenyl azide-based copolymer having a polydispersity index (PDI) of no more than about 1, about 1.1, about 1.2, about 1.3, about 1.4, or about 1.5.

In some embodiments, the surface of the medical device is coated with a phenyl azide-based copolymer having a polydispersity index (PDI) of between about 1 and 1.1. In some embodiments, the surface of the medical device is coated with a phenyl azide-based copolymer having a polydispersity index (PDI) of between about 1 and 1.2. In some embodiments, the surface of the medical device is coated with a phenyl azide-based copolymer having a polydispersity index (PDI) of between about 1 and 1.3. In some embodiments, the surface of the medical device is coated with a phenyl azide-based copolymer having a polydispersity index (PDI) of between about 1 and 1.4. In some embodiments, the surface of the medical device is coated with a phenyl azide-based copolymer having a polydispersity index (PDI) of between about 1 and 1.5. In some embodiments, the surface of the medical device is coated with a phenyl azide-based copolymer having a polydispersity index (PDI) of between about 1.1 and 1.2. In some embodiments, the surface of the medical device is coated with a phenyl azide-based copolymer having a polydispersity index (PDI) of between about 1.1 and 1.3. In some embodiments, the surface of the medical device is coated with a phenyl azide-based copolymer having a polydispersity index (PDI) of between about 1.1 and 1.4. In some embodiments, the surface of the medical device is coated with a phenyl azide-based copolymer having a polydispersity index (PDI) of between about 1.1 and 1.5. In some embodiments, the surface of the medical device is coated with a phenyl azide-based copolymer having a polydispersity index (PDI) of between about 1.2 and 1.3. In some embodiments, the surface of the medical device is coated with a phenyl azide-based copolymer having a polydispersity index (PDI) of between about 1.2 and 1.4. In some embodiments, the surface of the medical device is coated with a phenyl azide-based copolymer having a polydispersity index (PDI) of between about 1.2 and 1.5. In some embodiments, the surface of the medical device is coated with a phenyl azide-based copolymer having a polydispersity index (PDI) of between about 1.3 and 1.4. In some embodiments, the surface of the medical device is coated with a phenyl azide-based copolymer having a polydispersity index (PDI) of between about 1.3 and 1.5. In some embodiments, the surface of the medical device is coated with a phenyl azide-based copolymer having a polydispersity index (PDI) of between about 1.4 and 1.5. In some embodiments, the PDI is about 1. In some embodiments, the PDI is about 1.1. In some embodiments, the PDI is about 1.2. In some embodiments, the PDI is about 1.3. In some embodiments, the PDI is about 1.4. In some embodiments, the PDI is about 1.5. In some embodiments, the PDI is about 1.11. In some embodiments, the PDI is about 1.12. In some embodiments, the PDI is about 1.13. In some embodiments, the PDI is about 1.14. In some embodiments, the PDI is about 1.15. In some embodiments, the PDI is about 1.16. In some embodiments, the PDI is about 1.17. In some embodiments, the PDI is about 1.18. In some embodiments, the PDI is about 1.19. In some embodiments, the PDI is about 1.21. In some embodiments, the PDI is about 1.22. In some embodiments, the PDI is about 1.23. In some embodiments, the PDI is about 1.24. In some embodiments, the PDI is about 1.25.

In some embodiments, the medical device comprises a dental instrument or a medical instrument. In some embodiments, the medical device comprises an implant, an IV, a prosthesis, a suturing material, a valve, a stent, a catheter, a rod, a shunt, a scope, a contact lens, a tubing, a wiring, an electrode, a clip, a fastener, a syringe, a container, or a combination thereof. In some embodiments, the medical device is a contact lens. In some embodiments, the medical device is a catheter. In some embodiments, the catheter is an indwelling catheter. In some embodiments, the catheter comprises a uretic catheter or a Foley catheter. In some embodiments, the medical device is a scope. In some embodiments, the scope comprises a scope utilized in an image-guided surgery. In some embodiments, the scope comprises a scope utilized in endoscopy or laparoscopy.

In some embodiments, the medical device comprises auditory prostheses, artificial larynx, dental implants, mammary implants, penile implants, cranio/facial tendons, tendons, ligaments, menisci, or disks. In some embodiments, the medical device comprises artificial bones, artificial joints, or artificial organs. In some embodiments, the artificial organs comprise artificial pancreas, artificial hearts, artificial limbs, or heart valves. In some embodiments, the medical device comprises a bandage or a patch.

In some embodiments, the copolymer comprises zwitterionic copolymer. In some embodiments, the zwitterionic copolymer comprises polysulfobetaine.

In some embodiments, the biofouling is produced by a bacterium, a virus, and/or a fungus.

Non-Medical Devices

In some embodiments, a device described herein comprises a non-medical device. In some instances, a non-medical device comprises a marine vessel or an underwater construction. In some cases, a surface of a non-medical device for coating a compound described herein comprises a surface that is immersed in water. In some cases, the immersion is an immersion of at least 30 minutes, 1 hour, 6 hours, 12 hours, 1 day, 2 days, 3 days, 4 days, 5 days, 6 days, 7 days, 8 days, 9 days, 10 days, 11 days, 12 days, 13 days, 14 days, 15 days, 30 days, 1 month, 2 months, 3 months, 4 months, 5 months, 6 months, 7 months, 8 months, 9 months, 10 months, 11 months, 1 year, 2 years, 3 years, 4 years, 5 years, 10 years, or more.

In some instances, a device described herein comprises a marine vessel. In some instances, a surface of a marine vessel comprises a surface that is immersed in water. In some cases, a surface of a marine vessel comprises a surface that is immersed in water for at least 30 minutes, 1 hour, 6 hours, 12 hours, 1 day, 2 days, 3 days, 4 days, 5 days, 6 days, 7 days, 8 days, 9 days, 10 days, 11 days, 12 days, 13 days, 14 days, 15 days, 30 days, 1 month, 2 months, 3 months, 4 months, 5 months, 6 months, 7 months, 8 months, 9 months, 10 months, 11 months, 1 year, 2 years, 3 years, 4 years, 5 years, 10 years, or more. In some instances, the surface of a device for coating a compound described herein comprises the hull of a marine vessel.

In some instances, a device described herein comprises an underwater construction. In some instances, an underwater construction comprises an underwater cable, a current measurement instrument, or an offshore oil platform. In some cases, a device described herein comprises an underwater cable. In some cases, a device described herein comprises a current measurement instrument. In other cases, a device described herein comprises an offshore oil platform.

In some cases, an underwater construction is a construction in which the construction is immersed in water for at least 30 minutes, 1 hour, 6 hours, 12 hours, 1 day, 2 days, 3 days, 4 days, 5 days, 6 days, 7 days, 8 days, 9 days, 10 days, 11 days, 12 days, 13 days, 14 days, 15 days, 30 days, 1 month, 2 months, 3 months, 4 months, 5 months, 6 months, 7 months, 8 months, 9 months, 10 months, 11 months, 1 year, 2 years, 3 years, 4 years, 5 years, or more. In some cases, a surface of an underwater construction is a construction in which the surface is immersed in water for at least 30 minutes, 1 hour, 6 hours, 12 hours, 1 day, 2 days, 3 days, 4 days, 5 days, 6 days, 7 days, 8 days, 9 days, 10 days, 11 days, 12 days, 13 days, 14 days, 15 days, 30 days, 1 month, 2 months, 3 months, 4 months, 5 months, 6 months, 7 months, 8 months, 9 months, 10 months, 11 months, 1 year, 2 years, 3 years, 4 years, 5 years, 10 years, or more. In some instances, a device described herein comprises an underwater construction in which the surface is immersed in water for at least 30 minutes, 1 hour, 6 hours, 12 hours, 1 day, 2 days, 3 days, 4 days, 5 days, 6 days, 7 days, 8 days, 9 days, 10 days, 11 days, 12 days, 13 days, 14 days, 15 days, 30 days, 1 month, 2 months, 3 months, 4 months, 5 months, 6 months, 7 months, 8 months, 9 months, 10 months, 11 months, 1 year, 2 years, 3 years, 4 years, 5 years, 10 years, or more.

In some embodiments, a compound described herein is coated onto a device (e.g., a medical device or a non-medical device). In some cases, a compound described herein is coated directly onto a device (e.g., a medical device or a non-medical device). In other instances, a compound described herein is coated indirectly onto a device (e.g., a medical device or a non-medical device). In some cases, the coating comprises dip-coating. In other cases, the coating comprises spray coating.

In some embodiments, a compound described herein is coated onto a device (e.g., a medical device or a non-medical device) to reduce the formation of biofouling. In some cases, the formation of biofouling is reduced by about 10%, 20%, 30%, 40%, 50%, 60%, 70%, 80%, 90%, 95%, 99%, 99.5%, 99.9%, or more relative to a device not coated with the compound. In some instances, the formation of biofouling is reduced by about 10%, or more relative to a device not coated with the compound. In some instances, the formation of biofouling is reduced by about 20%, or more relative to a device not coated with the compound. In some instances, the formation of biofouling is reduced by about 30%, or more relative to a device not coated with the compound. In some instances, the formation of biofouling is reduced by about 40%, or more relative to a device not coated with the compound. In some instances, the formation of biofouling is reduced by about 50%, or more relative to a device not coated with the compound. In some instances, the formation of biofouling is reduced by about 60%, or more relative to a device not coated with the compound. In some instances, the formation of biofouling is reduced by about 70%, or more relative to a device not coated with the compound. In some instances, the formation of biofouling is reduced by about 80%, or more relative to a device not coated with the compound. In some instances, the formation of biofouling is reduced by about 90%, or more relative to a device not coated with the compound. In some instances, the formation of biofouling is reduced by about 95%, or more relative to a device not coated with the compound. In some instances, the formation of biofouling is reduced by about 99%, or more relative to a device not coated with the compound. In some instances, the formation of biofouling is reduced by about 99.5%, or more relative to a device not coated with the compound. In some instances, the formation of biofouling is reduced by about 99.9%, or more relative to a device not coated with the compound. In some instances, the compound is a compound that has a structure represented by a Formula (I):

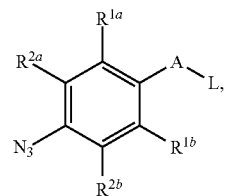

Formula (I)

wherein

A is selected from —C(=O)—, —S(=O)—, —S(=O)$_2$—, and —S(=O)(—NR$^3$)—;

L is selected from —OQ, —NR$^3$Q, and —N(R$^3$)$_2$Q$^+$;

Q is a structure represented by a formula:

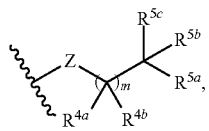

Z is selected from —CR$^{6a}$R$^{6b}$—, —C(=NH)—, and —C(=NH)NR$^7$—;

m is an integer selected from 0, 1, 2, 3, 4, 5, 6, 7, and 8;

each R$^{1a}$ and R$^{1b}$ is independently selected from hydrogen and halogen;

each R$^{2a}$ and R$^{2b}$ is independently selected from halogen, —CN, and optionally substituted C1-C6fluoroalkyl;

each R$^3$ is independently selected from hydrogen, optionally substituted C1-C4 alkyl, —X-optionally substituted C1-C4 alkyl, optionally substituted aryl, and —X-optionally substituted aryl;

X is —C(=O)—, —S(=O)—, or —S(=O)$_2$—;

each R$^{4a}$, R$^{4b}$, R$^{5a}$, R$^{5c}$, R$^{6a}$, and R$^{6b}$ is independently selected from hydrogen, halogen, —CN, —OR$^9$, optionally substituted C1-C4 alkyl, optionally substituted C1-C4 fluoroalkyl, optionally substituted aryl, —NR$^{8a}$R$^{8b}$, —NR$^{8a}$R$^{8b}$R$^{8c+}$, —S(=O)$_2$O$^-$, —S(=O)$_2$ OR$^9$, —C(=O)O$^-$, and —C(=O)OR$^9$;

R$^{5b}$ is —NR$^{10a}$R$^{10b}$ or —NR$^{10a}$R$^{10b}$R$^{10c+}$;

each R$^7$, R$^{8a}$, R$^{8b}$, R$^{8c}$, and R$^9$ is independently selected from hydrogen and optionally substituted C1-C4 alkyl, and optionally substituted aryl;

each R$^{10a}$ and R$^{10c}$ is independently selected from hydrogen, optionally substituted C1-C4 alkyl, optionally substituted aryl, -(optionally substituted C1-C8alkylene)S(=O)$_2$O$^-$, -(optionally substituted C1-C8alkylene)S(=O)$_2$OH, -(optionally substituted C1-C8alkylene)C(=O)O$^-$, and -(optionally substituted C1-C8alkylene)C(=O)OH; and R$^{10b}$ is (C=O)—C2-C6alkenyl, (S=O)—C2-C6alkenyl, or (S=O)$_2$—C2-C6alkenyl.

In some embodiments, the compound of Formula (I) has a structure selected from:

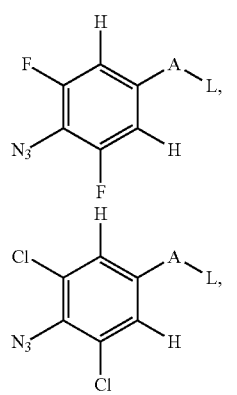

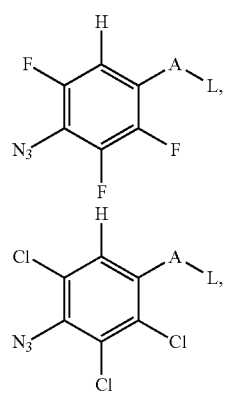

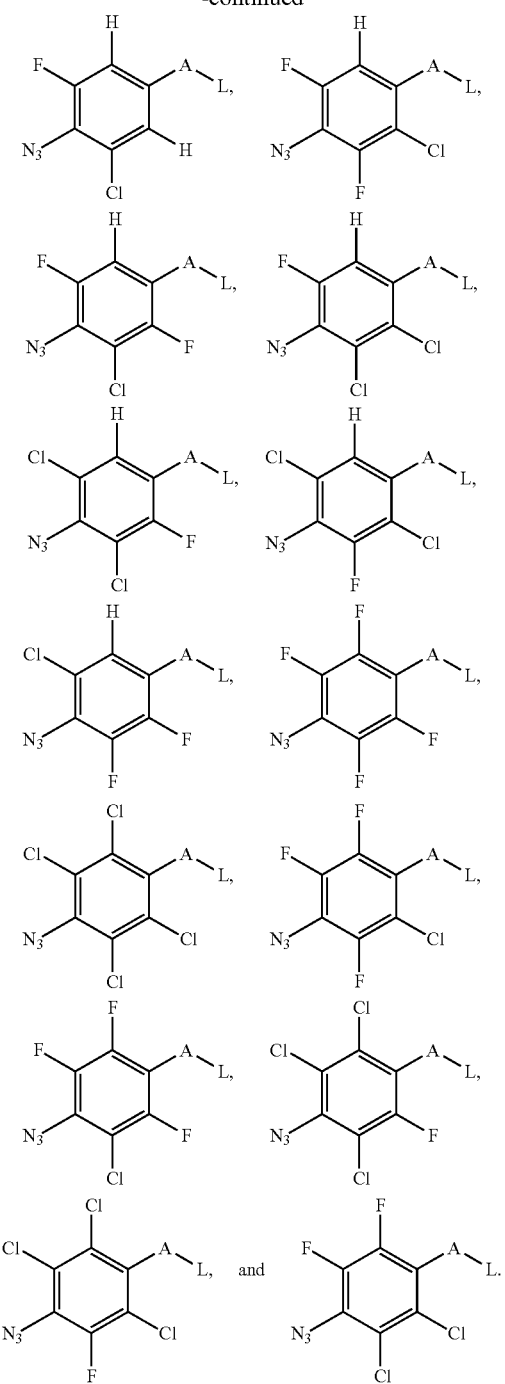

In some embodiments, the compound of Formula (I) has the structure selected from:

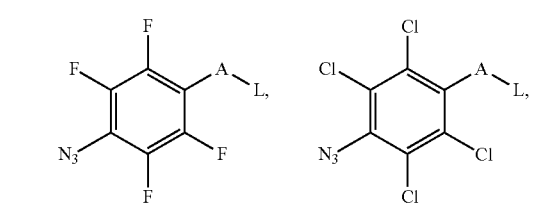

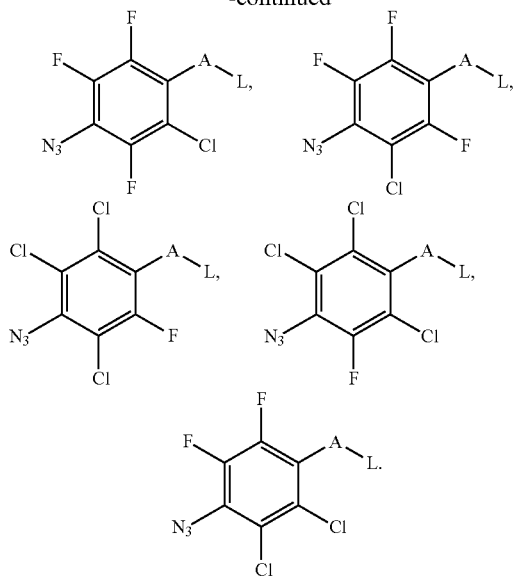

In some embodiments, the compound of Formula (I) has the following structure:

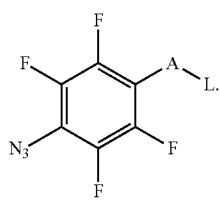

In some embodiments, the compound of Formula (I) has a structure selected from:

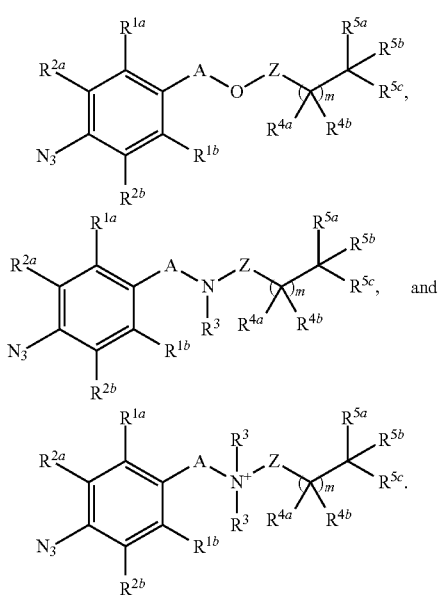

In some embodiments, the compound of Formula (I) has a structure selected from:

In some embodiments, each $R^{1a}$ and $R^{1b}$ is independently halogen. In some embodiments, each $R^{1a}$ and $R^{1b}$ is independently F or Cl. In some embodiments, each $R^{1a}$ and $R^{1b}$ is F. In some embodiments, each $R^{2a}$ and $R^{2b}$ is independently selected from halogen, —CN, and optionally substituted C1-C6fluoroalkyl. In some embodiments, each $R^{2a}$ and $R^{2b}$ is independently halogen. In some embodiments, each $R^{2a}$ and $R^{2b}$ is —CN. In some embodiments, each $R^{2a}$ and $R^{2b}$ is independently substituted C1-C6fluoroalkyl. In some embodiments, each $R^{2a}$ and $R^{2b}$ is —CF$_3$.

In some embodiments, each $R^{1a}$, $R^{1b}$, $R^{2a}$, and $R^{2b}$ is F.

In some embodiments, Z is selected from —CR$^{6a}$R$^{6b}$—, —C(=O)—, —C(=NH)—, and —C(=NH)NR$^7$—. In some embodiments, Z is —CR$^{6a}$R$^{6b}$—. In some embodiments, Z is —C(=O)—. In some embodiments, Z is —C(=NH)—. In some embodiments, Z is —C(=NH)NR$^7$—.

In some embodiments, each $R^3$ is independently selected from hydrogen, optionally substituted C1-C4 alkyl, —X-optionally substituted C1-C4 alkyl, optionally substituted aryl, and —X-optionally substituted aryl. In some embodiments, $R^3$ is hydrogen. In some embodiments, $R^3$ is optionally substituted C1-C4 alkyl. In some embodiments, $R^3$ is —X-optionally substituted C1-C4 alkyl. In some embodiments, $R^3$ is optionally substituted aryl. In some embodiments, $R^3$ is —X-optionally substituted aryl.

In some embodiments, X is —C(=O)—, —S(=O)—, or —S(=O)$_2$—. In some embodiments, X is —C(=O)—. In some embodiments, X is —S(=O)—. In some embodiments, X is —S(=O)$_2$—.

In some embodiments, each $R^{6a}$ and $R^{6b}$ is hydrogen.

In some embodiments, m is 0, 1, 2, 3, 4, or 5. In some embodiments, m is 0. In some embodiments, m is 1. In some embodiments, m is 2. In some embodiments, m is 3. In some embodiments, m is 4. In some embodiments, m is 5.

In some embodiments, $R^{5a}$ is hydrogen; $R^{5b}$ is —$NR^{10a}R^{10b}$; and $R^{5c}$ is hydrogen.

In some embodiments, the compound of Formula (I) has a structure of Formula (Ia):

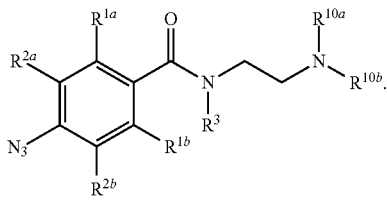

In some embodiments, the compound of Formula (I) has a structure of Formula (Ib):

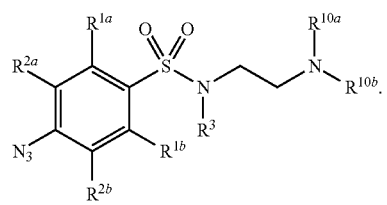

In some embodiments, $R^{10a}$ is hydrogen, optionally substituted C1-C4 alkyl, or optionally substituted aryl. In some embodiments, $R^{10a}$ is hydrogen. In some embodiments, $R^{10a}$ is optionally substituted C1-C4 alkyl. In some embodiments, $R^{10a}$ is —$CH_3$. In some embodiments, $R^{10a}$ is $CH_2$—$CH_3$. In some embodiments, $R^{10a}$ is optionally substituted aryl. In some embodiments, $R^{10a}$ is phenyl.

In some embodiments, $R^{10b}$ is —(C=O)—C2-C6alkenyl, (S=O)—C2-C6alkenyl, or (S=O)$_2$—C2-C6alkenyl. In some embodiments, $R^{10b}$ is —(C=O)—C2-C6alkenyl. In some embodiments, $R^{10b}$ is (S=O)—C2-C6alkenyl. In some embodiments, $R^{10b}$ is —(S=O)$_2$—C2-C6alkenyl.

In some embodiments, the compound of Formula (I) has the structure of:

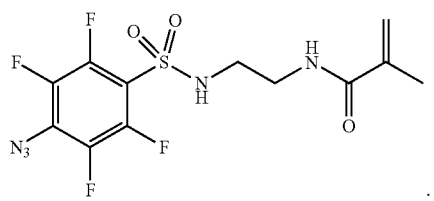

In some embodiments, a compound described above is a compound that has a structure represented by a Formula (II):

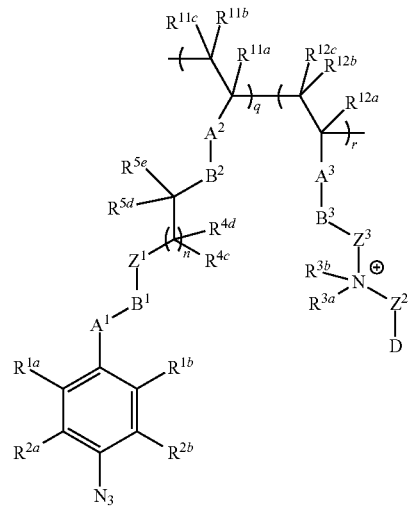

Formula (II)

wherein
each $R^{1a}$ and $R^{1b}$ is independently selected from hydrogen and halogen;
each $R^{2a}$ and $R^{2b}$ is independently selected from halogen, —CN, and optionally substituted C1-C6fluoroalkyl;
each $A^1$, $A^2$, and $A^3$ is independently selected from —C(=O)—, —S(=O)—, —S(=O)$_2$—, and —S(=O)(=$NR^{3c}$)—;
each $B^1$, $B^2$, and $B^3$ is independently selected from —O— and —$NR^{3c}$—;
D is —S(=O)$_2$O$^-$, —S(=O)$_2$OR$^{9a}$, —C(=O)O$^-$, or —C(=O)OR$^{9a}$;
$Z^1$ is —(CR$^{6c}$R$^{6d}$)$_s$—;
$Z^2$ is —(CR$^{6c}$R$^{6d}$)$_t$—;
$Z^3$ is —(CR$^{6c}$R$^{6d}$)$_p$—;
each $R^{3a}$ and $R^{3b}$ is independently selected from hydrogen, optionally substituted C1-C4 alkyl, and optionally substituted benzyl;
each $R^{3c}$ and $R^{3d}$ is independently selected from hydrogen, optionally substituted C1-C4 alkyl, —X-optionally substituted C1-C4 alkyl, optionally substituted C2-C6 alkenyl, and optionally substituted aryl;
X is —C(=O)—, —S(=O)—, or —S(=O)$_2$—;
each $R^{4c}$, $R^{4d}$, $R^{5d}$, $R^{5e}$, $R^{6c}$, and $R^{6d}$ is independently selected from hydrogen, halogen, —CN, —OR$^{9a}$, optionally substituted C1-C4 alkyl, optionally substituted C1-C4 fluoroalkyl, optionally substituted C2-C6 alkenyl, —$NR^{3c}R^{3d}$, —S(=O)$_2$O$^-$, —S(=O)$_2$OR$^{9a}$, —C(=O)O$^-$, and —C(=O)OR$^{9a}$;
each $R^{9a}$, $R^{11a}$, $R^{11b}$, $R^{11c}$, $R^{12a}$, $R^{12b}$, and $R^{12c}$ is independently selected from hydrogen, optionally substituted C1-C4 alkyl, and optionally substituted aryl;
n is an integer selected from 0, 1, 2, 3, 4, 5, and 6;
s is an integer selected from 1, 2, 3, 4, or 5;
t is an integer selected from 1, 2, 3, 4, or 5;
p is an integer selected from 1, 2, 3, 4, or 5;
q is an integer selected from 40-60;
r is an integer selected from 1-10; and
wherein the compounds of Formula (II) is charged or zwitterionic.

In some embodiments, each $R^{1a}$ and $R^{1b}$ is independently halogen. In some embodiments, each $R^{1a}$ and $R^{1b}$ is independently F or Cl. In some embodiments, each $R^{1a}$ and $R^{1b}$ is F. In some embodiments, each $R^{2a}$ and $R^{2b}$ is independently selected from halogen, —CN, and optionally substituted C1-C6fluoroalkyl. In some embodiments, each $R^{2a}$ and $R^{2b}$ is independently halogen. In some embodiments, each $R^{2a}$ and $R^{2b}$ is —CN. In some embodiments, each $R^{2a}$ and $R^{2b}$ is independently substituted C1-C6fluoroalkyl. In some embodiments, each $R^{2a}$ and $R^{2b}$ is —CF$_3$.

In some embodiments, each $R^{1a}$, $R^{1b}$, $R^{2a}$, and $R^{2b}$ is F.

In some embodiments, $A^1$ is —S(=O)$_2$—. In some embodiments, $A^1$ is —C(=O)—.

In some embodiments, $A^2$ is —S(=O)$_2$—. In some embodiments, $A^2$ is —C(=O)—.

In some embodiments, $A^3$ is —S(=O)$_2$—. In some embodiments, $A^3$ is —C(=O)—.

In some embodiments, each $B^1$ and $B^2$ is —NR$^{3c}$—.

In some embodiments, each $R^{3c}$ is independently hydrogen, optionally substituted C1-C4 alkyl, or optionally substituted aryl. In some embodiments, $R^{3c}$ is hydrogen. In some embodiments, $R^{3c}$ is optionally substituted C1-C4 alkyl. In some embodiments, $R^{3c}$ is —CH$_3$. In some embodiments, $R^{3c}$ is optionally substituted aryl. In some embodiments, $R^{3c}$ is optionally substituted phenyl.

In some embodiments, $B^3$ is —O—.

In some embodiments, D is —S(=O)$_2$OR$^{9a}$ or —C(=O)OR$^{9a}$. In some embodiments, D is —S(=O)$_2$OR$^{9a}$. In some embodiments, D is —C(=O)OR$^{9a}$.

In some embodiments, $R^{9a}$ is hydrogen or —CH$_3$. In some embodiments, $R^{9a}$ is hydrogen. In some embodiments, $R^{9a}$ is —CH$_3$.

In some embodiments, D is —S(=O)$_2$O$^-$ or —C(=O)O$^-$. In some embodiments, D is —S(=O)$_2$O$^-$. In some embodiments, D is —C(=O)O$^-$.

In some embodiments, each $R^6$ and $R^{6d}$ is hydrogen.

In some embodiments, each $R^{3a}$ and $R^{3b}$ is —CH$_3$.

In some embodiments, $R^{11a}$ is hydrogen or —CH$_3$. In some embodiments, $R^{11a}$ is hydrogen. In some embodiments, $R^{11a}$ is —CH$_3$.

In some embodiments, $R^{12a}$ is hydrogen or —CH$_3$. In some embodiments, $R^{11a}$ is hydrogen. In some embodiments, $R^{12a}$ is —CH$_3$.

In some embodiments, each $R^{11b}$, $R^{12b}$, and $R^{12c}$ is hydrogen.

In some embodiments, n is 0, 1, 2, 3, 4, or 5. In some embodiments, n is 0. In some embodiments, n is 1. In some embodiments, m is 2. In some embodiments, n is 3. In some embodiments, n is 4. In some embodiments, n is 5.

In some embodiments, s is 1, 2, 3, or 4. In some embodiments, s is 1. In some embodiments, s is 2. In some embodiments, s is 3. In some embodiments, s is 4.

In some embodiments, t is 1, 2, 3, or 4. In some embodiments, t is 1. In some embodiments, t is 2. In some embodiments, t is 3. In some embodiments, t is 4.

In some embodiments, p is 1, 2, 3, or 4. In some embodiments, p is 1. In some embodiments, p is 2. In some embodiments, p is 3. In some embodiments, p is 4.

In some embodiments, q is 40, 41, 42, 43, 44, 45, 46, 47, 48, 49, 50, 51, 52, 53, 54, 55, 56, 57, 58, 59, or 60. In some embodiments, q is 45, 46, 47, 48, 49, 50, 51, 52, 53, 54, or 55. In some embodiments, q is 45. In some embodiments, q is 46. In some embodiments, q is 47. In some embodiments, q is 48. In some embodiments, q is 49. In some embodiments, q is 50. In some embodiments, q is 51. In some embodiments, q is 52. In some embodiments, q is 53. In some embodiments, q is 54. In some embodiments, q is 55.

In some embodiments, r is 1, 2, 3, 4, 5, 6, 7, 8, 9, or 10. In some embodiments, r is 1. In some embodiments, r is 2. In some embodiments, r is 3. In some embodiments, r is 4. In some embodiments, r is 5. In some embodiments, r is 6. In some embodiments, r is 7. In some embodiments, r is 8. In some embodiments, r is 9. In some embodiments, r is 10.

In some embodiments, a compound described above is a compound that has a structure represented by a Formula (III):

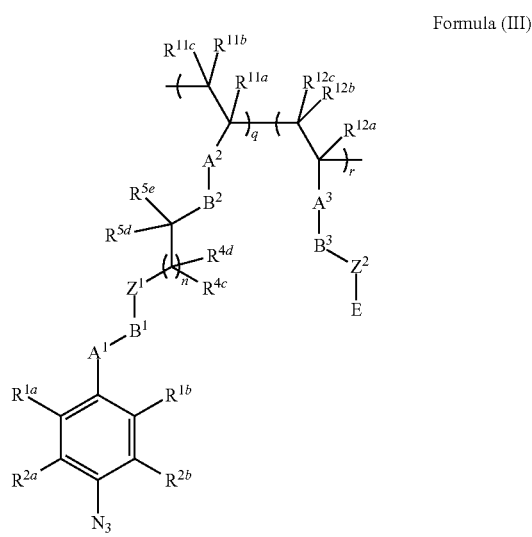

Formula (III)

wherein
each $R^{1a}$ and $R^{1b}$ is independently selected from hydrogen and halogen;
each $R^{2a}$ and $R^{2b}$ is independently selected from halogen, —CN, and optionally substituted C1-C6fluoroalkyl;
each $A^1$, $A^2$, and $A^3$ is independently selected from —C(=O)—, —S(=O)—, —S(=O)$_2$—, and —S(=O)(=NR$^{3c}$)—;
each $B^1$, $B^2$, and $B^3$ is independently selected from —O— and —NR$^{3c}$—;
$Z^1$ is —(CR$^{6c}$R$^{6d}$)$_s$—;
$Z^2$ is —(CR$^{6c}$R$^{6d}$)$_t$—;
E is —CN, —OR$^{9a}$, —NR$^{9a}$R$^{9b}$, —NR$^{9a}$R$^{9b}$R$^{9c+}$, optionally substituted C1-C4 alkyl, optionally substituted C1-C6fluoroalkyl, —S(=O)$_2$O$^-$, —S(=O)$_2$OR$^{9a}$, —C(=O)O$^-$, or —C(=O)OR$^{9a}$;
each $R^{4c}$, $R^{4d}$, $R^{5d}$, $R^{5e}$, $R^{6c}$, and $R^{6d}$ is independently selected from hydrogen, halogen, —CN, —OR$^{9a}$, optionally substituted C1-C4 alkyl, optionally substituted C1-C4 fluoroalkyl, optionally substituted C2-C6 alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;
each $R^{3c}$ and $R^{3d}$ is independently selected from hydrogen, optionally substituted C1-C4 alkyl, —X-optionally substituted C1-C4 alkyl, optionally substituted C2-C6 alkenyl, and optionally substituted aryl;
X is —C(=O)—, —S(=O)—, or —S(=O)$_2$—;
each $R^{9a}$, $R^{11a}$, $R^{11b}$, $R^{11c}$, $R^{12a}$, $R^{12b}$, and $R^{12c}$ is independently selected from hydrogen, optionally substituted C1-C4 alkyl, and optionally substituted aryl;
n is an integer selected from 0, 1, 2, 3, 4, 5, and 6;
s is an integer selected from 1, 2, 3, 4, or 5;
t is an integer selected from 1, 2, 3, 4, or 5;
q is an integer selected from 40-60; and
r is an integer selected from 1-10.

In some embodiments, each $R^{1a}$ and $R^{1b}$ is independently halogen. In some embodiments, each $R^{1a}$ and $R^{1b}$ is independently F or Cl. In some embodiments, each $R^{1a}$ and $R^{1b}$ is F. In some embodiments, each $R^{2a}$ and $R^{2b}$ is independently selected from halogen, —CN, and optionally substituted C1-C6fluoroalkyl. In some embodiments, each $R^{2a}$ and $R^{2b}$ is independently halogen. In some embodiments, each $R^{2a}$ and $R^{2b}$ is CN. In some embodiments, each $R^{2a}$ and $R^{2b}$ is independently substituted C1-C6fluoroalkyl. In some embodiments, each $R^{2a}$ and $R^{2b}$ is —$CF_3$.

In some embodiments, each $R^{1a}$, $R^{1b}$, $R^{2a}$, and $R^{2b}$ is F.

In some embodiments, $A^1$ is —$S(=O)_2$—. In some embodiments, $A^1$ is —$C(=O)$—.

In some embodiments, $A^2$ is —$S(=O)_2$—. In some embodiments, $A^2$ is —$C(=O)$—.

In some embodiments, $A^3$ is —$S(=O)_2$—. In some embodiments, $A^3$ is —$C(=O)$—.

In some embodiments, each $B^1$, $B^2$, and $B^3$ is —$NR^{3c}$—.

In some embodiments, each $R^{3c}$ is independently hydrogen, optionally substituted C1-C4 alkyl, or optionally substituted aryl. In some embodiments, $R^{3c}$ is hydrogen. In some embodiments, $R^{3c}$ is optionally substituted C1-C4 alkyl. In some embodiments, $R^{3c}$ is —$CH_3$. In some embodiments, $R^{3c}$ is optionally substituted aryl. In some embodiments, $R^{3c}$ is optionally substituted phenyl.

In some embodiments, E is —$NR^{9a}R^{9b}R^{9c+}$ or —$S(=O)_2OR^{9a}$.

In some embodiments, E is —$NR^{9a}R^{9b}R^{9c+}$. In some embodiments, each $R^{9a}$, $R^{9b}$, or $R^{9c}$ is independently H or —$CH_3$. In some embodiments, $R^{9a}$ is H. In some embodiments, $R^{9a}$ is —$CH_3$. In some embodiments, $R^{9b}$ is H. In some embodiments, $R^{9b}$ is —$CH_3$. In some embodiments, $R^{9c}$ is H. In some embodiments, $R^{9c}$ is —$CH_3$.

In some embodiments, E is —$S(=O)_2OR^{9a}$. In some embodiments, each $R^{9a}$ is H or —$CH_3$. In some embodiments, $R^{9a}$ is H. In some embodiments, $R^{9a}$ is —$CH_3$.

In some embodiments, each $R^{6c}$ and $R^{6d}$ is independently selected from hydrogen and —$CH_3$.

In some embodiments, each $R^{3a}$ and $R^{3b}$ is —$CH_3$.

In some embodiments, $R^{11a}$ is hydrogen or —$CH_3$. In some embodiments, $R^{11a}$ is hydrogen. In some embodiments, $R^{11a}$ is —$CH_3$.

In some embodiments, $R^{12a}$ is hydrogen or —$CH_3$. In some embodiments, $R^{12a}$ is hydrogen. In some embodiments, $R^{12a}$ is —$CH_3$.

In some embodiments, each $R^{11b}$, $R^{11c}$, $R^{12b}$, and $R^{12c}$ is hydrogen.

IV. Methods of Making

In a further aspect, described herein is a method of preparing a biofouling-resistant device, comprising:
   a) contacting a surface of a device with a mixture (e.g., a solution) comprising a copolymer; and
   b) treating the surface of the device of step a) with a light source for a time sufficient to undergo photografting of the copolymer onto the surface of the device, thereby making the biofouling-resistant device;
   wherein the copolymer comprises a phenyl azide-based copolymer; and wherein the copolymer has a number-average molecular weight of between about 10,000 and about 250,000.

In some embodiments, also described herein is a method of preparing a copolymer modified biofouling-resistant silicon-based device comprising:
   a) contacting a surface of a silicon-based device with a mixture (e.g., a solution) comprising a charged or zwitterion copolymer; and
   b) treating the surface of the device of step a) with a light source for a time sufficient to undergo photografting of the copolymer onto the surface of the silicon-based device, thereby generating the charged or zwitterion copolymer modified device;
   wherein the charged or zwitterion copolymer comprises a phenyl azide-based copolymer.

In some embodiments, also described herein is a method of preparing a charged or zwitterion copolymer modified biofouling-resistant device comprising:
   a) contacting a surface of a device with a mixture (e.g., a solution) comprising a charged or zwitterion copolymer; and
   a) treating the surface of the device of step a) with a light source for a time sufficient to undergo photografting of the copolymer onto the surface of the device, thereby generating the charged or zwitterion copolymer modified device;
   wherein the charged or zwitterion copolymer comprises a phenyl azide-based copolymer; and wherein the charged or zwitterion copolymer has a number-average molecular weight of between about 10,000 and about 250,000.

In some embodiments, the method comprises one-step grafting reaction that modifies the surface of a device.

In some embodiments, the device is a medical device described herein. In some embodiments, the device is a non-medical device described herein.

In some embodiments, the time sufficient to undergo photografting is at least 1 minute, at least 2 minutes, 3 minutes, 4 minutes, 5 minutes, 6 minutes, 7 minutes, 8 minutes, 9 minutes, 10 minutes, 15 minutes, 20 minutes, 25 minutes or 30 minutes.

In some embodiments, the light source is an ultraviolet light source. In some embodiments, the ultraviolet light source has an intensity of at least 500 $\mu W/cm^2$. In some embodiments, the ultraviolet light source has an intensity of at least 600 $\mu W/cm^2$. In some embodiments, the ultraviolet light source has an intensity of at least 700 $\mu W/cm^2$. In some embodiments, the ultraviolet light source has an intensity of at least 800 $\mu W/cm^2$. In some embodiments, the ultraviolet light source has an intensity of at least 900 $\mu W/cm^2$. In some embodiments, the ultraviolet light source has an intensity of at least 1000 $\mu W/cm^2$.

In some embodiments, the ultraviolet light source has a wavelength of between 240 nm and 280 nm, between 240 nm and 275 nm, between 240 nm and 270 nm, between 240 nm and 265 nm, between 240 nm and 260 nm, between 240 nm and 255 nm, between 240 nm and 250 nm, between 240 nm and 245 nm, between 250 nm and 280 nm, between 250 nm and 275 nm, between 250 nm and 270 nm, between 250 nm and 265 nm, between 250 nm and 260 nm, between 255 nm and 280 nm, between 255 nm and 275 nm, between 255 nm and 270 nm, between 255 nm and 265 nm, between 255 nm and 260 nm, between 260 nm and 280 nm, between 260 nm and 275 nm, between 260 nm and 270 nm, or between 270 nm and 280 nm.

In some embodiments, the ultraviolet light source has a wavelength of at least 240 nm, 245 nm, 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 275 nm or 280 nm. In some embodiments, the ultraviolet light source has a wavelength of no more than 240 nm, 245 nm, 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 275 nm or 280 nm.

In some embodiments, the mixture of step a) is an aqueous solution, an aqueous colloid, or an aqueous suspension. In some embodiments, the mixture of step a) is a non-aqueous solution, an aqueous colloid, or an aqueous suspension.

In some embodiments, the phenyl azide-based copolymer is a compound of Formula (II) or (III) described herein.

In some embodiments, the mixture comprising a charged or zwitterion copolymer has a concentration of the charged or zwitterion copolymer in the mixture between 1 mg/mL and 30 mg/mL.

In some embodiments, the concentration of the charged or zwitterion copolymer in the mixture is between 1 mg/mL and 25 mg/mL, between 1 mg/mL and 20 mg/mL, between 1 mg/mL and 15 mg/mL, between 1 mg/mL and 10 mg/mL, between 1 mg/mL and 5 mg/mL, between 5 mg/mL and 30 mg/mL, between 5 mg/mL and 25 mg/mL, between 5 mg/mL and 20 mg/mL, between 5 mg/mL and 15 mg/mL, between 5 mg/mL and 10 mg/mL, between 10 mg/mL and 30 mg/mL, between 10 mg/mL and 25 mg/mL, between 10 mg/mL and 20 mg/mL, between 10 mg/mL and 15 mg/mL, between 15 mg/mL and 30 mg/mL, between 15 mg/mL and 25 mg/mL, between 15 mg/mL and 20 mg/mL, between 20 mg/mL and 30 mg/mL, or between 20 mg/mL and 25 mg/mL.

In some embodiments, the concentration of the charged or zwitterion copolymer in the mixture is about 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14 mg/mL, 15 mg/mL, 16 mg/mL, 17 mg/mL, 18 mg/mL, 19 mg/mL, 20 mg/mL, 21 mg/mL, 22 mg/mL, 23 mg/mL, 24 mg/mL, 25 mg/mL, 26 mg/mL, 27 mg/mL, 28 mg/mL, 29 mg/mL, or 30 mg/mL.

In some embodiments, the concentration of the charged or zwitterion copolymer is between 0.1 to 1 mg per square centimeter of the device.

In some embodiments, the device comprises a polymer-based device. In some embodiments, the polymer-based device comprises a polyolefinic device. In some embodiments, the polyolefinic device comprises a device modified with polyethylene (PE), polypropylene (PP), polyamide (PA), polytetrafluoroethylene (PTFE), polyvinylidene fluoride (PVdF), polyvinyl chloride (PVC), or a combination thereof. In some embodiments, the device comprises a microporous device or a nonwoven device. In some embodiments, the device comprises a carbon-based device comprising a moiety capable of binding with a compound that has a structure of Formula (I), (II), or (III). In some embodiments, the carbon-based device comprises a polymer moiety. In some embodiments, the carbon-based device comprises a carbon-based polymer. In some embodiments, the carbon-based device comprises a polyolefin moiety. In some embodiments, the polyolefin moiety comprises a polyethylene (PE) moiety, a polypropylene (PP) moiety, a polyamide (PA) moiety, a polytetrafluoroethylene (PTFE) moiety, a polyvinylidene fluoride (PVdF) moiety, or a polyvinyl chloride (PVC) moiety.

In some embodiments, the device comprises a carbon-based device. In some embodiments, the carbon-based device comprises a carbon-based polymer. In some embodiments, the carbon-based device comprises a polyolefin moiety. In some embodiments, the polyolefin moiety comprises polyethylene moiety, polypropylene moiety, polyvinyl chloride moiety, polyvinylidene fluoride moiety, polytetrafluoroethylene moiety, polychlorotrifluoroethylene moiety, or polystyrene moiety. In some embodiments, the carbon-based polymer comprises polyamide moiety, polyurethane moiety, phenol-formaldehyde resin moiety, polycarbonate moiety, polychloroprene moiety, polyacrylonitrile moiety, polyimide moiety, or polyester moiety. In some embodiments, the carbon-based polymer comprises nylon. In some embodiments, the carbon-based polymer comprises polyethylene terephthalate.

In some embodiments, the device comprises a silicon-based device. In some embodiments, the silicon-based device comprises a silicon-based polymer moiety. In some embodiments, the device comprises a silicon-based device comprising a moiety capable of binding with a compound that has a structure of Formula (I), (II), or (III). In some embodiments, the silicon-based device comprises a polymer moiety. In some embodiments, the silicon-based device comprises a siloxane polymer moiety, a sesquisiloxane polymer moiety, a siloxane-silarylene polymer moiety, a silalkylene polymer moiety, a polysilane moiety, a polysilylene moiety, or a polysilazane moiety.

In some embodiments, the silicon-based device comprises a siloxane polymer moiety. In some embodiments, the silicon-based device comprises silicone polymer.

In some embodiments, the device comprises a carbon-based device or a silicon-based device.

In some embodiments, the copolymer comprises zwitterionic copolymer. In some embodiments, the zwitterionic copolymer comprises polysulfobetaine.

In some embodiments, the biofouling of the biofouling-resistant medical device described herein is produced by a bacterium, a virus, and/or a fungus.

V. Methods of Synthesis

Methods provided by the present disclosure also include methods of synthesizing a compound of Formula (II) comprising: reacting a compound of Formula (IV) or a salt or solvate thereof with a compound of Formula (V):

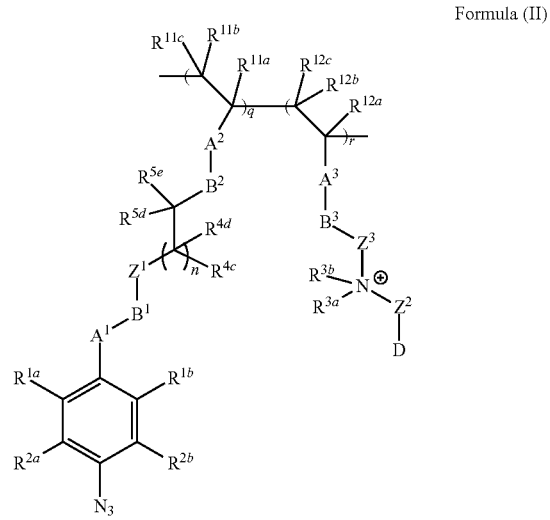

Formula (II)

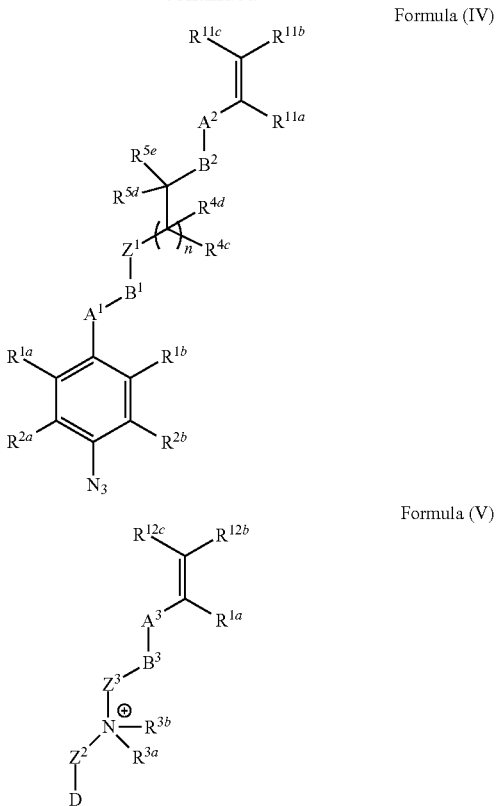

Formula (IV)

Formula (V)

wherein
each $R^{1a}$ and $R^{1b}$ is independently selected from hydrogen and halogen;
each $R^{2a}$ and $R^{2b}$ is independently selected from halogen, —CN, and optionally substituted C1-C6fluoroalkyl;
each $A^1$, $A^2$, and $A^3$ is independently selected from —C(=O)—, —S(=O)—, —S(=O)$_2$—, and —S(=O)(=NR$^{3c}$)—;
each $B^1$, $B^2$, and $B^3$ is independently selected from —O— and —NR$^{3c}$—;
D is —S(=O)$_2$O$^-$, —S(=O)$_2$OR$^{9a}$, —C(=O)O$^-$, or —C(=O)OR$^{9a}$;
$Z^1$ is —(CR$^{6c}$R$^{6d}$)$_s$—;
$Z^2$ is —(CR$^{6c}$R$^{6d}$)$_t$—;
$Z^3$ is —(CR$^{6c}$R$^{6d}$)$_p$—;
each $R^{3a}$ and $R^{3b}$ is independently selected from hydrogen, optionally substituted C1-C4 alkyl, and optionally substituted benzyl;
each $R^{3c}$ and $R^{3d}$ is independently selected from hydrogen, optionally substituted C1-C4 alkyl, —X-optionally substituted C1-C4 alkyl, optionally substituted C2-C6 alkenyl, and optionally substituted aryl;
X is —C(=O)—, —S(=O)—, or —S(=O)$_2$—;
each $R^{4c}$, $R^{4d}$, $R^{5d}$, $R^{5e}$, $R^{6c}$, and $R^{6d}$ is independently selected from hydrogen, halogen, —CN, —OH, optionally substituted C1-C4 alkyl, optionally substituted C1-C4 fluoroalkyl, optionally substituted C2-C6 alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;
each $R^{9a}$, $R^{11a}$, $R^{11b}$, $R^{11c}$, $R^{12a}$, $R^{12b}$, and $R^{12c}$ is independently selected from hydrogen, optionally substituted C1-C4 alkyl, and optionally substituted aryl;
n is an integer selected from 0, 1, 2, 3, 4, 5, and 6;
s is an integer selected from 1, 2, 3, 4, or 5;
t is an integer selected from 1, 2, 3, 4, or 5;
p is an integer selected from 1, 2, 3, 4, or 5;
q is an integer selected from 40-60;
r is an integer selected from 1-10; and
wherein the compounds of Formula (II) and Formula (V) are each charged or zwitterionic.

In some embodiments, each $R^{1a}$ and $R^{1b}$ is independently halogen. In some embodiments, each $R^{1a}$ and $R^{1b}$ is independently F or Cl. In some embodiments, each $R^{1a}$ and $R^{1b}$ is F. In some embodiments, each $R^{2a}$ and $R^{2b}$ is independently selected from halogen, —CN, and optionally substituted C1-C6fluoroalkyl. In some embodiments, each $R^{2a}$ and $R^{2b}$ is independently halogen. In some embodiments, each $R^{2a}$ and $R^{2b}$ is —CN. In some embodiments, each $R^{2a}$ and $R^{2b}$ is independently substituted C1-C6fluoroalkyl. In some embodiments, each $R^{2a}$ and $R^{2b}$ is —CF$_3$.

In some embodiments, each $R^{1a}$, $R^{1b}$, $R^{2a}$, and $R^{2b}$ is F.
In some embodiments, $A^1$ is —S(=O)$_2$—. In some embodiments, $A^1$ is —C(=O)—.
In some embodiments, $A^2$ is —S(=O)$_2$—. In some embodiments, $A^2$ is —C(=O)—.
In some embodiments, $A^3$ is —S(=O)$_2$—. In some embodiments, $A^3$ is —C(=O)—.
In some embodiments, each $B^1$ and $B^2$ is —NR$^{3c}$—.
In some embodiments, each $R^{3c}$ is independently hydrogen, optionally substituted C1-C4 alkyl, or optionally substituted aryl. In some embodiments, $R^{3c}$ is hydrogen. In some embodiments, $R^{3c}$ is optionally substituted C1-C4 alkyl. In some embodiments, $R^{3c}$ is —CH$_3$. In some embodiments, $R^{3c}$ is optionally substituted aryl. In some embodiments, $R^{3c}$ is optionally substituted phenyl.
In some embodiments, $B^3$ is —O—.
In some embodiments, D is —S(=O)$_2$OR$^{9a}$ or —C(=O)OR$^{9a}$. In some embodiments, D is —S(=O)$_2$OR$^{9a}$. In some embodiments, D is —C(=O)OR$^{9a}$.
In some embodiments, $R^{9a}$ is hydrogen or —CH$_3$. In some embodiments, $R^{9a}$ is hydrogen. In some embodiments, $R^{9a}$ is —CH$_3$.
In some embodiments, D is —S(=O)$_2$O$^-$ or —C(=O)O$^-$. In some embodiments, D is —S(=O)$_2$O$^-$.
In some embodiments, D is —C(=O)O$^-$.
In some embodiments, each $R^{6c}$ and $R^{6d}$ is hydrogen.
In some embodiments, each $R^{3a}$ and $R^{3b}$ is —CH$_3$.
In some embodiments, $R^{11a}$ is hydrogen or —CH$_3$. In some embodiments, $R^{11a}$ is hydrogen. In some embodiments, $R^{11a}$ is —CH$_3$.
In some embodiments, $R^{12a}$ is hydrogen or —CH$_3$. In some embodiments, $R^{11a}$ is hydrogen. In some embodiments, $R^{12a}$ is —CH$_3$.
In some embodiments, each $R^{11b}$, $R^{11c}$, $R^{12b}$, and $R^{12c}$ is hydrogen.
In some embodiments, n is 0, 1, 2, 3, 4, or 5. In some embodiments, n is 0. In some embodiments, n is 1. In some embodiments, m is 2. In some embodiments, n is 3. In some embodiments, n is 4. In some embodiments, n is 5.
In some embodiments, s is 1, 2, 3, or 4. In some embodiments, s is 1. In some embodiments, s is 2. In some embodiments, s is 3. In some embodiments, s is 4.
In some embodiments, t is 1, 2, 3, or 4. In some embodiments, t is 1. In some embodiments, t is 2. In some embodiments, t is 3. In some embodiments, t is 4.
In some embodiments, p is 1, 2, 3, or 4. In some embodiments, p is 1. In some embodiments, p is 2. In some embodiments, p is 3. In some embodiments, p is 4.
In some embodiments, q is 45, 46, 47, 48, 49, 50, 51, 52, 53, 54, or 55. In some embodiments, q is 45. In some embodiments, q is 46. In some embodiments, q is 47. In some embodiments, q is 48. In some embodiments, q is 49. In some embodiments, q is 50. In some embodiments, q is 51. In some embodiments, q is 52. In some embodiments, q is 53. In some embodiments, q is 54. In some embodiments, q is 55.

In some embodiments, r is 1, 2, 3, 4, 5, 6, 7, 8, 9, or 10. In some embodiments, r is 1. In some embodiments, r is 2. In some embodiments, r is 3. In some embodiments, r is 4. In some embodiments, r is 5. In some embodiments, r is 6. In some embodiments, r is 7. In some embodiments, r is 8. In some embodiments, r is 9. In some embodiments, r is 10.

In some embodiments, the compound of Formula (IV) has the structure of:

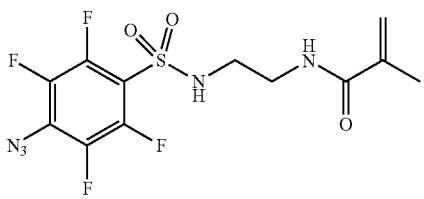

In some embodiments, the compound of Formula (V) has the structure of:

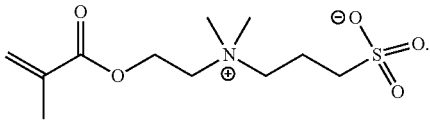 [SMILES: C=C(C)C(=O)OCC[N+](C)(C)CCCS(=O)(=O)[O-]]

Methods provided by the present disclosure also include methods of synthesizing a compound of Formula (III) comprising: reacting a compound of Formula (IV) or a salt or solvate thereof with a compound of Formula (VI):

Formula (III)

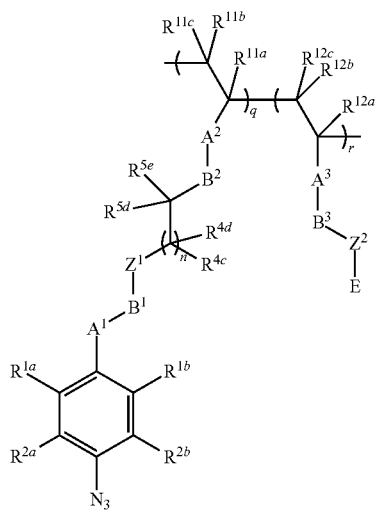

Formula (IV)

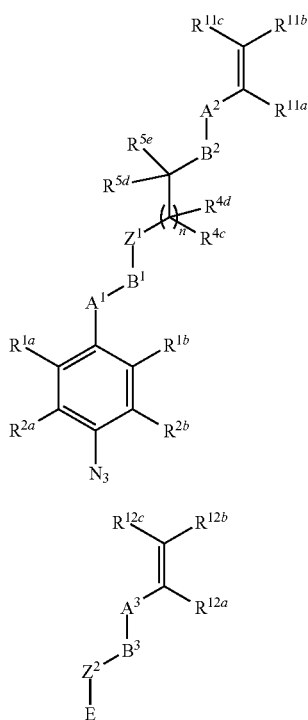

(Formula (VI))

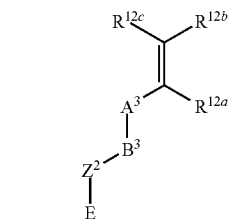

wherein
each $R^{1a}$ and $R^{1b}$ is independently selected from hydrogen and halogen;
each $R^{2a}$ and $R^{2b}$ is independently selected from halogen, —CN, and optionally substituted C1-C6 fluoroalkyl;
each $A^1$, $A^2$, and $A^3$ is independently selected from —C(=O)—, —S(=O)—, —S(=O)$_2$—, and —S(=O)(=N$R^{3c}$)—;
each $B^1$, $B^2$, and $B^3$ is independently selected from —O— and —N$R^{3c}$—;
$Z^1$ is —(C$R^{6c}R^{6d}$)$_s$—;
$Z^2$ is —(C$R^{6c}R^{6d}$)$_t$—;
E is —CN, —O$R^{9a}$, —N$R^{9a}R^{9b}$, —N$R^{9a}R^{9b}R^{9c+}$, optionally substituted C1-C4 alkyl, optionally substituted C1-C6 fluoroalkyl, —S(=O)$_2$O$^-$, —S(=O)$_2$O$R^{9a}$, —C(=O)O$^-$, or —C(=O)O$R^{9a}$;
each $R^{4c}$, $R^{4d}$, $R^{5d}$, $R^{5e}$, $R^{6c}$, and $R^{6d}$ is independently selected from hydrogen, halogen, —CN, —O$R^{9a}$, optionally substituted C1-C4 alkyl, optionally substituted C1-C4 fluoroalkyl, optionally substituted C2-C6 alkenyl, —N$R^{3c}R^{3d}$, —S(=O)$_2$O$^-$, —S(=O)$_2$O$R^{9a}$, —C(=O)O$^-$, and —C(=O)O$R^{9a}$;
each $R^{3c}$ and $R^{3d}$ is independently selected from hydrogen, optionally substituted C1-C4 alkyl, —X-optionally substituted C1-C4 alkyl, optionally substituted C2-C6 alkenyl, and optionally substituted aryl;
X is —C(=O)—, —S(=O)—, or —S(=O)$_2$—;
each $R^{9a}$, $R^{11a}$, $R^{11b}$, $R^{11c}$, $R^{12a}$, $R^{12b}$, and $12c$ is independently selected from hydrogen, optionally substituted C1-C4 alkyl, and optionally substituted aryl;
n is an integer selected from 0, 1, 2, 3, 4, 5, and 6;
s is an integer selected from 1, 2, 3, 4, or 5;
t is an integer selected from 1, 2, 3, 4, or 5;
q is an integer selected from 40-60; and
r is an integer selected from 1-10.

In some embodiments, each $R^{1a}$ and $R^{1b}$ is independently halogen. In some embodiments, each $R^{1a}$ and $R^{1b}$ is independently F or Cl. In some embodiments, each $R^{1a}$ and $R^{1b}$ is F. In some embodiments, each $R^{2a}$ and $R^{2b}$ is independently selected from halogen, —CN, and optionally substituted C1-C6fluoroalkyl. In some embodiments, each $R^{2a}$ and $R^{2b}$ is independently halogen. In some embodiments, each $R^{2a}$ and $R^{2b}$ is —CN. In some embodiments, each $R^{2a}$ and $R^{2b}$ is independently substituted C1-C6fluoroalkyl. In some embodiments, each $R^{2a}$ and $R^{2b}$ is —CF$_3$.

In some embodiments, each $R^{1a}$, $R^{1b}$, $R^{2a}$, and $R^{2b}$ is F.

In some embodiments, $A^1$ is —S(=O)$_2$—. In some embodiments, $A^1$ is —C(=O)—.

In some embodiments, $A^2$ is —S(=O)$_2$—. In some embodiments, $A^2$ is —C(=O)—.

In some embodiments, $A^3$ is —S(=O)$_2$—. In some embodiments, $A^3$ is —C(=O)—.

In some embodiments, each $B^1$, $B^2$, and $B^3$ is —NR$^{3c}$—.

In some embodiments, each $R^{3c}$ is independently hydrogen, optionally substituted C1-C4 alkyl, or optionally substituted aryl. In some embodiments, $R^{3c}$ is hydrogen. In some embodiments, $R^{3c}$ is optionally substituted C1-C4 alkyl. In some embodiments, $R^{3c}$ is —CH$_3$. In some embodiments, $R^{3c}$ is optionally substituted aryl. In some embodiments, $R^{3c}$ is optionally substituted phenyl.

In some embodiments, E is —NR$^{9a}$R$^{9b}$R$^{9c+}$ or —S(=O)$_2$OR$^{9a}$.

In some embodiments, E is —NR$^{9a}$R$^{9b}$R$^{9c+}$. In some embodiments, each $R^{9a}$, $R^{9b}$, or $R^{9c}$ is independently H or —CH$_3$. In some embodiments, $R^{9a}$ is H. In some embodiments, $R^{9a}$ is —CH$_3$. In some embodiments, $R^{9b}$ is H. In some embodiments, $R^{9b}$ is —CH$_3$. In some embodiments, $R^{9c}$ is H. In some embodiments, $R^{9c}$ is —CH$_3$.

In some embodiments, E is —S(=O)$_2$OR$^{9a}$. In some embodiments, each $R^{9a}$ is H or —CH$_3$. In some embodiments, $R^{9a}$ is H. In some embodiments, $R^{9a}$ is —CH$_3$.

In some embodiments, each $R^{6c}$ and $R^{6d}$ is independently selected from hydrogen and —CH$_3$.

In some embodiments, each $R^{3a}$ and $R^{3b}$ is —CH$_3$.

In some embodiments, $R^{11a}$ is hydrogen or —CH$_3$. In some embodiments, $R^{11a}$ is hydrogen. In some embodiments, $R^{11a}$ is —CH$_3$.

In some embodiments, $R^{12a}$ is hydrogen or —CH$_3$. In some embodiments, $R^{12a}$ is hydrogen. In some embodiments, $R^{12a}$ is —CH$_3$.

In some embodiments, each $R^{11b}$, $R^{11c}$, $R^{12b}$, and $R^{12c}$ is hydrogen.

In some embodiments, the compound of Formula (IV) has the structure of:

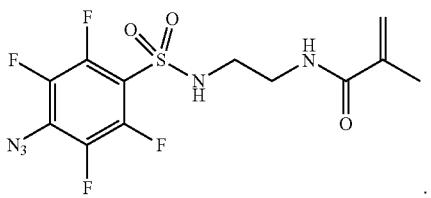 [SMILES: C=C(C)C(=O)NCCNS(=O)(=O)c1c(F)c(F)c(N=[N+]=[N-])c(F)c1F]

In some embodiments, the compound of Formula (VI) has the structure of:

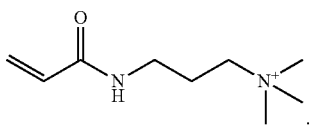

In some embodiments, the compound of Formula (VI) has the structure of:

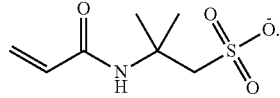

Any combination of the groups described above or below for the various variables is contemplated herein. Throughout the specification, groups and substituents thereof are chosen by one skilled in the field to provide stable moieties and compounds.

Properties of Biofouling-Resistant Coatings

In some embodiments, biofouling-resistant coatings disclosed herein have various properties that provide the superior function of the devices, including excellent flux, improved hydrophilicity, improved resistance to fouling, tunable surface charge properties, higher thermal stability, higher chemical stability, higher solvent stability, or a combination thereof. It is also understood that the coatings disclosed herein have other properties.

In some embodiments, a biofouling-resistant coating disclosed herein has a water receding angle of less than about 70°. In some embodiments, a biofouling-resistant coating disclosed herein has a water receding angle of less than about 65°. In some embodiments, a biofouling-resistant coating disclosed herein has a water receding angle of less than about 60°. In some embodiments, a biofouling-resistant coating disclosed herein has a water receding angle of less than about 55°. In some embodiments, a biofouling-resistant coating disclosed herein has a water receding angle of less than about 50°. In some embodiments, a biofouling-resistant coating disclosed herein has a water receding angle of less than about 45°. In some embodiments, a biofouling-resistant coating disclosed herein has a water receding angle of less than about 40°. In some embodiments, a biofouling-resistant coating disclosed herein has a water receding angle of less than about 35°. In some embodiments, a biofouling-resistant coating disclosed herein has a water receding angle of less than about 30°. In some embodiments, a biofouling-resistant coating disclosed herein has a water receding angle of less than about 25°. In some embodiments, a biofouling-resistant coating disclosed herein has a water receding angle of less than about 20°. In some embodiments, a biofouling-resistant coating disclosed herein has a water receding angle of less than about 15°. In some embodiments, a biofouling-resistant coating disclosed herein has a water receding angle of less than about 10°. In some embodiments, a biofouling-resistant coating disclosed herein has a water receding angle of less than about 5°. In some embodiments, a biofouling-resistant coating disclosed herein has a water receding angle of about 0°. In certain embodiments, the devices provided herein, coated by one or more biofouling-resistant coatings described herein have a high resistance of fouling.

In a further aspect, a biofouling-resistant coating disclosed herein exhibits an improvement in at least one property selected from resistance to fouling, hydrophilicity, surface charge, salt rejection, and roughness. In some embodiments, a biofouling-resistant coating disclosed herein demonstrates an improvement in at least one property selected from resistance to fouling, salt rejection, and hydrophilicity. In some embodiments, a biofouling-resistant coating disclosed herein demonstrates an improvement in resistance to fouling. In some embodiments, a biofouling-resistant coating disclosed herein demonstrates an improvement in hydrophilicity. In some embodiments, a biofouling-resistant coating disclosed herein demonstrates an improvement in surface charge. In some embodiments, a biofouling-resistant coating disclosed herein demonstrates an improvement in roughness. In some embodiments, a biofouling-resistant coating disclosed herein demonstrates reduced surface roughness. In some embodiments, a biofouling-resistant coating disclosed herein demonstrates an improvement in salt rejection.

In some embodiments, a biofouling-resistant coating disclosed herein comprising one or more compounds of Formula (I), (II), or (III) described herein prevents and/or reduces biofouling. In some instances, biofouling comprises microfouling or macrofouling. Microfouling comprises formation of microorganism adhesion (e.g., bacteria adhesion) and/or biofilm. Biofilm is a group of microorganism which adheres to a surface. In some instances, the adhered microorganisms are further embedded in a self-produced matrix of extracellular polymeric substance, which comprises a polymeric conglomeration of extracellular DNA, protein, and polysaccharides. Macrofouling comprises attachment of larger organism. In some instances a biofouling-resistant coating disclosed herein prevents and/or reduces microfouling. In some instances, a biofouling-resistant coating disclosed herein prevents and/or reduces bacterial adhesion. In some instances, a biofouling-resistant coating disclosed herein prevents and/or reduces biofilm. In other instances, a biofouling-resistant coating disclosed herein prevents and/or reduces macrofouling.

Microfouling

In some instances, microfouling is formed by bacteria or fungi. In some instances, microfouling is formed by bacteria. In some instances, a bacterium is a gram-positive bacterium or a gram-negative bacterium. In some cases, a bacterium is a marine bacterium.

In some cases, microfouling is formed by a gram-positive bacterium. Exemplary gram-positive bacteria include, but are not limited to, bacteria from the genus *Actinomyces, Arthrobacter, Bacillus, Clostridium, Corynebacterium, Enterococcus, Lactococcus, Listeria, Micrococcus, Mycobacterium, Staphylococcus*, or *Streptococcus*. In some instances, a gram-positive bacterium comprises *Actinomyces* spp., *Arthrobacter* spp., *Bacillus licheniformis, Clostridium difficile, Clostridium* spp., *Corynebacterium* spp., *Enterococcus faecalis, Lactococcus* spp., *Listeria monocytogenes, Micrococcus* spp., *Mycobacterium* spp., *Staphylococcus aureus, Staphylococcus epidermidis, Streptococcus pneumoniae*, or *Streptococcus pyogenes*.

In some instances, microfouling is formed by a gram-positive bacterium from the genus *Actinomyces, Arthrobacter, Bacillus, Clostridium, Corynebacterium, Enterococcus, Lactococcus, Listeria, Micrococcus, Mycobacterium, Staphylococcus*, or *Streptococcus*. In some instances, microfouling is formed by a gram-positive bacterium: *Actinomyces* spp., *Arthrobacter* spp., *Bacillus licheniformis, Clostridium difficile, Clostridium* spp., *Corynebacterium* spp., *Enterococcus faecalis, Lactococcus* spp., *Listeria monocytogenes, Micrococcus* spp., *Mycobacterium* spp., *Staphylococcus aureus, Staphylococcus epidermidis, Streptococcus pneumoniae*, or *Streptococcus pyogenes*.

In some instances, a biofouling-resistant coating disclosed herein is resistant to fouling. In some instances, a biofouling-resistant coating disclosed herein prevents and/or reduces microfouling on one or more of its surfaces. In some cases, a biofouling-resistant coating disclosed herein prevents and/or reduces microfouling formed by a gram-positive bacterium from the genus *Actinomyces, Arthrobacter, Bacillus, Clostridium, Corynebacterium, Enterococcus, Lactococcus, Listeria, Micrococcus, Mycobacterium, Staphylococcus*, or *Streptococcus*. In some cases, a biofouling-resistant coating disclosed herein prevents and/or reduces microfouling formed by a gram-positive bacterium: *Actinomyces* spp., *Arthrobacter* spp., *Bacillus licheniformis, Clostridium difficile, Clostridium* spp., *Corynebacterium* spp., *Enterococcus faecalis, Lactococcus* spp., *Listeria monocytogenes, Micrococcus* spp., *Mycobacterium* spp., *Staphylococcus aureus, Staphylococcus epidermidis, Streptococcus pneumoniae*, or *Streptococcus pyogenes*.

In some cases, microfouling comprises bacteria adhesion. In some instances, a biofouling-resistant coating disclosed herein prevents and/or reduces bacteria adhesion. In some cases, a biofouling-resistant coating disclosed herein prevents and/or reduces bacteria adhesion formed by a gram-positive bacterium from the genus *Actinomyces, Arthrobacter, Bacillus, Clostridium, Corynebacterium, Enterococcus, Lactococcus, Listeria, Micrococcus, Mycobacterium, Staphylococcus*, or *Streptococcus*. In some cases, a biofouling-resistant coating disclosed herein coated onto a material prevents and/or reduces bacteria adhesion formed by a gram-positive bacterium: *Actinomyces* spp., *Arthrobacter* spp., *Bacillus licheniformis, Clostridium difficile, Clostridium* spp., *Corynebacterium* spp., *Enterococcus faecalis, Lactococcus* spp., *Listeria monocytogenes, Micrococcus* spp., *Mycobacterium* spp., *Staphylococcus aureus, Staphylococcus epidermidis, Streptococcus pneumoniae*, or *Streptococcus pyogenes*.

In some cases, microfouling comprises biofilm. In some instances, a biofouling-resistant coating disclosed herein coated onto a material prevents and/or reduces biofilm. In some cases, a biofouling-resistant coating disclosed herein coated onto a material prevents and/or reduces biofilm formed by a gram-positive bacterium from the genus *Actinomyces, Arthrobacter, Bacillus, Clostridium, Corynebacterium, Enterococcus, Lactococcus, Listeria, Micrococcus, Mycobacterium, Staphylococcus*, or *Streptococcus*. In some cases, a biofouling-resistant coating disclosed herein coated onto a material prevents and/or reduces biofilm formed by a gram-positive bacterium: *Actinomyces* spp., *Arthrobacter* spp., *Bacillus licheniformis, Clostridium difficile, Clostridium* spp., *Corynebacterium* spp., *Enterococcus faecalis, Lactococcus* spp., *Listeria monocytogenes, Micrococcus* spp., *Mycobacterium* spp., *Staphylococcus aureus, Staphylococcus epidermidis, Streptococcus pneumoniae*, or *Streptococcus pyogenes*.

In some cases, microfouling is formed by a gram-negative bacterium. Exemplary gram-negative bacteria include, but are not limited to, bacteria from the genus *Alteromonas, Aeromonas, Desulfovibrio, Escherichia, Fusobacterium, Geobacter, Haemophilus, Klebsiella, Legionella, Porphyromonas, Proteus, Pseudomonas, Serratia, Shigella, Salmonella*, or *Vibrio*. In some instances, a gram-negative bacterium comprises *Alteromonas* spp., *Aeromonas* spp., *Desulfovibrio* spp., *Escherichia coli, Fusobacterium nucleatum, Geobacter* spp., *Haemophilus* spp., *Klebsiella* spp., *Legionella pneumophila, Porphyromonas* spp., *Pseudomonas aeruginosa, Proteus vulgaris, Proteus mirabilis, Proteus penneri, Serratia* spp., *Shigella dysenteriae, Shigella flexneri, Shigella boydii, Shigella sonnei, Salmonella bongori, Salmonella enterica*, or *Vibrio Cholerae*.

In some instances, microfouling is formed by a gram-negative bacterium from the genus *Alteromonas, Aeromonas, Desulfovibrio, Escherichia, Fusobacterium, Geobacter, Haemophilus, Klebsiella, Legionella, Porphyromonas, Pro-* teus, *Pseudomonas, Serratia, Shigella, Salmonella*, or *Vibrio*. In some instances, microfouling is formed by a gram-negative bacterium: *Alteromonas* spp., *Aeromonas* spp., *Desulfovibrio* spp., *Escherichia coli, Fusobacterium nucleatum, Geobacter* spp., *Haemophilus* spp., *Klebsiella* spp., *Legionella pneumophila, Porphyromonas* spp., *Pseudomonas aeruginosa, Proteus vulgaris, Proteus mirabilis, Proteus penneri, Serratia* spp., *Shigella dysenteriae, Shigella flexneri, Shigella boydii, Shigella sonnei, Salmonella bongori, Salmonella enterica*, or *Vibrio Cholerae*.

In some embodiments, a biofouling-resistant coating disclosed herein prevents and/or reduces microfouling formed by a gram-negative bacterium from the genus *Alteromonas, Aeromonas, Desulfovibrio, Escherichia, Fusobacterium, Geobacter, Haemophilus, Klebsiella, Legionella, Porphyromonas, Proteus, Pseudomonas, Serratia, Shigella, Salmonella*, or *Vibrio*. In some instances, a biofouling-resistant coating disclosed herein prevents and/or reduces microfouling formed by a gram-negative bacterium: *Alteromonas* spp., *Aeromonas* spp., *Desulfovibrio* spp., *Escherichia coli, Fusobacterium nucleatum, Geobacter* spp., *Haemophilus* spp., *Klebsiella* spp., *Legionella pneumophila, Porphyromonas* spp., *Pseudomonas aeruginosa, Proteus vulgaris, Proteus mirabilis, Proteus penneri, Serratia* spp., *Shigella dysenteriae, Shigella flexneri, Shigella boydii, Shigella sonnei, Salmonella bongori, Salmonella enterica*, or *Vibrio Cholerae*.

In some embodiments, microfouling comprises bacteria adhesion. In some embodiments, a biofouling-resistant coating disclosed herein prevents and/or reduces bacteria adhesion formed by a gram-negative bacterium from the genus *Alteromonas, Aeromonas, Desulfovibrio, Escherichia, Fusobacterium, Geobacter, Haemophilus, Klebsiella, Legionella, Porphyromonas, Proteus, Pseudomonas, Serratia, Shigella, Salmonella*, or *Vibrio*. In some instances, a biofouling-resistant coating disclosed herein prevents and/or reduces bacteria adhesion formed by a gram-negative bacterium: *Alteromonas* spp., *Aeromonas* spp., *Desulfovibrio* spp., *Escherichia coli, Fusobacterium nucleatum, Geobacter* spp., *Haemophilus* spp., *Klebsiella* spp., *Legionella pneumophila, Porphyromonas* spp., *Pseudomonas aeruginosa, Proteus vulgaris, Proteus mirabilis, Proteus penneri, Serratia* spp., *Shigella dysenteriae, Shigella flexneri, Shigella boydii, Shigella sonnei, Salmonella bongori, Salmonella enterica*, or *Vibrio Cholerae*.

In some instances, microfouling comprises biofilm. In some embodiments, a biofouling-resistant coating disclosed herein prevents and/or reduces biofilm formed by a gram-negative bacterium from the genus *Alteromonas, Aeromonas, Desulfovibrio, Escherichia, Fusobacterium, Geobacter, Haemophilus, Klebsiella, Legionella, Porphyromonas, Proteus, Pseudomonas, Serratia, Shigella, Salmonella*, or *Vibrio*. In some instances, a biofouling-resistant coating disclosed herein prevents and/or reduces biofilm formed by a gram-negative bacterium: *Alteromonas* spp., *Aeromonas* spp., *Desulfovibrio* spp., *Escherichia coli, Fusobacterium nucleatum, Geobacter* spp., *Haemophilus* spp., *Klebsiella* spp., *Legionella pneumophila, Porphyromonas* spp., *Pseudomonas aeruginosa, Proteus vulgaris, Proteus mirabilis, Proteus penneri, Serratia* spp., *Shigella dysenteriae, Shigella flexneri, Shigella boydii, Shigella sonnei, Salmonella bongori, Salmonella enterica*, or *Vibrio Cholerae*.

In some cases, microfouling is formed by a marine bacterium. In some instances, a marine bacterium comprises *Pseudoalteromonas* spp. or *Shewanella* spp. In some cases, microfouling is formed by *Pseudoalteromonas* spp. or *Shewanella* spp.

In some embodiments, a biofouling-resistant coating disclosed herein prevents and/or reduces microfouling formed by a marine bacterium. In some cases, a biofouling-resistant coating disclosed herein prevents and/or reduces microfouling formed by *Pseudoalteromonas* spp. or *Shewanella* spp.

In some instances, microfouling comprises bacteria adhesion. In some embodiments, a biofouling-resistant coating disclosed herein prevents and/or reduces bacteria adhesion formed by a marine bacterium. In some cases, a biofouling-resistant coating disclosed herein prevents and/or reduces bacteria adhesion formed by *Pseudoalteromonas* spp. or *Shewanella* spp.

In some instances, microfouling comprises biofilm. In some embodiments, a biofouling-resistant coating disclosed herein prevents and/or reduces biofilm formed by a marine bacterium. In some cases, a biofouling-resistant coating disclosed herein prevents and/or reduces biofilm formed by *Pseudoalteromonas* spp. or *Shewanella* spp.

In some embodiments, microfouling is formed by a fungus. Exemplary fungus includes, but is not limited to, *Candida albicans, Candida glabrata, Candida rugose, Candida parapsilosis, Candida tropicalis, Candida dubliniensis*, or *Hormoconis resinae*. In some cases, microfouling is formed by *Candida albicans, Candida glabrata, Candida rugose, Candida parapsilosis, Candida tropicalis, Candida dubliniensis*, or *Hormoconis resinae*.

In some embodiments, a biofouling-resistant coating disclosed herein prevents and/or reduces microfouling formed by a fungus. In some cases, a biofouling-resistant coating disclosed herein prevents and/or reduces microfouling formed by *Candida albicans, Candida glabrata, Candida rugose, Candida parapsilosis, Candida tropicalis, Candida dubliniensis*, or *Hormoconis resinae*.

In some instances, microfouling comprises bacteria adhesion. In some embodiments, a biofouling-resistant coating disclosed herein prevents and/or reduces bacteria adhesion formed by a fungus. In some cases, a biofouling-resistant coating disclosed herein prevents and/or reduces bacteria adhesion formed by *Candida albicans, Candida glabrata, Candida rugose, Candida parapsilosis, Candida tropicalis, Candida dubliniensis*, or *Hormoconis resinae*.

In some instances, microfouling comprises biofilm. In some embodiments, a biofouling-resistant coating disclosed herein prevents and/or reduces biofilm formed by a fungus. In some cases, a biofouling-resistant coating disclosed herein prevents and/or reduces biofilm formed by *Candida albicans, Candida glabrata, Candida rugose, Candida parapsilosis, Candida tropicalis, Candida dubliniensis*, or *Hormoconis resinae*.

Macrofouling

In some embodiments, macrofouling comprises calcareous fouling organism or non-calcareous fouling organism. A calcareous fouling organism is an organism with a hard body. In some cases, calcareous fouling organisms comprise barnacle, bryozoan, mollusk, polychaete, tube worm, or zebra mussel. A non-calcareous fouling organism comprises a soft body. Non-calcareous fouling organism comprises seaweed, hydroids, or algae.

In some instances, macrofouling is formed by a calcareous fouling organism. In some cases, macrofouling is formed by barnacle, bryozoan, mollusk, polychaete, tube worm, or zebra mussel.

In some embodiments, a biofouling-resistant coating disclosed herein prevents and/or reduces macrofouling formed by a calcareous fouling organism. In some instances, a biofouling-resistant coating disclosed herein prevents and/or reduces macrofouling formed by barnacle, bryozoan, mollusk, polychaete, tube worm, or zebra mussel.

In some cases, macrofouling is formed by a non-calcareous fouling organism. In some cases, macrofouling is formed by seaweed, hydroids, or algae.

In some embodiments, also disclosed herein are biofouling-resistant coating preventing and/or reducing macrofouling formed by a non-calcareous fouling organism. In some instances, a biofouling-resistant coating disclosed herein prevents and/or reduces macrofouling formed by seaweed, hydroids, or algae.

In some embodiments, a biofouling-resistant coating disclosed herein reduces the formation of biofouling on its surface. In some cases, the formation of biofouling on a surface of a device modified with a compound of Formula (I), (II), or (III) is reduced by about 10%, 20%, 30%, 40%, 50%, 60%, 70%, 80%, 90%, 95%, 99%, 99.5%, 99.9%, or more relative to the unmodified surface of a device. In some instances, the formation of biofouling is reduced by at least about 10%, 20%, 30%, 40%, 50%, 60%, 70%, 80%, 90%, 95%, 99%, 99.5%, 99.9%, or more relative to the unmodified surface of a device. In some instances, the formation of biofouling relative to the unmodified surface of a device is determined by comparing the amount of biofouling following a period of time of storage, use, and/or testing of the device(s). For example, the devices may be tested by exposing them to conditions conducive of biofouling formation (e.g., in vitro biofouling testing techniques known and practiced in the art). In some instances, the formation of biofouling is reduced by about 10%, or more relative to the unmodified surface of a device. In some instances, the formation of biofouling is reduced by about 20%, or more relative to the unmodified surface of a device. In some instances, the formation of biofouling is reduced by about 30%, or more relative to the unmodified surface of a device. In some instances, the formation of biofouling is reduced by about 40%, or more relative to the unmodified surface of a device. In some instances, the formation of biofouling is reduced by about 50%, or more relative to the unmodified surface of a device. In some instances, the formation of biofouling is reduced by about 60%, or more relative to the unmodified surface of a device. In some instances, the formation of biofouling is reduced by about 70%, or more relative to the unmodified surface of a device. In some instances, the formation of biofouling is reduced by about 80%, or more relative to the unmodified surface of a device. In some instances, the formation of biofouling is reduced by about 90%, or more relative to the unmodified surface of a device. In some instances, the formation of biofouling is reduced by about 95%, or more relative to the unmodified surface of a device. In some instances, the formation of biofouling is reduced by about 99%, or more relative to the unmodified surface of a device. In some instances, the formation of biofouling is reduced by about 99.5%, or more relative to the unmodified surface of a device. In some instances, the formation of biofouling is reduced by about 99.9%, or more relative to the unmodified surface of a device.

In some embodiments, a biofouling-resistant coating disclosed herein is further coated with an additional agent. In some instances, the additional agent is an antimicrobial agent. Exemplary antimicrobial agent comprises quaternary ammonium salts or tertiary amines. In some instances, the additional agent is a chemical disinfectant. Exemplary chemical disinfectant comprises sodium hypochlorite, sodium hydroxide, and benzalkonium chloride.

Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a component," "a polymer," or "a particle" includes mixtures of two or more such components, polymers, or particles, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that throughout the application, data is provided in a number of different formats and that this data represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance may or may not occur, and that the description includes instances where said event or circumstance occurs and instances where it does not.

As used herein, the terms "effective amount" and "amount effective" refer to an amount that is sufficient to achieve the desired result or to have an effect on an undesired condition.

The term "stable", as used herein, refers to compositions that are not substantially altered when subjected to conditions to allow for their production, detection, and, in certain aspects, their recovery, purification, and use for one or more of the purposes disclosed herein.

As used herein, the term "polymer" refers to a relatively high molecular weight organic compound, natural or synthetic, whose structure can be represented by a repeated small unit, the monomer (e.g., polyethylene, rubber, cellulose). Synthetic polymers are typically formed by addition or condensation polymerization of monomers. Unless indicated otherwise, polymer molecular weights are given in Daltons.

As used herein, the term "homopolymer" refers to a polymer formed from a single type of repeating unit (monomer residue).

As used herein, the term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers.

As used herein, the term "oligomer" refers to a relatively low molecular weight polymer in which the number of repeating units is between two and ten, for example, from two to eight, from two to six, or form two to four. In one aspect, a collection of oligomers can have an average number of repeating units of from about two to about ten, for example, from about two to about eight, from about two to about six, or form about two to about four.

As used herein, the term "cross-linked polymer" refers to a polymer having bonds linking one polymer chain to another.

As used herein, the term "porogen composition" or "porogen(s)" refers to any structured material that can be used to create a porous material.

"Oxo" refers to the =O substituent.

"Thioxo" refers to the =S substituent.

"Alkyl" refers to a straight or branched hydrocarbon chain radical, having from one to twenty carbon atoms, and which is attached to the rest of the molecule by a single bond. An alkyl comprising up to 10 carbon atoms is referred to as a C1-C10 alkyl, likewise, for example, an alkyl comprising up to 6 carbon atoms is a C1-C6 alkyl. Alkyls (and other moieties defined herein) comprising other numbers of carbon atoms are represented similarly. Alkyl groups include, but are not limited to, C1-C10 alkyl, C1-C9 alkyl, C1-C8 alkyl, C1-C7 alkyl, C1-C6 alkyl, C1-C5 alkyl, C1-C4 alkyl, C1-C3 alkyl, C1-C2 alkyl, C2-C8 alkyl, C3-C8 alkyl and C4-C8 alkyl. Representative alkyl groups include, but are not limited to, methyl, ethyl, n-propyl, 1-methylethyl (i-propyl), n-butyl, i-butyl, s-butyl, n-pentyl, 1,1-dimethylethyl (t-butyl), 3-methylhexyl, 2-methylhexyl, 1-ethyl-propyl, and the like. In some embodiments, the alkyl is methyl or ethyl. In some embodiments, the alkyl is —CH(CH3)2 or —C(CH3)3. Unless stated otherwise specifically in the specification, an alkyl group may be optionally substituted as described below. "Alkylene" or "alkylene chain" refers to a straight or branched divalent hydrocarbon chain linking the rest of the molecule to a radical group. In some embodiments, the alkylene is —CH2-, —CH2-CH2-, or —CH2-CH2-CH2-. In some embodiments, the alkylene is —CH2-. In some embodiments, the alkylene is —CH2-CH2-. In some embodiments, the alkylene is —CH2-CH2-CH2-.

"Alkoxy" refers to a radical of the formula —OR where R is an alkyl radical as defined. Unless stated otherwise specifically in the specification, an alkoxy group may be optionally substituted as described below. Representative alkoxy groups include, but are not limited to, methoxy, ethoxy, propoxy, butoxy, pentoxy. In some embodiments, the alkoxy is methoxy. In some embodiments, the alkoxy is ethoxy.

"Heteroalkylene" refers to an alkyl radical as described above where one or more carbon atoms of the alkyl is replaced with a O, N or S atom. "Heteroalkylene" or "heteroalkylene chain" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkyl groups include, but are not limited to —OCH2OMe, —OCH2-CH2OMe, or OCH2-CH2OCH2-CH2NH2.

Representative heteroalkylene groups include, but are not limited to —OCH2-CH2O—, OCH2-CH2OCH2-CH2O—, or OCH2-CH2OCH2-CH2OCH2-CH2O—.

"Alkylamino" refers to a radical of the formula —NHR or —NRR where each R is, independently, an alkyl radical as defined above. Unless stated otherwise specifically in the specification, an alkylamino group may be optionally substituted as described below.

The term "aromatic" refers to a planar ring having a delocalized π-electron system containing 4n+2 n electrons, where n is an integer. Aromatics can be optionally substituted. The term "aromatic" includes both aryl groups (e.g., phenyl, naphthalenyl) and heteroaryl groups (e.g., pyridinyl, quinolinyl).

"Aryl" refers to an aromatic ring wherein each of the atoms forming the ring is a carbon atom. Aryl groups can be optionally substituted. Examples of aryl groups include, but are not limited to phenyl, and naphthyl. In some embodiments, the aryl is phenyl. Depending on the structure, an aryl group can be a monoradical or a diradical (i.e., an arylene group). Unless stated otherwise specifically in the specification, the term "aryl" or the prefix "ar-" (such as in "aralkyl") is meant to include aryl radicals that are optionally substituted.

"Carboxy" refers to —CO2H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to:

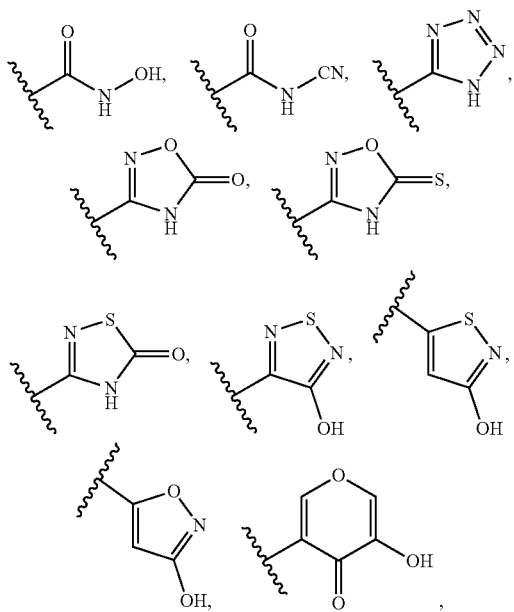

and the like.

"Cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms. Representative cycloalkyls include, but are not limited to, cycloalkyls having from three to ten carbon atoms, from three to eight carbon atoms, from three to six carbon atoms, or from three to five carbon atoms. Monocyclic cycicoalkyl radicals include, for example, cyclopropyl, cyclobutyl, cyclopentyl, cyclohexyl, cycloheptyl, and cyclooctyl. In some embodiments, the monocyclic cycicoalkyl is cyclopropyl, cyclobutyl, cyclopentyl or cyclohexyl. In some embodiments, the monocyclic cycicoalkyl is cyclopentyl. Polycyclic radicals include, for example, adamantyl, norbornyl, decalinyl, and 3,4-dihydronaphthalen-1(2H)-one. Unless otherwise stated specifically in the specification, a cycloalkyl group may be optionally substituted.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" refers to an alkoxy radical, as defined above, that is substituted by one or more halo radicals, as defined above, e.g., trifluoromethoxy, difluoromethoxy, fluoromethoxy, trichloromethoxy, 2,2,2-trifluoroethoxy, 1,2-difluoroethoxy, 3-bromo-2-fluoropropoxy, 1,2-dibromoethoxy, and the like. Unless stated otherwise specifically in the specification, a haloalkoxy group may be optionally substituted.

"Heterocycloalkyl" or "heterocyclyl" or "heterocyclic ring" refers to a stable 3- to 14-membered non-aromatic ring radical comprising 2 to 10 carbon atoms and from one to 4 heteroatoms selected from the group consisting of nitrogen, oxygen, and sulfur. Unless stated otherwise specifically in the specification, the heterocycloalkyl radical may be a monocyclic, or bicyclic ring system, which may include fused (when fused with an aryl or a heteroaryl ring, the heterocycloalkyl is bonded through a non-aromatic ring atom) or bridged ring systems. The nitrogen, carbon or sulfur atoms in the heterocyclyl radical may be optionally oxidized. The nitrogen atom may be optionally quaternized. The heterocycloalkyl radical is partially or fully saturated. Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. The term heterocycloalkyl also includes all ring forms of carbohydrates, including but not limited to monosaccharides, disaccharides and oligosaccharides. Unless otherwise noted, heterocycloalkyls have from 2 to 10 carbons in the ring. In some embodiments, heterocycloalkyls have from 2 to 8 carbons in the ring. In some embodiments, heterocycloalkyls have from 2 to 8 carbons in the ring and 1 or 2 N atoms. In some embodiments, heterocycloalkyls have from 2 to 10 carbons, 0-2 N atoms, 0-2 O atoms, and 0-1 S atoms in the ring. In some embodiments, heterocycloalkyls have from 2 to 10 carbons, 1-2 N atoms, 0-1 O atoms, and 0-1 S atoms in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

"Heteroaryl" refers to an aryl group that includes one or more ring heteroatoms selected from nitrogen, oxygen and sulfur. The heteroaryl is monocyclic or bicyclic. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, furazanyl, indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Illustrative examples of bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, heteroaryl is pyridinyl, pyrazinyl, pyrimidinyl, thiazolyl, thienyl, thiadiazolyl or furyl. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a C1-C9heteroaryl. In some embodiments, monocyclic heteroaryl is a C1-C5heteroaryl. In some embodiments, monocyclic heteroaryl is a 5-membered or 6-membered heteroaryl. In some embodiments, a bicyclic heteroaryl is a C6-C9heteroaryl.

The term "optionally substituted" or "substituted" means that the referenced group may be substituted with one or more additional group(s) individually and independently selected from alkyl, haloalkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, C1-C6alkylalkyne, halogen, acyl, acyloxy, —$CO_2H$, —$CO_2$alkyl, nitro, and amino, including mono- and di-substituted amino groups (e.g. $NH_2$, —NHR, —N(R)$_2$), and the protected derivatives thereof. In some embodiments, optional substituents are independently selected from alkyl, alkoxy, haloalkyl, cycloalkyl, halogen, —CN, —$NH_2$, —$NH(CH_3)$, —$N(CH_3)_2$, —OH, —$CO_2H$, and —$CO_2$alkyl. In some embodiments, optional substituents are independently selected from fluoro, chloro, bromo, iodo, —$CH_3$, —$CH_2$—$CH_3$, —$CF_3$, —$OCH_3$, and —$OCF_3$. In some embodiments, substituted groups are substituted with one or two of the preceding groups. In some embodiments, an optional substituent on an aliphatic carbon atom (acyclic or cyclic, saturated or unsaturated carbon atoms, excluding aromatic carbon atoms) includes oxo (=O). Compounds described herein can contain one or more double bonds and, thus, potentially give rise to cis/trans (E/Z) isomers, as well as other conformational isomers. Unless stated to the contrary, the compounds disclosed herein include all such possible isomers, as well as mixtures of such isomers.

In some embodiments, PSB and PFPA-PSB are used interchangeably and refer to poly(sulfobetaine methacrylate-co-perfluorophenylazide methacrylate).

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's R$^{2a}$ gents for Organic Synthesis, Volumes 1-17 (John Wiley and Sons, 1991), Rodd's Chemistry of Carbon Compounds, Volumes 1-5 and Supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

EXAMPLES

The following examples are provided for illustrative purposes only, and are intended to be purely exemplary of the disclosure and are not intended to limit the scope of the claims provided herein. Efforts have been made to ensure accuracy with respect to numbers (e.g., amounts, temperature, etc.), but some errors and deviations should be accounted for.

Materials

α-Bromoisobutyryl bromide, N-Boc-ethanolamine, Trifluoroacetic acid, 1,1,4,7,10,10-Hexamethyltriethylenetetramine (97%), [2-(Methacryloyloxy) ethyl] dimethyl-(3-sulfopropyl)ammonium hydroxide, tetrabutylammonium chloride, and cupper(I) chloride were used as received from Sigma Aldrich. Sodium bicarbonate, methylene chloride, magnesium sulfate, and 2,2,2-trifluoroethanol were purchased from Alfa Aesar. Sylgard 184 kit (Dow Corning) was obtained from Fisher Chemical.

The zwitterionic polymer, polysulfobetaine (PSB), was selected as an antifouling component of the coating. By adsorbing water electrostatically, PSB coatings form a thin hydration barrier that prevents organic material from adhering to its surface. Commonly used approaches to attach PSB coatings to surfaces such as radical-initiated graft polymerizations of PSB-methacrylate necessitate the use of oxygen-free conditions, preconditioning steps, or long reaction times that do not meet the scalability requirements. To circumvent the use of air-free graft polymerizations, we employed perfluorophenylazide (PFPA) as a molecular anchor to graft the PSB coating to the surface of polymeric materials under ambient conditions. When triggered with UV-light, PFPA moieties generate a highly reactive nitrene that forms covalent bonds with materials containing amines, C=C double bonds, and C—H bonds. With this method, it was surprisingly found that PSB is rapidly coated to a variety of substrates using UV light under ambient conditions with no preconditioning steps needed. In addition, it was unexpectedly found that water provided an optimal solvent for photografting of PFPA-PSB coating and that photografting of PFPA-PSB did not proceed well in the presence of organic solvents.

Example 1. Synthesis of ATRP Initiator 2-aminoethyl 2-bromoisobutyrate

ATRP initiator 2-aminoethyl 2-bromoisobutyrate was synthesized according to the following procedure. 5 g of 2-bromoisobutyryl bromide was added to a solution of 3.8 g of t-Boc-aminoethyl alcohol and 2.5 g of triethylamine in 12 ml methylene chloride in an ice bath. After 16 h, the salts were filtered off and the filtrate was extracted with saturated sodium bicarbonate solution. Methylene chloride phase was dried over magnesium sulfate and evaporated. The resulting t-Boc-aminoethyl 2-bromoisobutyrate was treated by 15 ml trifluoroacetic acid (TFA) for 2 h and crystallized upon addition of ethyl ether (yield 85%).

Example 2. Synthesis of Perfluorophenylazide Methacrylamide 1.00 g N-(3-amino-propyl)-methacrylamide and 1.41 g triethylamine was dissolved in 40 mL chloroform at 25° C. and stirred for 1 hour. The solution was then cooled to 0° C. Separately a solution of 1.45 g pentafluorobenzene sulfonyl chloride and 0.85 g triethylamine in 10 mL chloroform was also brought to 0° C., then slowly added to the reaction dropwise. The reaction mixture was placed in an ice bath and allowed to come to room temperature. After 24 hours, the reaction was washed 3× with DI water and the organic layer was evaporated under reduced pressure. The resulting product was then dissolved in 40 mL of 3:1 acetone:water. 1.5 g sodium azide was then added. After 24 hours, the reaction was partitioned with chloroform and water. The organic layer was washed 3× with DI water and evaporated under reduced pressure affording approximately 1.2 g of the perfluorophenylazide methacylamide product.

Example 3. Polymerization of poly(sulfobetaine methacrylate-co-perfluorophenylazide methacrylate)

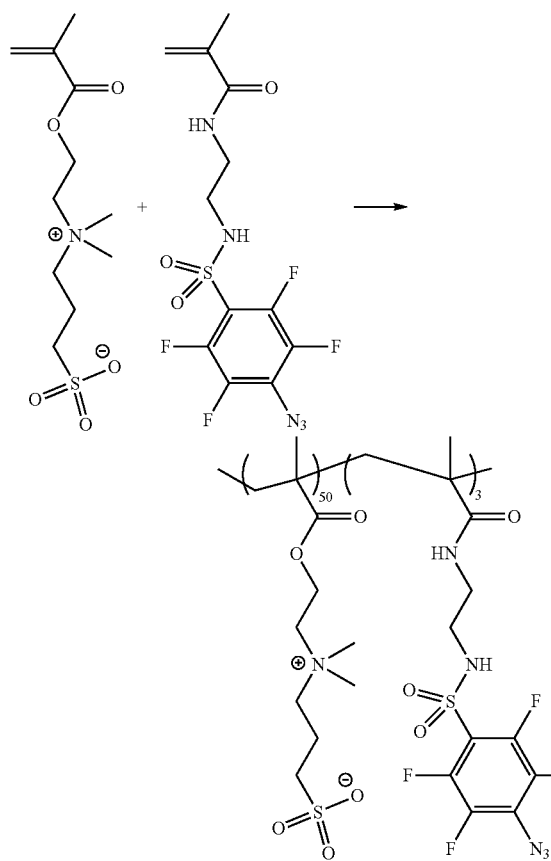

Poly(sulfobetaine methacrylate-co-perfluorophenylazide methacrylate) was synthesized as follows: 2 g sulfobetaine methacrylate monomer, 156 mg perfluorophenylazide methacrylamide monomer and 2 g tetrabutylammonium chloride were dissolved in 30 mL trifluoroethanol in a Schlenk flask and underwent two vacuum-argon cycles. Then, 14 mg Cu(I)Cl and 76 µL 1,1,4,7,10,10-Hexamethyltriethylenetetramine were added. The Schlenk flask was sealed with a rubber septum and another two vacuum-argon cycles were performed. Finally, 44 mg TFA protected 2-aminoethyl 2-bromoisobutyrate as ATRP initiator was dissolved in a small amount of trifluoroethanol (~0.5 mL) and syringe-injected into the Schlenk flask, followed by two additional vacuum-argon cycles. Polymerization was carried out at 60° C. under argon protection. After 24 h, the reaction mixture was cooled down to room temperature and the polymer was purified by performing membrane dialysis using a membrane with cut off molecular weight of 1000 Dalton. The resulting copolymer was freeze-dried before further use.

NMR spectra were recorded on a Bruker DPX300 spectrometer. Chemical shifts were calibrated to residual solvent signals. Molecular weights and dispersities were measured by gel permeation chromatography on a Shimadzu HPLC system with a refractive index detector S3 RID-10A, one Tosoh TSKGel guard column, and one Tosoh TSKGel G4000PW column. Eluent was 0.1 M $NaNO_3$+20 mM phosphate buffer pH 7+20% MeCN at 25° C. (flow rate 0.7 mL/min). Calibration was performed using near-monodisperse PEG standards from Polymer Laboratories. Light scattering was used to obtain the absolute molecular weight.

Example 4. Silicone Surface Modification and Characterization

Poly(sulfobetaine methacrylate-co-perfluorophenylazide methacrylate) was dissolved or suspended in DI water to prepare 2-20 mg/mL aqueous mixture. Silicone elastomer films were prepared by mixing 10:1 (by weight) base:crosslinker (Sylgard 184), followed by degassing under vacuum and subsequently crosslinking at 70° C. for 8 h. For anti-biofouling experiments, 2 mg/mL poly(sulfobetaine methacrylate-co-perfluorophenylazide methacrylate) aqueous mixture was spread onto a cured silicone elastomer surface and exposed to 254 nm UV light irradiation for 10 mins. Then the silicone elastomer surface was rinsed with large amounts of DI water to remove unreacted and physically adsorbed poly(sulfobetaine methacrylate-co-perfluorophenylazide methacrylate) molecules from the surface and stored underneath a layer of water before further use.

Contact angles of deionized water (18 MΩ/cm, Millipore) on polymer coatings were measured using a rame-hart Model 590 goniometer. Advancing angles ($\theta_{adv}$) were measured as water was supplied via a syringe, while receding angles ($\theta_{rec}$) were measured as water was removed via a syringe. The total drop volume was 5 µL, and the pump dispensing speed was 0.2 µL/s. Measurements were taken over three or more different locations on each surface, and the reported values are in the format of average ±standard deviation.

For surface modification, the following photoreaction takes place. First, PFPA decomposes by releasing $N_2$ to give the singlet phenylnitrene upon activation of the compound by UV light. The singlet phenylnitrene further undergoes C—H or N—H insertion, and C=C addition reactions which contributes to the covalent bond formation with the target surfaces (Liu, L.-H. et al. Perfluorophenyl azides: new applications in surface functionalization and nanomaterial synthesis. Accounts of Chemical Research 2010, 43 (11), 1434-1443). In this process, "the singlet phenylnitrene" reaction intermediate is a strong nucleophile and its stability is not affected by the existence of oxygen and water molecules.

Example 5. Substrates Modification and Characterization

Coating Substrates with PSB:

PDMS substrates were prepared by mixing a 10:1 ratio of elastomer to curing agent, followed by curing at 80° C. for 1 h. The PDMS disks were cut with a laser cutter into 3 mm diameter disks. 30 μL, of coating (PSB) mixture with concentrations ~2, 5, or 10 mg mL$^{-1}$ was placed and spread out on the surface of each disk. The PSB was then cross-linked on the discs by exposing them to 254 nm UV light for 10 min under sterile conditions, followed by rinsing with Milli-Q water and drying with air.

Contact Angle Visualization and Measurement:

Water contact angle on various substrates, such as PDMS, Nylon 66, polystyrene, polyvinyl chloride, and polyethylene was visualized by placing 17 μL, of Milli-Q water on the flat substrates at room temperature followed by imaging them. The images were analyzed using Fta32 version 2.1 software to measure the contact angle. To study the recovery of water contact angle on PDMS substrates, they were divided into two groups: (i) uncoated PDMS sheets, which were treated using $O_2$ plasma (Plasma Etch PE25-JW Plasma Cleaner, NV, US) for 1 min, followed by measuring water contact angle after 1, 2, 4, 7, and 10 days, and (ii) PDMS sheets that were coated with PSB, and the contact angle was similarly measured over time.

Profilometry:

A calibrated, mechanical 2-D profilometer (Dektak) was used to measure the roughness of polymer coating on PDMS substrates. The polymer is first coated as described above and placed under the measuring platform of the profilometer. A diamond stylus of 25 μm with a stylus angle 90° was traversed in a length of 1.7 mm for 60 s. Three measurements from one end of the coated polymer to the other end across the diameter were performed per sample. The measurements were then analyzed using Dektak V9 software to obtain roughness versus distance.

XPS studies were carried out on a Kratos AXIS Ultra DLD with a monochromatic Al Kα X-ray source operating at 10 mA and 15 kV. Survey spectra and individual high-resolution spectra were collected using pass energies of 160 and 20 eV, respectively. Data processing were performed using CasaXPS 2.3 software, and spectra binding energies were calibrated by assigning the hydrocarbon peak in the C1s high-resolution spectra to 284.6 eV Cell Culture:

NIH/3T3 fibroblast cells were cultured in cell culture flasks containing DMEM with 10% FBS and 1% P/S and passaged twice a week. For this purpose, a standard cell culture incubator (Thermo Fisher Scientific, PA, USA) was used to provide 5% $CO_2$ atmosphere and temperature=37° C. To conduct cell studies, 0.5% trypsin-EDTA was used to trypsinize fibroblast cells and count them using a hemocytometer, followed by seeding them on desirable substrates.

Cell Adhesion:

Trypsinized fibroblasts cells were seeded on PSB-coated 96-well plates by placing 100 μL, of the cell suspension (cell density 1×10$^5$ in 1 mL media) on the treated well plates, cultured for 24 h. Uncoated well plates were used as a control.

Cytotoxicity Evaluation:

To assess the cytotoxicity of un-crosslinked PSB, trypsinized fibroblasts cells were seeded on 96-well plates by placing 100 μL, of the cell suspension (cell density ~1×10$^5$ in 1 mL media) and cultured for 24 h, followed by adding a desired amount of un-crosslinked PSB to the media and further culturing for 72 h. The cytotoxicity of cross-linked PSB was evaluated by seeding 500 μL, of cell suspension (cell density ~2×10$^5$ in 1 mL media) in 24-well plates, culturing for 24 h, followed by placing PSB coated PDMS discs (diameter ~6 mm, height 3 mm) in the medium and further culturing for 72 h.

Metabolic Activity Assessment:

MTT 43-(4,5-Dimethylthiazol-2-yl)-2,5-Diphenyltetrazolium Bromide) (Thermo Fisher Scientific) stain solutions were prepared at a concentration ~5 mg mL$^{-1}$ in DPBS. Cell culture media were removed from the well plates, followed by one time rinsing with DPBS. The wells were then loaded with fresh media and MTT solution at a ratio of 9:1. The well plates were wrapped with aluminum foil and incubated for 4 h at 37° C. and 5% $CO_2$. After 4 h, the wells were aspirated with a pipette and 200 or 500 μL, of DMSO was added for 96- and 24-well plates, respectively. The well plates were wrapped with aluminum foil again and left on a rotator for 30 min, after which absorbance was recorded at 570 nm using a microplate reader (Synergy HTX multi-mode reader, BioTek, VT, USA).

Live/Dead Assay:

To assess the cell viability, a live/dead fluorescence assay was used. The staining solution was prepared by adding ethidium homodimer-1 (20 μL) and calcein AM (5 μL) to DPBS (10 mL). To perform the assay, the cells were incubated with 1 mL of the staining solution for approximately 20 min and imaged using a fluorescent microscope (Axio Observer 5, Zeiss, Germany) at excitation/emission wavelengths 494/515 nm for calcein and 528/617 nm for ethidium homodimer-1.

Protein Adsorption:

The protein adsorption was assessed by incubating 100 μg of 50 μg mL$^{-1}$ of Alexa Fluor™ 488 (AF)-conjugated BSA on each PDMS substrate for 1 h at 37° C. To inhibit the photodegradation of AF, aluminum foil was used to wrap the substrates. Then, the PDMS substrates were gently rinsed with Milli-Q water and imaged at a constant exposure time ~1.13 ms using a fluorescent microscope (Axio Observer 5, Zeiss, Germany) at excitation/emission wavelengths ~488/517 nm. ImageJ (National Institutes of Health, US) was used to quantify the emitted fluorescence via the mean gray value analysis tool. The average pixel brightness indirectly reflects the amount of protein adsorbed to the substrates. Background autofluorescence was eliminated using AF-free samples as control.

Bacterial Culture:

Bacterial species, *E. coli, S. epidermidis, S. aureus* Rosenbach, *S. aureus* (MRSA), *P. aeruginosa*, and *C. albicans* were used in this work. All strains were incubated at 30° C. at 150 rpm until a mid-exponential phase was reached, at which time the cells were harvested by centrifugation at 3800×g for 8 min. *E. coli* was grown on a Luria-Bertani (LB) broth, *S. epidermidis, P. aeruginosa*, and *S. aureus* Rosenbach were grown on nutrient broth; *S. aureus* (MRSA) was grown on a trypticase soy broth (TSB); and *C. albicans* was grown on a yeast mold (YM) broth. These initial cultures were then adjusted to an optical density of 1 at 600 nm and had an initial total cell number ranging from 1×10$^7$ cells per mL to 1×10$^8$ cells per mL.

Bacterial Adhesion:

55 mm diameter Petri dishes were filled with a 10:1 elastomer to curing agent (Sylgard 184) and allowed to cure at room temperature for at least 48 hours to form a 3 mm thick PDMS film on the bottom of the dishes. Modified plates were coated with a solution containing PFPA-PSB and irradiated with 254 nm UV light. Each modified and unmodified PDMS-lined dish was inoculated with 4 mL of bacterial or fungal suspension and incubated for 24-72 hours (shaken at 25 rpm) at 35° C. The bacterial or fungal suspension was then removed and stored for further microscopy. The Petri dishes were gently rinsed with sterile, deionized water using a Pasteur pipette, and covered in 4 mL of a dye solution (SYTO 9 live/dead Baclight Bacterial Viability Kit L13152, Molecular Probes) for 15 min. The SYTO 9 solution was prepared by dissolving the contents of component A of the kit in 30 mL of sterile, deionized water. After the staining was complete, the Petri dishes were gently rinsed with deionized water and imaged using a 4×CCD camera (Axiocam MRm System) attached to a Zeiss Axioskop 2 microscope with a 10× objective, 40× objective, a fluorescent lamp, and a blue excitation filter. During observation, the images were taken at an excitation range of 450-490 nm. The number of attached microorganisms on all fluorescent images were determined using ImageJ software.

Statistical analysis: The data were reported as mean values ±standard deviation of at least triplicate experiments. The one-way analysis of variance (ANOVA) and Tukey's multiple comparisons were used, and statistically significant differences were identified for p-values lower than 0.05 (*$p<0.05$), 0.01 ($p<0.01$), 0.001 (*$p<0.001$), and 0.0001 (****$p<0.0001$).

Example 6. Bacteria Adhesion Test

*Escherichia coli* was used as the model bacteria for this test. Pure bacterial cell cultures were suspended in Luria-Bertani (LB) broth and grown at 35° C. while being shaken at 150 rpm and incubated until a mid-exponential phase was reached, at which time the cells were harvested by centrifugation at 3800×g for 8 min. The cells were then re-suspended with fresh LB medium to a concentration of $4\times10^7$ cells/mL. Membrane coupons, of approximately 1 cm$^2$, were incubated in this bacterial suspension for 24 hr at 25 rpm and 35° C. The coupons were then removed from the suspension and gently rinsed with fresh LB broth using a Pasteur pipette. Once rinsed, the coupons were immersed in a dye solution (SYTO 9 live/dead Baclight Bacterial Viability Kit L13152, Molecular Probes) for 15 min. The SYTO 9 solution was prepared by dissolving the contents of component A of the kit in 30 mL of sterile distillated water. After the staining was complete, the coupons were gently rinsed with fresh LB broth and imaged using a microscope (Olympus BX51 microscope) equipped with a fluorescent lamp and green/red fluorescence filters and a 4×CCD camera attachment (FVIEW-II, Soft Imaging System, USA).

Example 7. Adsorption of BSA on PSB-Modified PDMS Substrates

Figure 6A:
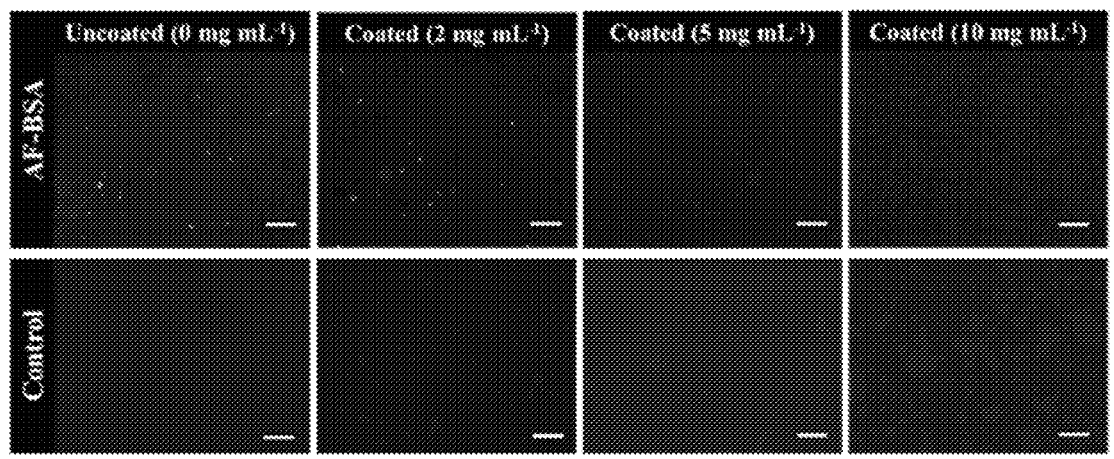
FIG. 6A illustrates fluorescent images of uncoated and PFPA-PSB coated PDMS substrates after incubation in a solution of AF-BSA. The bright spots are the protein molecules adsorbed to the PDMS substrates. The controls show similar substrates incubated in Milli-Q water.
Figure 6B:
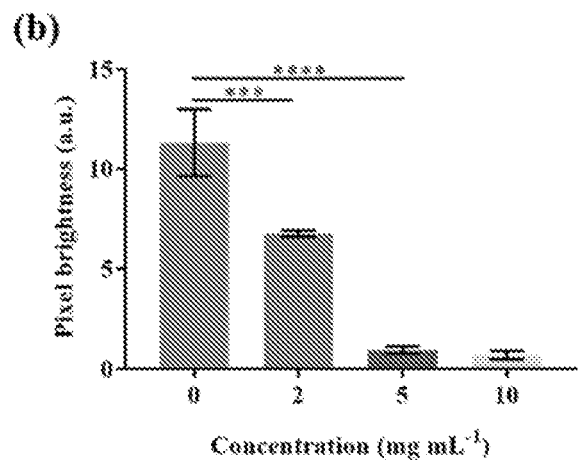
FIG. 6B illustrates pixel brightness of the PDMS substrates after incubation in the protein solution shows that PFPA-PSB coated PDMS reduces the protein adsorption to 0.

Assessment of the adsorption of BSA on PSB-modified PDMS substrates and comparison them with unmodified PDMS was shown. FIG. 6*a* presents the fluorescent images of substrates after incubation in Alexa Fluor™ bovine serum albumin (AF-BSA) followed by thorough rinsing with water. For an uncoated PDMS sheet, the adsorption of BSA is evident based on the AF green spots. Coating the substrate with PSB significantly decreases the number of green spots, and almost no adsorbed protein can be observed when the coating is performed from a PSB mixture with a concentration ≥5 mg mL$^{-1}$. The control experiments are the fluorescent images of uncoated and coated PDMS substrates incubated in milli-Q water, showing no bright spots. The BSA adsorption was quantified by measuring the average pixel brightness of images, which is shown in FIG. 6*b*. Coating the substrates with PSB decreases the pixel brightness by a factor of 2 when PSB coating mixture concentration is 2 mg mL$^{-1}$, and further increasing the PSB concentration reduces the protein adsorption by more than 1100%, almost completely eliminating the protein attachment to the substrates. The reduction of protein adsorption may be attributed to the formation of a bound water layer at the PSB-medium interfaces, significantly decreasing the electrostatic and hydrophobic interactions between the protein and substrate.

Example 8. Assessment of Cell Adhesion on PSB-Coated Cell Culture Well Plates

Figure 7A:
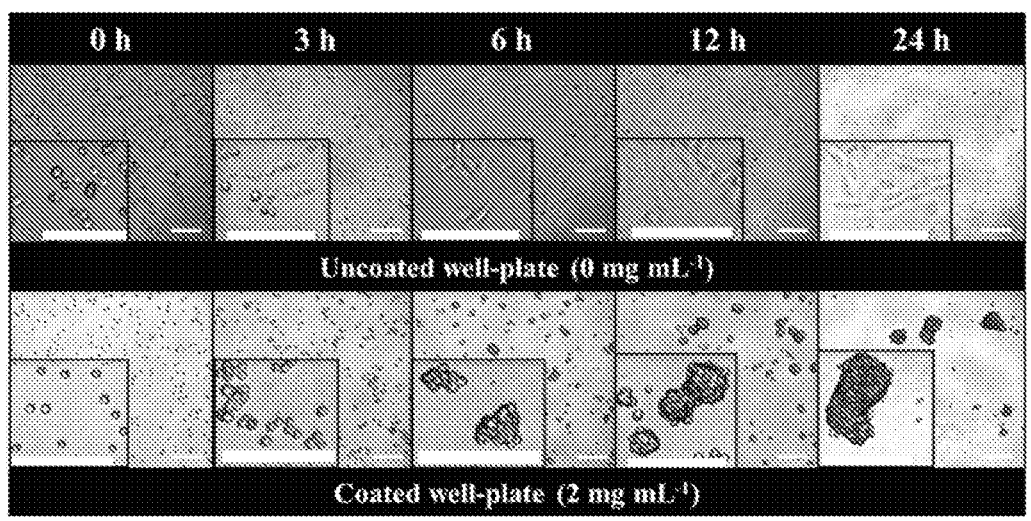
FIG. 7A illustrates bright field images of 2D NIH/3T3 fibroblast culture 0, 3, 6, 12, and 24 h post seeding on 96-well plates. Upper panel presents the cell behavior on unmodified PDMS substrates, indicating cell spreading initiated within ~3 h post seeding. After ~6 h, most of the cells are adhered and elongated on the unmodified PDMS substrate. In contrast, the PFPA-PSB coated PDMS substrates do not permit cell adhesion, maintaining the cells in the suspension form, which results in cell aggregation within a few hours post seeding.
Figure 7B:
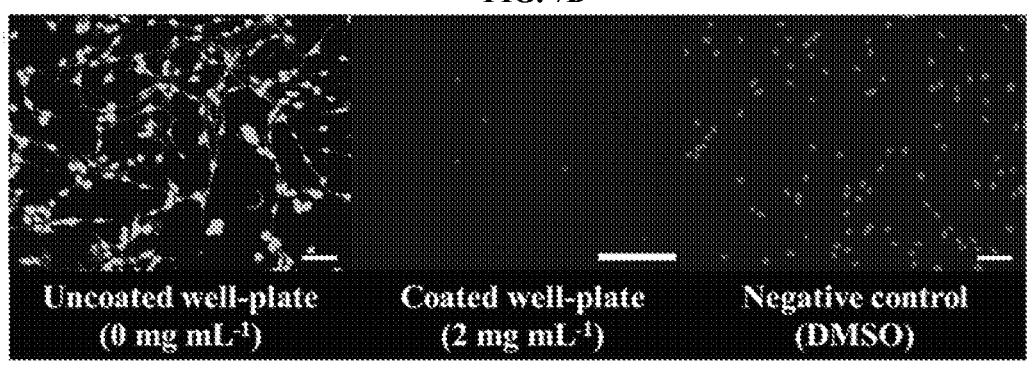
FIG. 7B illustrates live/dead staining of fibroblast cells after 24 h culture on the unmodified PDMS substrates shows that the cells adhere to the unmodified PDMS substrate and remain viable; however, no live cells were observed on PFPA-PSB coated PDMS substrates due to the lack of adhesion. The negative control shows that all the cells are dead in DMSO.
Figure 7C:
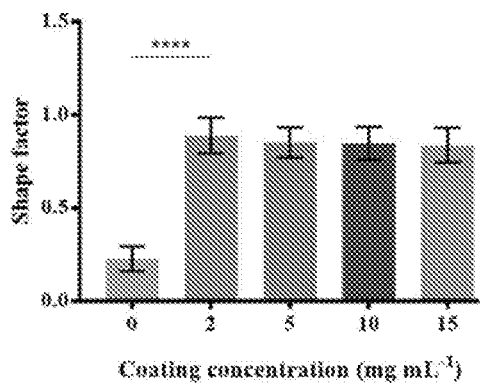
FIG. 7C illustrates shape factor of cells defined as $4\pi A/P^2$, where A is the cell surface area and P is the perimeter, is a measure of spreading (elongation) tendency, which shows that the cells cultured on the unmodified PDMS substrate undergoes spreading (shape factor near zero) and those cultured on the PFPA-PSB coated PDMS substrates are almost spherical (shape factor near one).
Figure 7D:
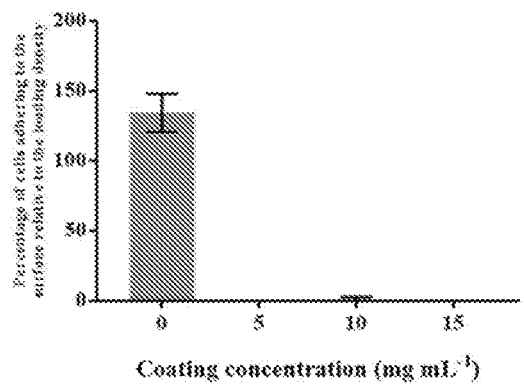
FIG. 7D illustrates the percent of cells adhered to unmodified PDMS substrates, showing the proliferation of adhered cells, compared with almost no cell attachment on PFPA-PSB modified PDMS substrates.

The behavior of NIH/3T3 fibroblast cells seeded on PSB-modified cell culture well-plates compared with uncoated wells was explored. Bright field images of uncoated wells (FIG. 7*a*) show that the cells tend to adhere and spread on the PDMS substrate within a few hours, whereas the PSB-modified wells completely inhibit the cell adhesion, resulting in cell detachment and aggregation in the medium. The insets of images show high magnification views of the cells for better visualization of their morphology. We have also stained the cells using a live/dead assay after 24 h of culture to assess their viability. Fibroblast cells cultured on uncoated well-plates and PSB-modified wells were fixed using the live/dead staining, as shown in FIG. 7*b*. While the uncoated wells permitted the attachment and survival of almost 100% of the cells, the PSB-modified substages prevented cell attachment, yielding cell death. The detached cells were washed off during the staining process. Note that the negative control includes the cell culture in DMSO, resulting in complete cell death. FIG. 7*c* presents the shape factor of cells, measured from $4\pi A/P^2$, where A is the cell surface area and P is the perimeter, obtained from analyzing at least 20 cells. When the shape factor is ~1, the cells adopt a spherical shape, and the elongated cells render the shape factor <<1, reaching 0 for a line. The shape factor of cells cultured on uncoated well plates is approximately 0.2, attesting to an elongated morphology as a result of cell spreading. At a PSB concentration >2 mg mL$^{-1}$, the shape factor of cells >0.85, showing a near-spherical morphology. Furthermore, the percentage of cell adhered to the substrate normalized with the seeded cells is presented in FIG. 7*d*, which shows while the uncoated substrate allows for cell proliferation (reflected in the values >100%), the coated substrates do not support adhesion.

Figure 8:
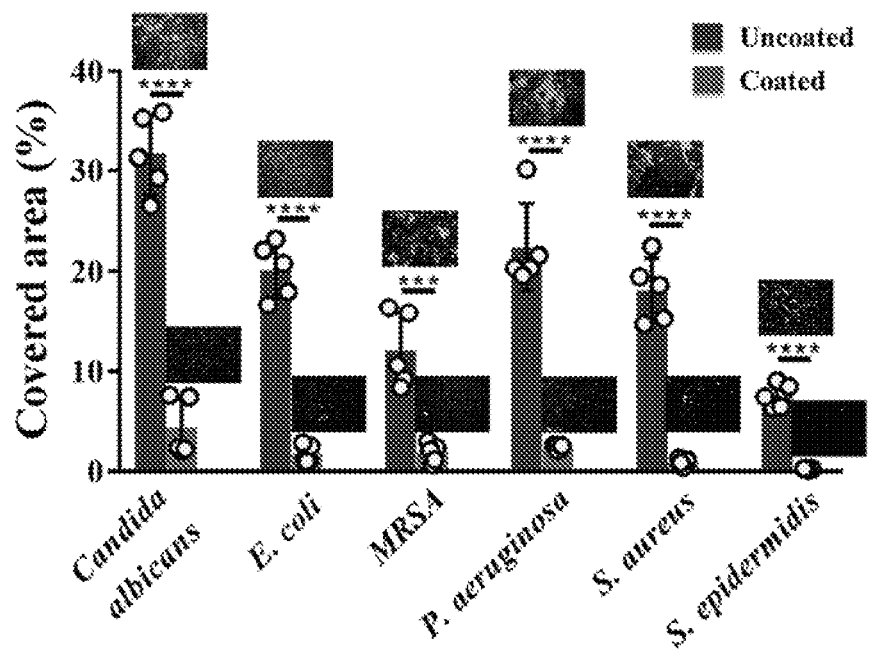
FIG. 8 illustrates the fluorescent microscopy images and quantitative analysis results from microbial adhesion after 24-48 hours of incubation on PFPA-PSB modified and unmodified surfaces.

Example 9. Fluorescent Microscopy Images and Quantitative Analysis of Microbial Adhesion Fluorescent microscopy images and quantitative analysis results from microbial adhesion after 24-48 hours of incubation on PSB-modified and unmodified surfaces were obtained (FIG. 8). Several gram-negative, gram-positive, biofilm forming strains and one fungus were incubated directly on bare and PSB coated PDMS sheets and analyzed with fluorescent microscopy. The PSB-modified surfaces exhibit significant decrease in bacterial and fungal adhesion and biofilm formation compared to the unmodified surface across all strains. The zwitterionic coating strongly binds water electrostatically, preventing adhesion of bacterial surface proteins that facilitate attachment and activation of the biofilm forming cascade.

Example 10. Assessment of Protein and Bacterial Adhesion on PSB-Coated PDMS Microfluidic Channels Under Flow Microfluidics systems utilizing a PDMS substrate provide a useful platform to study the effect of the PSB coating on protein and cellular adhesion under both static and flow conditions. Two sets of experiments were performed; fluorescent fibrinogen was chosen as a model protein and *Escherichia coli* containing Green Fluorescent Protein (GFP) was chosen as model bacteria. For these experiments, microfluidic channels of 1 mm diameter were fabricated. As PDMS is a relatively UV transparent material, the modified channels were obtained by flowing the PSB containing mixture into the channel and irradiating with UV light. DI water was then flowed through the channel to remove any unbound material.

Figure 9A:
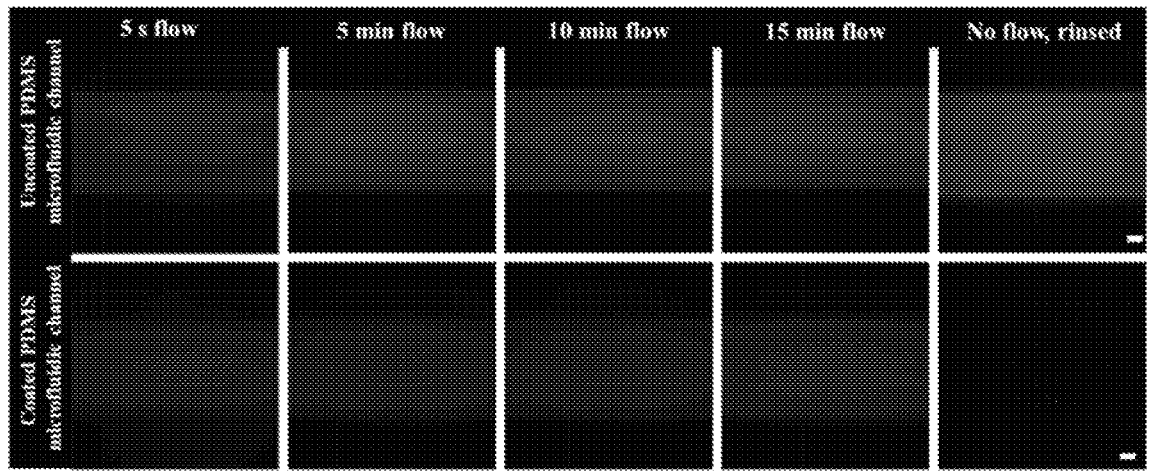
FIG. 9A illustrates fluorescent images of Alexa Fluor 488-conjugated fibrinogen flow in microfluidic channels. In 15 min, the intensity in uncoated channels significantly increases, showing a time-dependent, fast deposition of the protein in the channel. The PFPA-PSB coated channels remain resistant against protein adsorption, and upon rinsing with Milli-Q water, no adsorbed protein can be observed.
Figure 9B:
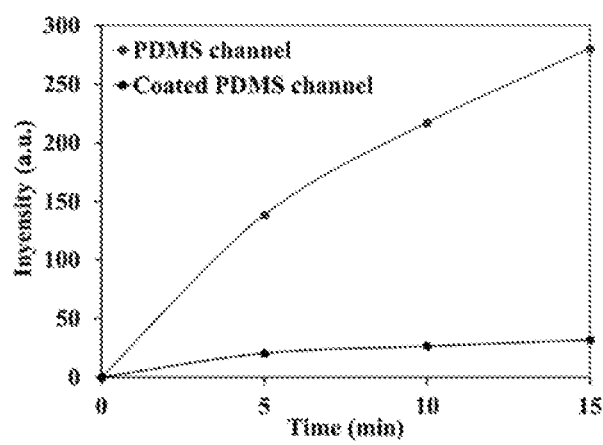
FIG. 9B illustrates quantification of fibrinogen adsorption to PDMS microfluidic channels under flow. Without PFPA-PSB coating, the channels undergo monotonic protein adsorption over time within 15 min; however, the PFPA-PSB coated channels do not show any significant protein adsorption. The arbitrary intensity of fluorescent, a measure of protein adsorption, shows that within 15 min, the fibrinogen deposition in the uncoated channel is 12000% more than the coated channel. Rinsing with water washes all the proteins in the PFPA-PSB coated channel.
Figure 9C:
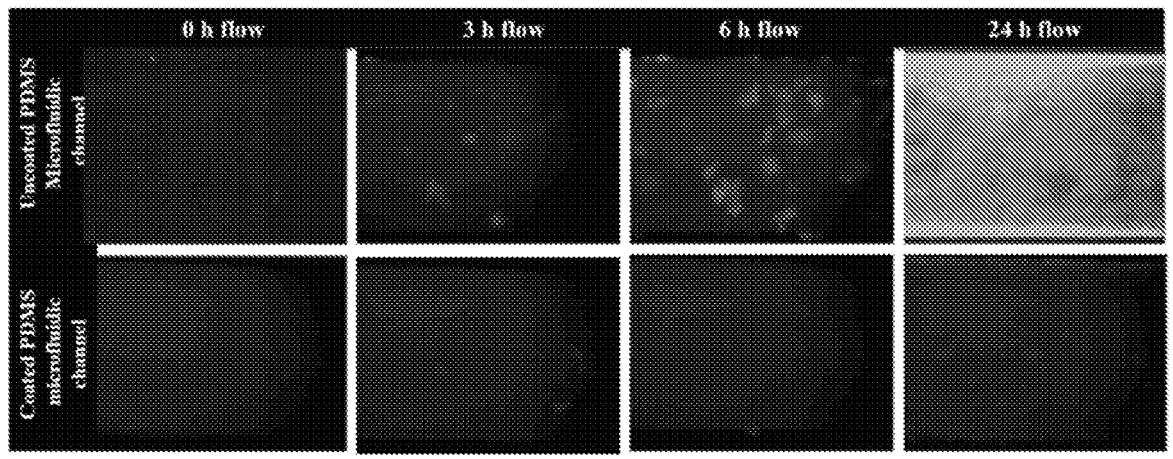
FIG. 9C illustrates adsorption of fluorescent (ATCC 25922GFP) *Escherichia coli* to the PDMS microfluidic channel under flow within 24 h shows that the uncoated channels permit a full coverage, whereas, the PFPA-PSB coated channels do not support bacterial adhesion.

Fluorescent fibrinogen was selected as the model protein for this study due to its availability and the role of fibrinogen in blood clotting, as discussed in the introduction. For both the flow and static experiments, a solution of 10 μg mL$^{-1}$ fluorescent fibrinogen in DI water was prepared. For the flow experiment (FIG. 9a), the microfluidic channels were placed under a microscope as the solution was extruded through a syringe via syringe pump at a rate of 10 ul/min. Images were taken at the time the channels were filled (0 minutes) and every 5 minutes after that with an exposure of 1 s. The increased fluorescence seen in each of the images compared to the first image of the sequence can be attribute to the adhesion of the fluorescent fibrinogen to the walls of the channel. The difference between the images of the bare PDMS and PSB-PDMS at 0 minutes is due to adhesion of the fluorescent fibrinogen as the channel was filled. Using ImageJ, the mean gray value representing the average fluorescent intensity for each image was determined and the percentage increase relative to the initial (0 Minute) image was calculated. The bare PDMS fluorescent intensity increased by 138.3%, 217.2%, and 280.3% for the 5, 10, and 15 minute images respectively. For the PSB-PDMS coated channel, there were fluorescent intensity increases of 20.5%, 26.5%, and 31.9% for the 5, 10, and 15 minute images respectively. For the static adhesion experiment (FIG. 9b), the channels were again filled with the 10 ug/mL solution of fluorescent fibrinogen in DI water. The solution was allowed to sit for 30 minutes before DI water was flowed through the channel at a rate of 10 ug/mL for 2 minutes to remove any unbound protein. An image was then taken of each channel at an exposure of 500 ms. There is significant adhesion to the bare PDMS channel and virtually no adhesion to the PSB-PDMS channel.

Example 11. Cytotoxicity of Un-Crosslinked and Crosslinked PSB

Figure 10A:
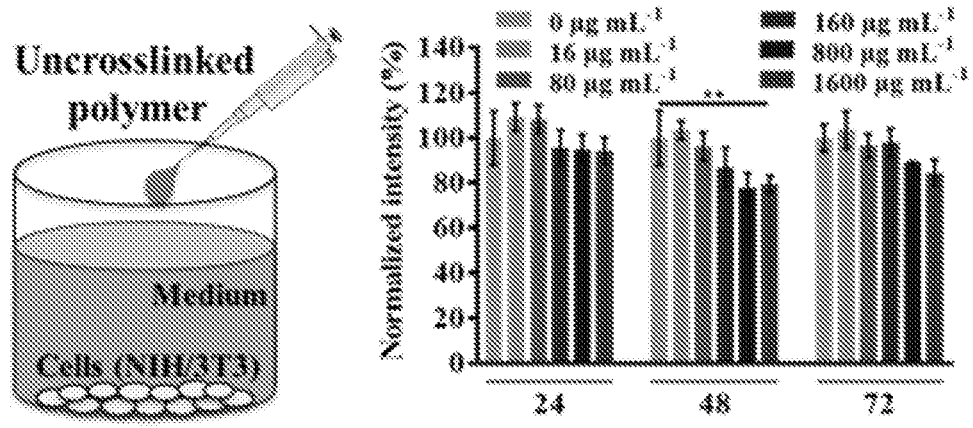
FIG. 10A illustrates assessing the cytotoxicity of un-crosslinked PSB by adding a desirable amount of the polymer to the cell culture media of 2D cultured fibroblast cells and measuring the metabolic activity of cells using MTT assay. Fluorescent intensity shows that the cells, regardless of the PSB concentration (up to 1.6 mg mL$^{-1}$) are able to well metabolize the cell membrane-permeable tetrazolium dye MTT, which attests to the insignificant effect of PSB on the cell viability.
Figure 10B:
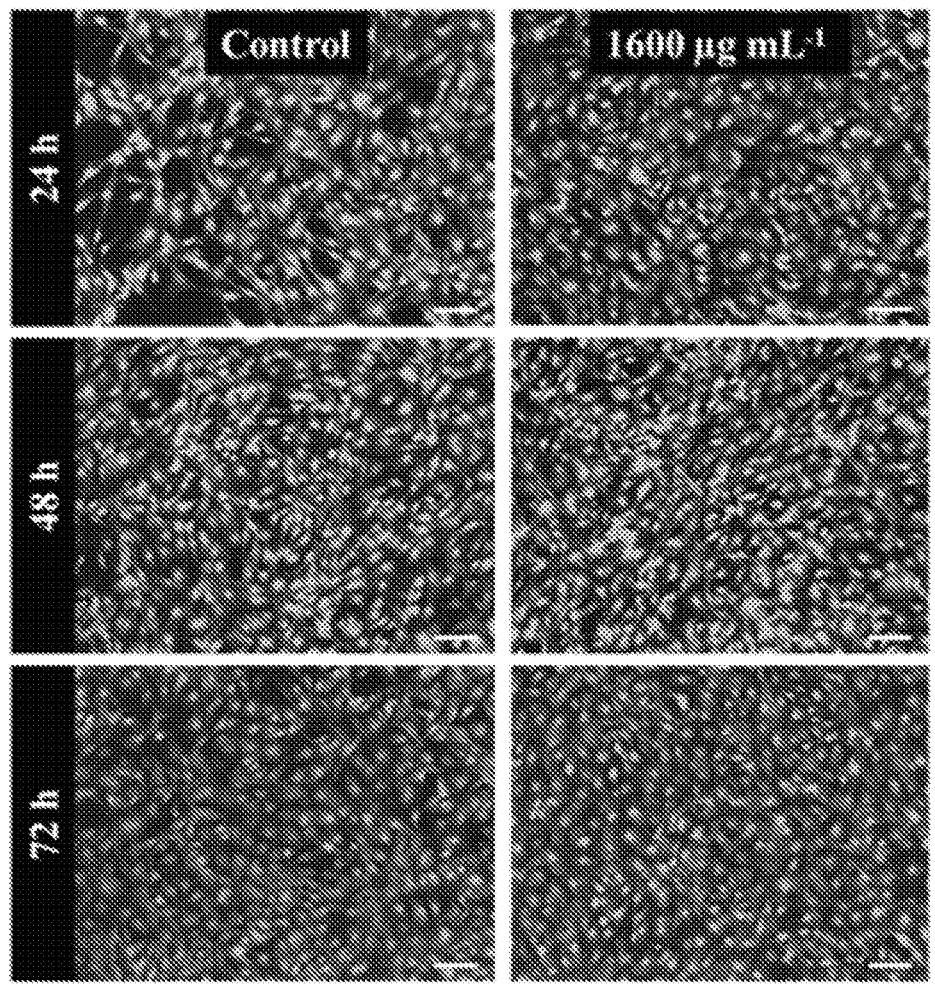
FIG. 10B illustrates live/dead staining of the fibroblast cells culture in 2D in the presence of un-crosslinked PBS shows a 100% viability of cells within 72 h. The controls show the cells cultured in the absence of PSB.
Figure 10C:
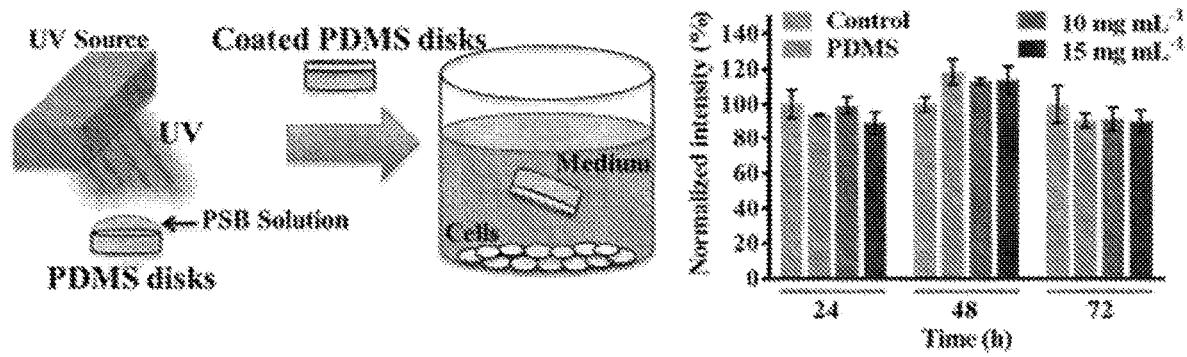
FIG. 10C illustrates the cytotoxicity of crosslinked PSB was investigated by coating it on PDMS discs, followed by incubating the discs in the cell culture media of 2D cultured fibroblast cells. The metabolic activity of the cells does not show any significant difference with the PSB-free control.
Figure 10D:
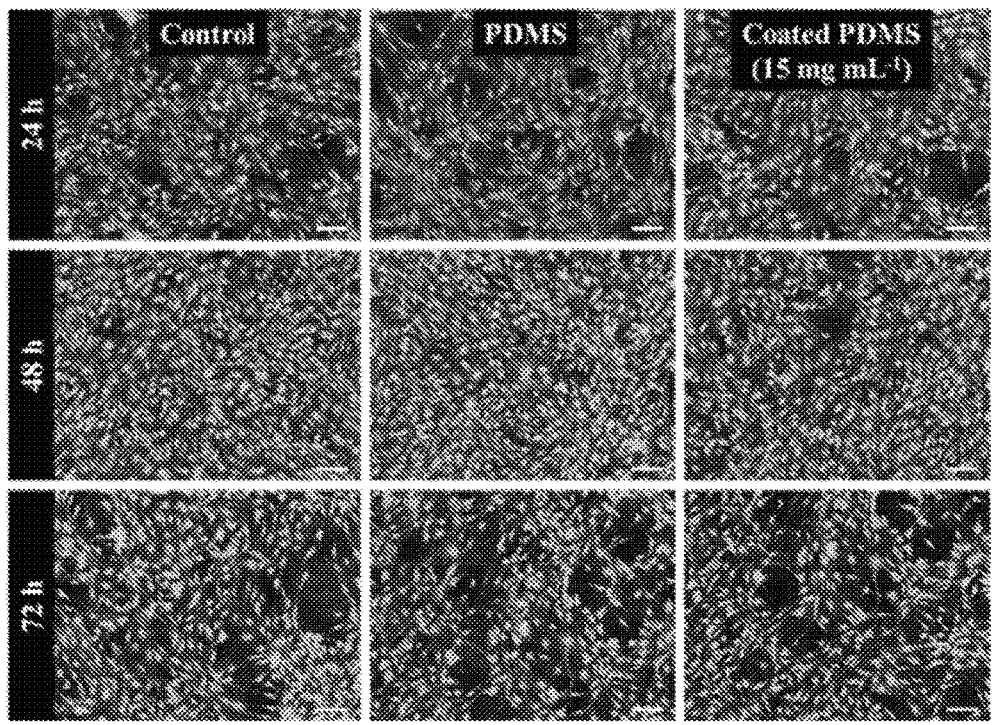
FIG. 10D depicts live/dead staining of the fibroblasts cells cultured in the presence of crosslinked PSB shows that almost no cell is compromised compared to the PSB-free controls. Accordingly, un-crosslinked and crosslinked PSB are both non-toxic for the cells, rendering this material suitable for coating medical devices that are in contact with cells.

The cytotoxicity of PSB before crosslinking was investigated by adding un-crosslinked PSB to the cell culture media and monitoring the behavior of 2D cultured fibroblast cells within 72 h, as shown schematically in FIG. 10a. The metabolic activity of cells is quantified based on the reduction of MTT by viable, metabolically active cells, reflected in the fluorescent intensity alteration due to the formation of intracellular purple formazan. The fluorescent intensity was normalized with the fluorescent intensity obtained from the cells in PSB-free media in days 1, 2, and 3, which shows that up to 1.6 mg mL$^{-1}$ of PSB does not induce any significant decrease in the metabolic activity of cells, i.e., PSB does not compromise the cell viability. Staining the cells using the live/dead assay, presented in FIG. 10b, shows that the behavior of cells exposed to un-crosslinked PSB is similar to PSB-free cells, which all exhibit a 100% viability. The toxicity of crosslinked PSB (coating) was also assessed by coating it on PDMS discs and incubating the discs in the cell culture media of 2D fibroblast cell culture, as schematically shown in FIG. 10c. The metabolic activity of cells incubated with the PDMS substrates or PSB-coated PDMS substrates in the media are identical to the control, attesting to the biosafety of the coatings. The live/dead staining (FIG. 10d) of the fibroblast cells incubated with the coated PDMS shows no sign of toxicity (dead cells), which further confirms that the crosslinked PSB does not impose any cytotoxicity to the cells. Accordingly, PSB provides a safe platform for coating substrates, e.g., medical devices, that are directly in contact with cells.

Example 12. Contact Lens Modification and Characterization

There are over 140 million wearers of contact lenses (CL) worldwide, roughly 50% percent of whom report dryness or discomfort resulting in as much as 26% of wearers to discontinue usage of the product within the first year. According to a study by Zion Market Research, the contact lens market was valued at 10.91 billion USD in 2017 and is expected to grow at a rate of 7.1% annually through 2024. There is therefore significant interest in next generation contact lenses with superior material and surface properties which reduce wearer discomfort.

Hydrogels have become the predominant material of choice for contact lenses due to their high oxygen permeability and wettability. Surface lubricity, lens hydration, oxygen permeability, and protein/bacterial adhesion are all factors that affect the frequency of contact lens discomfort. It has been shown that surface modification of the contact lenses leading to enhanced physical surface properties improves reported wearer comfort. While several promising surface modifications have been presented, most of the surface modification strategies employed require expensive chemicals/equipment or extended manufacturing times making it difficult to scale these processes at the low costs necessary for contact lenses.

Radical initiated polymerization through methacrylate/ methacrylamide linkages to produce a perfluorophenyl azide-polysulfobetaine (PFPA-PSB) copolymer was used for coating of contact lenses. The copolymer was mixed with water at different concentrations to make a coating mixture. The contact lenses are immersed in the coating mixture and the coating is grafted to the surface upon exposure to 254 nm UV light under ambient conditions.

Two forms of modified contact lenses were presented. The first, (PFPA-PSB modified) was simply immersed in a mixture of PFPA-PSB in DI water at a concentration of 10 mg/mL and subjected to 254 nm UV light for 15 minutes. The second, (ethanol treated, PFPA-PSB modified) was soaked in ethanol for 5 minutes prior to being immersed in the PFPA-PSB mixture and subject to UV light. Three different types of contact lenses were purchased for this work: Acuve Oasys (two week use), Acuve Moist (one day use), and Acuve Oasys with Hydraluxe (one day use). For each type of lens, a control sample, a PFPA-PSB Modified sample, and an ethanol treated, PFPA-PSB modified sample were used.

Figure 11:
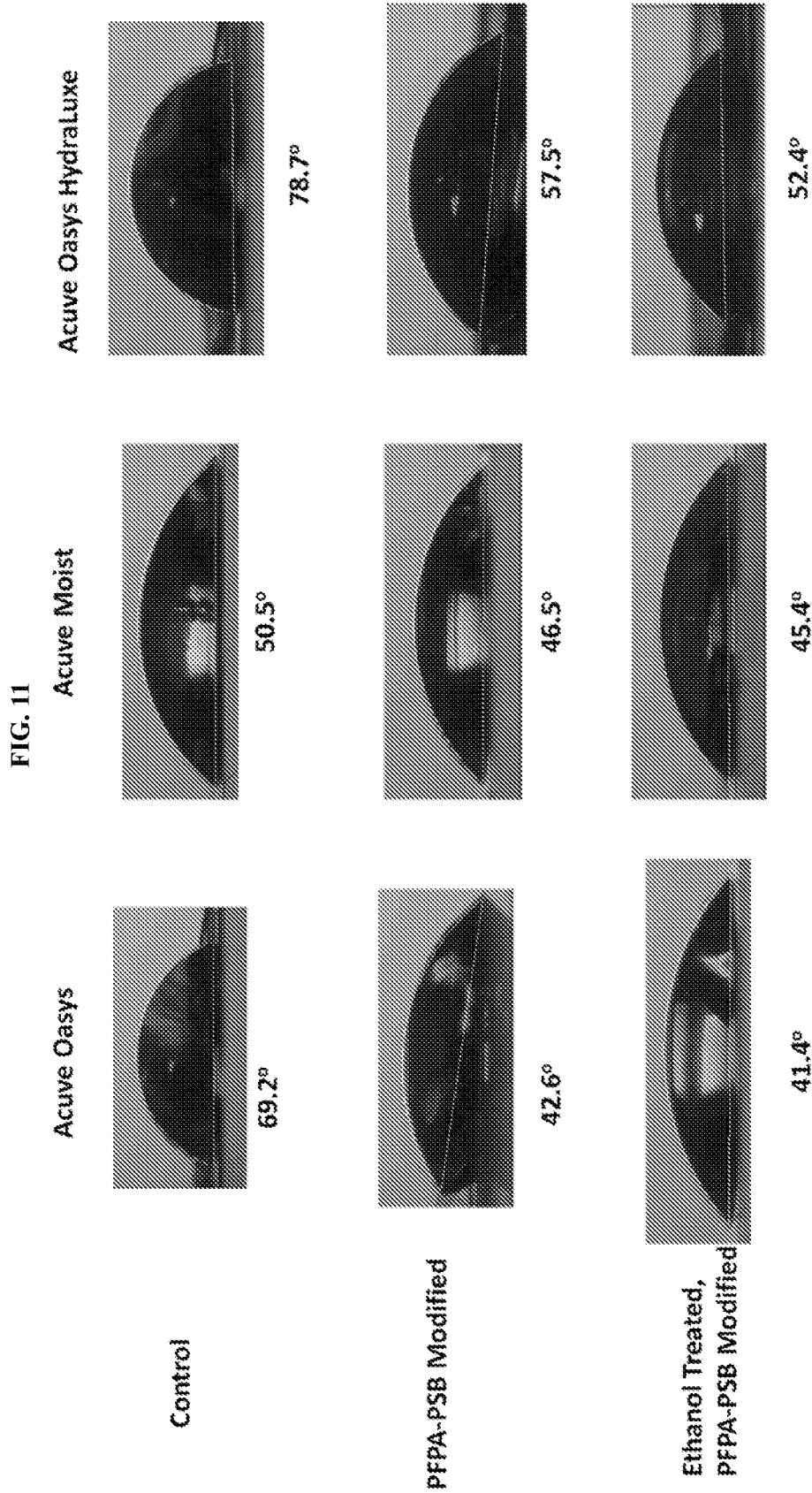
FIG. 11 illustrates contact angle measurements on control, PFPA-PSB modified, and ethanol treated, PFPA-PSB modified samples.

Contact angle measurements were taken using a goniometer and DI water (FIG. 11). In all cases, the modified samples exhibit a lower contact angle than the controls indicating that the modification induces a more hydrophilic surface.

Figure 12:
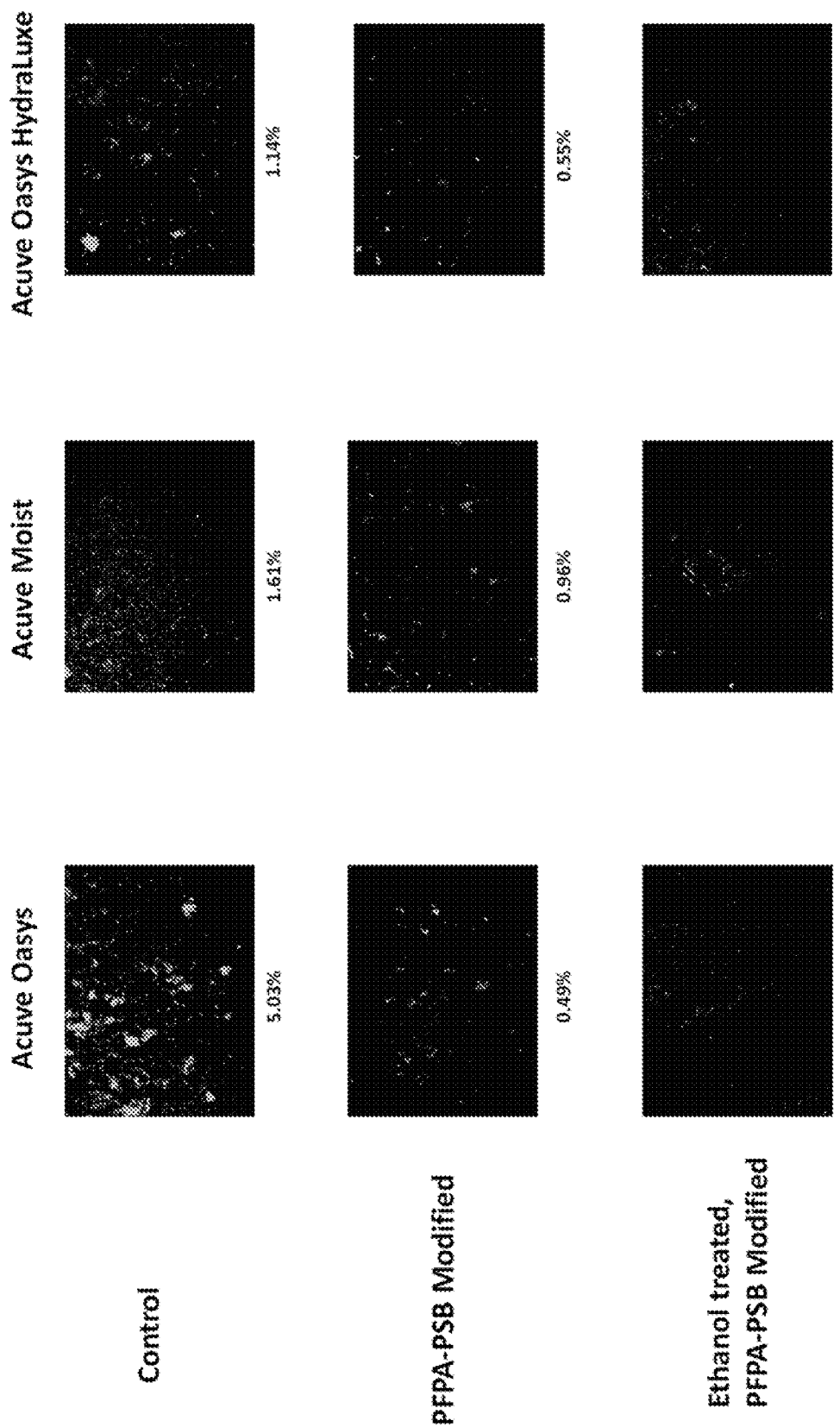
FIG. 12 illustrates bacterial adhesion images on control, PFPA-PSB modified, and ethanol treated, PFPA-PSB modified samples using *Escherichia coli*. The values presented next to the images are the average percent area coverage for the three images taken on each sample.

A bacterial adhesion test was then performed using *Escherichia coli*. Contact lens samples were incubated in a solution of *Escherichia coli* for 24 hours, then rinsed with DI water, stained using a SYTO 9 dye solution, and then rinsed again to remove any unbound dye. The samples were then imaged using a fluorescent microscope at 485 nm with 240 millisecond exposure. Three images were taken of each sample and the number of fluorescent pixels were quantified using imageJ to obtain a Percent Area Coverage value for each image. These values were averaged for each sample to obtain an Average Percent Area Coverage Value, which is presented in FIG. 12 along with one of the images taken for each sample.

Figure 13:
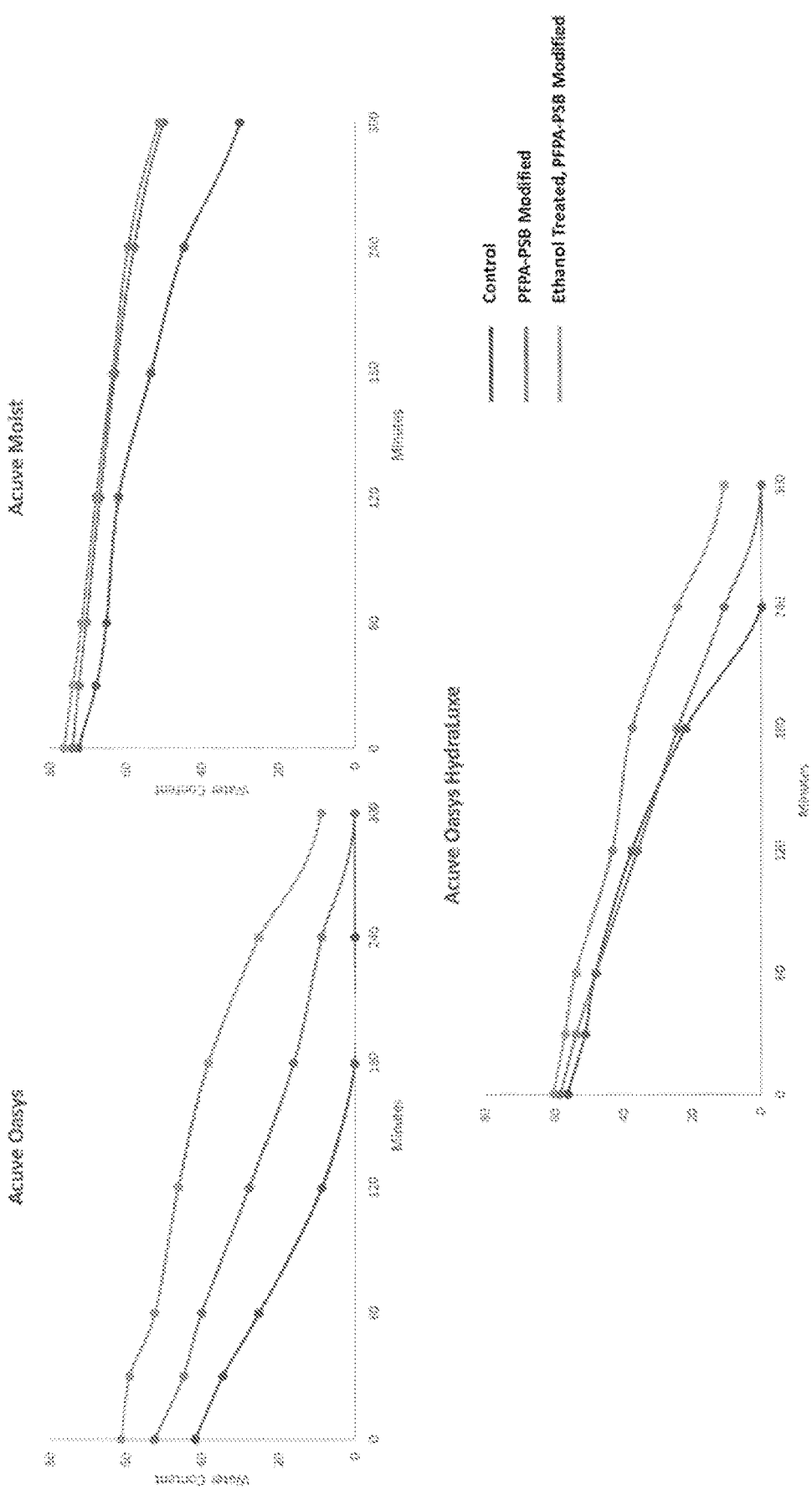
FIG. 13 illustrates a timed drying experiment on control, PFPA-PSB modified, and ethanol treated, PFPA-PSB modified samples using three different types of commercial contact lenses.

A timed drying experiment was then performed in which the contact lenses were immersed in DI water for 24 hours and then removed an allowed to dry in uncapped scintillation vials. The mass of each contact lens was recorded at 0 Minutes, 30 Minutes, 60 Minutes, 120 Minutes, 180 Minutes, 240 Minutes, and 300 Minutes. The contacts were then placed in a vacuum chamber overnight to remove any remaining water and obtain the dry weight of each lens. A Water Content value was then obtained by subtracting the dry weight from the observed weight at each time point and dividing that value by the observed weight. The results are presented in FIG. 13, it is clear in all cases that the modified samples exhibit superior water retention.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

Numbered Embodiments

The following embodiments recite nonlimiting permutations of combinations of features disclosed herein. Other permutations of combinations of features are also contemplated. In particular, each of these numbered embodiments is contemplated as depending from or relating to every previous or subsequent numbered embodiment, independent of their order as listed.

Embodiment 1 is a compound that has the structure of Formula (I):

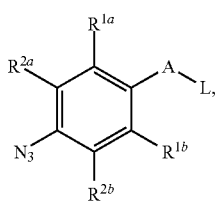

Formula (I)

wherein

A is selected from $-C(=O)-$, $-S(=O)-$, $-S(=O)_2-$, and $-S(=O)(-NR^3)-$;

L is selected from $-OQ$, $-NR^3Q$, and $-N(R^3)_2Q^+$;

Q is a structure represented by a formula:

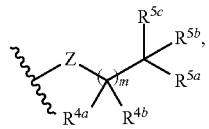

Z is selected from $-CR^{6a}R^{6b}-$, $-C(=O)-$, $-C(=NH)-$, and $-C(=NH)NR^7-$;

m is an integer selected from 0, 1, 2, 3, 4, 5, 6, 7, and 8;

each $R^{1a}$ and $R^{1b}$ is independently selected from hydrogen and halogen;

each $R^{2a}$ and $R^{2b}$ is independently selected from halogen, $-CN$, and optionally substituted C1-C6fluoroalkyl;

each $R^3$ is independently selected from hydrogen, optionally substituted C1-C4 alkyl, $-X$-optionally substituted C1-C4 alkyl, optionally substituted aryl, and $-X$-optionally substituted aryl;

X is $-C(=O)-$, $-S(=O)-$, or $-S(=O)_2-$;

each $R^{4a}$, $R^{4b}$, $R^{5a}$, $R^{5c}$, $R^{6a}$, and $R^{6b}$ is independently selected from hydrogen, halogen, $-CN$, $-OH$, optionally substituted C1-C4 alkyl, optionally substituted C1-C4 fluoroalkyl, optionally substituted aryl, $-NR^{8a}R^{8b}$, $-NR^{8a}R^{8b}R^{8c+}$, $-S(=O)_2O^-$, $-S(=O)_2 OR^9$, $-C(=O)O^-$, and $-C(=O)OR^9$;

$R^{5b}$ is $-NR^{10a}R^{10b}$ or $-NR^{10a}R^{10b}R^{10c+}$, each $R^7$, $R^{8a}$, $R^{8b}$, $R^{8c}$, and $R^9$ is independently selected from hydrogen and optionally substituted C1-C4 alkyl, and optionally substituted aryl;

each $R^{10a}$ and $R^{10c}$ is independently selected from hydrogen, optionally substituted C1-C4 alkyl, optionally substituted aryl, -(optionally substituted C1-C8alkylene)$S(=O)_2O^-$, -(optionally substituted C1-C8alkylene)$S(=O)_2OH$, -(optionally substituted C1-C8alkylene)$C(=O)O^-$, and -(optionally substituted C1-C8alkylene)$C(=O)OH$; and $R^{10b}$ is $-(C=O)-C2$-C6alkenyl, $(S=O)-C2$-C6alkenyl, or $(S=O)_2-C2$-C6alkenyl.

Embodiment 2 is the compound of embodiment 1, wherein the compound has a structure selected from:

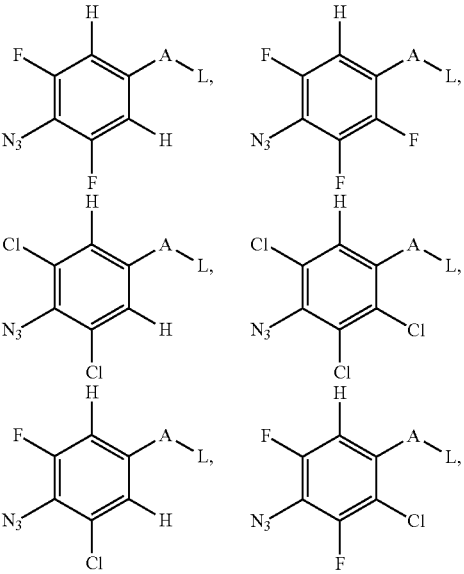

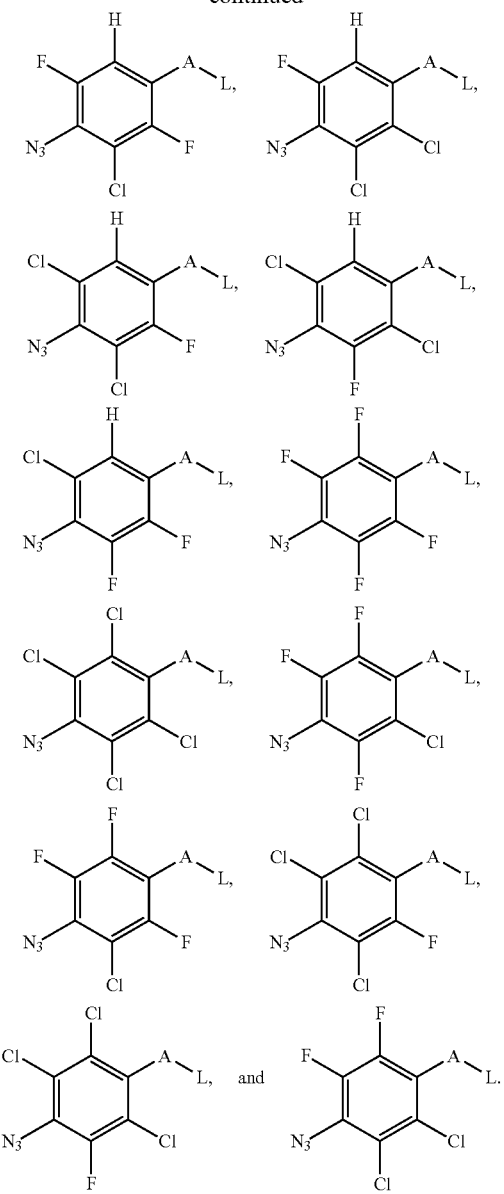

Embodiment 3 is the compound of embodiment 1 or 2, wherein the compound has a structure selected from:

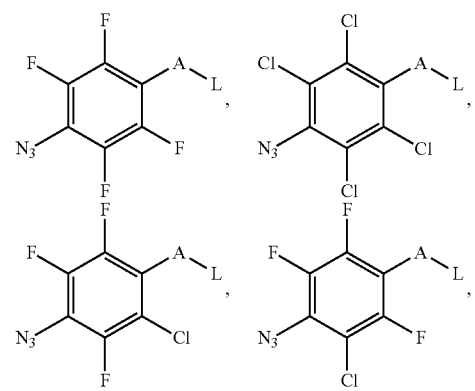

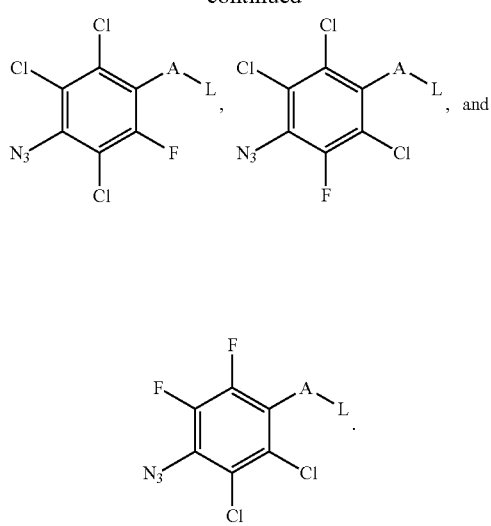

Embodiment 4 is the compound of any one of embodiments 1-3, wherein the compound has the following structure:

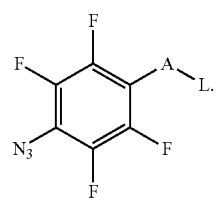

Embodiment 5 is the compound of embodiment 1, wherein the compound has the structure selected from:

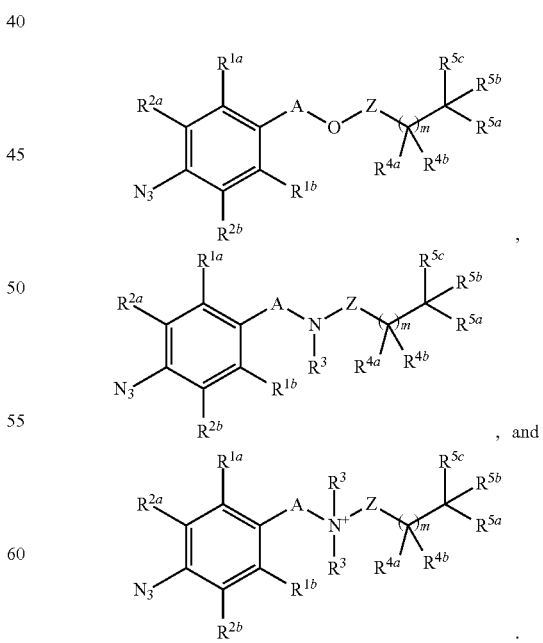

Embodiment 6 is the compound of embodiment 1, wherein the compound has the following structure:

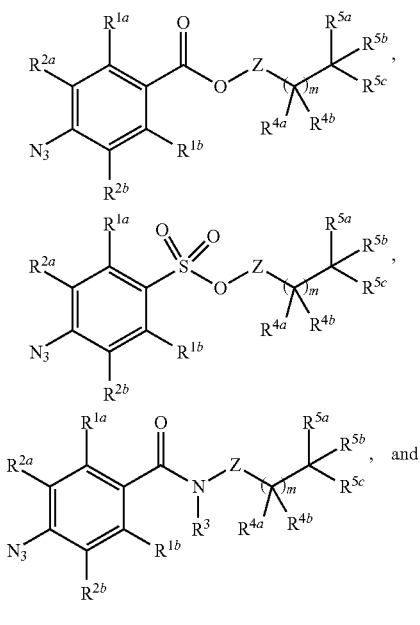

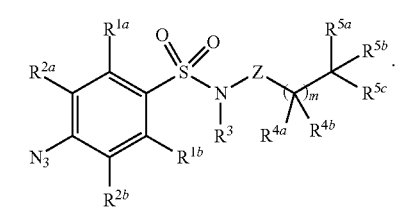

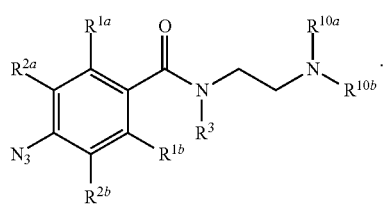

Embodiment 7 is the compound of embodiment 5 or 6, wherein $R^{1a}$, $R^{1b}$, $R^{2a}$, and $R^{2b}$ are each —F.

Embodiment 8 is the compound of any one of embodiments 1-7, wherein Z is —$CR^{6a}R^{6b}$—.

Embodiment 9 is the compound of embodiment 8, wherein $R^{6a}$ and $R^{6b}$ are each hydrogen.

Embodiment 10 is the compound of any one of embodiments 1-9, wherein m is 0, 1, 2, or 3.

Embodiment 11 is the compound of embodiment 10, wherein m is 0.

Embodiment 12 is the compound of any one of embodiments 1-11, wherein $R^{5a}$ is hydrogen; $R^{5b}$ is —$NR^{10a}R^{10b}$; and $R^{5c}$ is hydrogen.

Embodiment 13 is the compound of embodiment 1, wherein the compound has the structure of Formula (Ia):

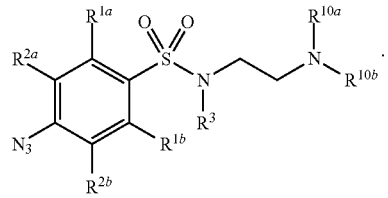

Embodiment 14 is the compound of embodiment 1, wherein the compound has the structure of Formula (Ib):

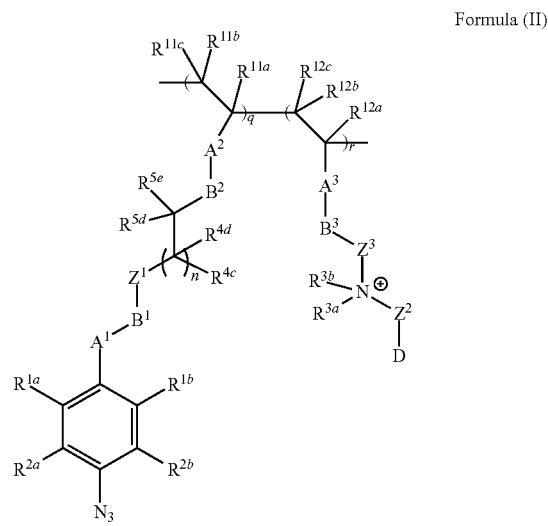

Embodiment 15 is the compound of embodiment 13 or 14, wherein $R^{10a}$ is hydrogen.

Embodiment 16 is the compound of any one of embodiments 13-15, wherein $R^3$ is hydrogen.

Embodiment 17 is a compound that has the structure of Formula (II):

Formula (II)

wherein
each $R^{1a}$ and $R^{1b}$ is independently selected from hydrogen and halogen;
each $R^{2a}$ and $R^{2b}$ is independently selected from halogen, —CN, and optionally substituted C1-C6fluoroalkyl;
each $A^1$, $A^2$, and $A^3$ is independently selected from —C(=O)—, —S(=O)—, —S(=O)$_2$—, and —S(=O)(=$NR^{3c}$)—;
each $B^1$, $B^2$, and $B^3$ is independently selected from —O— and —$NR^{3c}$—;
D is —S(=O)$_2$O$^-$, —S(=O)$_2$O$R^{9a}$, —C(=O)O$^-$, or —C(=O)O$R^{9a}$;
$Z^1$ is —$(CR^{6c}R^{6d})_s$—;
$Z^2$ is —$(CR^{6c}R^{6d})_t$—;
$Z^3$ is —$(CR^{6c}R^{6d})_p$—;
each $R^{3a}$ and $R^{3b}$ is independently selected from hydrogen, optionally substituted C1-C4 alkyl, and optionally substituted benzyl;
each $R^{3c}$ and $R^{3d}$ is independently selected from hydrogen, optionally substituted C1-C4 alkyl, —X-optionally substituted C1-C4 alkyl, optionally substituted C2-C6 alkenyl, and optionally substituted aryl;
X is —C(=O)—, —S(=O)—, or —S(=O)$_2$—;
each $R^{4c}$, $R^{4d}$, $R^{5d}$, $R^{5e}$, $R^{6c}$, and $R^{6d}$ is independently selected from hydrogen, halogen, —CN, —OH, optionally substituted C1-C4 alkyl, optionally substituted C1-C4 fluoroalkyl, optionally substituted C2-C6 alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;

each R$^{9a}$, R$^{11a}$, R$^{11b}$, R$^{12a}$, R$^{12b}$ and R$^{12c}$ is independently selected from hydrogen, optionally substituted C1-C4 alkyl, and optionally substituted aryl;

n is an integer selected from 0, 1, 2, 3, 4, 5, and 6;
s is an integer selected from 1, 2, 3, 4, or 5;
t is an integer selected from 1, 2, 3, 4, or 5;
p is an integer selected from 1, 2, 3, 4, or 5;
q is an integer selected from 40-60;
r is an integer selected from 1-10; and
wherein the compounds of Formula (II) is charged or zwitterionic.

Embodiment 18 is the compound of embodiment 17, wherein each R$^{1a}$ and R$^{1b}$ is independently halogen.

Embodiment 19 is the compound of embodiment 17 or 18, wherein each R$^{1a}$ and R$^{1b}$ is independently F or Cl.

Embodiment 20 is the compound of any one of embodiments 17-19, wherein R$^{1a}$ and R$^{1b}$ are each F.

Embodiment 21 is the compound of any one of embodiments 17-20, wherein each R$^{2a}$ and R$^{2b}$ is independently selected from halogen, —CN, and —CF$_3$;

Embodiment 22 is the compound of any one of embodiments 17-21, wherein each R$^{2a}$ and R$^{2b}$ is independently selected from F, Cl, —CN, and —CF$_3$;

Embodiment 23 is the compound of any one of embodiments 17-22, wherein R$^{2a}$ and R$^{2b}$ are each F.

Embodiment 24 is the compound of any one of embodiments 17-23, wherein A$^1$ is —S(=O)$_2$—; A$^2$ is —C(=O)—; and A$^3$ is —C(=O)—.

Embodiment 25 is the compound of embodiment 24, wherein B$^1$ and B$^2$ are each —NR$^{3c}$—.

Embodiment 26 is the compound of embodiment 25, wherein R$^{3c}$ is hydrogen or —CH$_3$.

Embodiment 27 is the compound of embodiment 26, wherein R$^{3c}$ is hydrogen.

Embodiment 28 is the compound of embodiment 24, wherein B$^3$ is —O—.

Embodiment 29 is the compound of any one of embodiments 17-28, wherein D is —S(=O)$_2$OR$^{9a}$ or —C(=O)OR$^{9a}$.

Embodiment 30 is the compound of embodiment 29 wherein R$^{9a}$ is hydrogen or —CH$_3$.

Embodiment 31 is the compound of any one of embodiments 17-28, wherein D is —S(=O)$_2$O$^-$ or —C(=O)O$^-$.

Embodiment 32 is the compound of embodiment 31, wherein D is —S(=O)$_2$O$^-$.

Embodiment 33 is the compound of any one of embodiments 17-32, wherein each R$^{6c}$ and R$^{6d}$ is hydrogen.

Embodiment 34 is the compound of any one of embodiments 17-33, wherein each R$^{3a}$ and R$^{3b}$ is —CH$_3$.

Embodiment 35 is the compound of any one of embodiments 17-34, wherein R$^{11a}$ is hydrogen or —CH$_3$.

Embodiment 36 is the compound of embodiment 35, wherein R$^{11a}$ is —CH$_3$.

Embodiment 37 is the compound of any one of embodiments 17-36, wherein R$^{12a}$ is hydrogen or —CH$_3$.

Embodiment 38 is the compound of embodiment 37, wherein R$^{12a}$ is —CH$_3$.

Embodiment 39 is the compound of any one of embodiments 17-38, wherein each R$^{11b}$, R$^{11c}$, R$^{12b}$, and R$^{12c}$ is hydrogen.

Embodiment 40 is a compound that has the structure of Formula (III):

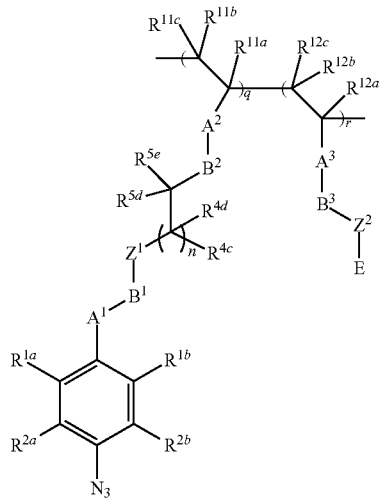

Formula (III)

wherein
each R$^{1a}$ and R$^{1b}$ is independently selected from hydrogen and halogen;
each R$^{2a}$ and R$^{2b}$ is independently selected from halogen, —CN, and optionally substituted C1-C6fluoroalkyl;
each A$^1$, A$^2$, and A$^3$ is independently selected from —C(=O)—, —S(=O)—, —S(=O)$_2$—, and —S(=O)(=NR$^{3c}$)—;
each B$^1$, B$^2$, and B$^3$ is independently selected from —O— and —NR$^{3c}$—;
Z$^1$ is —(CR$^{6c}$R$^{6d}$)$_s$—;
Z$^2$ is —(CR$^{6c}$R$^{6d}$)$_t$—;
E is —CN, —OR$^{9a}$, —NR$^{9a}$R$^{9b}$, —NR$^{9a}$R$^{9b}$R$^{9c+}$, optionally substituted C1-C4 alkyl, optionally substituted C1-C6fluoroalkyl, —S(=O)$_2$O$^-$, —S(=O)$_2$OR$^{9a}$, —C(=O)O$^-$, or —C(=O)OR$^{9a}$;
each R$^{4c}$, R$^{4d}$, R$^{5d}$, R$^{5e}$, R$^{6c}$, and R$^{6d}$ is independently selected from hydrogen, halogen, —CN, —OR$^{9a}$, optionally substituted C1-C4 alkyl, optionally substituted C1-C4 fluoroalkyl, optionally substituted C2-C6 alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;
each R$^{3c}$ and R$^{3d}$ is independently selected from hydrogen, optionally substituted C1-C4 alkyl, —X-optionally substituted C1-C4 alkyl, optionally substituted C2-C6 alkenyl, and optionally substituted aryl;
X is —C(=O)—, —S(=O)—, or —S(=O)$_2$—;
each R$^{9a}$, R$^{11a}$, R$^{11b}$, R$^{11c}$, R$^{12a}$, R$^{12b}$; and R$^{12c}$ is independently selected from hydrogen, optionally substituted C1-C4 alkyl, and optionally substituted aryl;
n is an integer selected from 0, 1, 2, 3, 4, 5, and 6;
s is an integer selected from 1, 2, 3, 4, or 5;
t is an integer selected from 1, 2, 3, 4, or 5;
q is an integer selected from 40-60; and
r is an integer selected from 1-10.

Embodiment 41 is the compound of embodiment 40, wherein each R$^{1a}$ and R$^{1b}$ is independently halogen.

Embodiment 42 is the compound of embodiment 40 or 41, wherein each R$^{1a}$ and R$^{1b}$ is independently F or Cl.

Embodiment 43 is the compound of any one of embodiments 40-42, wherein R$^{1a}$ and R$^{1b}$ are each F.

Embodiment 44 is the compound of any one of embodiments 40-43, wherein each R$^{2a}$ and R$^{2b}$ is independently selected from halogen, —CN, and —CF$_3$;

Embodiment 45 is the compound of any one of embodiments 40-44, wherein each $R^{2a}$ and $R^{2b}$ is independently selected from F, Cl, —CN, and —CF$_3$;

Embodiment 46 is the compound of any one of embodiments 40-45, wherein $R^{2a}$ and $R^{2b}$ are each F.

Embodiment 47 is the compound of any one of embodiments 40-46, wherein $A^1$ is —S(=O)$_2$—; $A^2$ is —C(=O)—; and $A^3$ is —C(=O)—.

Embodiment 48 is the compound of embodiment 47, wherein $B^1$ and $B^2$ are each —NR$^{3c}$—.

Embodiment 49 is the compound of embodiment 48, wherein $R^{3c}$ is hydrogen or —CH$_3$.

Embodiment 50 is the compound of embodiment 49, wherein $R^{3c}$ is hydrogen.

Embodiment 51 is the compound of embodiment 47, wherein $B^3$ is —NR$^{3c}$—.

Embodiment 52 is the compound of embodiment 51, wherein $R^{3c}$ is hydrogen.

Embodiment 53 is the compound of any one of embodiments 40-52, wherein E is —NR$^{9a}$R$^{9b}$R$^{9c+}$ or —S(=O)$_2$OR$^{9a}$.

Embodiment 54 is the compound of embodiment 53, wherein E is —NR$^{9a}$R$^{9b}$R$^{9c+}$.

Embodiment 55 is the compound of embodiment 54, wherein each $R^{9a}$, $R^{9b}$, or $R^{9c}$ is H or CH$_3$.

Embodiment 56 is the compound of embodiment 55, wherein each $R^{9a}$, $R^{9b}$, or $R^{9c}$ is H.

Embodiment 57 is the compound of embodiment 55, wherein each $R^{9a}$, $R^{9b}$, or $R^{9c}$ is —CH$_3$.

Embodiment 58 is the compound of embodiment 53, wherein E is —S(=O)$_2$OR$^{9a}$.

Embodiment 59 is the compound of embodiment 58, wherein $R^{9a}$ H or —CH$_3$.

Embodiment 60 is the compound of embodiment 59, wherein each $R^{9a}$ is H.

Embodiment 61 is the compound of embodiment 59, wherein each $R^{9a}$ is —CH$_3$.

Embodiment 62 is the compound of any one of embodiments 40-61, wherein each $R^{6c}$ and $R^{6d}$ is independently selected from hydrogen and —CH$_3$.

Embodiment 63 is the compound of any one of embodiments 40-62, wherein each $R^{3a}$ and $R^{3b}$ is —CH$_3$.

Embodiment 64 is the compound of any one of embodiments 40-63, wherein $R^{11a}$ is hydrogen or —CH$_3$.

Embodiment 65 is the compound of embodiment 64, wherein $R^{11a}$ is —CH$_3$.

Embodiment 66 is the compound of any one of embodiments 40-65, wherein $R^{12a}$ is hydrogen or —CH$_3$.

Embodiment 67 is the compound of embodiment 66, wherein $R^{12a}$ is —CH$_3$.

Embodiment 68 is the compound of any one of embodiments 40-67, wherein each $R^{11b}$, $R^{11c}$, $R^{12b}$, and $R^{12c}$ is hydrogen.

Embodiment 69 is a medical device coated with a compound of any one of embodiments 1-68.

Embodiment 70 is a biofouling-resistant medical device, wherein a surface of the medical device is coated with a phenyl azide-based copolymer having a number-average molecular weight of between about 10,000 and about 250,000.

Embodiment 71 is the biofouling-resistant medical device of embodiment 70, wherein the phenyl azide-based copolymer has a number-average molecular weight of between about 10,000 and about 20,000.

Embodiment 72 is the biofouling-resistant medical device of embodiment 70, wherein the phenyl azide-based copolymer has a number-average molecular weight of between about 10,000 and about 40,000.

Embodiment 73 is the biofouling-resistant medical device of embodiment 70, wherein the phenyl azide-based copolymer has a number-average molecular weight of between about 20,000 and about 60,000.

Embodiment 74 is the biofouling-resistant medical device of embodiment 70, wherein the phenyl azide-based copolymer has a number-average molecular weight of between about 40,000 and about 100,000.

Embodiment 75 is the biofouling-resistant medical device of embodiment 70, wherein the phenyl azide-based copolymer has a number-average molecular weight of between about 80,000 and about 160,000.

Embodiment 76 is the biofouling-resistant medical device of embodiment 70, wherein the phenyl azide-based copolymer has a number-average molecular weight of between about 120,000 and about 200,000.

Embodiment 77 is the biofouling-resistant medical device of embodiment 70, wherein the phenyl azide-based copolymer has a number-average molecular weight of between about 14,000 and about 21,000.

Embodiment 78 is the biofouling-resistant medical device of embodiment 70, wherein the phenyl azide-based copolymer has a number-average molecular weight of between about 15,000 and about 18,000.

Embodiment 79 is a biofouling-resistant medical device, wherein a surface of the medical device is coated with a phenyl azide-based copolymer having a polydispersity index (PDI) of between about 1 and 1.5.

Embodiment 80 is the biofouling-resistant medical device of embodiment 79, wherein the PDI is about 1.4, 1.3, 1.2, or 1.1.

Embodiment 81 is the biofouling-resistant medical device of embodiment 79, wherein the PDI is about 1.19.

Embodiment 82 is the biofouling-resistant medical device of any one of embodiments 70-81, wherein the medical device comprises a dental instrument or a medical instrument.

Embodiment 83 is the biofouling-resistant medical device of any one of embodiments 70-82, wherein the medical device comprises an implant, an IV, a prosthesis, a suturing material, a valve, a stent, a catheter, a rod, a shunt, a scope, a contact lens, a tubing, a wiring, an electrode, a clip, a fastener, a syringe, a container, or a combination thereof.

Embodiment 84 is the biofouling-resistant medical device of embodiment 83, wherein the medical device is a contact lens.

Embodiment 85 is the biofouling-resistant medical device of embodiment 83, wherein the medical device is a catheter.

Embodiment 86 is the biofouling-resistant medical device of embodiment 85, wherein the catheter is an indwelling catheter.

Embodiment 87 is the biofouling-resistant medical device of embodiment 85, wherein the catheter comprises a uretic catheter or a Foley catheter.

Embodiment 88 is the biofouling-resistant medical device of embodiment 83, wherein the medical device is a scope.

Embodiment 89 is the biofouling-resistant medical device of embodiment 88, wherein the scope comprises a scope utilized in an image-guided surgery.

Embodiment 90 is the biofouling-resistant medical device of embodiment 88, wherein the scope comprises a scope utilized in endoscopy or laparoscopy.

Embodiment 91 is the biofouling-resistant medical device of embodiment 82 or 83, wherein the medical device comprises auditory prostheses, artificial larynx, dental implants, mammary implants, penile implants, cranio/facial tendons, tendons, ligaments, menisci, or disks.

Embodiment 92 is the biofouling-resistant medical device of any one of embodiments 82, 83, or 91, wherein the medical device comprises artificial bones, artificial joints, or artificial organs.

Embodiment 93 is the biofouling-resistant medical device of embodiment 92, wherein the artificial organs comprise artificial pancreas, artificial hearts, artificial limbs, or heart valves.

Embodiment 94 is the biofouling-resistant medical device of any one of embodiments 70-81, wherein the medical device comprises a bandage or a patch.

Embodiment 95 is the biofouling-resistant medical device of any one of embodiments 70-94, wherein the copolymer comprises zwitterionic copolymer.

Embodiment 96 is the biofouling-resistant medical device of embodiment 95, wherein the zwitterionic copolymer comprises polysulfobetaine.

Embodiment 97 is the biofouling-resistant medical device of any one of embodiments 70-97, wherein the biofouling is produced by a bacterium, a virus, and/or a fungus.

Embodiment 98 is a method of preparing a biofouling-resistant medical device, comprising:
a) contacting a surface of a medical device with a mixture comprising a charged or zwitterion copolymer; and
b) treating the surface of the medical device of step a) with a light source for a time sufficient to undergo photografting of the charged or zwitterion copolymer onto the surface of the medical device, thereby making the biofouling-resistant medical device;
wherein the charged or zwitterion copolymer comprises a phenyl azide-based copolymer; and wherein the charged or zwitterion copolymer having a number-average molecular weight of between about 10,000 and about 250,000.

Embodiment 99 is a method of preparing a charged or zwitterion copolymer modified biofouling-resistant device comprising:
a) contacting a surface of a silicon-based device with a mixture (e.g., a solution) comprising a charged or zwitterion copolymer; and
b) treating the surface of the device of step a) with a light source for a time sufficient to undergo photografting of the charged or zwitterion copolymer onto the surface of the silicon-based device, thereby generating the charged or zwitterion copolymer modified device;
wherein the charged or zwitterion copolymer comprises a phenyl azide-based copolymer.

Embodiment 100 is a method of preparing a charged or zwitterion copolymer modified biofouling-resistant device comprising:
a) contacting a surface of a device with a mixture (e.g., a solution) comprising a charged or zwitterion copolymer; and
b) treating the surface of the device of step a) with a light source for a time sufficient to undergo photografting of the charged or zwitterion copolymer onto the surface of the device, thereby generating the charged or zwitterion copolymer modified device;
wherein the charged or zwitterion copolymer comprises a phenyl azide-based copolymer; and wherein the charged or zwitterion copolymer having a number-average molecular weight of between about 10,000 and about 250,000.

Embodiment 101 is the method of any one of embodiments 98-100, wherein the time sufficient to undergo photografting is at least 1 minute, at least 2 minutes, 3 minutes, 4 minutes, 5 minutes, 6 minutes, 7 minutes, 8 minutes, 9 minutes, 10 minutes, 15 minutes, 20 minutes, 25 minutes or 30 minutes.

Embodiment 102 is the method of any one of embodiments 98-101, wherein the light source is an ultraviolet light source.

Embodiment 103 is the method of embodiment 102, wherein the ultraviolet light source has an intensity of at least 900 μW/cm$^2$.

Embodiment 104 is the method of embodiment 102 or 103, wherein the ultraviolet light source has a wavelength of between 240 nm and 280 nm, between 240 nm and 275 nm, between 240 nm and 270 nm, between 240 nm and 265 nm, between 240 nm and 260 nm, between 240 nm and 255 nm, between 240 nm and 250 nm, between 240 nm and 245 nm, between 250 nm and 280 nm, between 250 nm and 275 nm, between 250 nm and 270 nm, between 250 nm and 265 nm, between 250 nm and 260 nm, between 255 nm and 280 nm, between 255 nm and 275 nm, between 255 nm and 270 nm, between 255 nm and 265 nm, between 255 nm and 260 nm, between 260 nm and 280 nm, between 260 nm and 275 nm, between 260 nm and 270 nm, or between 270 nm and 280 nm.

Embodiment 105 is the method of embodiment 102 or 103, wherein the ultraviolet light source has a wavelength of at least 240 nm, 245 nm, 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 275 nm or 280 nm.

Embodiment 106 is the method of any one of embodiments 98-100, wherein the mixture of step a) is an aqueous solution, an aqueous colloid, or an aqueous suspension.

Embodiment 107 is the method of any one of embodiments 98-100, wherein photografting of step b) is not affected by the presence of oxygen.

Embodiment 108 is the method of any one of embodiments 98-107, wherein the charged or zwitterion copolymer is a compound of any one of embodiments 17-68.

Embodiment 109 is the method of any one of the embodiments 98-108, wherein the mixture comprising a charged or zwitterion copolymer has a concentration of the charged or zwitterion copolymer in the mixture between 1 mg/mL and 30 mg/mL.

Embodiment 110 is the method of embodiment 109, wherein the concentration of the charged or zwitterion copolymer in the mixture is between 1 mg/mL and 25 mg/mL, between 1 mg/mL and 20 mg/mL, between 1 mg/mL and 15 mg/mL, between 1 mg/mL and 10 mg/mL, between 1 mg/mL and 5 mg/mL, between 5 mg/mL and 30 mg/mL, between 5 mg/mL and 25 mg/mL, between 5 mg/mL and 20 mg/mL, between 5 mg/mL and 15 mg/mL, between 5 mg/mL and 10 mg/mL, between 10 mg/mL and 30 mg/mL, between 10 mg/mL and 25 mg/mL, between 10 mg/mL and 20 mg/mL, between 10 mg/mL and 15 mg/mL, between 15 mg/mL and 30 mg/mL, between 15 mg/mL and 25 mg/mL, between 15 mg/mL and 20 mg/mL, between 20 mg/mL and 30 mg/mL, or between 20 mg/mL and 25 mg/mL.

Embodiment 111 is the method of embodiment 109, wherein the concentration of the charged or zwitterion copolymer in the mixture is about 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14 mg/mL, 15 mg/mL, 16 mg/mL, 17 mg/mL, 18 mg/mL, 19 mg/mL, 20 mg/mL, 21 mg/mL, 22 mg/mL, 23 mg/mL, 24 mg/mL, 25 mg/mL, 26 mg/mL, 27 mg/mL, 28 mg/mL, 29 mg/mL, or 30 mg/mL.

Embodiment 112 is the method of any one of embodiments 98-111, wherein the concentration of the charged or zwitterion copolymer is between 0.1 to 1 mg per square centimeter of the device.

Embodiment 113 is the method of embodiment 99, wherein the charged or zwitterion copolymer has a number-average molecular weight of between about 10,000 and about 250,000

Embodiment 114 is the method of any one of embodiments 98 or 100-113, wherein the charged or zwitterion copolymer has a number-average molecular weight of between about 10,000 and about 20,000.

Embodiment 115 is the method of any one of embodiments 98 or 100-113, wherein the charged or zwitterion copolymer has a number-average molecular weight of between about 10,000 and about 40,000.

Embodiment 116 is the method of any one of embodiments 98 or 100-113, wherein the charged or zwitterion copolymer has a number-average molecular weight of between about 20,000 and about 60,000.

Embodiment 117 is the method of any one of embodiments 98 or 100-113, wherein the charged or zwitterion copolymer has a number-average molecular weight of between about 40,000 and about 100,000.

Embodiment 118 is the method of any one of embodiments 98 or 100-113, wherein the charged or zwitterion copolymer has a number-average molecular weight of between about 80,000 and about 160,000.

Embodiment 119 is the method of any one of embodiments 98 or 100-113, wherein the charged or zwitterion copolymer has a number-average molecular weight of between about 120,000 and about 200,000.

Embodiment 120 is the method of any one of embodiments 98 or 100-113, wherein the charged or zwitterion copolymer has a number-average molecular weight of between about 14,000 and about 21,000.

Embodiment 121 is the method of any one of embodiments 98 or 100-113, wherein the charged or zwitterion copolymer has a number-average molecular weight of between about 15,000 and about 18,000.

Embodiment 122 is the method of embodiment 98 or 100, wherein the device comprises a carbon-based device or a silicon-based device.

Embodiment 123 is the method of embodiment 122, wherein the device comprises a silicon-based device.

Embodiment 124 is the method of embodiment 99 or 123, wherein the silicon-based device comprises a silicon-based polymer moiety.

Embodiment 125 is the method of embodiment 124, wherein the silicon-based polymer moiety comprises siloxane polymer moiety, sesquisiloxane polymer moiety, siloxane-silarylene polymer moiety, silalkylene polymer moiety, polysilane moiety, polysilylene moiety, or polysilazane moiety.

Embodiment 126 is the method of embodiment 101, wherein the silicon-based device comprises siloxane polymer moiety.

Embodiment 127 is the method of embodiment 98, wherein the device comprises a carbon-based device.

Embodiment 128 is the method of embodiment 127, wherein the carbon-based device comprises a carbon-based polymer.

Embodiment 129 is the method of embodiment 127, wherein the carbon-based device comprises a polyolefin moiety.

Embodiment 130 is the method of embodiment 129, wherein the polyolefin moiety comprises polyethylene moiety, polypropylene moiety, polyvinyl chloride moiety, polyvinylidene fluoride moiety, polytetrafluoroethylene moiety, polychlorotrifluoroethylene moiety, or polystyrene moiety.

Embodiment 131 is the method of embodiment 128, wherein the carbon-based polymer comprises polyamide moiety, polyurethane moiety, phenol-formaldehyde resin moiety, polycarbonate moiety, polychloroprene moiety, polyacrylonitrile moiety, polimide moiety, or polyester moiety.

Embodiment 132 is the method of embodiment 128, wherein the carbon-based polymer comprises nylon.

Embodiment 133 is the method of embodiment 128, wherein the carbon-based polymer comprises polyethylene terephthalate.

Embodiment 134 is the method of any one of embodiments 98-133, wherein the copolymer comprises zwitterionic copolymer.

Embodiment 135 is the method of embodiment 134, wherein the zwitterionic copolymer comprises polysulfobetaine.

Embodiment 136 is the method of any one of embodiments 98-135, wherein the biofouling is produced by a bacterium, a virus, and/or a fungus.

Embodiment 137 is a method for synthesizing a compound of Formula (II) comprising: reacting a compound of Formula (IV) or a salt or solvate thereof with a compound of Formula (V):

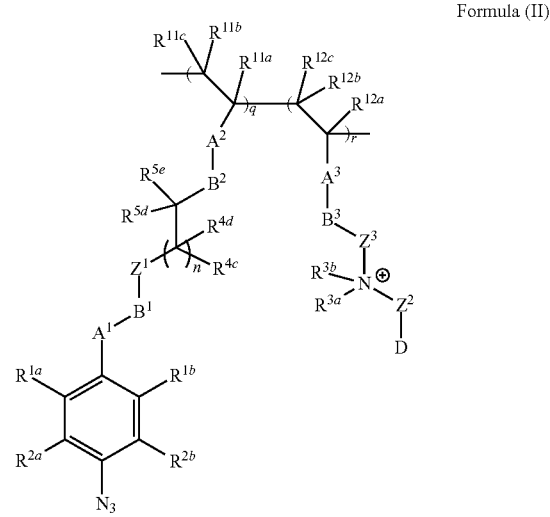

Formula (II)

-continued

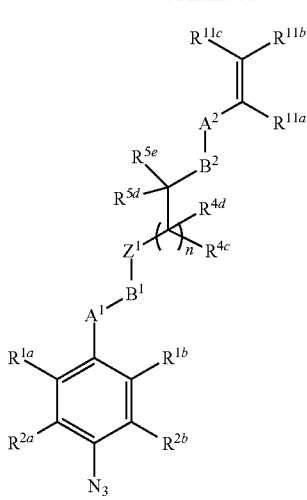

Formula (IV)

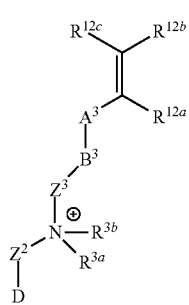

Formula (V)

wherein
each $R^{1a}$ and $R^{1b}$ is independently selected from hydrogen and halogen;
each $R^{2a}$ and $R^{2b}$ is independently selected from halogen, —CN, and optionally substituted C1-C6fluoroalkyl;
each $A^1$, $A^2$, and $A^3$ is independently selected from —C(=O)—, —S(=O)—, —S(=O)$_2$—, and —S(=O)(=NR$^{3c}$)—;
each $B^1$, $B^2$, and $B^3$ is independently selected from —O— and —NR$^{3c}$—;
D is —S(=O)$_2$O$^-$, —S(=O)$_2$OR$^{9a}$, —C(=O)O$^-$, or —C(=O)OR$^{9a}$;
$Z^1$ is —(CR$^{6c}$R$^{6d}$)$_s$—;
$Z^2$ is —(CR$^{6c}$R$^{6d}$)$_t$—;
$Z^3$ is —(CR$^{6c}$R$^{6d}$)$_p$—;
each $R^{3a}$ and $R^{3b}$ is independently selected from hydrogen, optionally substituted C1-C4 alkyl, and optionally substituted benzyl;
each $R^{3c}$ and $R^{3d}$ is independently selected from hydrogen, optionally substituted C1-C4 alkyl, —X-optionally substituted C1-C4 alkyl, optionally substituted C2-C6 alkenyl, and optionally substituted aryl;
X is —C(=O)—, —S(=O)—, or —S(=O)$_2$—;
each $R^{4c}$, $R^{4d}$, $R^{5d}$, $R^{5e}$, $R^{6c}$, and $R^{6d}$ is independently selected from hydrogen, halogen, —CN, —OH, optionally substituted C1-C4 alkyl, optionally substituted C1-C4 fluoroalkyl, optionally substituted C2-C6 alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;
each $R^{9a}$, $R^{11a}$, $R^{11b}$, $R^{11c}$, $R^{12a}$, $R^{12b}$, and $R^{12c}$ is independently selected from hydrogen, optionally substituted C1-C4 alkyl, and optionally substituted aryl;
n is an integer selected from 0, 1, 2, 3, 4, 5, and 6;
s is an integer selected from 1, 2, 3, 4, or 5;

t is an integer selected from 1, 2, 3, 4, or 5;
p is an integer selected from 1, 2, 3, 4, or 5;
q is an integer selected from 40-60;
r is an integer selected from 1-10; and
wherein the compounds of Formula (II) and Formula (V) are each independently charged or zwitterionic.

Embodiment 138 is the method of embodiment 137, wherein each $R^{1a}$ and $R^{1b}$ is independently halogen.

Embodiment 139 is the method of embodiment 137 or 138, wherein each $R^{1a}$ and $R^{1b}$ is independently F or Cl.

Embodiment 140 is the method of any one of embodiments 137-139, wherein $R^{1a}$ and $R^{1b}$ are each F.

Embodiment 141 is the method of any one of embodiments 137-140, wherein each $R^{2a}$ and $R^{2b}$ is independently selected from halogen, —CN, and —CF$_3$;

Embodiment 142 is the method of any one of embodiments 137-141, wherein each $R^{2a}$ and $R^{2b}$ is independently selected from F, Cl, —CN, and —CF$_3$;

Embodiment 143 is the method of any one of embodiments 137-142, wherein $R^{2a}$ and $R^{2b}$ are each F.

Embodiment 144 is the method of any one of embodiments 137-143, wherein $A^1$ is —S(=O)$_2$—; $A^2$ is —C(=O)—; and $A^3$ is —C(=O)—.

Embodiment 145 is the method of embodiment 144, wherein $B^1$ and $B^2$ are each —NR$^{3c}$—.

Embodiment 146 is the method of embodiment 145, wherein $R^{3c}$ is hydrogen or —CH$_3$.

Embodiment 147 is the method of embodiment 146, wherein $R^{3c}$ is hydrogen.

Embodiment 148 is the method of embodiment 144, wherein $B^3$ is —O—.

Embodiment 149 is the method of any one of embodiments 137-148, wherein D is —S(=O)$_2$OR$^9$a or —C(=O)OR$^{9a}$.

Embodiment 150 is the method of embodiment 149, wherein $R^{9a}$ is hydrogen or —CH$_3$.

Embodiment 151 is the method of any one of embodiments 137-148, wherein D is —S(=O)$_2$O$^-$ or —C(=O)O$^-$.

Embodiment 152 is the method of embodiment 151, wherein D is —S(=O)$_2$O$^-$.

Embodiment 153 is the method of any one of embodiments 137-152, wherein each $R^{6c}$ and $R^{6d}$ is hydrogen.

Embodiment 154 is the method of any one of embodiments 137-153, wherein each $R^{3a}$ and $R^{3b}$ is —CH$_3$.

Embodiment 155 is the method of any one of embodiments 137-154, wherein $R^{11a}$ is hydrogen or —CH$_3$.

Embodiment 156 is the method of embodiment 155, wherein $R^{11a}$ is —CH$_3$.

Embodiment 157 is the method of any one of embodiments 137-156, wherein $R^{12a}$ is hydrogen or —CH$_3$.

Embodiment 158 is the method of embodiment 157, wherein $R^{12a}$ is —CH$_3$.

Embodiment 159 is the method of any one of embodiments 137-158, wherein each $R^{11b}$, $R^{11c}$, $R^{12b}$, and $R^{12c}$ is hydrogen.

Embodiment 160 is a method for synthesizing a compound of Formula (III) comprising: reacting a compound of Formula (IV) or a salt or solvate thereof with a compound of Formula (VI):

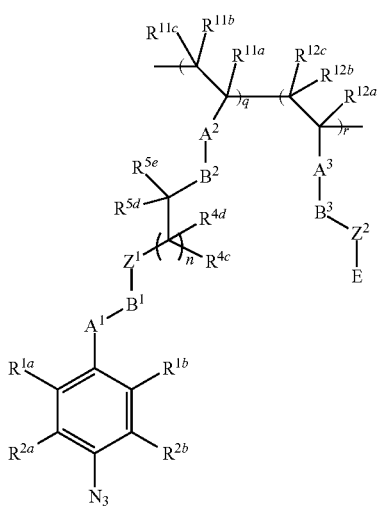

Formula (III)

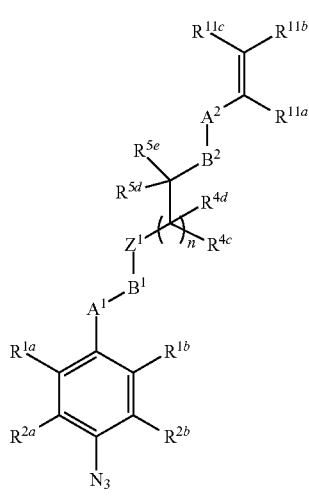

Formula (IV)

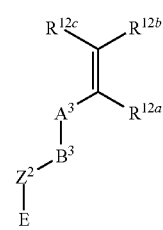

Formula (VI)

wherein
each $R^{1a}$ and $R^{1b}$ is independently selected from hydrogen and halogen;
each $R^{2a}$ and $R^{2b}$ is independently selected from halogen, —CN, and optionally substituted C1-C6 fluoroalkyl;
each $A^1$, $A^2$, and $A^3$ is independently selected from —C(=O)—, —S(=O)—, —S(=O)$_2$—, and —S(=O)(=NR$^{3c}$)—;
each $B^1$, $B^2$, and $B^3$ is independently selected from —O— and —NR$^{3c}$—;
$Z^1$ is —(CR$^{6c}$R$^{6d}$)$_s$—;
$Z^2$ is —(CR$^{6c}$R$^{6d}$)$_t$—;
E is —CN, —OR$^{9a}$, —NR$^{9a}$R$^{9b}$, —NR$^{9a}$R$^{9b}$R$^{9c+}$, optionally substituted C1-C4 alkyl, optionally substituted C1-C6fluoroalkyl, —S(=O)$_2$O$^-$, —S(=O)$_2$OR$^{9a}$, —C(=O)O$^-$, or —C(=O)OR$^{9a}$;
each $R^{4c}$, $R^{4d}$, $R^{5d}$, $R^{5e}$, $R^{6c}$, and $R^{6d}$ is independently selected from hydrogen, halogen, —CN, —OR$^{9a}$, optionally substituted C1-C4 alkyl, optionally substituted C1-C4 fluoroalkyl, optionally substituted C2-C6 alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;
each $R^{3c}$ and $R^{3d}$ is independently selected from hydrogen, optionally substituted C1-C4 alkyl, —X-optionally substituted C1-C4 alkyl, optionally substituted C2-C6 alkenyl, and optionally substituted aryl;
X is —C(=O)—, —S(=O)—, or —S(=O)$_2$—;
each $R^{9a}$, $R^{11a}$, $R^{11b}$, $R^{11c}$, $R^{12a}$, $R^{12b}$, and $R^{12c}$ is independently selected from hydrogen, optionally substituted C1-C4 alkyl, and optionally substituted aryl;
n is an integer selected from 0, 1, 2, 3, 4, 5, and 6;
s is an integer selected from 1, 2, 3, 4, or 5;
t is an integer selected from 1, 2, 3, 4, or 5;
q is an integer selected from 40-60; and
r is an integer selected from 1-10.

Embodiment 161 is the method of embodiment 160, wherein each $R^{1a}$ and $R^{1b}$ is independently halogen.

Embodiment 162 is the method of embodiment 160 or 161, wherein each $R^{1a}$ and $R^{1b}$ is independently F or Cl.

Embodiment 163 is the method of any one of embodiments 160-162, wherein $R^{1a}$ and $R^{1b}$ are each F.

Embodiment 164 is the method of any one of embodiments 160-163, wherein each $R^{2a}$ and $R^{2b}$ is independently selected from halogen, —CN, and —CF$_3$;

Embodiment 165 is the method of any one of embodiments 160-164, wherein each $R^{2a}$ and $R^{2b}$ is independently selected from F, Cl, —CN, and —CF$_3$;

Embodiment 166 is the method of any one of embodiments 160-165, wherein $R^{2a}$ and $R^{2b}$ are each F.

Embodiment 167 is the method of any one of embodiments 160-166, wherein $A^1$ is —S(=O)$_2$—; $A^2$ is —C(=O)—; and $A^3$ is —C(=O)—.

Embodiment 168 is the method of embodiment 167, wherein $B^1$ and $B^2$ are each —NR$^{3c}$—.

Embodiment 169 is the method of embodiment 168 wherein $R^{3c}$ is hydrogen or —CH$_3$.

Embodiment 170 is the method of embodiment 169, wherein $R^{3c}$ is hydrogen.

Embodiment 171 is the method of embodiment 170, wherein $B^3$ is —NR$^{3c}$—.

Embodiment 172 is the method of embodiment 171, wherein $R^{3c}$ is hydrogen.

Embodiment 173 is the method of any one of embodiments 160-172, wherein E is —NR$^{9a}$R$^{9b}$R$^{9c+}$ or —S(=O)$_2$OR$^{9a}$.

Embodiment 174 is the method of embodiment 173, wherein E is —NR$^{9a}$R$^{9b}$R$^{9c+}$.

Embodiment 175 is the method of embodiment 174, wherein each $R^{9a}$, $R^{9b}$, or $R^{9c}$ is H or —CH$_3$.

Embodiment 176 is the method of embodiment 175, wherein each $R^{9a}$, $R^{9b}$, or $R^{9c}$ is H.

Embodiment 177 is the method of embodiment 175, wherein each $R^{9a}$, $R^{9b}$, or $R^{9c}$ is —CH$_3$.

Embodiment 178 is the method of embodiment 173, wherein E is —S(=O)$_2$OR$^{9a}$.

Embodiment 179 is the method of embodiment 178, wherein $R^{9a}$ H or —CH$_3$.

Embodiment 180 is the method of embodiment 179, wherein each $R^{9a}$ is H.

Embodiment 181 is the method of embodiment 179, wherein each $R^{9a}$ is —CH$_3$.

Embodiment 182 is the method of any one of embodiments 160-181, wherein each $R^{6c}$ and $R^{6d}$ is independently selected from hydrogen and —CH$_3$.

Embodiment 183 is the method of any one of embodiments 160-182, wherein each $R^{3a}$ and $R^{3b}$ is —$CH_3$.

Embodiment 184 is the method of any one of embodiments 160-183, wherein $R^{11a}$ is hydrogen or —$CH_3$.

Embodiment 185 is the method of embodiment 184, wherein $R^{11a}$ is —$CH_3$.

Embodiment 186 is the method of any one of embodiments 160-185, wherein $R^{12a}$ is hydrogen or —$CH_3$.

Embodiment 187 is the method of embodiment 186, wherein $R^{12a}$ is —$CH_3$.

Embodiment 188 is the method of any one of embodiments 160-187, wherein each $R^{11b}$, $R^{11c}$, $R^{12b}$, and $R^{12c}$ is hydrogen.

Embodiment 189 is a charged or zwitterion copolymer modified biofouling-resistant device prepared by the method comprising:
  a) contacting a surface of a silicon-based device with a mixture (e.g., a solution) comprising a charged or zwitterion copolymer; and
  b) treating the surface of the device of step a) with a light source for a time sufficient to undergo photografting of the charged or zwitterion copolymer onto the surface of the silicon-based device, thereby generating the charged or zwitterion copolymer modified device; wherein the charged or zwitterion copolymer comprises a phenyl azide-based copolymer.

Embodiment 190 is a charged or zwitterion copolymer modified biofouling-resistant device prepared by the method comprising:
  a) contacting a surface of a device with a mixture (e.g., a solution) comprising a charged or zwitterion copolymer; and
  b) treating the surface of the device of step a) with a light source for a time sufficient to undergo photografting of the charged or zwitterion copolymer onto the surface of the device, thereby generating the charged or zwitterion copolymer modified device; wherein the charged or zwitterion copolymer comprises a phenyl azide-based copolymer;
  and wherein the charged or zwitterion copolymer having a number-average molecular weight of between about 10,000 and about 250,000.

Embodiment 191 is the device of embodiment 189 or 190, wherein the time sufficient to undergo photografting is at least 1 minute, at least 2 minutes, 3 minutes, 4 minutes, 5 minutes, 6 minutes, 7 minutes, 8 minutes, 9 minutes, 10 minutes, 15 minutes, 20 minutes, 25 minutes or 30 minutes.

Embodiment 192 is the device of any one of embodiments 189-191, wherein the light source is an ultraviolet light source.

Embodiment 193 is the device of embodiment 192, wherein the ultraviolet light source has an intensity of at least 900 µW/cm².

Embodiment 194 is the device of embodiment 192 or 193, wherein the ultraviolet light source has a wavelength of between 240 nm and 280 nm, between 240 nm and 275 nm, between 240 nm and 270 nm, between 240 nm and 265 nm, between 240 nm and 260 nm, between 240 nm and 255 nm, between 240 nm and 250 nm, between 240 nm and 245 nm, between 250 nm and 280 nm, between 250 nm and 275 nm, between 250 nm and 270 nm, between 250 nm and 265 nm, between 250 nm and 260 nm, between 255 nm and 280 nm, between 255 nm and 275 nm, between 255 nm and 270 nm, between 255 nm and 265 nm, between 255 nm and 260 nm, between 260 nm and 280 nm, between 260 nm and 275 nm, between 260 nm and 270 nm, or between 270 nm and 280 nm.

Embodiment 195 is the device of embodiment 192 or 193, wherein the ultraviolet light source has a wavelength of at least 240 nm, 245 nm, 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 275 nm or 280 nm.

Embodiment 196 is the device of embodiment 189 or 190, wherein the mixture of step a) is an aqueous solution, an aqueous colloid, or an aqueous suspension.

Embodiment 197 is the device of embodiment 189 or 190, wherein photografting of step b) is not affected by the presence of oxygen.

Embodiment 198 is the device of any one of embodiments 189-197, wherein the charged or zwitterion compound is a compound of any one of embodiments 1-68.

Embodiment 199 is the device of any one of the embodiments 189-198, wherein the mixture comprising a charged or zwitterion compound has a concentration of the charged or zwitterion compound in the mixture between 1 mg/mL and 30 mg/mL.

Embodiment 200 is the device of embodiment 199, wherein the concentration of the charged or zwitterion compound in the mixture is between 1 mg/mL and 25 mg/mL, between 1 mg/mL and 20 mg/mL, between 1 mg/mL and 15 mg/mL, between 1 mg/mL and 10 mg/mL, between 1 mg/mL and 5 mg/mL, between 5 mg/mL and 30 mg/mL, between 5 mg/mL and 25 mg/mL, between 5 mg/mL and 20 mg/mL, between 5 mg/mL and 15 mg/mL, between 5 mg/mL and 10 mg/mL, between 10 mg/mL and 30 mg/mL, between 10 mg/mL and 25 mg/mL, between 10 mg/mL and 20 mg/mL, between 10 mg/mL and 15 mg/mL, between 15 mg/mL and 30 mg/mL, between 15 mg/mL and 25 mg/mL, between 15 mg/mL and 20 mg/mL, between 20 mg/mL and 30 mg/mL, or between 20 mg/mL and 25 mg/mL.

Embodiment 201 is the device of embodiment 199, wherein the concentration of the charged or zwitterion compound in the mixture is about 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14 mg/mL, 15 mg/mL, 16 mg/mL, 17 mg/mL, 18 mg/mL, 19 mg/mL, 20 mg/mL, 21 mg/mL, 22 mg/mL, 23 mg/mL, 24 mg/mL, 25 mg/mL, 26 mg/mL, 27 mg/mL, 28 mg/mL, 29 mg/mL, or 30 mg/mL.

Embodiment 202 is the device of any one of embodiments 189-201, wherein the concentration of the charged or zwitterion compound is between 0.1 to 1 mg per square centimeter of the device.

Embodiment 203 is the device of embodiment 189, wherein the charged or zwitterion copolymer has a number-average molecular weight of between about 10,000 and about 250,000

Embodiment 204 is the device of any one of embodiments 190-202, wherein the charged or zwitterion copolymer has a number-average molecular weight of between about 10,000 and about 20,000.

Embodiment 205 is the device of any one of embodiments 190-202, wherein the charged or zwitterion copolymer has a number-average molecular weight of between about 10,000 and about 40,000.

Embodiment 206 is the device of any one of embodiments 190-202, wherein the charged or zwitterion copolymer has a number-average molecular weight of between about 20,000 and about 60,000.

Embodiment 207 is the device of any one of embodiments 190-202, wherein the charged or zwitterion copolymer has a number-average molecular weight of between about 40,000 and about 100,000.

Embodiment 208 is the device of any one of embodiments 190-202, wherein the charged or zwitterion copolymer has a number-average molecular weight of between about 80,000 and about 160,000.

Embodiment 209 is the device of any one of embodiments 190-202, wherein the charged or zwitterion copolymer has a number-average molecular weight of between about 120,000 and about 200,000.

Embodiment 210 is the device of any one of embodiments 190-202, wherein the charged or zwitterion copolymer has a number-average molecular weight of between about 14,000 and about 21,000.

Embodiment 211 is the device of any one of embodiments 190-202, wherein the charged or zwitterion copolymer has a number-average molecular weight of between about 15,000 and about 18,000.

Embodiment 212 is the device of embodiment 190, wherein the device comprises a carbon-based device or a silicon-based device containing a moiety capable of binding with the phenyl azide-zwitterion copolymer of any one of embodiments 17-68.

Embodiment 213 is the device of embodiment 212, wherein the device comprises a silicon-based device.

Embodiment 214 is the device of embodiment 189 or 213, wherein the silicon-based device comprises a polymer moiety.

Embodiment 215 is the device of embodiment 214, wherein the silicon-based device comprises a siloxane polymer moiety, a sesquisiloxane polymer moiety optionally having a ladder structure, a siloxane-silarylene polymer moiety, a silalkylene polymer moiety, a polysilane moiety, a polysilylene moiety, or a polysilazane moiety.

Embodiment 216 is the device of embodiment 215, wherein the silicon-based device comprises a siloxane polymer moiety.

Embodiment 217 is the device of embodiment 212, wherein the device comprises a carbon-based device.

Embodiment 218 is the device of embodiment 217, wherein the carbon-based device comprises a carbon-based polymer.

Embodiment 219 is the device of embodiment 217, wherein the carbon-based device comprises a polyolefin moiety.

Embodiment 220 is the device of embodiment 219, wherein the polyolefin moiety comprises polyethylene moiety, polypropylene moiety, polyvinyl chloride moiety, polyvinylidene fluoride moiety, polytetrafluoroethylene moiety, polychlorotrifluoroethylene moiety, or polystyrene moiety.

Embodiment 221 is the device of embodiment 218, wherein the carbon-based polymer comprises polyamide moiety, polyurethane moiety, phenol-formaldehyde resin moiety, polycarbonate moiety, polychloroprene moiety, polyacrylonitrile moiety, polimide moiety, or polyester moiety.

Embodiment 222 is the device of embodiment 218, wherein the carbon-based polymer comprises nylon.

Embodiment 223 is the device of embodiment 218, wherein the carbon-based polymer comprises polyethylene terephthalate.

Embodiment 224 is the device of any one of embodiments 189-223, wherein the device is resistant to fouling.

Embodiment 225 is the device of embodiment 224, wherein the device prevents and/or reduces biofouling.

Embodiment 226 is the device of embodiment 225, wherein biofouling comprises microfouling or macrofouling.

Embodiment 227 is the device of embodiment 226, wherein microfouling comprises biofilm and bacterial adhesion.

Embodiment 228 is the device of embodiment 226 or 227, wherein microfouling is formed by a bacterium or a fungus.

Embodiment 229 is the device of any one of embodiments 226-228, wherein microfouling is formed by a gram-positive bacterium.

Embodiment 230 is the device of embodiment 229, wherein the gram-positive bacterium comprises a bacterium from the genus *Actinomyces, Arthrobacter, Bacillus, Clostridium, Corynebacterium, Enterococcus, Lactococcus, Listeria, Micrococcus, Mycobacterium, Staphylococcus,* or *Streptococcus.*

Embodiment 231 is the device of embodiment 229 or 230, wherein the gram-positive bacterium comprises *Actinomyces* spp., *Arthrobacter* spp., *Bacillus licheniformis, Clostridium difficile, Clostridium* spp., *Corynebacterium* spp., *Enterococcus faecalis, Lactococcus* spp., *Listeria monocytogenes, Micrococcus* spp., *Mycobacterium* spp., *Staphylococcus aureus, Staphylococcus epidermidis, Streptococcus pneumoniae,* or *Streptococcus pyogenes.*

Embodiment 232 is the device of any one of embodiments 226-228, wherein microfouling is formed by a gram-negative bacterium.

Embodiment 233 is the device of embodiment 232, wherein the gram-negative bacterium comprises a bacterium from the genus *Alteromonas, Aeromonas, Desulfovibrio, Escherichia, Fusobacterium, Geobacter, Haemophilus, Klebsiella, Legionella, Porphyromonas, Proteus, Pseudomonas, Serratia, Shigella, Salmonella,* or *Vibrio.*

Embodiment 234 is the device of embodiment 232 or 233, wherein the gram-negative bacterium comprises *Alteromonas* spp., *Aeromonas* spp., *Desulfovibrio* spp., *Escherichia coli, Fusobacterium nucleatum, Geobacter* spp., *Haemophilus* spp., *Klebsiella* spp., *Legionella pneumophila, Porphyromonas* spp., *Pseudomonas aeruginosa, Proteus vulgaris, Proteus mirabilis, Proteus penneri, Serratia* spp., *Shigella dysenteriae, Shigella flexneri, Shigella boydii, Shigella sonnei, Salmonella bongori, Salmonella enterica,* or *Vibrio Cholerae.*

Embodiment 235 is the device of any one of embodiments 226-228, wherein the bacterium is a marine bacterium.

Embodiment 236 is the device of embodiment 235, wherein the marine bacterium comprises *Pseudoalteromonas* spp. or *Shewanella* spp.

Embodiment 237 is the device of any one of embodiments 226-228, wherein microfouling is formed by a fungus.

Embodiment 238 is the device of embodiment 237, wherein the fungus comprises *Candida albicans, Candida glabrata, Candida rugose, Candida parapsilosis, Candida tropicalis, Candida dubliniensis,* or *Hormoconis resinae.*

Embodiment 239 is the device of embodiment 226, wherein macrofouling comprises calcareous fouling organism or non-calcareous fouling organism.

Embodiment 240 is the device of embodiment 239, wherein calcareous fouling organism comprises barnacle, bryozoan, mollusk, polychaete, tube worm, or zebra mussel.

Embodiment 241 is the device of embodiment 239, wherein non-calcareous fouling organism comprises seaweed, hydroids, or algae.

Embodiment 242 is the device of any one of embodiments 189-241, wherein the formation of biofouling on a surface of a device is reduced by about 10%, 20%, 30%, 40%, 50%, 60%, 70%, 80%, 90%, 95%, 99%, 99.5%, 99.9%, or more relative to unmodified surface of a device.

Embodiment 243 is the device of any one of embodiments 189-242, wherein the device is further coated with an additional agent.

Embodiment 244 is the device of embodiment 243, wherein the additional agent is an antimicrobial agent.

Embodiment 245 is the device of embodiment 243, wherein the additional agent is a chemical disinfectant.

Embodiment I is a compound that has the structure of Formula (II):

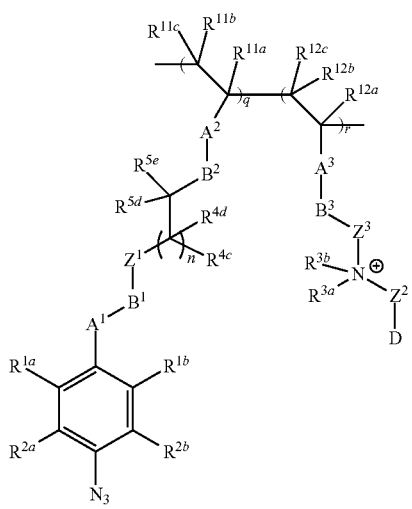

Formula (II)

wherein
each $R^{1a}$ and $R^{1b}$ is independently selected from hydrogen and halogen;
each $R^{2a}$ and $R^{2b}$ is independently selected from halogen, —CN, and optionally substituted C1-C6fluoroalkyl;
each $A^1$, $A^2$, and $A^3$ is independently selected from —C(=O)—, —S(=O)—, —S(=O)$_2$—, and —S(=O)(=NR$^{3c}$)—;
each $B^1$, $B^2$, and $B^3$ is independently selected from —O— and —NR$^{3c}$—;
D is —S(=O)$_2$O$^-$, —S(=O)$_2$OR$^{9a}$, —C(=O)O$^-$, or —C(=O)OR$^{9a}$;
$Z^1$ is —(CR$^{6c}$R$^{6d}$)$_s$—;
$Z^2$ is —(CR$^{6c}$R$^{6d}$)$_t$—;
$Z^3$ is —(CR$^{6c}$R$^{6d}$)$_p$—;
each $R^{3a}$ and $R^{3b}$ is independently selected from hydrogen, optionally substituted C1-C4 alkyl, and optionally substituted benzyl;
each $R^{3c}$ and $R^{3d}$ is independently selected from hydrogen, optionally substituted C1-C4 alkyl, —X-optionally substituted C1-C4 alkyl, optionally substituted C2-C6 alkenyl, and optionally substituted aryl;
X is —C(=O)—, —S(=O)—, or —S(=O)$_2$—;
each $R^{4c}$, $R^{4d}$, $R^{5d}$, $R^{5e}$, $R^{6c}$, and $R^{6d}$ is independently selected from hydrogen, halogen, —CN, —OH, optionally substituted C1-C4 alkyl, optionally substituted C1-C4 fluoroalkyl, optionally substituted C2-C6 alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;
each $R^{9a}$, $R^{11a}$, $R^{11b}$, $R^{11c}$, $R^{12a}$, $R^{12b}$, and $R^{12c}$ is independently selected from hydrogen, optionally substituted C1-C4 alkyl, and optionally substituted aryl;
n is an integer selected from 0, 1, 2, 3, 4, 5, and 6;

s is an integer selected from 1, 2, 3, 4, or 5;
t is an integer selected from 1, 2, 3, 4, or 5;
p is an integer selected from 1, 2, 3, 4, or 5;
q is an integer selected from 40-60;
r is an integer selected from 1-10; and
wherein the compounds of Formula (II) is charged or zwitterionic.

Embodiment II is the compound of embodiment I, wherein each $R^{1a}$ and $R^{1b}$ is independently halogen.

Embodiment III is the compound of embodiment I, wherein each $R^{2a}$ and $R^{2b}$ is independently selected from halogen, —CN, and —CF$_3$;

Embodiment IV is the compound of embodiment I, wherein $A^1$ is —S(=O)$_2$—; $A^2$ is —C(=O)—; and $A^3$ is —C(=O)—.

Embodiment V is the compound of embodiment IV, wherein $B^1$ and $B^2$ are each —NR$^{3c}$— and wherein $B^3$ is —O—.

Embodiment VI is the compound of embodiment V, wherein D is —S(=O)$_2$O$^-$.

Embodiment VII is the compound of embodiment I, wherein each $R^{6c}$ and $R^{6d}$ is hydrogen and wherein each $R^{3a}$ and $R^{3b}$ is —CH$_3$.

Embodiment VIII is a compound that has the structure of Formula (III):

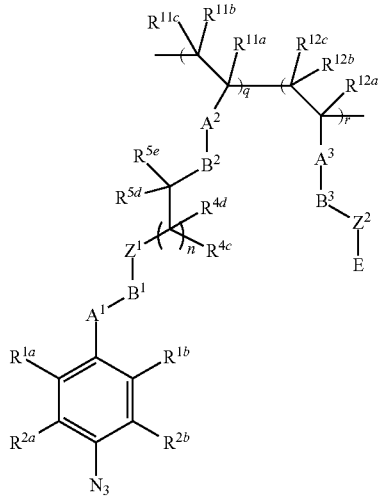

Formula (III)

wherein
each $R^{1a}$ and $R^{1b}$ is independently selected from hydrogen and halogen;
each $R^{2a}$ and $R^{2b}$ is independently selected from halogen, —CN, and optionally substituted C1-C6fluoroalkyl;
each $A^1$, $A^2$, and $A^3$ is independently selected from —C(=O)—, —S(=O)—, —S(=O)$_2$—, and —S(=O)(=NR$^{3c}$)—;
each $B^1$, $B^2$, and $B^3$ is independently selected from —O— and —NR$^{3c}$—;
$Z^1$ is —(CR$^{6c}$R$^{6d}$)$_s$—;
$Z^2$ is —(CR$^{6c}$R$^{6d}$)$_t$—;
E is —CN, —OR$^{9a}$, —NR$^{9a}$R$^{9b}$, —NR$^{9a}$R$^{9b}$R$^{9c+}$, optionally substituted C1-C4 alkyl, optionally substituted C1-C6fluoroalkyl, —S(=O)$_2$O$^-$, —S(=O)$_2$OR$^{9a}$, —C(=O)O$^-$, or —C(=O)OR$^{9a}$;
each $R^{4c}$, $R^{4d}$, $R^{5d}$, $R^{5e}$, $R^{6c}$, and $R^{6d}$ is independently selected from hydrogen, halogen, —CN, —OR$^{9a}$, optionally substituted C1-C4 alkyl, optionally substituted C1-C4 fluoroalkyl, optionally substituted C2-C6 alkenyl, —$NR^{3c}R^{3d}$, —$S(=O)_2O^-$, —$S(=O)_2OR^{9a}$, —$C(=O)O^-$, and —$C(=O)OR^{9a}$;

each $R^{3c}$ and $R^{3d}$ is independently selected from hydrogen, optionally substituted C1-C4 alkyl, —X-optionally substituted C1-C4 alkyl, optionally substituted C2-C6 alkenyl, and optionally substituted aryl;

X is —$C(=O)$—, —$S(=O)$—, or —$S(=O)_2$—;

each $R^{9a}$, $R^{11a}$, $R^{11b}$, $R^{11c}$, $R^{12a}$, $R^{12b}$, and $R^{12c}$ is independently selected from hydrogen, optionally substituted C1-C4 alkyl, and optionally substituted aryl;

n is an integer selected from 0, 1, 2, 3, 4, 5, and 6;
s is an integer selected from 1, 2, 3, 4, or 5;
t is an integer selected from 1, 2, 3, 4, or 5;
q is an integer selected from 40-60; and
r is an integer selected from 1-10.

Embodiment IX is the compound of embodiment VIII, wherein each $R^{1a}$ and $R^{1b}$ is independently halogen.

Embodiment X is the compound of embodiment VIII, wherein each $R^{2a}$ and $R^{2b}$ is independently selected from halogen, —CN, and —$CF_3$;

Embodiment XI is the compound of embodiment VIII, wherein $A^1$ is —$S(=O)_2$—; $A^2$ is —$C(=O)$—; and $A^3$ is —$C(=O)$—.

Embodiment XII is the compound of embodiment XI, wherein $B^1$ and $B^2$ are each —$NR^{3c}$— and wherein $B^3$ is —$NR^{3c}$—.

Embodiment XIII is the compound of embodiment XII, wherein E is —$NR^{9a}R^{9b}R^{9c+}$.

Embodiment XIV is the compound of embodiment XIII, wherein each $R^{9a}$, $R^{9b}$, or $R^{9c+}$ is H or —$CH_3$.

Embodiment XV is a medical device coated with a compound that has the structure of Formula (II):

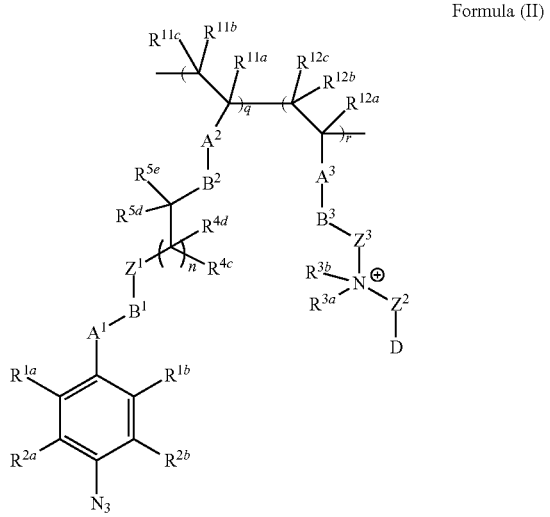

Formula (II)

wherein
each $R^{1a}$ and $R^{1b}$ is independently selected from hydrogen and halogen;
each $R^{2a}$ and $R^{2b}$ is independently selected from halogen, —CN, and optionally substituted C1-C6fluoroalkyl;
each $A^1$, $A^2$, and $A^3$ is independently selected from —$C(=O)$—, —$S(=O)$—, —$S(=O)_2$—, and —$S(=O)(=NR^{3c})$—;
each $B^1$, $B^2$, and $B^3$ is independently selected from —O— and —$NR^{3c}$—;

D is —$S(=O)_2O^-$, —$S(=O)_2OR^{9a}$, —$C(=O)O^-$, or —$C(=O)OR^{9a}$;
$Z^1$ is —$(CR^{6c}R^{6d})_s$—;
$Z^2$ is —$(CR^{6c}R^{6d})_t$—;
$Z^3$ is —$(CR^{6c}R^{6d})_p$—;
each $R^{3a}$ and $R^{3b}$ is independently selected from hydrogen, optionally substituted C1-C4 alkyl, and optionally substituted benzyl;
each $R^{3c}$ and $R^{3d}$ is independently selected from hydrogen, optionally substituted C1-C4 alkyl, —X-optionally substituted C1-C4 alkyl, optionally substituted C2-C6 alkenyl, and optionally substituted aryl;
X is —$C(=O)$—, —$S(=O)$—, or —$S(=O)_2$—;
each $R^{4c}$, $R^{4d}$, $R^{5d}$, $R^{5e}$, $R^{6c}$, and $R^{6d}$ is independently selected from hydrogen, halogen, —CN, —OH, optionally substituted C1-C4 alkyl, optionally substituted C1-C4 fluoroalkyl, optionally substituted C2-C6 alkenyl, —$NR^{3c}R^{3d}$, —$S(=O)_2O^-$, —$S(=O)_2OR^{9a}$, —$C(=O)O^-$, and —$C(=O)OR^{9a}$;
each $R^{9a}$, $R^{11a}$, $R^{11b}$, $R^{11c}$, $R^{12a}$, $R^{12b}$, and $R^{12c}$ is independently selected from hydrogen, optionally substituted C1-C4 alkyl, and optionally substituted aryl;
n is an integer selected from 0, 1, 2, 3, 4, 5, and 6;
s is an integer selected from 1, 2, 3, 4, or 5;
t is an integer selected from 1, 2, 3, 4, or 5;
p is an integer selected from 1, 2, 3, 4, or 5;
q is an integer selected from 40-60;
r is an integer selected from 1-10; and wherein the compounds of Formula (II) is charged or zwitterionic.

Embodiment XVI is the medical device of embodiment XV, wherein each $R^{1a}$ and $R^{1b}$ is independently halogen.

Embodiment XVII is the medical device of embodiment XV, wherein each $R^{2a}$ and $R^{2b}$ is independently selected from halogen, —CN, and —$CF_3$;

Embodiment XVIII is the medical device of embodiment XV, wherein $A^1$ is —$S(=O)_2$—; $A^2$ is —$C(=O)$—; and $A^3$ is —$C(=O)$—.

Embodiment XIX is the medical device of embodiment XVIII, wherein $B^1$ and $B^2$ are each —$NR^{3c}$— and wherein $B^3$ is —O—.

Embodiment XX is the medical device of embodiment XIX, wherein D is —$S(=O)_2O^-$.

Embodiment XXI is the medical device of embodiment XV, wherein each $R^{6c}$ and $R^{6d}$ is hydrogen and wherein each $R^{1a}$ and $R^{1b}$ is —$CH_3$.

Embodiment XXII is the medical device of embodiment XV, wherein the medical device comprises an implant, an IV, a prosthesis, a suturing material, a valve, a stent, a catheter, a rod, a shunt, a scope, a contact lens, a tubing, a wiring, an electrode, a clip, a fastener, a syringe, a container, or a combination thereof.

Embodiment XXIII is a biofouling-resistant medical device, wherein a surface of the medical device is coated with a phenyl azide-based copolymer that has a number-average molecular weight of between about 10,000 and about 250,000.

Embodiment XXIV is the biofouling-resistant medical device of embodiment XXIII, wherein the phenyl azide-based copolymer has a number-average molecular weight of between about 10,000 and about 20,000.

Embodiment XXV is the biofouling-resistant medical device of embodiment XXIII, wherein the phenyl azide-based copolymer has a polydispersity index (PDI) of between about 1 and 1.5.

Embodiment XXVI is the biofouling-resistant medical device of embodiment XXIII, wherein the medical device comprises an implant, an IV, a prosthesis, a suturing material, a valve, a stent, a catheter, a rod, a shunt, a scope, a contact lens, a tubing, a wiring, an electrode, a clip, a fastener, a syringe, a container, or a combination thereof.

Embodiment XXVII is the biofouling-resistant medical device of embodiment XXVI, wherein the medical device is a catheter.

Embodiment XXVIII is the biofouling-resistant medical device of embodiment XXVII, wherein the catheter is an indwelling catheter.

Embodiment XXIX is the biofouling-resistant medical device of embodiment XXIII, wherein the copolymer comprises polysulfobetaine.

Embodiment XXX is the biofouling-resistant medical device of embodiment XXIII, wherein the biofouling is produced by a bacterium, a virus, and/or a fungus.

What is claimed is:

1. A phenyl azide-based copolymer comprising a compound of formula (IV):

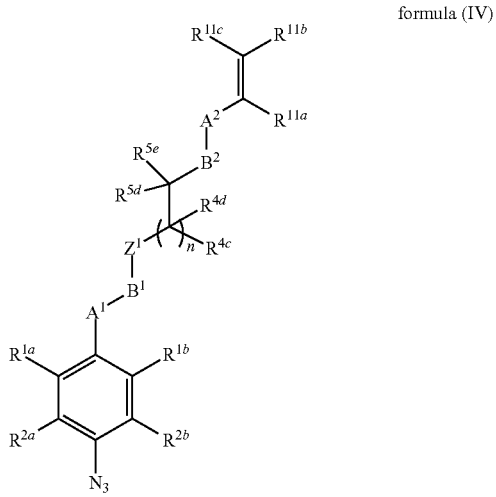

formula (IV)

wherein each $R^{1a}$ and $R^{1b}$ is independently selected from hydrogen and halogen;

each $R^{2a}$ and $R^{2b}$ is independently selected from halogen, —CN, and optionally substituted $C_1$-$C_6$ fluoroalkyl;

$A^1$ is —S(=O)$_2$—;

$A^2$ is —C(=O)—;

each $B^1$ and $B^2$ is independently selected from —O— and —NR$^{3c}$—;

$Z^1$ is —(CR$^{6c}$R$^{6d}$)$_s$—); each $R^{4c}$, $R^{4d}$, $R^{5d}$, $R^{5e}$, $R^{6c}$ and $R^{6d}$ is independently selected from hydrogen, halogen, —CN, —OR$^{9a}$, optionally substituted $C_1$-$C_4$ alkyl, optionally substituted $C_1$-$C_4$ fluoroalkyl, optionally substituted $C_2$-$C_6$ alkenyl, —NR$^{3c}$R$^{3d}$, —S(=O)$_2$O$^-$, —S(=O)$_2$OR$^{9a}$, —C(=O)O$^-$, and —C(=O)OR$^{9a}$;

each $R^{3c}$ and $R^{3d}$ is independently selected from hydrogen, optionally substituted $C_1$-$C_4$ alkyl, —X—, optionally substituted $C_1$-$C_4$ alkyl, optionally substituted $C_2$-$C_6$ alkenyl, and optionally substituted aryl;

X is —C(=O)—, —S(=O)—, or —S(=O)$_2$—;

each $R^{9a}$, $R^{11a}$, $R^{11b}$, and $R^{11c}$ is independently selected from hydrogen, optionally substituted $C_1$-$C_4$ alkyl, and optionally substituted aryl;

n is an integer selected from 0, 1, 2, 3, 4, 5, and 6; and s is an integer selected from 1, 2, 3, 4, and 5.

2. The phenyl azide-based copolymer of claim 1, wherein $R^{1a}$ and $R^{1b}$ are each F.

3. The phenyl azide-based copolymer of claim 1, wherein $R^{2a}$ and $R^{2b}$ are each F.

4. The phenyl azide-based copolymer of claim 1, wherein $B^1$ and $B^2$ are each —NR$^{3c}$—; and wherein $R^{3c}$ in —NR$^{3c}$— is hydrogen or —CH$_3$.

5. The phenyl azide-based copolymer of claim 4, wherein $R^{3c}$ in —NR$^{3c}$— is hydrogen.

6. The phenyl azide-based copolymer of claim 1, wherein each $R^{6c}$ and $R^{6d}$ is independently selected from hydrogen and -CH$_3$.

7. The phenyl azide-based copolymer of claim 1, wherein each $R^{5d}$ and $R^{5e}$ is hydrogen and n is 0.

8. The phenyl azide-based copolymer of claim 1, wherein $R^{11a}$ is hydrogen or —CH$_3$.

9. The phenyl azide-based copolymer of claim 1, wherein each $R^{11b}$ and $R^{11c}$ is hydrogen.

10. The phenyl azide-based copolymer of claim 1, wherein the phenyl azide-based copolymer comprises a monomer comprising sulfobetaine.

11. The phenyl azide-based copolymer of claim 10, wherein the monomer is sulfobetaine methacrylate.

12. The phenyl azide-based copolymer of claim 11, wherein the phenyl azide-based copolymer is formed from a reaction of the sulfobetaine methacrylate and the compound of formula (IV).

13. The phenyl azide-based copolymer of claim 1, wherein the phenyl azide-based copolymer comprises sulfobetaine methacrylate-co-perfluorophenylazide methacrylate.

14. The phenyl azide-based copolymer of claim 1, wherein the phenyl azide-based copolymer consists of sulfobetaine methacrylate-co-perfluorophenylazide methacrylate.

15. A biofouling resistant coating comprising the phenyl azide-based copolymer of claim 1.

16. The biofouling resistant coating of claim 15, wherein the biofouling resistant coating is configured to be coated onto a medical device.

17. A medical device coated with a compound that has the structure of the phenyl azide-based copolymer of claim 1.

18. The medical device of claim 17, wherein the medical device comprises an implant, an IV, a prosthesis, a suturing material, a valve, a stent, a catheter, a rod, a shunt, a scope, a contact lens, a tubing, a wiring, an electrode, a clip, a fastener, a syringe, a container for storage of one or more other medical devices, or a combination thereof.

19. The medical device of claim 18, wherein the medical device comprises the tubing.

* * * * *